(12) United States Patent
Hafez et al.

(10) Patent No.: US 12,305,235 B2
(45) Date of Patent: May 20, 2025

(54) METHODS FOR DETECTING IMMUNE CELL DNA AND MONITORING IMMUNE SYSTEM

(71) Applicant: Natera, Inc., San Carlos, CA (US)

(72) Inventors: Dina M. Hafez, Los Altos, CA (US); Prashanthi Natarajan, Foster City, CA (US); Raheleh Salari, San Carlos, CA (US); Ryan Swenerton, Millbrae, CA (US); Bernhard Zimmermann, Manteca, CA (US)

(73) Assignee: Natera, Inc., San Carlos, CA (US)

( * ) Notice: Subject to any disclaimer, the term of this patent is extended or adjusted under 35 U.S.C. 154(b) by 818 days.

(21) Appl. No.: 17/616,536

(22) PCT Filed: May 29, 2020

(86) PCT No.: PCT/US2020/035216
§ 371 (c)(1),
(2) Date: Dec. 3, 2021

(87) PCT Pub. No.: WO2020/247263
PCT Pub. Date: Dec. 10, 2020

(65) Prior Publication Data
US 2022/0251654 A1    Aug. 11, 2022

Related U.S. Application Data

(60) Provisional application No. 62/857,966, filed on Jun. 6, 2019.

(51) Int. Cl.
C12Q 1/68     (2018.01)
C12Q 1/6881   (2018.01)
C12Q 1/6844   (2018.01)

(52) U.S. Cl.
CPC .......... *C12Q 1/6881* (2013.01); *C12Q 1/6844* (2013.01); *C12Q 2600/156* (2013.01); *C12Q 2600/16* (2013.01)

(58) Field of Classification Search
None
See application file for complete search history.

(56) References Cited

U.S. PATENT DOCUMENTS

| | | | |
|---|---|---|---|
| 4,040,785 | A | 8/1977 | Kim et al. |
| 4,683,195 | A | 7/1987 | Mullis et al. |

(Continued)

FOREIGN PATENT DOCUMENTS

| | | | |
|---|---|---|---|
| CN | 1650032 | A | 8/2005 |
| CN | 1674028 | A | 9/2005 |

(Continued)

OTHER PUBLICATIONS

US 8,501,409 B2, 08/2013, Simen et al. (withdrawn)

(Continued)

*Primary Examiner* — Aaron A Priest

(57) ABSTRACT

The disclosure herein provides methods and compositions for detecting or monitoring immune cell populations in biological samples. The methods and compositions disclosed herein are particularly useful for detecting or monitoring immune cell populations in patients suffering from a disease or undergoing treatment of a disease resulting in depletion of immune cells. In particular, the present disclosure provides method for using multiplex PCR combined with next-generation DNA sequencing to detect DNA containing recombined V(D)J gene segments which can be used to detect immune cells.

16 Claims, 13 Drawing Sheets

Specification includes a Sequence Listing.

(56) References Cited

U.S. PATENT DOCUMENTS

| | | |
|---|---|---|
| 4,942,124 A | 7/1990 | Church et al. |
| 5,486,477 A | 1/1996 | Carver |
| 5,635,366 A | 6/1997 | Cooke et al. |
| 5,648,220 A | 7/1997 | Bianchi et al. |
| 5,716,776 A | 2/1998 | Bogart |
| 5,753,467 A | 5/1998 | Jensen et al. |
| 5,824,467 A | 10/1998 | Mascarenhas |
| 5,854,033 A | 12/1998 | Lizardi |
| 5,860,917 A | 1/1999 | Comanor et al. |
| 5,891,734 A | 4/1999 | Gill et al. |
| 5,952,170 A | 9/1999 | Stroun et al. |
| 5,962,223 A | 10/1999 | Whiteley et al. |
| 5,972,602 A | 11/1999 | Hyland et al. |
| 5,976,790 A | 11/1999 | Pinkel et al. |
| 5,994,148 A | 11/1999 | Stewart et al. |
| 6,001,611 A | 12/1999 | Will |
| 6,025,128 A | 2/2000 | Veltri et al. |
| 6,066,454 A | 5/2000 | Lipshutz et al. |
| 6,100,029 A | 8/2000 | Lapidus et al. |
| 6,108,635 A | 8/2000 | Herren et al. |
| 6,124,120 A | 9/2000 | Lizardi |
| 6,143,496 A | 11/2000 | Brown et al. |
| 6,156,504 A | 12/2000 | Gocke et al. |
| 6,180,349 B1 | 1/2001 | Ginzinger |
| 6,235,472 B1 | 2/2001 | Landegren et al. |
| 6,214,558 B1 | 4/2001 | Shuber et al. |
| 6,221,603 B1 | 4/2001 | Mahtani |
| 6,258,540 B1 | 7/2001 | Lo et al. |
| 6,300,077 B1 | 10/2001 | Shuber et al. |
| 6,329,179 B1 | 12/2001 | Kopreski |
| 6,335,167 B1 | 1/2002 | Pinkel et al. |
| 6,440,706 B1 | 8/2002 | Vogelstein et al. |
| 6,479,235 B1 | 11/2002 | Schumm et al. |
| 6,489,135 B1 | 12/2002 | Parrott et al. |
| 6,605,451 B1 | 8/2003 | Marmaro et al. |
| 6,617,137 B2 | 9/2003 | Dean et al. |
| 6,720,140 B1 | 4/2004 | Hartley et al. |
| 6,794,140 B1 | 9/2004 | Goldsborough |
| 6,807,491 B2 | 10/2004 | Pavlovic et al. |
| 6,858,412 B2 | 2/2005 | Willis et al. |
| 6,927,028 B2 | 8/2005 | Lo et al. |
| 6,852,487 B1 | 10/2005 | Barany et al. |
| 6,958,211 B2 | 10/2005 | Vingerhoets et al. |
| 6,964,847 B1 | 11/2005 | Englert |
| 7,035,739 B2 | 4/2006 | Schadt et al. |
| 7,058,517 B1 | 6/2006 | Denton et al. |
| 7,058,616 B1 | 6/2006 | Larder et al. |
| 7,101,663 B2 | 9/2006 | Godfrey et al. |
| 7,153,656 B2 | 12/2006 | Nolan et al. |
| 7,218,764 B2 | 5/2007 | Vaisberg et al. |
| 7,297,485 B2 | 11/2007 | Bornarth et al. |
| 7,332,277 B2 | 2/2008 | Dhallan |
| 7,410,764 B2 | 8/2008 | Gocke et al. |
| 7,414,118 B1 | 8/2008 | Mullah et al. |
| 7,442,506 B2 | 12/2008 | Dhallan |
| 7,459,273 B2 | 12/2008 | Jones et al. |
| 7,645,576 B2 | 1/2010 | Lo et al. |
| 7,655,399 B2 | 2/2010 | Cantor et al. |
| 7,700,325 B2 | 4/2010 | Cantor et al. |
| 7,718,367 B2 | 5/2010 | Lo et al. |
| 7,718,370 B2 | 6/2010 | Dhallan |
| 7,741,463 B2 | 6/2010 | Gormley et al. |
| 7,727,720 B2 | 9/2010 | Dhallan |
| 7,790,418 B2 | 9/2010 | Mayer |
| 7,805,282 B2 | 9/2010 | Casey |
| 7,838,647 B2 | 11/2010 | Hahn et al. |
| 7,981,609 B2 | 7/2011 | Rubin et al. |
| 7,888,017 B2 | 8/2011 | Quake |
| 8,008,018 B2 | 9/2011 | Quake et al. |
| 8,024,128 B2 | 9/2011 | Rabinowitz |
| 8,133,719 B2 | 3/2012 | Drmanac et al. |
| 8,137,912 B2 | 5/2012 | Kapur et al. |
| 8,173,370 B2 | 5/2012 | Oeth et al. |
| 8,168,389 B2 | 6/2012 | Shoemaker et al. |
| 8,236,503 B2 | 8/2012 | Faham et al. |
| 8,195,415 B2 | 10/2012 | Fan et al. |
| 8,296,076 B2 | 11/2012 | Fan et al. |
| 8,304,187 B2 | 11/2012 | Fernando |
| 8,318,430 B2 | 11/2012 | Chuu et al. |
| 8,318,434 B2 | 11/2012 | Cuppens et al. |
| 8,323,897 B2 | 12/2012 | Andersen et al. |
| 8,372,584 B2 | 2/2013 | Shoemaker et al. |
| 8,389,557 B2 | 3/2013 | Singh et al. |
| 8,389,578 B2 | 3/2013 | Went et al. |
| 8,450,063 B2 | 5/2013 | Dube et al. |
| 8,467,976 B2 | 8/2013 | Lo et al. |
| 8,515,679 B2 | 8/2013 | Rabinowitz et al. |
| 8,532,930 B2 | 9/2013 | Rabinowitz et al. |
| 8,679,741 B2 | 3/2014 | Hoyal-Wrightson et al. |
| 8,682,592 B2 | 3/2014 | Rabinowitz et al. |
| 8,703,652 B2 | 4/2014 | Quake et al. |
| 8,706,422 B2 | 4/2014 | Lo et al. |
| 8,748,103 B2 | 6/2014 | Faham et al. |
| 8,822,153 B2 | 9/2014 | Hayes et al. |
| 8,825,412 B2 | 9/2014 | Rabinowitz et al. |
| 9,005,894 B2 | 4/2015 | Ladner et al. |
| 9,051,602 B2 | 6/2015 | Oliphant et al. |
| 9,085,798 B2 | 7/2015 | Chee |
| 9,206,475 B2 | 12/2015 | Gerdes et al. |
| 9,228,234 B2 | 1/2016 | Rabinowitz et al. |
| 9,323,888 B2 | 4/2016 | Rava et al. |
| 9,404,150 B2 | 8/2016 | Lee et al. |
| 9,424,392 B2 | 8/2016 | Rabinowitz et al. |
| 9,453,257 B2 | 9/2016 | Hoyal-Wrightson et al. |
| 9,476,095 B2 | 10/2016 | Vogelstein et al. |
| 9,487,829 B2 | 11/2016 | Vogelstein et al. |
| 9,493,828 B2 | 11/2016 | Rava et al. |
| 9,506,119 B2 | 11/2016 | Faham et al. |
| 9,598,731 B2 | 3/2017 | Talasaz |
| 9,677,118 B2 | 6/2017 | Zimmermann et al. |
| 10,017,810 B2 | 7/2018 | Tafrate et al. |
| 10,041,127 B2 | 8/2018 | Talasaz |
| 10,061,890 B2 | 8/2018 | Rabinowitz et al. |
| 10,081,839 B2 | 9/2018 | Rabinowitz et al. |
| 10,083,273 B2 | 9/2018 | Rabinowitz et al. |
| 10,174,369 B2 | 1/2019 | Rabinowitz et al. |
| 10,179,937 B2 | 1/2019 | Babiarz et al. |
| 10,227,652 B2 | 3/2019 | Rabinowitz et al. |
| 10,240,202 B2 | 3/2019 | Rabinowitz et al. |
| 10,260,096 B2 | 4/2019 | Rabinowitz et al. |
| 10,266,893 B2 | 4/2019 | Rabinowitz et al. |
| 10,308,981 B2 | 6/2019 | Sparks et al. |
| 10,316,362 B2 | 6/2019 | Babiarz et al. |
| 10,351,906 B2 | 7/2019 | Zimmermann et al. |
| 10,392,664 B2 | 8/2019 | Rabinowitz et al. |
| 10,450,597 B2 | 10/2019 | Tafrate et al. |
| 10,522,242 B2 | 12/2019 | Rabinowitz et al. |
| 10,526,658 B2 | 1/2020 | Babiarz et al. |
| 10,538,814 B2 | 1/2020 | Babiarz et al. |
| 10,557,172 B2 | 2/2020 | Babiarz et al. |
| 10,597,708 B2 | 3/2020 | Zimmermann et al. |
| 10,597,709 B2 | 3/2020 | Zimmermann et al. |
| 10,597,723 B2 | 3/2020 | Babiarz et al. |
| 10,655,180 B2 | 5/2020 | Babiarz et al. |
| 10,711,309 B2 | 7/2020 | Rabinowitz et al. |
| 10,731,220 B2 | 8/2020 | Babiarz et al. |
| 10,774,380 B2 | 9/2020 | Ryan et al. |
| 10,793,912 B2 | 10/2020 | Babiarz et al. |
| 10,894,976 B2 | 1/2021 | Stray et al. |
| 11,111,543 B2 | 9/2021 | Rabinowitz et al. |
| 11,111,544 B2 | 9/2021 | Rabinowitz et al. |
| 11,111,545 B2 | 9/2021 | Babiarz et al. |
| 11,130,995 B2 | 9/2021 | Quake et al. |
| 2001/0051341 A1 | 12/2001 | Lo et al. |
| 2001/0053519 A1 | 12/2001 | Fodor et al. |
| 2002/0006622 A1 | 1/2002 | Bradley et al. |
| 2002/0107640 A1 | 8/2002 | Ideker et al. |
| 2002/0119478 A1 | 8/2002 | Umansky et al. |
| 2002/0182622 A1 | 12/2002 | Nakamura et al. |
| 2003/0009295 A1 | 1/2003 | Markowitz et al. |
| 2003/0040620 A1 | 2/2003 | Langmore et al. |
| 2003/0044388 A1 | 3/2003 | Lo et al. |
| 2003/0065535 A1 | 4/2003 | Karlov et al. |
| 2003/0077586 A1 | 4/2003 | Pavlovic et al. |

(56) References Cited

U.S. PATENT DOCUMENTS

| | | |
|---|---|---|
| 2003/0087276 A1 | 5/2003 | Kopreski et al. |
| 2003/0101000 A1 | 5/2003 | Bader et al. |
| 2003/0119004 A1 | 6/2003 | Wenz et al. |
| 2003/0138780 A1 | 7/2003 | Gill et al. |
| 2003/0211489 A1 | 11/2003 | Shen et al. |
| 2003/0228613 A1 | 12/2003 | Bornarth et al. |
| 2003/0232348 A1 | 12/2003 | Jones et al. |
| 2003/0232353 A1 | 12/2003 | Kennedy et al. |
| 2004/0009518 A1 | 1/2004 | Lo et al. |
| 2004/0033596 A1 | 2/2004 | Threadgill et al. |
| 2004/0067493 A1 | 4/2004 | Matsuzaki et al. |
| 2004/0096874 A1 | 5/2004 | Neville et al. |
| 2004/0115629 A1 | 6/2004 | Panzer et al. |
| 2004/0117346 A1 | 6/2004 | Stoffel et al. |
| 2004/0126760 A1 | 7/2004 | Broude |
| 2004/0137470 A1 | 7/2004 | Dhallan et al. |
| 2004/0146866 A1 | 7/2004 | Fu |
| 2004/0157243 A1 | 8/2004 | Huang et al. |
| 2004/0185495 A1 | 9/2004 | Schueler et al. |
| 2004/0197797 A1 | 10/2004 | Inoko et al. |
| 2004/0209299 A1 | 10/2004 | Pinter et al. |
| 2004/0229231 A1 | 11/2004 | Frudakis et al. |
| 2004/0236518 A1 | 11/2004 | Pavlovic et al. |
| 2004/0259100 A1 | 12/2004 | Gunderson et al. |
| 2005/0009069 A1 | 1/2005 | Liu et al. |
| 2005/0043894 A1 | 2/2005 | Fernandez |
| 2005/0049793 A1 | 3/2005 | Paterlini-Brechot |
| 2005/0053950 A1 | 3/2005 | Ubani et al. |
| 2005/0064476 A1 | 3/2005 | Huang et al. |
| 2005/0079521 A1 | 4/2005 | Beaulieu et al. |
| 2005/0079535 A1 | 4/2005 | Kirchgesser et al. |
| 2005/0123914 A1 | 6/2005 | Katz et al. |
| 2005/0130173 A1 | 6/2005 | Leamon et al. |
| 2005/0142577 A1 | 6/2005 | Jones et al. |
| 2005/0144664 A1 | 6/2005 | Smith et al. |
| 2005/0164241 A1 | 7/2005 | Hahn et al. |
| 2005/0164252 A1 | 7/2005 | Yeung |
| 2005/0216207 A1 | 9/2005 | Kermani |
| 2005/0221341 A1 | 10/2005 | Shimkets et al. |
| 2005/0227263 A1 | 10/2005 | Green et al. |
| 2005/0250111 A1 | 11/2005 | Xie et al. |
| 2005/0255508 A1 | 11/2005 | Casey et al. |
| 2005/0272073 A1 | 12/2005 | Vaisberg et al. |
| 2005/0282185 A1 | 12/2005 | Lo et al. |
| 2006/0019278 A1 | 1/2006 | Lo et al. |
| 2006/0040300 A1 | 2/2006 | Dapprich et al. |
| 2006/0046258 A1 | 3/2006 | Lapidus et al. |
| 2006/0051799 A1 | 3/2006 | Iwaki et al. |
| 2006/0052945 A1 | 3/2006 | Rabinowitz et al. |
| 2006/0057618 A1 | 3/2006 | Piper et al. |
| 2006/0068394 A1 | 3/2006 | Langmore et al. |
| 2006/0088574 A1 | 4/2006 | Manning et al. |
| 2006/0094010 A1 | 5/2006 | Giles et al. |
| 2006/0099614 A1 | 5/2006 | Gill et al. |
| 2006/0121452 A1 | 6/2006 | Dhallan |
| 2006/0134662 A1 | 6/2006 | Pratt et al. |
| 2006/0141499 A1 | 6/2006 | Sher et al. |
| 2006/0229823 A1 | 8/2006 | Liu |
| 2006/0210997 A1 | 9/2006 | Myerson et al. |
| 2006/0216153 A1 | 9/2006 | Wobben et al. |
| 2006/0216738 A1 | 9/2006 | Wada et al. |
| 2006/0228721 A1 | 10/2006 | Leamon et al. |
| 2006/0248031 A1 | 11/2006 | Kates et al. |
| 2006/0281105 A1 | 12/2006 | Li et al. |
| 2006/0292599 A1 | 12/2006 | Ritz et al. |
| 2007/0020640 A1 | 1/2007 | McCloskey et al. |
| 2007/0027636 A1 | 2/2007 | Rabinowitz |
| 2007/0031857 A1 | 2/2007 | Makarov et al. |
| 2007/0037166 A1 | 2/2007 | Wohlgemuth et al. |
| 2007/0042384 A1 | 2/2007 | Li et al. |
| 2007/0059700 A1 | 3/2007 | Tao et al. |
| 2007/0059707 A1 | 3/2007 | Cantor et al. |
| 2007/0122805 A1 | 5/2007 | Cantor et al. |
| 2007/0128624 A1 | 6/2007 | Gormley et al. |
| 2007/0134658 A1 | 6/2007 | Bohmer et al. |
| 2007/0178478 A1 | 8/2007 | Dhallan |
| 2007/0178501 A1 | 8/2007 | Rabinowitz et al. |
| 2007/0184467 A1 | 8/2007 | Rabinowitz et al. |
| 2007/0202525 A1 | 8/2007 | Quake et al. |
| 2007/0202536 A1 | 8/2007 | Yamanishi et al. |
| 2007/0207466 A1 | 9/2007 | Cantor et al. |
| 2007/0212689 A1 | 9/2007 | Bianchi et al. |
| 2007/0243549 A1 | 10/2007 | Bischoff |
| 2007/0259351 A1 | 11/2007 | Chinitz |
| 2008/0020390 A1 | 1/2008 | Mitchell |
| 2008/0026390 A1 | 1/2008 | Stoughton et al. |
| 2008/0038733 A1 | 2/2008 | Bischoff et al. |
| 2008/0050739 A1 | 2/2008 | Stoughton et al. |
| 2008/0070792 A1 | 3/2008 | Stoughton |
| 2008/0071076 A1 | 3/2008 | Hahn et al. |
| 2008/0085836 A1 | 4/2008 | Kearns et al. |
| 2008/0090239 A1 | 4/2008 | Shoemaker et al. |
| 2008/0096766 A1 | 4/2008 | Lee |
| 2008/0102455 A1 | 5/2008 | Poetter |
| 2008/0138809 A1 | 6/2008 | Kapur et al. |
| 2008/0182244 A1 | 7/2008 | Tafas et al. |
| 2008/0193927 A1 | 8/2008 | Mann et al. |
| 2008/0220422 A1 | 9/2008 | Shoemaker et al. |
| 2008/0234142 A1 | 9/2008 | Lietz |
| 2008/0243398 A1 | 10/2008 | Rabinowitz et al. |
| 2008/0280292 A1 | 11/2008 | Wangh et al. |
| 2008/0286783 A1 | 11/2008 | Hosono et al. |
| 2008/0299562 A1 | 12/2008 | Oeth et al. |
| 2008/0305473 A1 | 12/2008 | Chowdary et al. |
| 2009/0023190 A1 | 1/2009 | Lao et al. |
| 2009/0029377 A1 | 1/2009 | Lo et al. |
| 2009/0053719 A1 | 2/2009 | Lo et al. |
| 2009/0087847 A1 | 4/2009 | Lo et al. |
| 2009/0098534 A1 | 4/2009 | Weier et al. |
| 2009/0099041 A1 | 4/2009 | Church et al. |
| 2009/0143570 A1 | 6/2009 | Jiang et al. |
| 2009/0176662 A1 | 7/2009 | Rigatti et al. |
| 2009/0221620 A1 | 9/2009 | Luke et al. |
| 2009/0228299 A1 | 9/2009 | Kangarloo et al. |
| 2009/0263800 A1 | 10/2009 | Wohlgemuth et al. |
| 2009/0280479 A1 | 11/2009 | Hoon et al. |
| 2009/0317817 A1 | 12/2009 | Oeth et al. |
| 2010/0035232 A1 | 2/2010 | Ecker et al. |
| 2010/0041048 A1 | 2/2010 | Diehl et al. |
| 2010/0086914 A1 | 4/2010 | Bentley et al. |
| 2010/0105049 A1 | 4/2010 | Ehrich et al. |
| 2010/0112575 A1 | 5/2010 | Fan et al. |
| 2010/0112586 A1 | 5/2010 | Stoughton et al. |
| 2010/0112590 A1 | 5/2010 | Lo et al. |
| 2010/0120038 A1 | 5/2010 | Mir et al. |
| 2010/0124751 A1 | 5/2010 | Quake et al. |
| 2010/0129792 A1 | 5/2010 | Makrigiorgos et al. |
| 2010/0129874 A1 | 5/2010 | Mitra et al. |
| 2010/0138165 A1 | 6/2010 | Fan et al. |
| 2010/0171954 A1 | 7/2010 | Quake et al. |
| 2010/0173394 A1 | 7/2010 | Colston et al. |
| 2010/0184043 A1 | 7/2010 | Mitchell et al. |
| 2010/0184069 A1 | 7/2010 | Fernando et al. |
| 2010/0184152 A1 | 7/2010 | Sandler |
| 2010/0196892 A1 | 8/2010 | Quake et al. |
| 2010/0203538 A1 | 8/2010 | Dube et al. |
| 2010/0216151 A1 | 8/2010 | Lapdus et al. |
| 2010/0216153 A1 | 8/2010 | Lapidus et al. |
| 2010/0248231 A1 | 9/2010 | Wei et al. |
| 2010/0255492 A1 | 10/2010 | Quake et al. |
| 2010/0256013 A1 | 10/2010 | Quake et al. |
| 2010/0273159 A1 | 10/2010 | Melo |
| 2010/0273219 A1 | 10/2010 | May et al. |
| 2010/0273678 A1 | 10/2010 | Alexandre et al. |
| 2010/0285478 A1 | 11/2010 | Chen et al. |
| 2010/0285537 A1 | 11/2010 | Zimmermann |
| 2010/0291572 A1 | 11/2010 | Stoughton et al. |
| 2010/0291635 A1 | 11/2010 | Peleg |
| 2010/0323352 A1 | 12/2010 | Lo et al. |
| 2011/0015096 A1 | 1/2011 | Chiu |
| 2011/0033862 A1 | 2/2011 | Rabinowitz et al. |
| 2011/0039724 A1 | 2/2011 | Lo et al. |
| 2011/0045462 A1 | 2/2011 | Fu et al. |
| 2011/0064824 A1 | 3/2011 | Lascoste et al. |

(56) References Cited

U.S. PATENT DOCUMENTS

| | | |
|---|---|---|
| 2011/0071031 A1 | 3/2011 | Khripin et al. |
| 2011/0086769 A1 | 4/2011 | Oliphant et al. |
| 2011/0092763 A1 | 4/2011 | Rabinowitz et al. |
| 2011/0105353 A1 | 5/2011 | Lo et al. |
| 2011/0130558 A1 | 6/2011 | Ritt et al. |
| 2011/0151442 A1 | 6/2011 | Fan et al. |
| 2011/0159499 A1 | 6/2011 | Hindson et al. |
| 2011/0160078 A1 | 6/2011 | Fodor et al. |
| 2011/0178719 A1 | 7/2011 | Rabinowitz et al. |
| 2011/0201507 A1 | 8/2011 | Rava et al. |
| 2011/0212446 A1 | 9/2011 | Wang et al. |
| 2011/0212846 A1 | 9/2011 | Spier |
| 2011/0224087 A1 | 9/2011 | Quake et al. |
| 2011/0246083 A1 | 10/2011 | Fan et al. |
| 2011/0251149 A1 | 10/2011 | Perrine et al. |
| 2011/0288780 A1 | 11/2011 | Rabinowitz et al. |
| 2011/0294699 A1 | 12/2011 | Lee et al. |
| 2011/0300608 A1 | 12/2011 | Ryan et al. |
| 2011/0301854 A1 | 12/2011 | Curry et al. |
| 2011/0312503 A1 | 12/2011 | Chuu et al. |
| 2012/0003635 A1 | 1/2012 | Lo et al. |
| 2012/0003637 A1 | 1/2012 | Lo et al. |
| 2012/0010085 A1 | 1/2012 | Rava et al. |
| 2012/0034603 A1 | 2/2012 | Oliphant et al. |
| 2012/0034685 A1 | 2/2012 | Sparks et al. |
| 2012/0058902 A1* | 3/2012 | Livingston ......... C07K 14/7051 |
| | | 506/7 |
| 2012/0108460 A1 | 5/2012 | Quake et al. |
| 2012/0122701 A1 | 5/2012 | Ryan et al. |
| 2012/0165203 A1 | 6/2012 | Quake et al. |
| 2012/0185176 A1 | 7/2012 | Rabinowitz et al. |
| 2012/0190020 A1 | 7/2012 | Oliphant et al. |
| 2012/0190021 A1 | 7/2012 | Oliphant et al. |
| 2012/0190557 A1 | 7/2012 | Oliphant et al. |
| 2012/0191358 A1 | 7/2012 | Oliphant et al. |
| 2012/0196754 A1 | 8/2012 | Quake et al. |
| 2012/0208706 A1 | 8/2012 | Downing et al. |
| 2012/0214678 A1 | 8/2012 | Rava et al. |
| 2012/0220466 A1* | 8/2012 | Fire ..................... C12Q 1/6881 |
| | | 506/2 |
| 2012/0264121 A1 | 10/2012 | Rava et al. |
| 2012/0264618 A1 | 10/2012 | Nygren |
| 2012/0270212 A1 | 10/2012 | Rabinowitz et al. |
| 2012/0270739 A1 | 10/2012 | Rava et al. |
| 2012/0295810 A1 | 11/2012 | Quake et al. |
| 2012/0295819 A1 | 11/2012 | Leamon et al. |
| 2013/0017549 A1 | 1/2013 | Hong |
| 2013/0022973 A1 | 1/2013 | Hansen et al. |
| 2013/0024127 A1 | 1/2013 | Stuelpnagel |
| 2013/0034546 A1 | 2/2013 | Rava et al. |
| 2013/0040375 A1 | 2/2013 | Sparks et al. |
| 2013/0060483 A1 | 3/2013 | Struble et al. |
| 2013/0069869 A1 | 3/2013 | Akao et al. |
| 2013/0085681 A1 | 4/2013 | Deciu et al. |
| 2013/0090250 A1 | 4/2013 | Sparks et al. |
| 2013/0116130 A1 | 5/2013 | Fu et al. |
| 2013/0123120 A1 | 5/2013 | Zimmermann et al. |
| 2013/0130923 A1 | 5/2013 | Ehrich et al. |
| 2013/0172211 A1 | 7/2013 | Oliphant et al. |
| 2013/0178373 A1 | 7/2013 | Rabinowitz et al. |
| 2013/0190653 A1 | 7/2013 | Alvarez Ramos |
| 2013/0196862 A1 | 8/2013 | Rabinowitz et al. |
| 2013/0210644 A1 | 8/2013 | Stoughton et al. |
| 2013/0225422 A1 | 8/2013 | Rabinowitz et al. |
| 2013/0252824 A1 | 9/2013 | Rabinowitz |
| 2013/0253369 A1 | 9/2013 | Rabinowitz et al. |
| 2013/0253842 A1* | 9/2013 | Sherwood ............... G16B 30/00 |
| | | 702/19 |
| 2013/0261004 A1 | 10/2013 | Ryan et al. |
| 2013/0274116 A1 | 10/2013 | Rabinowitz et al. |
| 2013/0303461 A1 | 11/2013 | Iafrate et al. |
| 2013/0323731 A1 | 12/2013 | Lo et al. |
| 2013/0325360 A1 | 12/2013 | Deciu et al. |
| 2014/0032128 A1 | 1/2014 | Rabinowitz et al. |
| 2014/0038830 A1 | 2/2014 | Srinivasan et al. |
| 2014/0051585 A1 | 2/2014 | Prosen et al. |
| 2014/0065621 A1 | 3/2014 | Mhatre et al. |
| 2014/0066317 A1 | 3/2014 | Talasaz |
| 2014/0087385 A1 | 3/2014 | Rabinowitz et al. |
| 2014/0094373 A1 | 4/2014 | Zimmermann et al. |
| 2014/0100126 A1 | 4/2014 | Rabinowitz |
| 2014/0100134 A1 | 4/2014 | Rabinowitz et al. |
| 2014/0106975 A1 | 4/2014 | Stoughton et al. |
| 2014/0141981 A1 | 5/2014 | Zimmermann et al. |
| 2014/0154682 A1 | 6/2014 | Rabinowitz et al. |
| 2014/0155274 A1 | 6/2014 | Xie et al. |
| 2014/0162269 A1 | 6/2014 | Rabinowitz |
| 2014/0186848 A1* | 7/2014 | Robins ................. C12Q 1/6881 |
| | | 435/6.12 |
| 2014/0193816 A1 | 7/2014 | Rabinowitz et al. |
| 2014/0206552 A1 | 7/2014 | Rabinowitz et al. |
| 2014/0227705 A1 | 8/2014 | Vogelstein et al. |
| 2014/0256558 A1 | 9/2014 | Varley et al. |
| 2014/0256569 A1 | 9/2014 | Rabinowitz et al. |
| 2014/0272956 A1 | 9/2014 | Huang et al. |
| 2014/0274740 A1 | 9/2014 | Srinivasan et al. |
| 2014/0287934 A1 | 9/2014 | Szelinger et al. |
| 2014/0296081 A1 | 10/2014 | Diehn et al. |
| 2014/0322716 A1* | 10/2014 | Robins ................. C12Q 1/6881 |
| | | 435/6.12 |
| 2014/0329245 A1 | 11/2014 | Spier et al. |
| 2014/0336060 A1 | 11/2014 | Rabinowitz |
| 2015/0017652 A1* | 1/2015 | Robins ................. C12Q 1/6881 |
| | | 435/6.12 |
| 2015/0051087 A1 | 2/2015 | Rabinowitz et al. |
| 2015/0064695 A1 | 3/2015 | Katz et al. |
| 2015/0086477 A1 | 3/2015 | Mitchell et al. |
| 2015/0087535 A1 | 3/2015 | Patel |
| 2015/0147815 A1 | 5/2015 | Babiarz et al. |
| 2015/0197786 A1 | 7/2015 | Osborne et al. |
| 2015/0211050 A1 | 7/2015 | Iafrate et al. |
| 2015/0218656 A1* | 8/2015 | Kirsch ................. C12Q 1/6886 |
| | | 506/2 |
| 2015/0232938 A1 | 8/2015 | Mhatre |
| 2015/0265995 A1 | 9/2015 | Head et al. |
| 2015/0299812 A1 | 10/2015 | Talasaz |
| 2015/0315657 A1 | 11/2015 | Rhodes et al. |
| 2015/0322507 A1 | 11/2015 | Zimmermann et al. |
| 2015/0329891 A1 | 11/2015 | Tan et al. |
| 2016/0002731 A1* | 1/2016 | Robins ................. C12Q 1/6886 |
| | | 702/19 |
| 2016/0024493 A1* | 1/2016 | Robins ................. C12Q 1/6846 |
| | | 506/9 |
| 2016/0032396 A1 | 2/2016 | Diehn et al. |
| 2016/0046986 A1 | 2/2016 | Eltoukhy et al. |
| 2016/0115541 A1 | 4/2016 | Schutz et al. |
| 2016/0138011 A1* | 5/2016 | Dewitt ................. C12N 15/1065 |
| | | 506/4 |
| 2016/0145682 A1 | 5/2016 | Woodward et al. |
| 2016/0186239 A1 | 6/2016 | Sinha |
| 2016/0186253 A1 | 6/2016 | Talasaz et al. |
| 2016/0201124 A1 | 7/2016 | Donahue et al. |
| 2016/0239602 A1 | 8/2016 | Shendure et al. |
| 2016/0244838 A1 | 8/2016 | Babiarz et al. |
| 2016/0257993 A1 | 9/2016 | Fu et al. |
| 2016/0289740 A1 | 10/2016 | Fu et al. |
| 2016/0289753 A1 | 10/2016 | Osborne et al. |
| 2016/0312276 A1 | 10/2016 | Fu et al. |
| 2016/0319345 A1 | 11/2016 | Gnerre et al. |
| 2016/0369333 A1 | 12/2016 | Babiarz et al. |
| 2017/0011166 A1 | 1/2017 | Rabinowitz et al. |
| 2017/0037469 A1* | 2/2017 | Robins ................. C12Q 1/6881 |
| 2017/0107576 A1 | 4/2017 | Babiarz et al. |
| 2017/0114411 A1 | 4/2017 | Mitchell et al. |
| 2017/0121716 A1 | 5/2017 | Rodi et al. |
| 2017/0152561 A1 | 6/2017 | Hamamah et al. |
| 2017/0218458 A1 | 8/2017 | Fan et al. |
| 2017/0275689 A1 | 9/2017 | Maguire et al. |
| 2017/0283788 A1 | 10/2017 | Khoja et al. |
| 2017/0292149 A1* | 10/2017 | Sherwood ............... C12Q 1/6811 |
| 2017/0314014 A1 | 11/2017 | Green et al. |
| 2017/0335391 A1* | 11/2017 | Emerson ................. C12Q 1/6809 |
| 2017/0342477 A1 | 11/2017 | Jensen et al. |
| 2017/0362649 A1 | 12/2017 | Lieberman-Aiden et al. |

(56) References Cited

U.S. PATENT DOCUMENTS

| | | | |
|---|---|---|---|
| 2017/0362653 A1* | 12/2017 | Robins | C12Q 1/6886 |
| 2018/0023128 A1 | 1/2018 | Yanai et al. | |
| 2018/0025109 A1 | 2/2018 | Rabinowitz et al. | |
| 2018/0127744 A1 | 5/2018 | Hu et al. | |
| 2018/0148777 A1 | 5/2018 | Kirkizlar et al. | |
| 2018/0155775 A1 | 6/2018 | Zimmermann et al. | |
| 2018/0155776 A1 | 6/2018 | Zimmermann et al. | |
| 2018/0155779 A1 | 6/2018 | Zimmermann et al. | |
| 2018/0155785 A1 | 6/2018 | Rabinowitz et al. | |
| 2018/0155786 A1 | 6/2018 | Rabinowitz et al. | |
| 2018/0155792 A1 | 6/2018 | Rabinowitz et al. | |
| 2018/0171409 A1 | 6/2018 | Rabinowitz et al. | |
| 2018/0171420 A1 | 6/2018 | Babiarz et al. | |
| 2018/0173845 A1 | 6/2018 | Sigurjonsson et al. | |
| 2018/0173846 A1 | 6/2018 | Sigurjonsson et al. | |
| 2018/0187241 A1 | 7/2018 | Selvaraj et al. | |
| 2018/0201995 A1 | 7/2018 | Rabinowitz et al. | |
| 2018/0208984 A1* | 7/2018 | Looney | C12Q 1/6869 |
| 2018/0237841 A1 | 8/2018 | Stray et al. | |
| 2018/0251553 A1 | 9/2018 | McGranahan et al. | |
| 2018/0265917 A1 | 9/2018 | Barany et al. | |
| 2018/0288982 A1 | 10/2018 | Sinha | |
| 2018/0298439 A1 | 10/2018 | Ryan et al. | |
| 2018/0300448 A1 | 10/2018 | Rabinowitz et al. | |
| 2019/0010543 A1 | 1/2019 | Babiarz et al. | |
| 2019/0085374 A1* | 3/2019 | Lowman | C12Q 1/686 |
| 2019/0106737 A1 | 4/2019 | Underhill | |
| 2019/0106751 A1 | 4/2019 | Zimmermann et al. | |
| 2019/0185913 A1 | 6/2019 | Zimmermann et al. | |
| 2019/0185936 A1 | 6/2019 | Babiarz et al. | |
| 2019/0194743 A1 | 6/2019 | Ryan et al. | |
| 2019/0194758 A1 | 6/2019 | Babiarz et al. | |
| 2019/0194759 A1 | 6/2019 | Babiarz et al. | |
| 2019/0203290 A1 | 7/2019 | Rabinowitz et al. | |
| 2019/0203294 A1 | 7/2019 | Babiarz et al. | |
| 2019/0211391 A1 | 7/2019 | Rabinowitz et al. | |
| 2019/0211392 A1 | 7/2019 | Rabinowitz et al. | |
| 2019/0211393 A1 | 7/2019 | Rabinowitz et al. | |
| 2019/0211399 A1 | 7/2019 | Rabinowitz et al. | |
| 2019/0211402 A1 | 7/2019 | Babiarz et al. | |
| 2019/0211406 A1 | 7/2019 | Babiarz et al. | |
| 2019/0249241 A1 | 8/2019 | Rabinowitz et al. | |
| 2019/0256894 A1 | 8/2019 | Zimmermann et al. | |
| 2019/0256906 A1 | 8/2019 | Rabinowitz et al. | |
| 2019/0256907 A1 | 8/2019 | Ryan et al. | |
| 2019/0256908 A1 | 8/2019 | Rabinowitz et al. | |
| 2019/0256909 A1 | 8/2019 | Rabinowitz et al. | |
| 2019/0256912 A1 | 8/2019 | Rabinowitz et al. | |
| 2019/0256916 A1 | 8/2019 | Babiarz et al. | |
| 2019/0256917 A1 | 8/2019 | Babiarz et al. | |
| 2019/0256919 A1 | 8/2019 | Babiarz et al. | |
| 2019/0256924 A1 | 8/2019 | Vogelstein et al. | |
| 2019/0256931 A1 | 8/2019 | Babiarz et al. | |
| 2019/0264277 A1 | 8/2019 | Rabinowitz et al. | |
| 2019/0264280 A1 | 8/2019 | Rabinowitz et al. | |
| 2019/0264288 A1 | 8/2019 | Rabinowitz et al. | |
| 2019/0271043 A1 | 9/2019 | Babiarz et al. | |
| 2019/0276888 A1 | 9/2019 | Rabinowitz et al. | |
| 2019/0284623 A1 | 9/2019 | Rabinowitz et al. | |
| 2019/0300950 A1 | 10/2019 | Rabinowitz et al. | |
| 2019/0309358 A1 | 10/2019 | Rabinowitz et al. | |
| 2019/0309359 A1 | 10/2019 | Zimmermann et al. | |
| 2019/0309365 A1 | 10/2019 | Babiarz et al. | |
| 2019/0316177 A1 | 10/2019 | Zimmermann et al. | |
| 2019/0316184 A1 | 10/2019 | Zimmermann et al. | |
| 2019/0316200 A1 | 10/2019 | Rabinowitz et al. | |
| 2019/0323076 A1 | 10/2019 | Rabinowitz et al. | |
| 2019/0360036 A1 | 11/2019 | Rabinowitz et al. | |
| 2020/0024653 A1 | 1/2020 | Bethke | |
| 2020/0032323 A1 | 1/2020 | Talasaz et al. | |
| 2020/0109449 A1 | 4/2020 | Stamm et al. | |
| 2020/0123612 A1 | 4/2020 | Babiarz et al. | |
| 2020/0126634 A1 | 4/2020 | Sigurjonsson et al. | |
| 2020/0140950 A1 | 5/2020 | Babiarz et al. | |
| 2020/0149111 A1 | 5/2020 | Babiarz et al. | |
| 2020/0157629 A1 | 5/2020 | Babiarz et al. | |
| 2020/0172977 A1 | 6/2020 | Rabinowitz et al. | |
| 2020/0181697 A1 | 6/2020 | Rabinowitz et al. | |
| 2020/0190570 A1 | 6/2020 | Ryan et al. | |
| 2020/0190573 A1 | 6/2020 | Rabinowitz et al. | |
| 2020/0190591 A1 | 6/2020 | Rabinowitz et al. | |
| 2020/0208196 A1 | 7/2020 | Zimmermann et al. | |
| 2020/0208221 A1 | 7/2020 | Babiarz et al. | |
| 2020/0224273 A1 | 7/2020 | Rabinowitz et al. | |
| 2020/0232036 A1 | 7/2020 | Rabinowitz et al. | |
| 2020/0232037 A1 | 7/2020 | Babiarz et al. | |
| 2020/0248264 A1 | 8/2020 | Rabinowitz et al. | |
| 2020/0248266 A1 | 8/2020 | Swanton et al. | |
| 2020/0316498 A1 | 10/2020 | Mitchell | |
| 2020/0318191 A1 | 10/2020 | Babiarz et al. | |
| 2020/0347454 A1 | 11/2020 | Babiarz et al. | |
| 2020/0350034 A1 | 11/2020 | Rabinowitz et al. | |
| 2020/0362415 A1 | 11/2020 | Rabinowitz et al. | |
| 2020/0407788 A1 | 12/2020 | Ryan et al. | |
| 2020/0407798 A1 | 12/2020 | Babiarz et al. | |
| 2021/0009990 A1 | 1/2021 | Stray et al. | |
| 2021/0025005 A1 | 1/2021 | Babiarz et al. | |
| 2021/0054459 A1 | 2/2021 | Rabinowitz et al. | |
| 2021/0071246 A1 | 3/2021 | Zimmermann et al. | |
| 2021/0139969 A1 | 5/2021 | Mitchell et al. | |
| 2021/0139983 A1 | 5/2021 | Mitchell et al. | |
| 2021/0139988 A1 | 5/2021 | Mitchell et al. | |
| 2021/0155988 A1 | 5/2021 | Rabinowitz et al. | |
| 2021/0172015 A1* | 6/2021 | Berka | C12Q 1/6886 |
| 2021/0189498 A1 | 6/2021 | Babiarz et al. | |
| 2021/0198733 A1 | 7/2021 | Moshkevich et al. | |
| 2021/0198742 A1 | 7/2021 | Rabinowitz et al. | |
| 2021/0198743 A1 | 7/2021 | Rabinowitz et al. | |
| 2021/0222230 A1 | 7/2021 | Zimmermann et al. | |
| 2021/0222240 A1 | 7/2021 | Moshkevich et al. | |
| 2021/0257048 A1 | 8/2021 | Zimmermann et al. | |
| 2021/0269879 A1 | 9/2021 | Mitchell et al. | |
| 2021/0324463 A1 | 10/2021 | Rabinowitz et al. | |
| 2021/0327538 A1 | 10/2021 | Egilsson et al. | |
| 2021/0327542 A1 | 10/2021 | Ryan et al. | |
| 2021/0355536 A1 | 11/2021 | Rabinowitz et al. | |
| 2022/0002802 A1* | 1/2022 | Looney | C12N 15/1072 |
| 2022/0025455 A1 | 1/2022 | Zimmermann et al. | |
| 2022/0025456 A1 | 1/2022 | Rabinowitz et al. | |
| 2022/0033908 A1 | 2/2022 | Rabinowitz et al. | |
| 2022/0033909 A1 | 2/2022 | Babiarz et al. | |
| 2022/0042103 A1 | 2/2022 | Rabinowitz et al. | |
| 2022/0056509 A1 | 2/2022 | Zimmermann | |
| 2022/0056534 A1 | 2/2022 | Rivers | |
| 2022/0009866 A1 | 3/2022 | Rabinowitz et al. | |
| 2022/0073978 A1 | 3/2022 | Rabinowitz et al. | |
| 2022/0073979 A1 | 3/2022 | Rabinowitz et al. | |
| 2022/0073983 A1* | 3/2022 | Looney | C12Q 1/6881 |

FOREIGN PATENT DOCUMENTS

| | | |
|---|---|---|
| CN | 101675169 A | 3/2010 |
| CN | 104736722 A | 6/2015 |
| CN | 105229175 A | 1/2016 |
| EP | 0270017 A2 | 6/1988 |
| EP | 1325963 A1 | 7/2003 |
| EP | 1524321 A1 | 4/2005 |
| EP | 1325963 B1 | 9/2006 |
| EP | 1524321 B1 | 7/2009 |
| EP | 2163622 A1 | 3/2010 |
| EP | 2128169 A1 | 12/2010 |
| EP | 2902500 A1 | 8/2015 |
| EP | 3026124 A1 | 6/2016 |
| EP | 3285193 A1 | 2/2018 |
| EP | 2877594 B1 | 12/2019 |
| EP | 3187597 B1 | 6/2020 |
| EP | 3134541 B1 | 8/2020 |
| EP | 3760730 A1 | 1/2021 |
| EP | 3760731 A1 | 1/2021 |
| EP | 3760732 A1 | 1/2021 |
| EP | 3824470 | 5/2021 |
| EP | 3443119 B1 | 2/2022 |
| GB | 2488358 | 8/2012 |
| JP | 2965699 | 8/1999 |

(56) References Cited

FOREIGN PATENT DOCUMENTS

| | | |
|---|---|---|
| JP | 2002-530121 A | 9/2002 |
| JP | 2002-300894 A | 10/2002 |
| JP | 2003/521252 A | 7/2003 |
| JP | 2004502466 A | 1/2004 |
| JP | 2004533243 A | 11/2004 |
| JP | 2005514956 A | 5/2005 |
| JP | 2005160470 A | 6/2005 |
| JP | 2006-254912 A | 9/2006 |
| JP | 2008-263974 A | 11/2008 |
| JP | 2008/271980 A | 11/2008 |
| JP | 2010-509922 A | 4/2010 |
| JP | 2011/508662 A | 3/2011 |
| JP | 2011/516069 A | 5/2011 |
| JP | 2015-535681 | 12/2015 |
| RU | 2290078 C1 | 12/2006 |
| WO | 95/01796 | 1/1995 |
| WO | 1996036736 A2 | 11/1996 |
| WO | 98/39474 | 9/1998 |
| WO | 98/44151 | 10/1998 |
| WO | 00/18957 | 4/2000 |
| WO | 2001007640 A2 | 2/2001 |
| WO | 0134844 A1 | 5/2001 |
| WO | 01/57269 A2 | 8/2001 |
| WO | 2001/079851 A1 | 10/2001 |
| WO | 200190419 A2 | 11/2001 |
| WO | 2002004672 A2 | 1/2002 |
| WO | 02/44411 A1 | 6/2002 |
| WO | 2002055985 A2 | 7/2002 |
| WO | 02/070751 A1 | 9/2002 |
| WO | 2002076377 | 10/2002 |
| WO | 02/090505 A2 | 11/2002 |
| WO | 03/000919 A2 | 1/2003 |
| WO | 03/018757 A3 | 3/2003 |
| WO | 03/020974 A3 | 3/2003 |
| WO | 2003031646 A1 | 4/2003 |
| WO | 2003/050532 A1 | 6/2003 |
| WO | 2003062441 A1 | 7/2003 |
| WO | 2003/102595 A1 | 12/2003 |
| WO | 2003/106623 A2 | 12/2003 |
| WO | 2004/051218 A2 | 6/2004 |
| WO | 2004069849 A2 | 8/2004 |
| WO | 2004070005 A2 | 8/2004 |
| WO | 2004070007 A2 | 8/2004 |
| WO | 2004087863 A2 | 10/2004 |
| WO | 2005003375 A2 | 1/2005 |
| WO | 2005021793 A1 | 3/2005 |
| WO | 2005023091 A2 | 3/2005 |
| WO | 2005030999 A1 | 4/2005 |
| WO | 2005035725 A2 | 4/2005 |
| WO | 2005/039389 A3 | 5/2005 |
| WO | 2005100401 A2 | 10/2005 |
| WO | 2005123779 A2 | 12/2005 |
| WO | 2007145612 A1 | 6/2006 |
| WO | 2006110855 A2 | 10/2006 |
| WO | 2006/128192 A2 | 11/2006 |
| WO | 2007/011903 A3 | 1/2007 |
| WO | 2007/052006 A1 | 5/2007 |
| WO | 2007057647 A1 | 5/2007 |
| WO | 2007062164 A3 | 5/2007 |
| WO | 2007/073171 A2 | 6/2007 |
| WO | 2007070280 A2 | 6/2007 |
| WO | 2007070482 A2 | 6/2007 |
| WO | 2007075836 A2 | 7/2007 |
| WO | 2007/092473 A2 | 8/2007 |
| WO | 2007086935 A2 | 8/2007 |
| WO | 2007/117256 A1 | 10/2007 |
| WO | 2007117039 A1 | 10/2007 |
| WO | 2007132167 A2 | 11/2007 |
| WO | 2007/147073 A2 | 12/2007 |
| WO | 2007/147076 A2 | 12/2007 |
| WO | 2007140417 A2 | 12/2007 |
| WO | 2007147074 A2 | 12/2007 |
| WO | 2007147079 A2 | 12/2007 |
| WO | 2008024473 A2 | 2/2008 |
| WO | 2008048931 A1 | 4/2008 |
| WO | 2008/061213 A2 | 5/2008 |
| WO | 2008051928 A2 | 5/2008 |
| WO | 2008056937 A1 | 5/2008 |
| WO | 2008059578 A1 | 5/2008 |
| WO | 2008079374 A2 | 7/2008 |
| WO | 2008081451 A2 | 7/2008 |
| WO | 2008084405 A2 | 7/2008 |
| WO | 2008115427 A2 | 9/2008 |
| WO | 2008115497 A2 | 9/2008 |
| WO | 2008118988 A1 | 10/2008 |
| WO | 2008135837 A2 | 11/2008 |
| WO | 2008157264 A2 | 12/2008 |
| WO | 2009009769 A2 | 1/2009 |
| WO | 2009013492 A1 | 1/2009 |
| WO | 2009013496 A1 | 1/2009 |
| WO | 2009019215 A1 | 2/2009 |
| WO | 2009019455 A2 | 2/2009 |
| WO | 2009/032779 A2 | 3/2009 |
| WO | 2009/036525 A2 | 3/2009 |
| WO | 2009030100 A1 | 3/2009 |
| WO | 2009032781 A2 | 3/2009 |
| WO | 2009033178 A1 | 3/2009 |
| WO | 2009049889 A1 | 4/2009 |
| WO | 2009017784 A2 | 5/2009 |
| WO | 2009064897 A2 | 5/2009 |
| WO | 2009091934 A1 | 7/2009 |
| WO | 2009092035 A2 | 7/2009 |
| WO | 2009/105531 A1 | 8/2009 |
| WO | 2009099602 A1 | 8/2009 |
| WO | 2009100029 A1 | 8/2009 |
| WO | 2009117122 A2 | 9/2009 |
| WO | 2009120808 A2 | 10/2009 |
| WO | 2009145828 A2 | 12/2009 |
| WO | 2009146335 A1 | 12/2009 |
| WO | 2010014920 A1 | 2/2010 |
| WO | 2010017214 A1 | 2/2010 |
| WO | 2010/033639 A2 | 3/2010 |
| WO | 2010/033652 A1 | 3/2010 |
| WO | 2010033578 A2 | 3/2010 |
| WO | 2010042831 A2 | 4/2010 |
| WO | 2010045617 A2 | 4/2010 |
| WO | 2010075459 | 7/2010 |
| WO | 2010/088288 A2 | 8/2010 |
| WO | 2010115016 A1 | 10/2010 |
| WO | 2010115154 A1 | 10/2010 |
| WO | 2010118016 A2 | 10/2010 |
| WO | 2010/127186 A1 | 11/2010 |
| WO | 2011/023078 A1 | 3/2011 |
| WO | 2011/032078 A1 | 3/2011 |
| WO | 2011041485 A1 | 4/2011 |
| WO | 2011/051283 A1 | 5/2011 |
| WO | 2011/057061 A1 | 5/2011 |
| WO | 2011057094 | 5/2011 |
| WO | 2011/090556 A1 | 7/2011 |
| WO | 2011087760 | 7/2011 |
| WO | 2011102998 A2 | 8/2011 |
| WO | 2011109440 A1 | 9/2011 |
| WO | 2011140433 A2 | 11/2011 |
| WO | 2011146632 A1 | 11/2011 |
| WO | 2012/019200 A2 | 2/2012 |
| WO | 2012/028746 A1 | 3/2012 |
| WO | 2013030577 | 3/2012 |
| WO | 2012042374 A2 | 4/2012 |
| WO | 2013052557 A2 | 4/2012 |
| WO | 2012/058488 A1 | 5/2012 |
| WO | 201283250 | 6/2012 |
| WO | 2012088456 A2 | 6/2012 |
| WO | 20120071621 | 6/2012 |
| WO | 2012108920 A1 | 8/2012 |
| WO | 2012/142531 A2 | 10/2012 |
| WO | 2007/149791 A2 | 12/2012 |
| WO | 2013/045432 A2 | 4/2013 |
| WO | 2013/049892 A1 | 4/2013 |
| WO | 2013/078470 A2 | 5/2013 |
| WO | 2013/086464 A1 | 6/2013 |
| WO | 2013/123220 A1 | 8/2013 |
| WO | 2013/138510 A1 | 9/2013 |
| WO | 2013/138510 A9 | 9/2013 |
| WO | 20130130848 | 9/2013 |

(56) References Cited

FOREIGN PATENT DOCUMENTS

| | | |
|---|---|---|
| WO | 2013/159035 A2 | 10/2013 |
| WO | 2013/169339 A1 | 11/2013 |
| WO | 2013/177220 A1 | 11/2013 |
| WO | 2013/181651 A1 | 12/2013 |
| WO | 2014/004726 A1 | 1/2014 |
| WO | 2014/014497 A1 | 1/2014 |
| WO | 20140018080 | 1/2014 |
| WO | 2014/035986 A1 | 3/2014 |
| WO | 2014/122288 A1 | 8/2014 |
| WO | 2014/145078 A1 | 9/2014 |
| WO | 2014/145232 A2 | 9/2014 |
| WO | 2014/149134 A2 | 9/2014 |
| WO | 2014/150300 A2 | 9/2014 |
| WO | 2014/151117 A1 | 9/2014 |
| WO | 2014/194113 A2 | 12/2014 |
| WO | 2015134552 A1 | 3/2015 |
| WO | 2015/048535 A1 | 4/2015 |
| WO | 2015/100427 A1 | 7/2015 |
| WO | 2015/148494 A1 | 10/2015 |
| WO | 2015/164432 A1 | 10/2015 |
| WO | 2016/009059 A1 | 1/2016 |
| WO | 2016009224 A1 | 1/2016 |
| WO | 2016/063122 A1 | 4/2016 |
| WO | 2016/065295 A1 | 4/2016 |
| WO | 2016/077313 A1 | 5/2016 |
| WO | 2016/123698 A1 | 8/2016 |
| WO | 2016/138080 A1 | 9/2016 |
| WO | 2016/176662 A1 | 11/2016 |
| WO | 2016/183106 A1 | 11/2016 |
| WO | 2016/193490 A1 | 12/2016 |
| WO | 2017/058784 A1 | 4/2017 |
| WO | 2017/181146 A1 | 10/2017 |
| WO | 2017/181202 A2 | 10/2017 |
| WO | 2017/190106 A1 | 11/2017 |
| WO | 2017205540 A1 | 11/2017 |
| WO | 2018/009723 A1 | 1/2018 |
| WO | 2018/083467 A1 | 5/2018 |
| WO | 2018/085603 A1 | 5/2018 |
| WO | 2018/106798 A1 | 6/2018 |
| WO | 2018/136562 A2 | 7/2018 |
| WO | 2018/156418 A1 | 8/2018 |
| WO | 2018/237081 A1 | 12/2018 |
| WO | 2019/046817 A1 | 3/2019 |
| WO | 2019/118926 A1 | 6/2019 |
| WO | 2019/140298 A1 | 7/2019 |
| WO | 2019/161244 A1 | 8/2019 |
| WO | 2019/200228 A1 | 10/2019 |
| WO | 2019/241349 A1 | 12/2019 |
| WO | 2020/010255 A1 | 1/2020 |
| WO | 2020/018522 A1 | 1/2020 |
| WO | 2020/041449 A1 | 2/2020 |
| WO | 2020/076957 A1 | 4/2020 |
| WO | 2020/106987 A1 | 5/2020 |
| WO | 2020/131699 A2 | 6/2020 |
| WO | 2020/214547 A1 | 10/2020 |
| WO | 2020/247263 A1 | 12/2020 |
| WO | 2021/055968 A1 | 3/2021 |
| WO | 2007100911 A2 | 9/2021 |
| WO | 2021/243045 A1 | 12/2021 |
| WO | 2022/015676 A1 | 1/2022 |

OTHER PUBLICATIONS

Bau, Stephan, et al., "Targeted next-generation sequencing by specific capture of multiple genomic loci using low-volume microfluidic DNA arrays", Anal Bioanal Chem, 2009, 171-175.
Lanman, et al., "Analytical and Clinical Validation of a Digital Sequencing Panel for Quantitative, Highly Accurate Evaluation of Cell-Free Circulating Tumor DNA", PLoS One, 2015, 1-27.
Lee, et al., "ERBB2 kinase domain mutation in the lung squamous cell carcinoma", Cancer Letters, 2006, 89-94.
Park, et al., "First-Line Erlotinib Therapy Until and Beyond Response Evaluation Criteria in Solid Tumors Progression in Asian Patients With Epidermal Growth Factor Receptor Mutation-Positive Non-Small-Cell Lung Cancer", JAMA Oncol., 2015, 305-312.
Tseng, Jeng-Sen, et al., "Dynamic Plasma EGFR Mutation Status as a Predictor of EGFR-TKI Efficacy in Patients with fGFR-Mutant Lung Adenocarcinoma", Thorac Oncol., 2015, 603-610.
"European Application No. 014198110, European Search Report Mailed Apr. 28, 2015, 3 pages."
PRNewswire (Research Suggests Daily Consumption of Orange Juice Can Reduce Blood Pressure and May Provide Beneficial Effects to Blood Vessel Function: New Study Identified Health Benefits in Orange Juice, Dec. 8, 2010), 3 pages.
"Abstracts for CNAPS III Circulating Nucleic Acids in Plasma and Serum and Serum Proteomics", Clinical Chemistry, vol. 49, No. 11, 2003, 33 pages.
"Abstracts for CNAPS IV Circulating Nucleic Acids in Plasma/Serum", Fourth International Conference on Circulating Nucleic Acids in Plasma/Serum (CNAPS-IV), 2005, 40 pages.
"How Many Carbs in a Potato?, [Online]", New Health Guide, Nov. 1, 2014, 3 pages.
"Random variable", The Penguin Dictionary of Mathematics, 2008, 1 page.
Abaan, O. D et al., "The Exomes of the NCI-60 Panel: A Genomic Resource for Cancer Biology and Systems Pharmacology", Cancer Res., vol. 73, No. 14, Jul. 15, 2013, 4372-4382.
Abbosh, C. et al., "Phylogenetic ctDNA analysis depicts early-stage lung cancer evolution", Nature, vol. 545, May 25, 2017, 446-451.
Abd-Elsalam, Kamel A., "Bioinformatic Tools And Guideline for PCR Primer Design", African Journal of Biotechnology, vol. 2, 2003, pp. 91-95.
Abidi, S. et al., "Leveraging XML-based electronic medical records to extract experiential clinical knowledge: An automated approach to generate cases for medical case-based reasoning systems", International Journal of Medical Informatics, 68(1-3), 2002, 187-203.
Academic Press, "Fixed Medium", 1996, 1 pg.
Adalsteinsson, V. A. et al., "Scalable whole-exome sequencing of cell-free DNA reveals high concordance with metastatic tumors", Nature Communications, vol. 18, No. 1324, 2017, 13 pages.
Adinolfi, M. et al., "Rapid Detection of Aneuploidies by Microsatellite and the Quantitative Fluorescent Polymerase Chain Reaction", Prenatal Diagnosis, vol. 17, No. 13, 1997, 1299-1311.
Agarwal, Ashwin et al., "Commercial Landscape of Noninvasive Prenatal Testing in the United States", Prenatal Diagnosis, 33, 2013, 521-531.
Agbor-Enoh, S. et al., "Donor-derived cell-free DNA predicts allograft failure and mortality after lung transplantation", EBioMedicine, vol. 40, 2019, 541-553.
Alaeddini, R. et al., "Forensic implications of genetic analyses from degraded DNA—A review", Forensic Science International: Genetics, vol. 4, 2010, 148-157.
Alberts, B. et al., "Chapter 20: Germ Cells and Fertilization", Molecular Biology of the Cell, Fourth Edition, 2002, 1127-1156.
Alberts, B. et al., "Chapter 4: DNA and Chromosomes", Molecular Biology of the Cell, Fourth Edition, 2002, 191-234.
Alizadeh, Mehdi et al., "Quantitative Assessment of Hematopoietic Chimerism after Bone Marrow Transplantation by Real-time Quantitative Polymerase Chain Reaction", Blood, vol. 99, No. 12, Jun. 15, 2002, 4618-4625.
Alkan, Can et al., "Personalized Copy Number and Segmental Duplication Maps Using Next-Generation Sequencing", Nature Genetics, 41, 10, 2009, 1061-1068.
Allaire, F R., "Mate selection by selection index theory", Theoretical Applied Genetics, 57(6), 1980, 267-272.
Allan, J. et al., "Micrococcal Nuclease Does Not Substantially Bias Nucleosome Mapping", Journal of Molecular Biology, vol. 417, Jan. 30, 2012, 152-164.
Allawi, Hatim T. et al., "Thermodynamics of internal C•T Mismatches in DNA", Nucleic Acids Research, 26 (11), 1998, 2694-2701.
Ambardar, S. et al., "High Throughput Sequencing: An Overview of Sequencing Chemistry", Indian J. Microbiol., vol. 56, No. 4, 2016, 394-404.

(56) References Cited

OTHER PUBLICATIONS

Amicucci, P. et al., "Prenatal Diagnosis of Myotonic Dystrophy Using Fetal DNA Obtained from Maternal Plasma", Clinical Chemistry, vol. 46, No. 2, 2000, 301-302.
Andras, S. C. et al., "Strategies for Signal Amplification in Nucleic Acid Detection", Molecular Biotechnology, vol. 19, 2001, 29-44.
Anker, P. et al., "Circulating DNA in Plasma or Serum", Medicina, vol. 60, 2000, 699-702.
Anker, P. et al., "Detection of circulating tumour DNA in the blood (plasma/serum) of cancer patients", Cancer and Metastasis Reviews, vol. 18, 1999, 65-73.
Anker, P. et al., "The Second International Symposium on Circulating Nucleic Acids in Plasma and Serum (CNAPS-2) held in conjunction with the 6th Annual Scientific Symposium of the Hong Kong Cancer Institute", Clinical Chemistry, vol. 47, No. 2, 2001, 361-370.
Ansorge, Wilhelm J., "Next-generation DNA Sequencing Techniques", New Biotechnology, vol. 25, No. 4, Feb. 2, 2009, 195-203.
Antonarakis, S. E. et al., "Chromosome 21 And Down Syndrome: From Genomics To Pathophysiology", Nature Reviews Genetics, vol. 5, Oct. 2004, 725-738.
Aoki, Yasuhiro, "Statistical and Probabilistic Bases of Forensic DNA Testing", The Journal of the Iwate Medical Association, 2002, vol. 54, p. 81-94.
Arandjelovic, M. et al., "Two-Step Multiplex Polymerase Chain Reaction improves the Speed and Accuracy of Genotyping Using DNA from Noninvasive and Museum Samples", Molecular Ecology Resources, vol. 9, 2009, pp. 28-36.
Ashoor, G. et al., "Fetal fraction in maternal plasma cell-free DNA at 11-13 weeks' gestation: relation to maternal and fetal characteristics", Ultrasound in Obstetrics and Gynecology, vol. 41, 2013, 26-32.
Ashoor, Ghalia et al., "Chromosome-Selective Sequencing of Maternal Plasma Cell-Free DNA for First-Trimester Detection of Trisomy 21 and Trisomy 18", American Journal of Obstetrics & Gynecology, 206, 2012, 322.e1-322.e5.
Ashoor, Ghalia et al., "Fetal Fraction in Maternal Plasma Cell-Free DNA at 11-13 Weeks' Gestation: Effect of Maternal and Fetal Factors", Fetal Diagnosis Therapy, 2012, 1-7.
Auld, D. S., "Use of Chelating Agents to Inhibit Enzymes", Methods in Enzymology, vol. 158, 1988, 110-114.
Avent, Neil D. et al., "Cell-free Fetal DNA in The Maternal Serum And Plasma: Current And Evolving Applications", Current Opinion in Obstretrics and Gynecology, vol. 21, No. 2, Apr. 1, 2009, 175-179.
Avgidou, K. et al., "Prospective first-trimester screening for trisomy 21 in 30,564 pregnancies", American Journal of Obstetrics and Gynecology, vol. 192, 2005, 1761-1767.
Ayala, et al., "Long-Term Follow-Up of Donor Chimerism Tolerance After Human Liver Transplantation", Liver Transplantation, vol. 15, No. 6,, May 28, 2009, 581-591.
Bada, Michael A. et al., "Computational Modeling of Structural Experimental Data", Methods in Enzymology,317, 2000, 470-491.
Bai, H. et al., "Detection and Clinical Significance of Intratumoral EGFR Mutational Heterogeneity in Chinese Patients with Advanced Non-Small Cell Lung Cancer", PLOS One, vol. 8, No. 2, Feb. 2013, 7 pages.
Balavoine, Guillaume, "Identification of Members of Several Homeobox Genes in a Planarian Using a Ligation-Mediated Polymerase Chain Reaction Technique", Nucleic Acids Research, vol. 24, 1996, pp. 1547-1553.
Balduini, et al., "Utility of Biochemical Markers in The Follow-up Heart Transplant Recipients", Transplantation Proceedings, vol. 35, No. 8, Dec. 1, 2003, 3075-3078.
Bale, J. R. et al., "Reducing Birth Defects: Meeting the Challenge in the Developing World", Institute of Medicine of the National Academies, 2003, 270 pgs.
Ballif, B. C. et al., "Detection of Low-Level Mosaicism by Array CGH in Routine Diagnostic Specimens", American Journal of Medical Genetics Part A, vol. 140A, 2006, 2757-2767.
Banfi, G. et al., "The role of ethylenediamine tetraacetic acid (EDTA) as in vitro anticoagulant for diagnostic purposes", Clin. Chem., vol. 45, No. 5, 2007, 565-576.
Barbazuk, et al., "SNP Discovery via 454 Transcriptome Sequencing", The Plant Journal, vol. 51, Jul. 27, 2007, 910-918.
Barra, G. B. et al., "EDTA-mediated inhibition of DNases protects circulating cell-free DNA from ex vivo degradation in blood samples", Clinical Biochemistry, vol. 48, 2015, 976-981.
Barski, A. et al., "High-Resolution Profiling of Histone Methylations in the Human Genome", Cell, vol. 129, May 18, 2007, 823-837.
Bartlett, John M. et al., "PCR Protocols", PCR Protocols, vol. 226, 2003, 519 pages.
Bashashati, A. et al., "Distinct evolutionary trajectories of primary high-grade serous ovarian cancers revealed through spatial mutational profiling", Journal of Pathology, vol. 231, 2013, 21-34.
Bauer, M. et al., "A prospective analysis of cell-free fetal DNA concentration in maternal plasma as an indicator for adverse pregnancy outcome", Prenatal Diagnosis, vol. 26, 2006, 831-836.
Baxter, L. L et al., "Discovery and genetic localization of Down syndrome cerebellar phenotypes using the Ts65Dn mouse", Human Molecular Genetics, vol. 9, No. 2, Jan. 2000, 195-202.
Baxter-Lowe, et al., "Tracking Microchimeric DNA In Plasma To Diagnose And Manage Organ Transplant Rejection", Clinical Chemistry, vol. 52, No. 4, Apr. 1, 2006, 559-561.
Beaumont, Mark A et al., "The Bayesian Revolution in Genetics", Nature Reviews Genetics, 5, 2004, 251-261.
Beck, et al., "Next Generation Sequencing of Serum Circulating Nucleic Acids from Patients with Invasive Ductal Breast Cancer Reveals Differences to Healthy and Nonmalignant Controls", Molecular Cancer Research, vol. 8, No. 3, Mar. 1, 2010, 335-342.
Beck, J. et al., "Digital Droplet PCR for Rapid Quantification of Donor DNA in the Circulation of Transplant Recipients as a Potential Universal Biomarker of Graft Injury", Clinical Chemistry, vol. 59, No. 12, 2013, 1732-1741.
Beck, J. et al., "Profile of the Circulating DNA in Apparently Healthy Individuals", Clinical Chemistry, vol. 55, No. 4, 2009, 730-738.
Beer, Alan E. et al., "The Biological Basis of Passage of Fetal Cellular Material into the Maternal Circulation", Annals New York Academy of Sciences, 731, 1994, 21-35.
Beerenwinkel, et al., "Methods for Optimizing Antiviral Combination Therapies", Bioinformatics, 19(1), 2003, i16-i25.
Beerenwinkel, N. et al., "Geno2pheno: estimating phenotypic drug resistance from HIV-1 genotypes", Nucleic Acids Research, 31(13), 2003, 3850-3855.
Belostotsky, Dmitry A. et al., "Plant Systems Biology", Methods in Molecular Biology, vol. 553, Aug. 25, 2009, 3-408.
Bender, et al., "A Multiplex SNP Typing Approach For The DNA Pyrosequencing Technology", International Congress Series, vol. 1288, Apr. 20, 2006, 73-75.
Benjamini, Y. et al., "Controlling the False Discovery Rate: A Practical and Powerful Approach to Multiple Testing", Journal of the Royal Statistical Society, Series B (Methodological), vol. 57, No. 1, 1995, 289-300.
Benn, P. et al., "Non-Invasive Prenatal Testing for Aneuploidy: Current Status and Future Prospects", Ultrasound Obstet Gynecol, 42, 2013, 15-33.
Benn, P et al., "Non-Invasive prenatal Diagnosis for Down Syndrome: the Paradigm Will Shift, but Slowly", Ultrasound Obstet. Gynecol., 39, 2012, 127-130.
Bennett, S. T. et al., "Toward the $1000 human genome", Pharmacogenomics, vol. 6, No. 4, 2005, 373-382.
Bentley, et al., "High-resolution, High-throughput HLA Genotyping by Next-generation Sequencing", Tissue Antigens, vol. 74, No. 5, Nov. 1, 2009, 393-403.
Bentley, David R et al., "Accurate Whole Human Genome Sequencing Using Reversible Terminator Chemistry", Nature, 456, 6, 2008, 53-59.
Bergen, A. W. et al., "Effects of DNA mass on multiple displacement whole genome amplification and genotyping performance", BMC Biotechnology, vol. 5, No. 24, Sep. 16, 2005, 11 pgs.

(56) References Cited

OTHER PUBLICATIONS

Bermudez, M. et al., "Single-cell sequencing and mini-sequencing for preimplantation genetic diagnosis", Prenatal Diagnosis, 23, 2003, 669-677.
Beroud, C. et al., "Prenatal diagnosis of spinal muscular atrophy by genetic analysis of circulating fetal cells", The Lancet, vol. 361, Mar. 22, 2003, 1013-1014.
Bevinetto, Gina , Bevinetto (5 Foods All Pregnant Women Need, American Baby, available at http://www.parents.com/pregnancy/mybody/nutrition/5greatpregnancyfoods/, Apr. 15, 2008), 8 pgs.
Bianchi, D W. et al., "Fetal gender and aneuploidy detection using fetal cells maternal blood: analysis of NIFTY I data", Prenat Diagn 2002; 22, 2002, 609-615.
Bianchi, D W. et al., "Insights Into Fetal and Neonatal Development Through Analysis of Cell-Free RNA in Body Fluids", Early Human Development, vol. 86, No. 11, Nov. 2010, 747-752.
Bianchi, D. W. , "Circulating Fetal DNA: Its Origin and Diagnostic Potential—A Review", Placenta, vol. 25, Supplemental A, May 2004, S93-S101.
Bianchi, D. W. et al., "Genome-Wide Fetal Aneuploidy Detection by Maternal Plasma DNA Sequencing", Obstetrics & Gynecology, vol. 119, No. 5, May 2012, 890-901.
Bianchi, D. W. , "Review: Fetal Cells in the Maternal Circulation: Feasibility for Prenatal Diagnosis", British Journal of Haematology, vol. 105, 1999, 574-583.
Binladen, J. et al., "The Use of Coded PCR Primers Enables High-Throughput Sequencing of Multiple Homolog Amplification Products by 454 Parallel Sequencing", PLOS One, Issue 2, Feb. 2007, 9 pages.
Birch, Lyndsey et al., "Accurate and Robust Quantification of Circulating Fetal and Total DNA in Maternal Plasma from 5 to 41 Weeks of Gestation", Clinical Chemistry, 51(2), 2005, 312-320.
Birkenkamp-Demtroder, K. et al., "Abstract 3653: Sequencing of plasma cfDNA from patients with locally advanced bladder cancer for surveillance and therapeutic efficacy monitoring", Cancer Research, vol. 78, No. 13 Supplement, Jul. 2019, 1 page.
Bischoff, F. Z. et al., "Cell-free fetal DNA in maternal blood: kinetics, source and structure", Human Reproduction Update, vol. 11, No. 1, 2005, 59-67.
Bischoff, F. Z. et al., "Intact fetal cells in maternal plasma: are they really there?", Lancet, vol. 361, 2003, 139-140.
Bisignano, et al., "PGD and Aneuploidy Screening for 24 Chromosomes: Advantages and Disadvantages of Competing Platforms", Reproductive BioMedicine Online, 23, 2011, 677-685.
Blomquist, T M. et al., "Targeted RNA-Sequencing with Competitive Multiplex-PCR Amplicon Libraries", Plos One, vol. 8, Issue 11, Nov. 2013, 14 pages.
Blow, N. , "The personal side of genomics", Nature, vol. 449, Oct. 4, 2007, 627-630.
Board, R.E. et al., "Detection of BRAF mutations in the tumour and serum of patients enrolled in the AZD6244 (ARRY-142886) advanced melanoma phase II study", British Journal of Cancer, vol. 101, 2009, 1724-1730.
Bodenreider, O. , "The Unified Medical Language System (UMLS): Integrating Biomedical Terminology", Nucleic Acids Research, 32, (Database issue), 2004, D267-D270.
Bordoni, et al., "Evaluation Of Human Gene Variant Detection In Amplicon Pools By The GS-FLX Parallel Pyrosequencer", BMC Genomics, vol. 9, Oct. 8, 2008, 1-8.
Boudsocq, F. et al., "Sulfolobus solfataricus P2 DNA polymerase IV (Dpo4): an archael DinB-like DNA polymerase with lesion-bypass properties akin to eukaryotic poln", Nucleic Acids Research, vol. 29, No. 22, 2001, 4607-4616.
Bouma, B. N. et al., "Human Blood Coagulation Factor", The Journal of Biological Chemistry, vol. 252, No. 18, 1977, 6432-6437.
Brastianos, P. K. et al., "Genomic Characterization of Brain Metastases Reveals Branched Evolution and Potential Therapeutic Targets", Cancer Discovery, vol. 5, Sep. 26, 2015, 1164-1177.
Breithaupt, Holger , "The Future of Medicine", EMBO Reports, 21(61), 2001, 465-467.
Brinza, D. et al., "2SNP: scalable phasing based on 2-SNP haplotypes", Bioinformatics, vol. 22, No. 3, 2006, 371-373.
Brockman, et al., "Quality Scores And SNP Detection In Sequencing-by-synthesis Systems", Genome Research, vol. 18, No. 5, May 1, 2008, 763-770.
Broude, N E. et al., "High-Level Multiplex DNA Amplification", Antisense & Nucleic Acid Drug Development, vol. 11, 2001, 327-332.
Broude, N. E. et al., "High Multiplexity PCR Based on PCR Suppression", DNA Amplification Current Technologies and Applications, 2004, 61-76.
Broude, N. E. et al., "Multiplex Allele-specific Target Amplification based on PCR Suppression", PNAS, vol. 98, No. 1, Jan. 2, 2001, 206-211.
Brownie, Jannine et al., "The Elimination of Primer-Dimer Accumulation in PCR", Nucleic Acids Research, 25(16), 1997, 3235-3241.
Browning, S. R. et al., "Rapid and Accurate Haplotype Phasing and Missing-Data Inference for Whole-Genome Association Studies By Use of Localized Haplotype Clustering", The American Journal of Human Genetics, vol. 81, Nov. 2007, 1084-1097.
Bryant, A. P., "Terminology of Sugars", Ind. Eng. Chem., vol. 26, No. 2, 1933, 231.
Burkey, B. F. et al., "Hepatic apolipoprotein J is secreted as a lipoprotein", Journal of Lipid Research, vol. 33, 1992, 1517-1526.
Burkova, E. E. et al., "Extremely Stable Soluble High Molecular Mass Multi-Protein Complex with DNase Activity in Human Placental Tissue", PLOS One, vol. 9, No. 11: e011234, Nov. 26, 2014, 26 pages.
Burnham, P. et al., "Myriad Applications of Circulating Cell-Free DNA in Precision Organ Transplant Monitoring", Annals of the American Thoracic Society, vol. 14, Supplement 3, Sep. 2017, S237-S241.
Bustamante-Aragones, Ana et al., "New Strategy for The Prenatal Detection/Exclusion of Paternal Cystic Fibrosis Mutations in Maternal Plasma", Journal of Cystic Fibrosis, vol. 7, Issue 6, Nov. 1, 2008, 505-510.
Butler, et al., "Cardiovascular Magnetic Resonance In The Diagnosis Of Acute Heart Transplant Rejection: A Review", Journal of Cardiovascular Magnetic Resonance, vol. 11, No. 1, Mar. 12, 2009, 1-11.
Butler, J. et al., "The Development of Reduced Size STR Amplicons as Tools for Analysis of Degraded DNA*", Journal of Forensic Sciences, vol. 48, No. 5, 2003, 1054-1064.
Butt, A. N. et al., "Overview of Circulating Nucleic Acids in Plasma/Serum: Update on Potential Prognostic and Diagnostic Value in Diseases Excluding Fetal Medicine and Oncology", Ann. N.Y. Acad. Sci., vol. 1137, 2008, 236-242.
Cairns, Paul et al., "Homozygous Deletions of 9p21 in Primary Human Bladder Tumors Detected by Comparative Multiplex Polymerase Chain Reaction", Cancer Research, 54, 1994, 1422-1424.
Caliendo, Angela , "Multiplex PCR and Emerging Technologies for the Detection of Respiratory Pathogens", Clinical Infectious Diseases, 52(4), 2011, S326-S330.
Calin, G. A. et al., "A MicroRNA Signature Associated with Prognosis and Progression in Chronic Lymphocytic Leukemia", N Engl J Med, vol. 353, 2005, 1793-1801.
Campbell, P. J. et al., "Subclonal phylogenetic structures in cancer revealed by ultra-deep sequencing", PNAS, vol. 105, No. 35, Sep. 2, 2008, 13081-13086.
Canick, J. A. et al., "The impact of maternal plasma DNA fetal fraction on next generation sequencing tests for common fetal aneuploidies", Prenatal Diagnosis, vol. 33, 2013, 667-674.
Cansar, , "Hs-578-T—Copy Number Variation—Cell Line Synopsis", ICR Cancer Research UK, Retrieved on Mar. 26, 2018 from https://cansar.icr.ac.uk/cansar/cell-lines/Hs-578-T/copy_number_variation/chromosome_8/, Mar. 26, 2018, 50 pgs.
Cao, Y. et al., "Clinical Evaluation of Branched DNA Signal Amplification for Quantifying HIV Type 1 in Human Plasma", AIDS Research and Human Retroviruses, vol. 11, No. 3, 1995, 353-361.

(56) References Cited

OTHER PUBLICATIONS

Carnevale, Alessandra et al., "Attitudes of Mexican Geneticists Towards Prenatal Diagnosis and Selective Abortion", American Journal of Medical Genetics, 75, 1998, 426-431.
Carvalho, B. et al., "Exploration, normalization, and genotype calls of high-density oligonucleotide SNP array data", Biostatistics, vol. 8, No. 2, 2007, 485-499.
Casbon, J. A. et al., "A method for counting PCR template molecules with application to next-generation sequencing", Nucleic Acids Research, vol. 39, No. 12, Apr. 13, 2011, 1-8.
Castleberry, C. D. et al., "Quantification of Circulating Cell-Free DNA in Pediatric Heart Transplant Recipients", Journal of Heart and Lung Transplantation, vol. 30, No. 4, Apr. 1, 2011, S139.
Chakraborty, R. et al., "Paternity Exclusion by DNA Markers: Effects of Paternal Mutations", Journal of Forensic Sciences, vol. 41, No. 4, Jul. 1996, 671-677.
Chan, Allen K. et al., "Cell-free Nucleic Acids In Plasma, Serum And Urine: A New Tool In Molecular Diagnosis", Annals of Clinical Biochemistry, vol. 40, Issue 2, Mar. 1, 2003, 122-130.
Chan, K.C. et al., "Size Distributions of Maternal and Fetal DNA in Maternal Plasma", Clinical Chemistry, vol. 50, No. 1, 2004, 88-92.
Chang, H.W. et al., "Assessment of Plasma DNA Levels, Allelic Imbalance, and CA 125 as Diagnostic Tests for Cancer", Journal of the National Cancer Institute, vol. 94, No. 22, Nov. 20, 2002, 1697-1703.
Chavali, Sreenivas et al., "Oligonucleotide Properties Determination And Primer Designing: A Critical Examination of Predictions", Bioinformatics, vol. 21, 2005, pp. 3918-3925.
Chen, E. et al., "Noninvasive Prenatal Diagnosis of Fetal Trisomy 18 and Trisomy 13 by Maternal Plasma DNA Sequencing", PLoS One, 6(7), e21791, 2011, 7 pgs.
Chen, Bing-Yuan et al., "PCR Cloning Protocols", PCR Cloning Protocols, vol. 192, 2002, 434 pages.
Chen, C. P. et al., "Fetal DNA in maternal plasma: the prenatal detection of a paternally inherited fetal aneuploidy", Prenatal Diagnosis, vol. 20, 2000, 353-357.
Chen, X. Q. et al., "Microsatallite alterations in plasma DNA of small cell lung cancer patients", Nature Medicine, vol. 2, No. 9, Sep. 1996, 1033-1035.
Chetty, Shilpa et al., "Uptake of Noninvasive Prenatal Testing (NIPT) in Women Following Positive Aneuploidy Screening", Prenatal Diagnosis,33, 2013, 542-546.
Cheung, S. W. et al., "Rapid Publication: Microarray-Based CGH Detects Chromosomal Mosaicism Not Revealed by Conventional Cytogenetics", American Journal of Medical Genetics Part A, vol. 143A, 2007, 1679-1686.
Cheung, V. G. et al., "Whole genome amplification using a degenerate oligonucleotide primer allows hundreds of genotypes to be performed on less than one nanogram of genomic DNA", Proceedings of the National Academy of Sciences, USA, vol. 93, Dec. 1996, 14676-14679.
Chim, S. S. et al., "Detection and Characterization of Placental MicroRNAs in Maternal Plasma", Clinical Chemistry, vol. 54, No. 3, 2008, 482-490.
Chinnapapagari, S. K. et al., "Treatment of Maternal Blood Samples with Formaldehyde Does Not Alter the Proportion of Circulatory Fetal Nucleic Acids (DNA and mRNA) in Maternal Plasma", Clinical Chemistry, vol. 51, No. 3, 2005, 653-655.
Chitty, L. S. et al., "Noninvasive Prenatal Screening for Genetic Diseases Using Massively Parallel Sequencing of Maternal Plasma DNA", Cold Spring Harbor Perspectives in Medicine, vol. 5, No. 9, 2015, 20 pages.
Chiu, R. et al., "Non-Invasive Prenatal Assessment of Trisomy 21 by Multiplexed Maternal Plasma DNA Sequencing: Large Scale Validity Study", BMJ, 342, c7401, 2011, 9 pgs.
Chiu, R.W.K. et al., "Hypermethylation of RASSF1A in Human and Rhesus Placentas", The American Journal of Pathology, vol. 170, No. 3, Mar. 2007, 941-950.

Chiu, Rossa W. et al., "Effects of Blood-Processing Protocols on Fetal and Total DNA Quantification in Maternal Plasma", Clinical Chemistry, 47(9), 2001, 1607-1613.
Chiu, Rossa W.K. et al., "Maternal Plasma DNA Analysis with Massively Parallel Sequencing by Litigation for Noninvasive Prenatal Diagnosis of Trisomy 21", Clinical Chemistry, 56, 3, 2010, 459-463.
Chiu, Rossa W.K. et al., "Non-Invasive Prenatal Diagnosis by Single Molecule Counting Technologies", Trends in Genetics, 25 (7), 2009, 324-331.
Chiu, Rossa W.K. et al., "Noninvasive Prenatal Diagnosis of Fetal Chromosomal Aneuploidy by Massively Parallel Genomic Sequencing of DNA in Maternal Plasma (with Supporting Information)", PNAS, vol. 105, No. 51, 2008, 20458-20463.
Choi, M. et al., "Genetic diagnosis by whole exome capture and massively parallel DNA sequencing", PNAS, vol. 106, No. 45, Nov. 10, 2009, 19096-19101.
Choi, Y. et al., "Comparison of phasing strategies for whole human genomes", PLOS Genetics, Apr. 5, 2018, 26 pages.
Chu, T. et al., "Statistical Considerations for Digital Approaches to Non-Invasive Fetal Genotyping", Bioinformatics (Advance Access publication), 26 (22), 2010, 2863-2866.
Chu, Tianjiao et al., "Statistical Model for Whole Genome Sequencing and its Application to Minimally Invasive Diagnosis of Fetal Genetic Disease", Bioinformatics, 25(10), 2009, 1244-1250.
Chu, Tianjiao et al., "A Novel Approach Toward the Challenge of Accurately Quantifying Fetal DNA in Maternal Plasma", Prenatal Diagnosis,30, 2010, 1226-1229.
Chung, G. T. et al., "Lack of Dramatic Enrichment of Fetal DNA in Maternal Plasma by Formaldehyde Treatment", Clinical Chemistry, vol. 51, No. 3, 2005, 655-658.
Church, et al., "Multiplex DNA Sequencing", Science, vol. 240, No. 4849, Apr. 8, 1988, 185-188.
Ciriello, G. et al., "Emerging landscape of oncogenic signatures across human cancers", Nature Genetics, vol. 45, No. 10, Oct. 2013, 1127-1135.
Clausen, F. B. et al., "Improvement in fetal DNA extraction from maternal plasma. Evaluation of the NucliSens Magnetic Extraction system and the QIAamp DSP Virus Kit in comparison with the QIAamp DNA Blood Mini Kit", Prenatal Diagnosis, vol. 27, 2007, 6-10.
Cole, Neal W. et al., "Hyperglycemia-Induced Membrane Lipid Peroxidation and Elevated Homocysteine Levels Are Poorly Attenuated by Exogenous Folate in Embryonic Chick Brains", Comparative Biochemistry and Physiology, Part B, 150, 2008, 338-343.
Colella, S. et al., "QuantiSNP: an Objectives Bayes Hidden-Markov Model to Detect and Accurately Map Copy Number Variation Using SNP Genotyping Data", Nucleic Acids Research, 35 (6), 2007, 2013-2025.
Conlin, L. K. et al., "Mechanisms of mosaicism, chimerism and uniparental disomy identified by single nucleotide polymorphism array analysis", Human Molecular Genetics, vol. 19, No. 7, Jan. 6, 2010, 1263-1275.
Coombes, R. C. , "Abstract P4-01-02: Early detection of residual breast cancer through a robust, scalable and personalized analysis of circulating tumour DNA (ctDNA) antedates overt metastatic recurrence", Cancer Research, vol. 79, No. 4 Supplement, Feb. 15, 2019.
Cossu, Gianfranco et al., "Rh D/d Genotyping by Quantitative Polymerase Chain Reaction and Capillary Zone Electrophoresis", Electrophoresis, 17, 1996, 1911-1915.
Couraud, S. et al., "Noninvasive Diagnosis of Actionable Mutations by Deep Sequencing of Circulating Free DNA in lung Cancer from Never-Smokers: A Proof-of-Concept Study from BioCAST / IFCT-1002", Clinical Cancer Research, vol. 20, No. 17, Jul. 10, 2014, 4613-4624.
Couraud, S. et al., "Supplementary Data for Noninvasive Diagnosis of Actionable Mutations by Deep Sequencing of Circulating Free DNA in lung Cancer from Never-Smokers: A Proof-of-Concept Study from BioCAST / IFCT-1002", 2014, 13 pages.
Coyle, J. F. et al., "Standards for detailed clinical models as the basis for medical data exchange and decision support", International Journal of Medical Informatics, 69(2-3), 2003, 157-174.

(56) References Cited

OTHER PUBLICATIONS

Craig, D. W. et al., "Identification of genetic variants using barcoded multiplexed sequencing", Nature Methods, vol. 5, Oct. 2008, 887-893.
Crespo-Leiro, et al., "Gene Expression Profiling for Monitoring Graft Rejection in Heart Transplant Recipients", Transplantation Proceedings, vol. 41, No. 6, Jul. 1, 2009, 2240-2243.
Cronn, R. et al., "Multiplex sequencing of plant chloroplast genomes using Solexa sequencing-by-synthesis technology", Nucleic Acids Research, vol. 36, No. 19, Aug. 27, 2008, 11 pgs.
Cross, Jillian et al., "Resolution of trisomic mosaicism in prenatal diagnosis: estimated performance of a 50K SNP microarray", Prenat Diagn 2007; 27, 2007, 1197-1204.
Cunningham, K. S. et al., "An approach to endomyocardial biopsy interpretation", Journal of Clinical Pathology, vol. 59, No. 2, Mar. 2006, 121-129.
Dahl, et al., "Multigene Amplification and Massively Parallel Sequencing for Cancer Mutation Discovery", Proceedings of the National Academy of Sciences, vol. 104, No. 22, May 29, 2007, 9387-9392.
Dambrin, et al., "A New Rejection Criteria In The Heterotopically Placed Rat Heart By Non-invasive Measurement Of Dp/Dtmax", The Journal of Heart and Lung Transplantation, vol. 18, No. 6, Jun. 18, 1999, 524-531.
D'Aquila, Richard et al., "Maximizing sensitivity and specificity of PCR by pre-amplification heating", Nucleic Acids Research, 19(13), 1991, p. 3749.
Daruwala, Raoul-Sam et al., "A Versatile Statistical Analysis Algorithm to Detect Genome Copy Number Variation", PNAS, 101(46), 2004, 16292-16297.
Dawson, S.J. et al., "Analysis of Circulating Tumor DNA to Monitor Metastatic Breast Cancer", The New England Journal of Medicine, vol. 368, No. 13, Mar. 28, 2013, 1199-1209.
De Bruin, E. et al., "Spatial and temporal diversity in genomic instability processes defines lung cancer evolution", Science, vol. 346, No. 6206, Oct. 10, 2014, 251-256.
De Jong, M. M. et al., "Genes other than BRCA 1 and BRCA2 involved in breast cancer susceptibility", J. Med. Genet., vol. 39, 2009, 225-242.
De Vries, et al., "Diagnostic genome profiling in mental retardation", Am J Hum Genet, 77, published online Aug. 30, 2005, 2005, 606-616.
Deangelis, M. et al., "Solid-phase Reversible Immobilization for the Isolation of PCR Products", Nucleic Acids Research, 23 (22), 1995, 4742-4743.
Deb, Mahua et al., "Development of a Multiplexed PCR Detection Method for Barley and Cereal Yellow Dwarf Viruses, Wheat Spindle Streak Virus, Wheat Streak Mosaic Virus and Soil-Borne Wheat Mosaic Virus", Journal of Virological Methods, vol. 148, 2008, pp. 17-24.
Delaneau, O. et al., "Shape-IT: new rapid and accurate algorithm for haplotype inference", BMC Bioinformatics, vol. 9, No. 540, Dec. 16, 2008, 14 pages.
Delgado, P. O. et al., "Characterization of cell-free circulating DNA in plasma in patients with prostate cancer", Tumor Biol., vol. 34, 983-986, 2013.
Deng, S. et al., "TNER: A Novel Background Error Suppression Method for Mutation Detection in Circulating Tumor DNA", bioRxiv, http://dx.doi.org/10.1101/214379, Nov. 5, 2017, 12 pgs.
Deutsch, S. et al., "Detection of aneuploidies by paralogous sequence quantification", J Med Genet, vol. 41, 2004, 908-915.
Devaney, S. et al., "Noninvasive Fetal Sex Determination Using Cell-Free Fetal DNA: A Systematic Review and Meta-analysis", JAMA, 306 (6), 2011, 627-636.
Dhallan, et al., "Methods to Increase the Percentage of Free Fetal DNA Recovered from the Maternal Circulation", JAMA, 291(9), 2004, 1114-1119.
Dhallan, Ravinder et al., "A non-invasive test for prenatal diagnosis based on fetal DNA present in maternal blood: a preliminary study", The Lancet, 369, 2007, 474-481.
Di, X. et al., "Dynamic model based algorithms for screening and genotyping", Bioinformatics, vol. 21, No. 9, 2005, 1958-1963.
Dias-Santagata, D. et al., "BRAF V600E Mutations Are Common in Pleomorphic Xanthoastrocytoma: Diagnostic and Therapeutic Implications", PLoS One, vol. 6, No. 3, Mar. 2011, 9 pages.
Dickover, R. E. et al., "Optimization of Specimen-Handling Procedures for Accurate Quantitation of Levels of Human Immunodeficiency Virus RNA in Plasma by Reverse Transcriptase PCR", Journal of Clinical Microbiology, vol. 36, No. 4, 1998, 1070-1073.
Dieffenbach, C W. et al., "General concepts for PCR primer design", Genome Research. PCR methods and Applications vol. 3, 1993, S30-S37.
Diehl, F. et al., "Circulating mutant DNA to assess tumor dynamics", Nature Medicine, vol. 14, No. 9, Jul. 31, 2008, 985-990.
Diehl, F. et al., "Detection and quantification of mutations in the plasma of patients with colorectal tumors", PNAS, vol. 102, No. 45, Nov. 8, 2005, 16368-16373.
Dietmaier, W. et al., "Multiple Mutation Analyses in Single Tumor Cells with Improved Whole Genome Amplification", American Journal of Pathology, vol. 154, No. 1, Jan. 1999, 83-95.
Ding, C et al., "Direct molecular haplotyping of long-range genomic DNA with M1-PCR", PNAS 100(13), 2003, 7449-7453.
Ding, C. et al., "MS analysis of single-nucleotide differences in circulating nucleic acids: Application to noninvasive prenatal diagnosis", PNAS, vol. 101, No. 29, Jul. 20, 2004, 10762-10767.
Dodge, Y., "Bayes' Theorem", The Concise Encyclopedia of Statistics, 2008, 30-31.
Dohm, J. et al., "Substantial Biases in Ultra-Short Read Data Sets From High-Throughput DNA Sequencing", Nucleic Acids Research, 36 (16), e105, 2008, 10 pgs.
Dolganov, Gregory et al., "A Novel Method of Gene Transcript Profiling in Airway Biopsy Homogenates Reveals Increased Expression of a Na—K+ -Cl-Cotransporter (NKCC1) in Asthmatic Subjects", Genome Res., 11, 2001, 1473-1483.
Donaghue, C. et al., "Detection of mosaicism for primary trisomies in prenatal samples by QF-PCR and karyotype analysis", Prenatal Diagnosis, vol. 25, 2005, 65-72.
Donohoe, Gerard G et al., "Rapid Single-Tube Screening of the C282Y Hemochromatosis Mutation by Real-Time Multiplex Allele-specific PCR without Fluorescent Probes", Clinical Chemistry, 46, 10, 2000, 1540-1547.
Donoso, P. et al., "Current Value of Preimplantation Genetic Aneuploidy Screening in IVF", Human Reproduction Update, 13(1), 2007, 15-25.
Doostzadeh, et al., "High Throughput Automated Allele Frequency Estimation by Pyrosequencing", PLoS One, vol. 3, No. 7, Jul. 16, 2008, 1-4.
Dorit, D. L., "cDNA Amplification Using One-sided (Anchored) Pcr", Current Protocols in Molecular Biology, vol. 17, 1992, pp. 15.6.1-15.6.10.
Dorit, Robert L. et al., "One-sided Anchored Polymerase Chain Reaction for Amplification and Sequencing of Complementary DNA", Methods in Enzymology, vol. 218 1993, pp. 36-47.
Dowd, P. et al., "On the mechanism of the anticlotting action of vitamin R quinone", Proc. Natl. Acad. Sci. USA, vol. 92, 1995, 8171-8175.
Downward, J., "Targeting RAS Signalling Pathways in Cancer Therapy", Nature Reviews, vol. 3, Jan. 2003, 11-22.
Dressman, D. et al., "Transforming single DNA molecules into fluorescent magnetic particles for detection and enumeration of genetic variations", PNAS, vol. 100, No. 15, Jul. 22, 2003, 8817-8822.
Echeverri, et al., "Caffeine's Vascular Mechanisms of Action", International Journal of Vascular Medicine vol. 2010(2010), 10 pages, Aug. 25, 2010.
Edwards, M. C. et al., "Multiplex PCR: Advantages, Development, and Applications", Genome Research, vol. 3, 1994, S65-S75.
Efron, B. et al., "Bootstrap Methods for Standard Errors, Confidence Intervals, and Other Measures of Statistical Accuracy", Statistical Science, vol. 1, No. 1, 1986, 54-77.

(56) References Cited

OTHER PUBLICATIONS

Ehrich, Mathias et al., "Noninvasive Detection of Fetal Trisomy 21 by Sequencing of DNA in Maternal Blood: A Study in a Clinical Setting", American Journal of Obstetrics & Gynecology, 204, 2011, 205.e1-205.e11.
Eichler, H., "Mild Course of Fetal Rh D Haemolytic Disease due to Maternal Alloimmunisation to Paternal HLA Class I and II Antigens", Vox Sang, 68, 1995, 243-247.
Ellison, Aaron M., "Bayesian Inference in Ecology", Ecology Letters, vol. 7, 2004, 509-520.
Ellonen, P. et al., "Development of SNP Microarray for Supplementary Paternity Testing", International Congress Series, 1261, 2004, 12-14.
Elnifro, Elfath M., "Multiplex PCR: Optimization and Application in Diagnostic Virology", Clinical Microbiology Reviews, vol. 13, 2000, pp. 559-570.
Eltoukhy, H. et al., "Modeling and Base-Calling for DNA Sequencing-By-Synthesis", IEEE, 2006, II-1032-II-1035.
EP06838311.6, "European Communication and Extended European Search Report", mailed Dec. 30, 2008, 8 pgs.
EP08742125.1, "European Communication pursuant to Article 94(3) EPC and Examination Report", mailed Feb. 12, 2010, 5 pgs.
Erijman, Ariel et al., "Transfer-PCR (TPCR): A Highway For DNA Cloning and Protein Engineering", Journal of Structural Biology, vol. 175, 2011, pp. 171-177.
Erlich, R. L. et al., "Next-generation sequencing for HLA typing of class I loci", BMC Genomics, vol. 12, No. 42, 2011, 13 pages.
Eronen, L. et al., "HaploRec: efficient and accurate large-scale reconstruction of haplotypes", BMC Bioinformatics, vol. 7, No. 542, Dec. 22, 2006, 18 pages.
European Commission, , "The 7th International Conference on Circulating Nucleic Acids in Plasma and Serum (CNAPS VII) in Madrid—Spain", The International Conference on Circulating Nucleic Acids in Plasma and Serum, Oct. 24, 2011, 2 pgs.
Everitt, B. S., "Medical Statistics From A to Z", 2003, 3 pages.
Fackenthal, J. D. et al., "Aberrant RNA splicing and its functional consequences in cancer cells", Disease Models & Mechanisms, vol. 1, 2008, 37-42.
Faham, M. et al., "Deep-sequencing approach for minimal residual disease detection in acute lymphoblastic leukemia", Blood Journal, vol. 120, No. 26, Dec. 20, 2012, 5173-5180.
Falcon, O., "Screening for trisomy 21 by fetal tricuspid regurgitation, nuchal translucency and maternal serum free b-hCG and PAPP-A at 11 + 0 to 13 + 6 weeks", Ultrasound Obstet Gynecol, vol. 27, 2006, 151-155.
Fan, et al., "Whole-genome molecular haplotyping of single cells", Nature Biotechnology, vol. 29, No. 1, Jan. 1, 2011, 51-57.
Fan, C H. et al., "Detection of Aneuploidy with Digital Polymerase Chain Reaction", Analytical Chemistry, vol. 79, No. 19, Oct. 1, 2007, 7576-7579.
Fan, Christina H. et al., "Non-Invasive Prenatal Measurement of the Fetal Genome", Nature, doi:10.1038/nature11251, 2012, 26 pgs.
Fan, Christina H et al., "Noninvasive Diagnosis of Fetal Aneuploidy by Shotgun Sequencing DNA from Maternal Blood", PNAS, 105, 42, 2008, 16266-16271.
Fan, H. C. et al., "In Principle Method for Noninvasive Determination of the Fetal Genome", Nat. Prec., 2010, 16 pgs.
Fan, H. C. et al., "Microfluidic digital PCR enables rapid prenatal diagnosis of fetal aneuploidy", American Journal of Obstetrics & Gynecology, vol. 200, May 2009, 543.e1-543.e7.
Fan, H. Christina et al., "Sensitivity of Noninvasive Prenatal Detection of Fetal Aneuploidy from Maternal Plasma Using Shotgun Sequencing Is Limited Only by Counting Statistics", PLoS One, vol. 5, Issue 5 (e10439), May 3, 2010, 1-6.
Fan, J.-B. et al., "Highly Parallel SNP Genotyping", Cold Spring Harbor Symposia on Quantitative Biology, vol. LXVIII, Feb. 2003, 69-78.
Fan, Jian-Bing et al., "Highly Parallel Genomic Assay", Nature Reviews, 7, 2006, 632-644.

Fat Secret, "5 Foods to Never Eat", https://www.fatsecret.com/calories-nutrition/food/white-bread/carboyhydrate (printed from internet Nov. 1, 2014)., 2 pages.
Fazio, Gennaro et al., "Identification of RAPD Markers Linked to Fusarium Crown and Root Rot Resistance (Frl) in Tomato", Euphytica 105, 1999, 205-210.
Fiorentino, F. et al., "Development and Clinical Application of a Strategy for Preimplantation Genetic Diagnosis of Single Gene Disorders Combined with HLA Matching", Molecular Human Reproduction (Advance Access publication), 10 (6), 2004, 445-460.
Fiorentino, F et al., "Strategies and Clinical Outcome of 250 Cycles of Preimplantation Genetic Diagnosis for Single Gene Disorders", Human Reproduction, 21, 3, 2006, 670-684.
Fiorentino, Francesco et al., "Short Tandem Repeats Haplotyping of the HLA Region in Preimplantation HLA Matching", European Journal of Human Genetics, 13, 2005, 953-958.
Fitzgerald, , "Intravascular Ultrasound Imaging Of Coronary Arteries: Is Three Layers The Norm?", Circulation, vol. 86, No. 1, Jul. 1, 1992, 154-158.
Ford, E. et al., "A method for generating highly multiplexed ChIP-seq libraries", BMC Research Notes, vol. 7, No. 312, May 22, 2014, 1-5.
Forejt, et al., "Segmental trisomy of mouse chromosome 17: introducing an alternative model of Down's syndrome", Genomics, 4(6), 2003, 647-652.
Forshew, et al., "Noninvasive Identification and Monitoring of Cancer Mutations by Targeted Deep Sequencing of Plasma DNA", Noninvasive identification and monitoring of cancer mutations by targeted deep sequencing of plasma DNA. Sci. Transl. Med. 4, 136 30 (2012)., 1-12.
Forshew, T. et al., "Supplementary Materials for Noninvasive Identification and Monitoring of Cancer Mutations by Targeted Deep Sequencing of Plasma DNA", Sci. Transl. Med, vol. 4, May 30, 2012, 20 pgs.
Fortina, P. et al., "Detection of the most common mutations causing beta-thalassemia in Mediterraneans using a multiplex amplification refractory mutation system (MARMS)", Genome Res., vol. 2, 1992, 163-166.
Fortina, P. et al., "DOP-PCR Amplification of Whole Genomic DNA and Microchip-Based Capillary Electrophoresis", Methods in Molecular Biology: Capillary Electrophoresis of Nucleic Acids, vol. II Practical Applications of Capillary Electrophoresis, 2001, 211-219.
Fouquet, C et al., "Rapid and Sensitive p53 Alteration Analysis in Biopsies from Lung Cancer Patients Using a Functional Assay and A Universal Oligonudeotide Array: A Prospective Study", Clinical Cancer Research, vol. 10, May 15, 2004, 3479-3489.
Universal Oligonudeotide Array: A Prospective Study, Clinical Cancer Research, vol. 10, May 15, 2004, 3479-3489.
Fournie, et al., "Plasma DNA As A Marker Of Cancerous Cell Death. Investigations In Patients Suffering From Lung Cancer And In Nude Mice Bearing Human Tumours", Cancer Letters, vol. 91, No. 2, May 8, 1995, 221-227.
Fredriksson, et al., "Multiplex amplification of all coding sequences within 10 cancer genes by Gene-Collector", Nucleic Acids Research, 2007, vol. 35, No. 7 e47, 1-6.
Fredriksson, M et al., "Assessing Hematopoietic Chimerism After Allogeneic Stem Cell Transplantation by Multiplexed SNP Genotyping Using Microarrays and Quantitive Analysis of SNP Alleles", Leukemia, vol. 18, Issue 2, Dec. 4, 2003, 255-266.
Freeman, Jennifer L. et al., "Copy Number Variation: New Insights in Genome Diversity", Genome Research, 16, 2006, 949-961.
Frohman, M A. et al., "On Beyond Classic RACE (Rapid Amplification of cDNA Ends)", Genome Research, vol. 4, 1994, S40-S58.
Frost, Mackenzie S et al., "Differential Effects of Chronic Pulsatile Versus Chronic Constant Maternal Hyperglycemia on Fetal Pancreatic B-Cells", Journal of Pregnancy, 2012,, Article ID 812094, 2012, 8.
Fu, G. K. et al., "Counting individual DNA molecules by the stochastic attachment of diverse labels", PNAS, vol. 108, No. 22, May 31, 2011, 9026-9031.

(56) References Cited

OTHER PUBLICATIONS

Fu, G. K et al., "Digital Encoding of Cellular mRNAs Enabling Precise and Absolute Gene Expression Measurement by Single-Molecule Counting", Analytical Chemistry, vol. 86, Mar. 3, 2014, 2867-2870.

Fu, Yao-Wen et al., "Presence Of Donor-and-recipientderived Dna Microchimerism In The Cell-free Blood Samples Of Renal Transplantation Recipients Associates With The Acceptance Of Transplanted Kidneys", Asian Journal of Andrology, vol. 8, No. 4, Jul. 1, 2006, 477-482.

Gadi, V. K. et al., "Soluble Donor DNA Concentrations in Recipient Serum Correlate with Pancreas-Kidney Rejection", Clinical Chemistry, vol. 52, No. 3, 2006, 379-382.

Ganshirt-Ahlert, D. et al., "Ratio of Fetal to Maternal DNA is Less Than 1 in 5000 at different Gestational Ages in Maternal Blood", Clinical Genetics,38, 1990, 38-43.

Ganshirt-Ahlert, D. et al., "Fetal DNA in Uterine Vein Blood", Obstetrics & Gynecology, 80 (4), 1992, 601-603.

Ganshirt-Ahlert, Dorothee et al., "Three Cases of 45,X/46,XYnf Mosaicism", Human Genetics, 76, 1987, 153-156.

Gao, et al., "Relation Of Donor Age And Preexisting Coronary Artery Disease On Angiography And Intracoronary Ultrasound To Later Development Of Accelerated Allograft Coronary Artery Disease", The American Journal of Cardiology, vol. 29, No. 3, Mar. 1, 1997, 623-629.

Gao, F. et al., "Characterizing Immunoglobulin Repertoire from Whole Blood by a Personal Genome Sequencer", PLOS One, vol. 8, No. 9, Sep. 13, 2013, 8 pgs.

Gao, Ming et al., "Characterization of dull1, a Maize Gene Coding for a Novel Starch Synthase", The Plant Cell, vol. 10, 1998, pp. 399-412.

Garcia Moreira, V. et al., "Cell-Free DNA as a Noninvasive Acute Rejection Marker in Renal Transplantation", Clinical Chemistry, vol. 55, No. 11, 2009, 1958-1966.

Garcia-Murillas, I. et al., "Mutation tracking in circulating tumor DNA predicts relapse in early breast cancer", Science Translational Medicine, vol. 7, No. 302, Aug. 26, 2015, 34 pgs.

Gardina, P. et al., "Ploidy Status and Copy Number Aberrations in Primary Glioblastomas Defined by Integrated Analysis of Allelic Ratios, Signal Ratios and Loss of Heterozygosity Using 500K SNP Mapping Arrays", BMC Genomics, 9 (489), (doi: 10.1186/1471-2164-9-489), 2008, 16 pgs.

Gautier, E. et al., "Fetal RhD genotyping by maternal serum analysis: A two-year experience", American Journal of Obstetrics and Gynecology, vol. 192, 2005, 666-669.

Geifman-Holtzman, et al., "Prenatal Diagnosis: Update On Invasive Versus Noninvasive Fetal Diagnostic Testing From Maternal Blood", Expert Review of Molecular Diagnostics, vol. 8, No. 6, Nov. 1, 2008, 727-751.

Geiss, G. K. et al., "Direct multiplexed measurement of gene expression with color-coded probe pairs", Nature Biotechnology, vol. 26, No. 3, Feb. 17, 2008, 317-325.

Ghanta, Sujana et al., "Non-Invasive Prenatal Detection of Trisomy 21 Using Tandem Single Nucleotide Polymorphisms", PLoS One, 5 (10), 2010, 10 pgs.

Gholami, M. et al., "A tailed PCR procedure for cost-effective, two-order multiplex sequencing of candidate genes in polyploid plants", Plant Biotechnology Journal, vol. 10, 2012, 635-645.

Gielis, E. M. et al., "Cell-Free DNA: An Upcoming Biomarker in Transplantation", American Journal of Transplantation, vol. 15, 2015, 2541-2551.

Gielis, E. M. et al., "Plasma donor-derived cell-free DNA kinetics after kidney transplantation using a single tube multiplex PCR assay", PLOS One, vol. 13, No. 12, e0208207, Dec. 6, 2018, 16 pgs.

Gineikiene, Egle et al., "Single Nucleotide Polymorphism-based System Improves The Applicability Of Quantitative PCR For Chimerism Monitoring", Journal of Molecular Diagnostics, vol. 11, No. 1, Jan. 1, 2009, 66-74.

Gingeras, et al., "Fifty Years of Molecular (DNA/RNA) Diagnostics", Clinical Chemistry, vol. 51, No. 3, Jan. 13, 2005, 661-671.

Girnita, Diana M. et al., "Disparate Distribution of 16 Candidate Single Nucleotide Polymorphisms Among Racial and Ethnic Groups of Pediatric Heart Transplant Patients", Transplantation, vol. 82, No. 12, Dec. 27, 2006, 1774-1780.

Gjertson, David W. et al., "Assessing Probability of Paternity and the Product Rule in DNA Systems", Genetica, 96, 1995, 89-98.

Gnirke, A. et al., "Solution hybrid selection with ultra-long oligonucleotides for massively parallel targeted sequencing", Nature Biotechnology, vol. 27, No. 2, Feb. 2009, 182-189.

Go, A. T. et al., "Non-invasive aneuploidy detection using free fetal DNA and RNA in maternal plasma: recent progress and future possibilities", Human Reproduction Update, vol. 17, No. 3, 2011, 372-382.

Goncalves-Primo, A. et al., "Investigation of Apoptosis-Related Gene Expression Levels in Preimplantation Biopsies as Predictors of Delayed Kidney Graft Function", Transplantation, vol. 97, No. 12, Jun. 27, 2014.

Gordon, et al., "Disease-Specific Motifs Can Be Identified In Circulating Nucleic Acids From Live Elk And Cattle Infected With Transmissible Spongiform Encephalopathies", Nucleic Acids Research, vol. 37. No. 2, Feb. 1, 2009, 550-556.

Gorringe, et al., "Large-scale Genomic Analysis of Ovarian Carcinomas", Molecular oncology, vol. 3, No. 2, Apr. 1, 2009, 157-164.

Gouya, et al., "Coronary Artery Stenosis In High-risk Patients: 64-section Ct And Coronary Angiography—Prospective Study And Analysis of Discordance", Radiology, vol. 252, No. 2, Aug. 1, 2009, 377-385.

Greenwalt, T. et al., "The Quantification of Fetomaternal Hemorrhage by an Enzyme-Linked Antibody Test with Glutaraldehyde Fixation", Vox Sang, 63, 1992, 268-271.

Gregory, et al., "Comparison of Sixty-Four-Slice Multidetector Computed Tomographic Coronary Sngiography To Coronary Angiography With Intravascular Ultrasound For The Detection Of Transplant Vasculopathy", The American Journal of Cardiology, vol. 98, No. 7, Aug. 4, 2006, 877-884.

Griffiths, A. J. et al., "An Introduction to Genetic Analysis", Sixth Edition, 1996, 5 pages.

Grskovic, M. et al., "Validation of a Clinical-Grade Assay to Measure Donor-Derived Cell-Free DNA in Solid Organ Transplant Recipients", The Journal of Molecular Diagnostics, vol. 18, No. 6 + Supplemental Appendix S1, Nov. 2016, 890-902.

Grunewald, H. , "Optimization of Polymerase Chain Reactions", Methods in Biology, vol. 226, 2003, 89-99.

Gu, H. et al., "Diagnostic role of microRNA expression profile in the serum of pregnant women with fetuses with neural tube defects", Journal of Neurochemistry, vol. 122, 2012, 641-649.

Guerra, J. , "Terminal Contributions for Duplex Oligonucleotide Thermodynamic Properties in the Context of Nearest Neighbor Models", Biopolymers, 95(3), (2010), 2011, 194-201.

Guetta, Esther et al., "Analysis of Fetal Blood Cells in the Maternal Circulation: Challenges, Ongoing Efforts, and Potential Solutions", Stem Cells and Development, 13, 2004, 93-99.

Guichoux, et al., "Current Trends in Microsatellite Genotyping", Molecular Ecology Resources, 11, 2011, 591-911.

Gunderson, K. L. et al., "A genome-wide scalable SNP genotyping assay using microarray technology", Nature Genetics, vol. 37, No. 5, May 2005, 549-554.

Gundry, C. N. et al., "Base-pair neutral homozygotes can be discriminated by calibrated high-resolution melting of small amplicons", Nucleic Acids Research, vol. 36, No. 10, Apr. 29, 2008, 3401-3408.

Guo, H et al., "A Specific and Versatile Genome Walking Technique", Gene, vol. 381, 2006, 18-23.

Gwee, Pai-Chung et al., "Simultaneous Genotyping of Seven Single-nucleotide Polymorphisms in the Mdr1 Gene by Single-tube Multiplex Minisequencing", Pai-Chung Gwee. et al., "Simultaneous Genotyping of Seven Single-nucleotide Polymorphisms in the Mdr1 Gene by Single-tube Multiplex Minisequencing", Clinical chemistry, Apr. 2003, vol. 49, Issue. 3, pp. 672-676., Apr. 1, 2003, 672-676.

Hahn, et al., "Non-invasive Prenatal Diagnostics Using Next Generation Sequencing: Technical, Legal And Social Challenges", Expert Opinion on Medical Diagnostics, vol. 6, No. 6, Nov. 1, 2012, 517-528.

(56) References Cited

OTHER PUBLICATIONS

Hahn, S. et al., "Current applications of single-cell PCR", CMLS Cellular and Molecular. Life Sciences, vol. 57, 2000, 96-105.
Hahn, S. et al., "Quantification of Circulating DNA: In the Preparation Lies the Rub", Clinical Chemistry, vol. 47, No. 9, 2001, 1577-1578.
Halford, William P. , "The Essential Prerequisites for Quantitative RT-PCR", Nature Biotechnology, vol. 17, 1999, 1 page.
Hall, M. , "Panorama Non-Invasive Prenatal Screening for Microdeletion Syndromes", Apr. 1, 2014 (Apr. 1, 2014), XP055157224, Retrieved from the Internet: URL:http://www.panoramatest.com/sites/default/files/files/PanoramaMicrodeletionsWhite Paper-2.pdf [retrieved on Dec. 8, 2014].
Han, S-W et al., "Predictive and Prognostic Impact of Epidermal Growth Factor Receptor Mutation in Non-Small-Cell Lung Cancer Patients Treated With Gefitinib", Journal of Clinical Oncology, vol. 23, No. 11, Apr. 10, 2005, 2493-2501.
Handley, D. et al., "Noninvasive prenatal chromosomal aneuploidy detection using plasma cell-free nucleic acid", Expert Rev Obstet. Gynecol, vol. 5, No. 5, 2010, 581-590.
Handyside, et al., "Isothermal whole genome amplification from single and small numbers of cells: a new era for preimplantation genetic diagnosis of inherited disease", Molecular Human Reproduction vol. IO, No. 10 pp. 767-772, 2004.
Hao, T. B. et al., "Circulating cell-free DNA in serum as a biomarker for diagnosis and prognostic prediction of colorectal cancer", British Journal of Cancer, vol. 111, Aug. 26, 2014, 1482-1489.
Hara, Eiji et al., "Subtractive eDNA cloning using oligo(dT)3o-latex and PCR: isolation of eDNA clones specific to undifferentiated human embryonal carcinoma cells", Nucleic Acids Research, 19(25), 1991, 7097-7104.
Hardenbol, P. , "Multiplexed Genotyping With Sequence-Tagged Molecular Inversion Probes", Nature Biotechnology, 21 (6), 2003, 673-678.
Hardenbol, Paul et al., "Highly multiplexed molecular inversion probe genotyping: Over 10,000 targeted SNPs genotyped in a singled tube assay", Genome Research, 15, 2005, 269-275.
Harismendy, O. et al., "Method for Improving Sequence Coverage Uniformity of Targeted Genomic Intervals Amplified by LR-PCR Using Illumina GA Sequencing-By-Synthesis Technology", Bio Techniques, 46(3), 2009, 229-231.
Harper, J. C. et al., "Recent Advances and Future Developments in PGD", Prenatal Diagnosis, 19, 1999, 1193-1199.
Harton, G.L. et al., "Preimplantation Genetic Testing for Marfan Syndrome", Molecular Human Reproduction, 2 (9), 1996, 713-715.
Hartwell, L. H. et al., "Chapter 11: The Direct Detection of Genotype Distinguishes Individual Genomes", Genetics: From Genes To Genomes, Second Edition, 2004, 371-414.
Hartwell, L. H. et al., "Chapter 13: Chromosomal Rearrangements and Changes in Chromosome Number Reshape Eukaryotic Genomes", Genetics: From Genes To Genomes, Second Edition, 2004, 441-486.
Hattori, M. et al., "The DNA sequence of human chromosome 21", Nature, vol. 405, May 18, 2000, 311-319.
Hawkins, T. et al., "Whole genome amplification—applications and advances", Current Opinion in Biotechnology, 13, 2002, 65-67.
Hayden, et al., "Multiplex-Ready PCR: A new method for multiplexed SSR and SNP genotyping", BMC Genomics 2008, 9(80), 1-12.
He, QZ et al., "A method for improving the accuracy of non-invasive prenatal screening by cell-free foetal DNA size selection", British Journal of Biomedical science, vol. 75, No. 3, Jul. 2018, 133-138.
Heaton, Paul R. et al., "Heminested PCR Assay for Detection of Six Genotypes of Rabies and Rabies-related Viruses", Journal of Clinical Microbiology, vol. 35, 1997, pp. 2762-2766.
Heidary, M. et al., "The dynamic range of circulating tumor DNA in metastatic breast cancer", Breast Cancer Research, vol. 16, No. 421, 2014, 10 pages.

Hellani, A. et al., "Clinical Application of Multiple Displacement Amplification in Preimplantation Genetic Diagnosis", Reproductive BioMedicine Online, 10 (3), 2005, 376-380.
Hellani, Ali et al., "Multiple displacement amplification on single cell and possible PGD applications", Molecular Human Reproduction, 10(11), 2004, 847-852.
Henegariu, O. et al., "Multiplex PCR: Critical Parameters and Step-by-Step Protocol", Biotechniques, vol. 23, 1997, pp. 504-511.
Hidestrand, M. et al., "Highly Sensitive Noninvasive Cardiac Transplant Rejection Monitoring Using Targeted Quantification of Donor-Specific Cell-Free Deoxyribonucleic Acid", Journal of the American College of Cardiology, vol. 63, No. 12, 1224-1226, 2014.
Hoberman, Rose et al., "A Probabilistic Approach for SNP Discovery in High-throughput Human Resequencing Data", Genome Research, vol. 19, Jul. 15, 2009, 1542-1552.
Hochberg, et al., "A Novel Rapid Single Nucleotide Polymorphism (SNP)-Based Method For Assessment Of Hematopoietic Chimerism After Allogeneic Stem Cell Transplantation", Blood, vol. 101, No. 1, Jan. 1, 2003, 363-369.
Hodges, et al., "Genome-wide In Situ Exon Capture For Selective Resequencing", Nature Genetics, vol. 39, No. 12, Nov. 4, 2007, 1522-1527.
Hodgkinson, C. L. et al., "Tumorigenicity and genetic profiling of circulating tumor cells in small-cell lung cancer", Nature Medicine, vol. 20, No. 8, Aug. 2014, 897-905.
Hoffmann, Steven et al., "Donor Genomics Influence Graft Events: The Effect Of Donor Polymorphisms On Acute Rejection And Chronic Allograft Nephropathy", Kidney International, vol. 66, No. 4, Oct. 1, 2004, 1686-1693.
Hojsgaard, S. et al., "Bifrost—Block recursive models induced from relevant knowledge, observations, and statistical techniques", Computational Statistics & Data Analysis, 19(2), 1995, 155-175.
Hollas, B. et al., "A stochastic approach to count RN A molecules using DNA sequencing methods", Lecture Notes in Computer Science, vol. 2812, 2003, 55-62.
Holleley, et al., "Multiplex Manager 1.0: a Cross-Platform Computer Program that Plans and Optimizes Multiplex PCR" BioTechniques46:511-517 (Jun. 2009), 511-517.
Hollox, E. et al., "Extensive Normal Copy Number Variation of a β-Defensin Antimicrobial-Gene Cluster", Am. J. Hum. Genet., 73, 2003, 591-600.
Holt, et al., "Detecting SNPS And Estimating Allele Frequencies In Clonal Bacterial Populations By Sequencing Pooled DNA", Bioinformatics, vol. 25, No. 16, Aug. 15, 2009, 2074-2075.
Homer, et al., "Resolving Individuals Contributing Trace Amounts of DNA to Highly Complex Mixtures Using High-Density SNP Genotyping Microarrays", PLOS Genetics, 4(8), 2008, 9 pgs.
Hoogendoorn, Bastiaan et al., "Genotyping Single Nucleotide Polymorphisms by Primer Extension and High Performance Liquid Chromatography", Hum Genet, 104, 1999, 89-93.
Horai, et al., "Novel Implantable Device To Detect Cardiac Allograft Rejection", Circulation, vol. 120, No. Suppl 1, Sep. 15, 2009, 185-190.
Hornak, M. et al., "Aneuploidy Detection in Pigs Using Comparative Genomic Hybridization: From the Oocytes to Blastocysts", PLoS One, vol. 7, No. 1, Jan. 2012, 6 pages.
Hosmillo, Myra D. et al., "Development of Universal SYBR Green Real-time RT-PCR for The Rapid Detection and Quantitation of Bovine and Porcine Toroviruses", Journal of Virological Methods, vol. 168, 2010, pp. 212-217.
Hosono, S. et al., "Unbiased Whole-Genome Amplification Directly From Clinical Samples", Genome Research, vol. 13, 2003, 954-964.
Hospital, F. et al., "A General Algorithm to Compute Multilocus Genotype Frequencies Under Various Mating Systems" vol. 12, No. 6, Jan. 1, 1996 (Jan. 1, 1996), pp. 455-462.
Hou, X. et al., "Analysis of the Repertoire Features of TCR Beta Chain CDR3 in Human by High-Throughput Sequencing", Cellular Physiology and Biochemistry, vol. 39, Jul. 21, 2019, 651-667.
Howie, et al., "Fast and accurate genotype imputation in genome-wide association studies through pre-phasing", Nature Genetics, vol. 44, No. 8, Jul. 22, 2012, 955-959.

(56) References Cited

OTHER PUBLICATIONS

Howie, B. N. et al., "A Flexible and Accurate Genotype Imputation Method for the Next Generation of Genome-Wide Association Studies", PLoS Genetics, vol. 5, No. 6, Jun. 2009, 15 pages.

Hu, Dong Gui et al., "Aneuploidy Detection in Single Cells Using DNA Array-Based Comparative Genomic Hybridization", Molecular Human Reproduction, 10(4), 2004, 283-289.

Hu, Hao et al., "Mutation Screening in 86 Known X-linked Mental Retardation Genes by Droplet-based Multiplex Pcr and Massive Parallel Sequencing", Hao Hu. et al., "Mutation Screening in 86 Known X-linked Mental Retardation Genes by Droplet-based Multiplex Pcr and Massive Parallel Sequencing", Hugo J, Dec. 2009, vol. 3, pp. 41-49., Dec. 1, 2009, 41-49.

Hu, Y. et al., "Detection of Extrahepatic Hepatitis C Virus Replication by a Novel, Highly Sensitive, Single-Tube Nested Polymerase Chain Reaction", Am. J. Clin Pathol., vol. 119, 2003, 95-100.

Huang, D. J. et al., "Reliable detection of Trisomy 21 using MALDI-TOF mass spectrometry", Genetics in Medicine, vol. 8, Nov. 2006, 728-734.

Huang, D. J. et al., "Use of an Automated Method Improves the Yield and Quality of Cell-Free Fetal DNA Extracted from Maternal Plasma", Clinical Chemistry, vol. 51, No. 12, 2005, 2419-2420.

Huang, J. et al., "Whole genome DNA copy number changes identified by high density oligonucleotide arrays", Human Genomics, vol. 1, No. 4, May 2004, 287-299.

Hubacek, et al., "Detection of Donor DNA After Heart Transplantation: How Far Could It Be Affected by Blood Transfusion and Donor Chimerism?", Transplantation Proceedings, vol. 39, Jun. 1, 2007, 1593-1595.

Hug, H. et al., "Measurement of the number of molecules of a single mRNA species in a complex mRNA preparation", J. Theor. Biol., vol. 221, 2003, 615-624.

Hultin, E. et al., "Competitive enzymatic reaction to control allele-specific extensions", Nucleic Acids Research, vol. 33, No. 5, Mar. 14, 2005, 1-10.

Hung, E.C.W. et al., "Detection of circulating fetal nucleic acids: a review of methods and applications", J. Clin. Pathol., vol. 62, 2009, 308-313.

Hyndman, D L. et al., "PCR Primer Design", Methods in Molecular Biology, vol. 226, Second Edition, 2003, 81-88.

Ido, Yasuo et al., "Hyperglycemia-Induced Apoptosis in Human Umbilical Vein Endothelial Cells: Inhibition by the AMP-Activated Protein Kinase Activation", Diabetes, 51, 2002, 159-167.

Illumina, "Automated GoldenGate™ Genotyping on the BeadStation 500", Pub. No. 970-2004-002, 2004, 2 pages.

Illumina, "Genomic Sequencing", Data Sheet: Sequencing, 2010, 38939-38944.

Illumina, "GoldenGate" Assay Workflow: Illumina's GoldenGate assay protocol provides high-quality, high-multiplex genotyping results with a streamlined workflow, Pub. No. 370-2004-006, 2004, 2 pages.

Illumina, "HiSeq 2500 Sequencing System", System Specification Sheet: Sequencing, available via URL https://www.illumina.com/documents/products/datasheets/datasheet_hiseq2500.pdf, 2015, 4 pgs.

Illumina, "History of Sequencing by Synthesis", https://www.illumina.com/science/technology/next-generation-sequencing/illumina-sequencing-history.html, 2020, 3 pages.

Illumina, "Illumina Extends BeadArray Technology to Address Wider Range of SNP Genotyping Projects; New Microarray Offerings Enable Genotyping at 384 and 786 Multiplex", Businesswire, May 4, 2004, 2 pages.

Illumina, "Illumina® Beadstation 500: A Scalable System That Grows With Your Research Requirements", Pub. No. 970-2005-003, Jul. 1, 2005, 4 pages.

Illumina, "Illumina Announces Benchtop SNP Genotyping System", Press Release, Nov. 5, 2003, 3 pages.

Illumina, "Illumina Begins Shipment of BeadStation 500G Benchtop Genotyping System", Press Release, Apr. 15, 2004, 3 pages.

Illumina, "MiSeq System Information Sheet", 2018, 3 pgs.

Illumina, "Patent Owner Illumina's Preliminary Response To Petition", Oct. 17, 2018, 75 pgs.

Illumina, "Petition for Inter Partes Review of U.S. Pat. No. 8,682,592", Jun. 13, 2019, 91 pages.

Illumina, "Plaintiff/Counterclaim Defendant Illumina, Inc.'S Amended Patent L.R. 3-3 Preliminary Invalidity Contentions for U.S. Pat. No. 8,682,592", Oct. 30, 2018, 22 pages.

Illumina, "Plaintiff/Counterclaim-Defendant Illumina, Inc.'s Patent L.R. 3-3 Contentions for U.S. Patent Preliminary Invalidity Contentions for U.S. Pat. No. 8,682,592", Oct. 9, 2018, 81 pages.

Illumina, "Preparing Samples for Sequencing Genomic DNA", Part # 11251892 Rev. A, 2007, 18 pages.

Illumina, "Preparing Samples for Sequencing Genomic DNA", Part # 1003806 Rev. A, 2007, 20 pages.

Illumina, "Products & Services", Product Literature, Mar. 21, 2007, 3 pages.

Illumina, "Technology: Solexa Sequencing Technology", May 21, 2007, 1 page.

Illumina, "TruSeq™ RNA and DNA Library Preparation Kits v2", Data Sheet: Illumina® Sequencing, 2014, 4.

Illumina Catalog, "Paired-End Sample Preparation Guide, Illumina Catalog# PE-930-1 001, Part# 1005063 Rev. E", 2011, 1-40.

Illumina, Inc., "Declaration of David Peters, Ph.D. in Support of Petition for Inter Partes Review of U.S. Pat. No. 8,682,592", Jun. 13, 2019, 136 pages.

*Illumina, Inc. V. Natera, Inc.*, "Order Re: Claim Construction", Jan. 30, 2019, 16 pgs.

Imielinski, M. et al., "Mapping the Hallmarks of Lung Adenocarcinoma with Massively Parallel Sequencing", Cell, vol. 150, Sep. 14, 2012, 1107-1120.

Ingman, et al., "SNP Frequency Estimation Using Massively Parallel Sequencing of Pooled DNA", European Journal of Human Genetics, vol. 17, No. 3, Oct. 15, 2008, 383-386.

Innan, H. et al., "The Pattern of Polymorphism on Human Chromosome 21", Genome Research, vol. 13, 2003, 1158-1168.

Interewicz, B. et al., "DNA Released from Ischemic and Rejecting Organs as an Indicator of Graft Cellular Damage", Annals of Transplantation, vol. 9, No. 2, May 1, 2004, 42-45.

International Human, Genome Sequencing Consortium , "Finishing the Euchromatic Sequence of the Human Genome", Nature, vol. 431, Oct. 21, 2004, 931-945.

Ishii, et al., "Optimization of Annealing Temperature To Reduce Bias Caused by a Primer Mismatch in Multitemplate PCR", Applied and Environmental Microbiology, Aug. 2001, p. 3753-3755.

Iskow, R. C. et al., "Natural Mutagenesis of Human Genomes by Endogenous Retrotransposons", Cell, vol. 141, Jun. 25, 2010, 1253-1261.

Ivanov, M. et al., "Non-random fragmentation patterns in circulating cell-free DNA reflect epigenetic regulation", BMC Genomics, vol. 16 (Suppl 13):S1, Jun. 2015, 12 pgs.

Jabara, C. B. et al., "Accurate sampling and deep sequencing of the HIV-1 protease gene using a Primer ID", PNAS, vol. 108, No. 50, Dec. 13, 2011, 20166-20171.

Jahr, S. et al., "DNA Fragments in the Blood Plasma of Cancer Patients: Quantitations and Evidence for Their Origin from Apoptotic and Necrotic Cells", Cancer Research, vol. 61, Feb. 15, 2001, 1659-1665.

Jamal-Hanjani, M. et al., "Detection of ubiquitous and heterogeneous mutations in cell-free DNA from patients with early-stage non-small-cell lung cancer", Annals of Oncology, vol. 27, No. 5, Jan. 28, 2016, 862-867.

Jamal-Hanjani, M. et al., "Tracking Genomic Cancer Evolution for Precision Medicine: The Lung TRACERx Study", PLOS Biology, vol. 12, No. 7, Jul. 2014, 1-7.

Jamal-Hanjani, M. et al., "Tracking the Evolution of Non-Small-Cell Lung Cancer", The New England Journal of Medicine, vol. 376, No. 22, Jun. 1, 2017, 2109-2121.

Jarvie, T. , "Next generation sequencing technologies", Drug Discovery Today: Technologies, vol. 2, No. 3, 2005, 255-260.

Jen, J. et al., "An Overview on the Isolation and Analysis of Circulating Tumor DNA in Plasma and Serum", Annals New York Academy of Sciences, 2000, 8-12.

(56) References Cited

OTHER PUBLICATIONS

Jenkins, S. et al., "High-throughput SNP genotyping", Comparative and Functional Genomics, vol. 3, Dec. 5, 2001, 57-66.
Jennings, C. et al., "Investigation of Effects of Acid Citrate Dextrose and EDTA on Ability to Quantitatively Culture Human Immunodeficiency Virus", Journal of Clinical Microbiology, vol. 38, No. 9, 2000, 3522.
Jett, K. et al., "Clinical and genetic aspects of neurofibromatosis 1", Genetics In Medicine, vol. 12, No. 1, Jan. 2010, 11 pages.
Jewesburty, E.C.O., "Reactions after Transfusion of Stored Blood", The British Medical Journal, vol. 1, No. 4191, 1941, 664-665.
Jiang, P. et al., "The Long and Short of Circulating Cell-Free DNA and the Ins and Outs of Molecular Diagnostics", Trends in Genetics, vol. 32, No. 6, Jun. 2016, 360-371.
Johnson, D. S. et al., "Genome-Wide Mapping of in Vivo Protein-DNA Interactions", Science, vol. 316, Jun. 8, 2007, 1497-1502.
Johnson, D.S. et al., "Comprehensive Analysis of Karyotypic Mosaicism Between Trophectoderm and Inner Cell Mass", Molecular Human Reproduction, 16(12), 2010, 944-949.
Johnson, J. B. et al., "Differential mechanisms of complementmediated neutralization of the closely related paramyxoviruses simian virus 5 and mumps virus", Virology, vol. 376, No. 1, 2008, 112-123.
Johnson, K. L. et al., "Interlaboratory Comparison of Fetal Male DNA Detection from Common Maternal Plasma Samples by Real-Time PC", Clinical Chemistry, vol. 50, No. 3, 2004, 516-521.
Johnson D.S, et al., "Preclinical Validation of a Microarray Method for Full Molecular Karyotyping of Blastomeres in a 24-h Protocol", Human Reproduction, 25 (4), 2010, 1066-1075.
Jung, K. et al., "Cell-free DNA in the blood as a solid tu1nor biomarker—A critical appraisal of the literature", Clinica Chimica Acta, vol. 411, 2010, 1611-1624.
Juppner, H. et al., "Functional Properties of the PTH/PTHrP Receptor", Bone, vol. 17, No. 2 Supplement, Aug. 1995, 39S-42S.
Kalendar, Ruslan et al., "Java Web Tools for PCR, in Silico PCR, and Oligonucleotide Assembly and Analysis", Genomics, vol. 98, 2011, pp. 137-144.
Kamat, A. A. et al., "Quantification of total plasma cell-free DNA in ovarian cancer using real-time PCR", Ann N Y Acad Sci., vol. 1075, Sep. 2006, 230-234.
Kamel, A. M. et al., "A simple strategy for breakpoint fragment determination in chronic myeloid leukemia", Cancer Genetics and Cytogenetics, vol. 122, 2000, 110-115.
Kane, M. et al., "Application of Less Primer Method to Commercial Kits", Forensic Science International: Genetics Supplement Series, vol. 1, Issue 1, 2008, 41-43.
Kane, M., "Application of Less Primer Method To Multiplex PCR", International Congress Series, vol. 1288, 2006, pp. 694-696.
Kanou, et al., "Cell-free DNA in human ex vivo lung perfusate as a potential biomarker to predict the risk of primary graft dysfunction in lung transplantation", The Journal of Heart and Lung Transplantation, vol. 36, No. 45, 2017, S187.
Kapadia, Samir R. et al., "Impact of Intravascular Ultrasound in Understanding Transplant Coronary Artery Disease", Current Opinion In Cardiology, vol. 14, No. 2, Mar. 1, 1999, 1-19.
Kaplinski, Lauris et al., "MultiPLX: Automatic Grouping and Evaluation of PCR Primers", Bioinformatics, 21(8), 2005, 1701-1702.
Karger, et al., "DNA Sequencing By Capillary Electrophoresis" Electrophoresis, vol. 30, Supplement 1, Jun. 1, 2009, 1-11.
Karoui, Noureddine E. et al., "Getting More from Digital SNP Data", Statistics in Medicine, vol. 25, Issue 18, Jan. 5, 2006, 3124-3133.
Kass, et al., "Diagnosis Of Graft Coronary Artery Disease", Current Opinion in Cardiology, vol. 22, No. 2, Mar. 1, 2007, 139-145.
Kathiresan, Sekar et al., "Genome-wide Association of Early-onset Myocardial Infarction With Common Single Nucleotide Polymorphisms, Common Copy Number Variants, and Rare Copy Number Variants", Nature Genetics, vol. 41, No. 3, Mar. 1, 2009, 1-23.
Kazakov, V.I. et al., "Extracellular DNA in the Blood of Pregnant Women", Tsitologia, vol. 37, No. 3, 1995, 1-8.

Keith, L. et al., "Clinical Experience With the Prevention of Rh-Isoimmunization: A Historical Comparative Analysis", American Journal of Reproductive Immunology, vol. 5, 1984, 84-89.
Keller, M. C. et al., "Non-Pathological Paternal Isodisomy of Chromosome 2 Detected From a Genome-Wide SNP Scan", American Journal of Medical Genetics, Part A, 2009, 1823-1826.
Kennedy, S. R. et al., "Detecting ultralow-frequency mutations by Duplex Sequencing", Nature Protocols, vol. 9, No. 11, 2014, 2586-2606.
Kibbe, Warren A., "Oligocalc: An Online Oligonucleotide Properties Calculator", Nucleic Acids Research, vol. 35, 2007, pp. W43-W46.
Kiernan, J. A., "Formaldehyde, formalin, paraformaldehyde and glutaraldehyde: What they are and what they do.", Microscopy Today, vol. 1, 2000, 8-12.
Kijak, G. et al., "Discrepant Results in the Interpretation of HIV-1 Drug-Resistance Genotypic Data Among Widely Used Algorithms", HIV Medicine, 4, 2003, 72-78.
Kim, H. et al., "Whole-genome and multisector exome sequencing of primary and post-treatment glioblastoma reveals patterns of tumor evolution", Genome Research, vol. 25, No. 3, Feb. 3, 2015, 316-327.
Kimmel, G. et al., "Gerbil: Genotype resolution and block identification using likelihood", PNAS, vol. 102, No. 1, Jan. 4, 2005, 158-162.
Kinde, I. et al., "Detection and quantification of rare mutations with massively parallel sequencing", PNAS, vol. 108, No. 23, Jun. 7, 2011, 9530-9535.
Kinnings, S. L. et al., "Factors affecting levels of circulating cell-free fetal DNA in maternal plasma and their implications for noninvasive prenatal testing", Prenatal Diagnosis, vol. 35, 2015, 816-822.
Kircher, Martin et al., "Improved Base Calling for the Illumina Genome Analyzer Using Machine Learning Strategies", Genome Biology, vol. 10, Issue 8, Article No. R83, Aug. 14, 2009, 83.2-83.9.
Kirkizlar, E. et al., "Detection of Clonal and Subclonal Copy-Number Variants in Cell-Free DNA from Patients with Breast Cancer Using a Massively Multiplexed PCR Methodology", Translational Oncology, vol. 8, No. 5, Oct. 2015, pp. 407-416.
Kirkness, E. F. et al., "Sequencing of isolated sperm cells for direct haplotyping of a human genome", Genome Research, vol. 23, 2013, 826-832.
Kivioja, T. et al., "Counting absolute number of molecules using unique molecular identifiers", Nature Proceedings, Apr. 14, 2011, 18 pgs.
Kivioja, T et al., "Counting absolute numbers of molecules using unique molecular identifiers", Nature Methods, Advance Online Publication, Nov. 20, 2011, 1-5.
Kivioja, T. et al., "Counting absolute numbers of molecules using unique molecular identifiers", Nature Methods, vol. 9, No. 1, Jan. 2012, 72-76.
Kobashigawa, et al., "Multicenter Intravascular Ultrasound Validation Study Among Heart Transplant Recipients", Journal of the American College of Cardiology, vol. 45, No. 9, May 3, 2005, 1532-1537.
Koboldt, et al., "VarScan: Variant Detection In Massively Parallel Sequencing Of Individual And Pooled Samples", Bioinformatics, vol. 25, No. 17, Jun. 19, 2009, 2283-2285.
Koelman, et al., "Donor-derived Soluble HLA Plasma Levels Can Not Be Used To Monitor Graft Rejection In Heart Transplant Recipients", Transplant Immunology, vol. 8, No. 1, Mar. 1, 2000, 57-64.
Kohler, C. et al., "Levels of plasma circulating cell free nuclear and mitochondrial DNA as potential biomarkers for breast tumors", Molecular Cancer, vol. 8, No. 105, Nov. 17, 2009, 9 pages.
Koide, K. et al., "Fragmentation of cell-free fetal DNA in plasma and urine of pregnant women", Prenatal Diagnosis, vol. 25, 2005, 604-607.
Koldehoff, Michael et al., "Quantitative analysis of chimerism after allogeneic stem cell transplantation by real-time polymerase chain reaction with single nucleotide polymorphisms, standard tandem repeats, and Y-chromosome-specific sequences", American Journal of Hematology, vol. 81, No. 10, Jul. 12, 2006, 735-746.

(56) References Cited

OTHER PUBLICATIONS

Konfortov, B A et al., "A High-Resolution Happy Map of Dictyostelium discoideum Chromosome 6", Genome Research, vol. 10, No. 11, Nov. 2000, 1737-1742.
Konfortov, Bernard A. et al., "An Efficient Method for Multi-Locus Molecular Haplotyping", Nucleic Acids Research, 35(1), e6, 2007, 8 pgs.
Kopreski, MS et al., "Detection of mutant K-ras DNA in plasma or serum of patients with colorectal cancer", British Journal of Cancer, vol. 76, No. 10, 1997, 1293-1299.
Koressaar, Triinu et al., "Enhancements and Modifications of Primer Design Program Primer3", Bioinformatics, vol. 23, 2007, pp. 1289-1291.
Korn, et al., "Integrated Genotype Calling And Association Analysis Of SNPS, Common Copy Number Polymorphisms And Rare CNVS", Nature Genetics, vol. 40, No. 10, Oct. 1, 2008, 1253-1260.
Krjutskov, K. et al., "Development of a single tube 640-plex genotyping method for detection of nucleic acid variations on microarrays", Nucleic Acids Research, vol. 36, No. 12, May 23, 2008, 7 pages.
Kuhn, H. et al., "Rolling-circle amplification under topological constraints", Nucleic Acids Research, vol. 30, No. 2, 2002, 574-580.
Kukita, Y. et al., "High-fidelity target sequencing of individual molecules identified using barcode sequences: de nova detection and absolute quantitation of mutations in plasma cell-free DNA from cancer patients" DNA Research, vol. 22, No. 4, Jun. 29, 2015, 269-277.
Kuliev, Anver et al., "Thirteen Years' Experience on Preimplantation Diagnosis: Report of the Fifth International Symposium on Preimplantation Genetics", Reproductive BioMedicine Online, 8, 2, 2004, 229-235.
Kumar, P. et al., "Ethylenegycol-Bis-(B-Aminoethylether)Tetraacetate as a Blood Anticoagulant: Preservation of Antigen-Presenting Cell Function and Antigen-Specific Proliferative Response of Peripheral Blood Mononuclear Cells from Stored Blood", Clinical and Diagnostic Laboratory Immunology, vol. 7, No. 4, 2000, 578-583.
Kunishima, S. et al., "First description of somatic mosaicism in MYH9 disorders", British Journal of Haematology, vol. 128, 2005, 360-365.
Kwok, P. Y. , "High-throughput genotyping assay approaches", Pharmacogenomics, vol. 1, No. 1, 2000, 1-5.
Lambert, et al., "Quantification of Maternal Microchimerism by HLA-Specific Real-time Polymerase Chain Reaction", Arthritis and Rheumatism, vol. 50, No. 3, Mar. 1, 2004, 906-914.
Lambert-Messerlian, G. et al., "Adjustment of Serum Markers in First Trimester Screening", Journal of Medical Screening, 16 (2), 2009, 102-103.
Landegren, U. et al., "Padlock and proximity probes for in situ and array-based analyses: tools for the post-genomic era", Comparative and Functional Genomics, vol. 4, 2003, 525-530.
Lander, E. S. et al., "Initial sequencing and analysis of the human genome", Nature, vol. 409, Feb. 15, 2001, 860-921.
Langmore, J. , "Quality Control and Pre-Qualifications of NGS Libraries Made from Clinical Samples", ABRF 2013 Satellite Workshop, Mar. 2, 2013, 35 pages.
Lapaire, O. et al., "Array-CGH analysis of cell-free fetal DNA in 10 mL of amniotic fluid supernatant", Prenatal Diagnosis, vol. 27, May 17, 2007, 616-621.
Lapierre, J.M. et al., "Analysis of uncultured amniocytes by comparative genomic hybridization: a prospective prenatal study", Prenatal Diagnosis, vol. 20, 2000, 123-131.
Lardeux, Frederic et al., "Optimization of a Semi-nested Multiplex PCR to Identify Plasmodium Parasites in Wild-Caught Anopheles in Bolivia, and Its Application to Field Epidemiological Studies", Transactions of the Royal Society of Tropical Medicine and Hygiene, vol. 102, 2008, pp. 485-492.
Larsen, J. B. et al., "Single-step Nested Multiplex PCR to Differentiate Between Various Bivalve Larvae", Marine Biology, vol. 146, 2005, pp. 1119-1129.
Lasken, R. S. et al., "Whole genome amplification: abundant supplies of DNA from precious samples or clinical specimens", Trends in Biotechnology, vol. 21, No. 12, Dec. 2003, 531-535.
Lathi, Ruth B. et al., "Informatics Enhanced SNP Microarray Analysis of 30 Miscarriage Samples Compared to Routine Cytogenetics", PLoS One, 7(3), 2012, 5 pgs.
Lavebrat, et al., "Single Nucleotide Polymorphism (SNP) Allele Frequency Estimation in DNA Pools Using Pyrosequencing", Nature Protocols, vol. 1, No. 6, Jan. 11, 2007, 2573-2582.
Lavebratt, Catharina et al., "Pyrosequencing-based SNP Allele Frequency Estimation In DNA Pools", Human Mutation, vol. 23, Issue 1, Dec. 19, 2003, 92-97.
Lavrentieva, I et al., "High Polymorphism Level of Genomic Sequences Flanking Insertion Sites of Human Endogenous Retroviral Long Terminal Repeats", FEBS Letters, vol. 443, No. 3, Jan. 29, 1999, 341-347.
Leamon, John H. et al., "A massively parallel PicoTiterPlate based platform for discrete picoliter-scale polymerase chain reactions", Electrophoresis, vol. 24, No. 21, Nov. 1, 2003, 3769-3777.
Leary, R. J. et al., "Development of Personalized Tumor Biomarkers Using Massively Parallel Sequencing", Science Translational Medicine, vol. 2, No. 20, Feb. 24, 2010, 1-8.
Leary, Rebecca J et al., "Detection of Chromosomal Alterations in the Circulation of Cancer Patients with Whole-Genome Sequencing", Science Translational Medicine, 4, 162, 2012, 12.
Lecomte, T. et al., "Detection of Free-Circulating Tumor-Associated DNA in Plasma of Colorectal Cancer Patients and Its Association With Prognosis", Int. J. Cancer, vol. 100, 2002, 542-548.
Lee, J et al., "Anchored Multiplex PCR Enables Sensitive and Specific Detection of Variants in Circulating Tumor DNA by Next-Generation Sequencing", DOI:https://doi.org/10.1016/j.cancergen.2017.04.049, Cancer Genetics 214-215, 2017, 47.
Lee, T. et al., "Down syndrome and cell-free fetal DNA in archived maternal serum", AmJ Obstet Gynecol, vol. 187, No. 5, 1217-1221, Nov. 2002.
Lee, T.H. et al., "Quantitation of genomic DNA in plasma and serum samples: higher concentrations of genomic DNA found in serum than in plasma", Transfusion, vol. 41, Feb. 2001, 276-282.
Levsky, J. M. et al., "Fluorescence in situ hybridization: past, present and future", Journal of Cell Science, vol. 116, No. 14, 2003, 2833-2838.
Levsky, Jeffrey M. et al., "Efficacy of Coronary Ct Angiography: Where We Are, Where We Are Going and Where We Want to Be", Journal Of Cardiovascular Computed Tomography, vol. 3, Supplement 2, Nov. 2, 2009, s99-s108.
Li, et al., "Detection of SNPs in the Plasma of Pregnant Women and in the Urine of Kidney Transplant Recipients by Mass Spectrometry", Annals of the New York Academy of Sciences, vol. 1075, Sep. 5, 2006, 144-147.
Li, et al., "Mapping Short DNA Sequencing Reads And Calling Variants Using Mapping Quality Scores", Genome Research, vol. 18, No. 11, Aug. 19, 2008, 1851-1858.
Li, et al., "Multiplex Padlock Targeted Sequencing Reveals Human Hypermutable CpG Variations", Genome Research, vol. 19, No. 9, Jun. 12, 2009, 1606-1615.
Li, et al., "SOAP2: An Improved Ultrafast Tool For Short Read Alignment", Bioinformatics, vol. 25, No. 15, Aug. 1, 2009, 1966-1967.
Li, B. , "Highly Multiplexed Amplicon Preparation for Targeted Re-Sequencing of Sample Limited Specimens Using the Ion AmpliSeq Technology and Semiconductor Sequencing", Proceedings of the Annual Meeting of the American Society of Human Genetics [retrieved on Oct. 30, 2012]. Retrieved from the Internet: <URL: http://www.ashg.org/2012meeting/abstracts/fulltext/f120121811. htm>, 2012, 1 pg.
Li, R. et al., "SNP detection for massively parallel whole-genome resequencing", Genome Research, vol. 19, 2009, 1124-1132.
Li, Y. et al., "Detection of Paternally Inherited Fetal Point Mutations for b-Thalassemia Using Size-Fractionated Cell-Free DNA in Maternal Plasma", JAMA, vol. 293, No. 7, Apr. 13, 2005, 843-849.

(56) References Cited

OTHER PUBLICATIONS

Li, Y. et al., "Non-Invasive Prenatal Diagnosis Using Cell-Free Fetal DNA in Maternal Plasma from PGD Pregnancies", Reproductive BioMedicine Online, 19 (5), 2009, 714-720.
Li, Ying et al., "Detection of Donor-specific DNA Polymorphisms in the Urine of Renal Transplant Recipients", Clinical Chemistry, vol. 49, No. 4, Apr. 1, 2003, 655-658.
Li, Ying et al., "Ready detection of donor-specific single-nucleotide polymorphisms in the urine of renal transplant recipients by matrix-assisted laser desorption/ionization time-of-flight mass spectrometry", Ying Li et al., "Ready detection of donor-specific single-nucleotide polymorphisms in the urine of renal transplant recipients by matrix-assisted laser desorption/ionization time-of-flight mass spectrometry", Clin Chem, Oct. 2005, vol. 51,Issue. 10,pp. 1903-1904, Oct. 1, 2005, 1903-1904.
Li, Ying et al., "Size Separation of Circulatory DNA in Maternal Plasma Permits Ready Detection of Fetal DNA Polymorphisms", Clinical Chemistry, 50, 6, 2004, 1002-1011.
Liao, Gary J.W. et al., "Targeted Massively Parallel Sequencing of Maternal Plasma DNA Permits Efficient and Unbiased Detection of Fetal Alleles", Clinical Chemistry, 57 (1), 2011, 92-101.
Liao, J. et al., "An Alternative Linker-Mediated Polymerase Chain Reaction Method Using a Dideoxynucleotide to Reduce Amplification Background", Analytical Biochemistry 253, 137-139 (1997).
Lichtenstein, A. V. et al., "Circulating Nucleic Acids and Apoptosis", Annals New York Academy of Sciences, vol. 945, Aug. 1, 2001, 239-249.
Liew, Michael et al., "Genotyping of Single-Nucleotide Polymorphisms", Clinical Chemistry, 50(7), 2004, 1156-1164.
Life Technologies, "Ion AmpliSeq Comprehensive Cancer Panel", 2012, 2 pgs.
Life Technologies, "Ion AmpliSeq™ Designer provides full flexibility to sequence genes of your choice", 2012, 4 pages.
Liljedahl, Ulrika et al., "Detecting Imbalanced Expression Of SNP Alleles by Minisequencing On Microarrays", BMC Biotechnology, vol. 4, Article No. 24, Oct. 22, 2004, 1-10.
Lindberg, J. et al., "Exome Sequencing of Prostate Cancer Supports the Hypothesis of Independent Tumour Origins", European Urology, vol. 63, 2013, 347-353.
Lindroos, Katatina et al., "Genotyping SNPs by Minisequencing Primer Extension Using Oligonucleotide Microarrays", Methods in Molecular Biology, 212, Single Nucleotide Polymorphisms: Methods and Protocols, P-K Kwok (ed.), Humana Press, Inc., Totowa, NJ, 2003, 149-165.
Lo, et al., "Digital PCR for the Molecular Detection of Fetal Chromosomal Aneuploidy", PNAS, vol. 104, No. 32, Aug. 7, 2007, 13116-13121.
Lo, et al., "Fetal Nucleic Acids in Maternal Blood: the Promises", Clin. Chem. Lab. Med., 50(6), 2012, 995-998.
Lo, et al., "Free Fetal DNA in Maternal Circulation", JAMA, 292(23), (Letters to the Editor), 2004, 2835-2836.
Lo, et al., "Next-generation Sequencing Of Plasma/Serum DNA: An Emerging Research And Molecular Diagnostic Tool", Clinical Chemistry, vol. 55, No. 4, Apr. 1, 2009, 607-608.
Lo, "Non-Invasive Prenatal Diagnosis by Massively parallel Sequencing of Maternal Plasma DNA", Open Biol 2: 120086, 2012, 1-5.
Lo, et al., "Prenatal Sex Determination by DNA Amplification from Maternal Peripheral Blood", The Lancet, 2, 8676, 1989, 1363-1365.
Lo, et al., "Presence Of Donor-specific Dna In Plasma Of Kidney And Liver-transplant Recipients", Lancet, vol. 351, No. 9112, May 2, 1998, 1329-1330.
Lo, et al., "Rapid Clearance of Fetal DNA from Maternal Plasma", Am. J. Hum. Genet., 64, 1999, 218-224.
Lo, et al., "Strategies for the Detection of Autosomal Fetal DNA Sequence from Maternal Peripheral Blood", Annals New York Academy of Sciences,731, 1994, 204-213.
Lo, et al., "Two-way cell traffic between mother and fetus: biologic and clinical implications", Blood, 88(11), Dec. 1, 1996, 4390-4395.
Lo, Y M. et al., "Circulating Nucleic Acids in Plasma and Serum: An Overview", Annals of the New York Academy of Sciences, vol. 945, Sep. 1, 2001, 1-7.
Lo, Y. , "Noninvasive prenatal detection of fetal chromosomal aneuploidies by maternal plasma nucleic acid analysis: a review of the current state of the art", BJOG An International Journal of Obstetrics and Gynaecology, vol. 116, 2009, 152-157.
Lo, Y.M. Dennis , "Fetal Nucleic Acids in Maternal Plasma: Toward the Development of Noninvasive Prenatal Diagnosis of Fetal Chromosomal Aneuploidies", Ann. N.Y. Acad. Sci., 1137, 2008, 140-143.
Lo, Y.M. Dennis et al., "Maternal Plasma DNA Sequencing Reveals the Genome-Wide Genetic and Mutational Profile of the Fetus", Science Translational Medicine,, 2 (61), 2010, 13.
Lo, Y.M. Dennis et al., "Plasma placental RNA allelic ratio permits noninvasive prenatal chromosomal aneuploidy detection", Nature Medicine, 13 (2), 2007, 218-223.
Lo, Y.M. Dennis et al., "Presence of Fetal DNA in Maternal Plasma and Serum", The Lancet, 350, 1997, 485-487.
Lo, Y.M. Dennis et al., "Quantitative Analysis of Fetal DNA in Maternal Plasma and Serum: Implications for Noninvasive Prenatal Diagnosis", Am. J. Hum. Genet., 62, 1998, 768-775.
Lo, Y.M.D. , "Fetal DNA in Maternal Plasma: Biology and Diagnostic Applications", Clinical Chemistry, vol. 46, No. 12, 2000, 1903-1906.
Lo, Y.M.D et al., "Prenatal diagnosis: progress through plasma nucleic acids", Nature Reviews, vol. 8, 2007, 71-77.
Lo, Y-M D. , "Non-invasive prenatal diagnosis using fetal cells in maternal blood", J. Clin. Pathol., vol. 47, 1994, 1060-1065.
Lo, Y-M.D et al., "Detection of Single-Copy Fetal DNA Sequence from Maternal Blood", The Lancet, 335, 1990, 1463-1464.
Lo, Y-M.D et al., "Prenatal Determination of Fetal Rhesus D Status by DNA Amplification of Peripheral Blood of Rhesus-Negative Mothers", Annals New York Academy of Sciences, 731, 1994, 229-236.
Lo, Y-M.D. et al., "Detection of Fetal RhD Sequence from Peripheral Blood of Sensitized RhD-Negative Pregnant Women", British Journal of Haematology, 87, 1994, 658-660.
Lo, Y-M.D. et al., "Prenatal Determination of Fetal RhD Status by Analysis of Peripheral Blood of Rhesus Negative Mothers", The Lancet, 341, 1993, 1147-1148.
Loh, Elwyn , "Anchored PCR: Amplification with Single-sided Specificity", Methods, vol. 2, 1991, pp. 11-19.
Lovmar, L. et al., "Quantitative evaluation by minisequencing and microarrays reveals accurate multiplexed SNP genotyping of whole genome amplified DN", Nucleic Acids Research, vol. 31, No. 21, 2003,, 9 pgs.
Lu, I. et al., "Establishment of a system based on universal multiplex-PCR for screening genetically modified crops", Anal. Bioanal. Chem, vol. 396, Oct. 24, 2009, 2055-2064.
Lu, S. et al., "Probing Meiotic Recombination and Aneuploidy of Single Sperm Cells by Whole-Genome Sequencing", Science, vol. 338, Dec. 21, 2012, 1627-1630.
Lui, Y. Y. et al., "Predominant Hematopoietic Origin of Cell-Free DNA in Plasma and Serum after Sex-Mismatched Bone Marrow Transplantation", Clinical Chemistry, vol. 48, vol. 3, 2002, 421-427.
Lui, Yanni Y. et al., "Circulating DNA in Plasma and Serum: Biology, Preanalytical Issues And Diagnostic Applications", Clinical Chemistry and Laboratory Medicine, vol. 40, No. 10, Oct. 29, 2002, 962-968.
Lui, Yanni Y. et al., "Origin of Plasma Cell-Free DNA after Solid Organ Transplantation", Clinical Chemistry, vol. 49, No. 3, Mar. 1, 2003, 495-496.
Lun, Fiona M. et al., "Microfluidics Digital PCR Reveals A Higher Than Expected Fraction Of Fetal DNA In Maternal Plasma", Clinical Chemistry, vol. 54, No. 10, Aug. 14, 2008, 1664-1672.
Lun, Fiona M. et al., "Noninvasive Prenatal Diagnosis of Monogenic Diseases by Digital Size Selection and Relative Mutation Dosage on DNA in Maternal Plasma", PNAS, 105(50), 2008, 19920-19925.
Ma, Xiaotu et al., "Rise and fall of subclones from diagnosis to relapse in pediatric B-acute lymphoblastic leukaemia", Nature Communications, vol. 6, Mar. 19, 2015, 1-12.

(56) References Cited

OTHER PUBLICATIONS

Mackiewicz, D. et al., "Distribution of Recombination Hotspots in the Human Genome—A Comparison of Computer Simulations with Real Data", PLOS One, vol. 8, No. 6, Jun. 2013, 11 pages.
Magbanua, M. J. et al., "Abstract PD2-01: Personalized serial circulating tumor DNA (ctDNA) analysis in high-risk early stage breast cancer patients to monitor and predict response to neoadjuvant therapy and outcome in the I-SPY 2 Trial", Cancer Research, vol. 79, No. 4 Supplement, Feb. 15, 2019.
Mamon, H. et al., "Letters to the Editor: Preferential Amplification of Apoptotic DNA from Plasma: Potential for Enhancing Detection of Minor DNA Alterations in Circulating DNA", Clinical Chemistry, vol. 54, No. 9, 2008, 1582-1584.
Maniatis, T. et al., "In: Molecular Cloning: A Laboratory Manual", Cold Spring Harbor Laboratory, New York, Thirteenth Printing, 1986, 458-459.
Mansfield, Elaine S , "Diagnosis of Down Syndrome and Other Aneuploidies Using Quantitative Polymerase Chain Reaction and Small Tandem Repeat Polymorphisms", Human Molecular Genetics, 2, 1, 1993, 43-50.
Mardis, E. R. , "The impact of next-generation sequencing technology on genetics", Trends in Genetics, vol. 24, No. 3, Feb. 11, 2008, 133-141.
Marguiles, M. et al., "Genome Sequencing in Open Microfabricated High Density Picoliter Reactors", Nature, vol. 437, No. 7057, Sep. 15, 2005, 376-380.
Margulies, M. et al., "Genome sequencing in microfabricated high-density picolitre reactors", Nature, vol. 437, Sep. 15, 2005, 376-380.
Margulies, M. et al., "Genome sequencing in microfabricated high-density picolitre reactors plus Supplemental Methods", Nature, vol. 437, Sep. 15, 2005, 40 pgs.
Marianes, Alexis E. et al., "Targets of Somatic Hypermutation within Immunoglobulin Light Chain Genes in Zebrafish", Immunology, vol. 132, 2010, pp. 240-255.
Markoulatos, P. et al., "Multiplex Polymerase Chain Reaction: A Practical Approach", Journal of Clinical Laboratory Analysis, vol. 16, 2002, 47-51.
Maron, Jill L. et al., "Cell-free Fetal DNA Plasma Extraction and Real-time Polymerase Chain Reaction Quantification", Methods In Molecular Medicine, vol. 132, Aug. 1, 2007, 51-63.
Marshutina, N. V. et al., "Comparative Clinical and Diagnostic Significance of Some Serological Tumor Associated Markers for Different Histological Types of Lung Cancer", Russian Oncological Journal, vol. 3, 2010, 13-16.
Martinez-Lopez, J. et al., "Real-time PCR Quantification of Haematopoietic Chimerism after Transplantation: A Comparison Between TaqMan And Hybridization Probes Technologies", International Journal of Laboratory Hematology, vol. 32, Issue 1, Part 1, May 12, 2009, e17-e25.
Martins, et al., "Quantification Of Donor-derived DNA In Serum: A New Approach Of Acute Rejection Diagnosis In A Rat Kidney Transplantation Model", Transplantation Proceedings, vol. 37, No. 1,, Jan. 1, 2005, 87-88.
Masuzaki, H. et al., "Detection of cell free placental DNA in maternal plasma: direct evidence from three cases of confined placental mosaicism", J Med Genet, vol. 41, 2004, 289-292.
Matsubara, T. et al., "Pantropic Retroviral Vectors Integrate and Express In Cells of the Malaria Mosquito, Anopheles Gambiae", PNAS, vol. 93, 1996, pp. 6181-6185.
Matsuzaki, H. et al., "Genotyping over 100,000 SNPs on a pair of oligonucleotide arrays", Nature Methods, vol. 1, No. 2, Nov. 2004, 109-111.
May, Robert M. , "How Many Species Are There on Earth?", Science, 241, Sep. 16, 1988, 1441-1449.
McBride, D. et al., "Use of Cancer-Specific Genomic Rearrangements to Quantify Disease Burden in Plasma from Patients with Solid Tumors", Genes, Chromosomes & Cancer, vol. 49, Aug. 19, 2010, 1062-1069.

McCloskey, M. L. et al., "Encoding PCR Products with Batch-stamps and Barcodes", Biochem Genet., vol. 45, Oct. 23, 2007, 761-767.
McCray, Alexa T. et al., "Aggregating UMLS Semantic Types for Reducing Conceptual Complexity", MEDINFO 2001: Proceedings of the 10th World Congress on Medical Informatics (Studies in Health Technology and Informatics, 84, V. Patel et al. (eds.), IOS Press Amsterdam, 2001, 216-220.
McDonald, B. R. et al., "Abstract P4-01-21: Multiplexed targeted digital sequencing of circulating tumor DNA to detect minimal residual disease in early and locally advanced breast cancer", Cancer Research, vol. 79, No. 4 Supplement, Feb. 15, 2019.
McDonald, J. P. et al., "Novel thermostable Y-family polymerases: applications for the PCR amplification of damaged or ancient DNAs", Nucleic Acids Research, vol. 34, No. 4, 2006, 1102-1111.
Mennuti, M. et al., "Is It Time to Sound an Alarm About False-Positive Cell-Free DNA Testing for Fetal Aneuploidy?", American Journal of Obstetrics, 2013, 5 pgs.
Merriam-Webster, "Medical Definition of Stimulant", http://www.merriam-webster.com/medical/stimulant, Mar. 14, 2016, 7 pages.
Merriam-Webster, "Universal Definition", Merriam-Webster.com, 3 pages.
Mersy, et al., "Noninvasive Detection of Fetal Trisomy 21: Systematic Review and Report of Quality and Outcomes of Diagnostic Accuracy Studies Performed Between 1997 and 2012", Human Reproduction Update, 19(4), 2013, 318-329.
Mertes, F. et al., "Targeted enrichment of genomic DNA regions for next-generation sequencing", Briefings in Functional Genomics, vol. 10, No. 6, Nov. 26, 2011, 374-386.
Messmer, Trudy O. et al., "Application of a Nested, Multiplex PCR to Psittacosis Outbreaks", Journal of Clinical Microbiology, vol. 35, No. 8, 1997, pp. 2043-2046.
Metzker, M. L. et al., "Polymerase Chain Reaction", Encyclopedia of Medical Devices and Instrumentation, vol. 5, Second Edition, 2006, 380-387.
Metzker, M. L. et al., "Quantitation of Mixed-Base Populations of HIV-1 Variants by Automated DNA Sequencing with Bodipy* Dye-Labeled Primers", BioTechniques, vol. 25, Sep. 1998, 446-462.
Meuzelaar, Linda S. et al., "Megaplex PCR: A Strategy for Multiplex Amplification", Nature Methods, vol. 4, 2007, pp. 835-837.
Meyer, M et al., "Illumina Sequencing Library Preparation for Highly Multiplexed Target Capture and Sequencing", Cold Spring Harbor Protocols, vol. 2010, Issue 6, Jun. 2010, 1-10.
Meyerson, M. et al., "Advances in understanding cancer genomes through second-generation sequencing", Nature Reviews: Genetics, vol. 11, Oct. 2010, 685-696.
Mikkelsen, T. S. et al., "Genome-wide maps of chromatin state in pluripotent and lineage-committed cells", Nature, vol. 448, No. 2, Aug. 2007, 553-562.
Milani, et al., "Genotyping Single Nucleotide Polymorphisms By Multiplex Minisequencing Using Tag-arrays", DNA Microarrays for Biomedical Research, vol. 529, Jan. 16, 2009, 215-229.
Miller, Robert , "Hyperglycemia-Induced Changes in Hepatic Membrane Fatty Acid Composition Correlate with Increased Caspase-3 Activities and Reduced Chick Embryo Viability", Comparative Biochemistry and Physiology, Part B, 141, 2005, 323-330.
Miller, Robert R. , "Homocysteine-Induced Changes in Brain Membrane Composition Correlate with Increased Brain Caspase-3 Activities and Reduced Chick Embryo Viability", Comparative Biochemistry and Physiology Part B, 136, 2003, 521-532.
Miner, B. E. et al., "Molecular barcodes detect redundancy and contamination in hairpin-bisulfite PCR", Nucleic Acids Research, vol. 32, No. 17, 30 Sep. 2004, 1-4.
Minkoff, E. et al., "Stem Cells, Cell Division, and Cancer", Biology Today Third Edition, Chapter 12, 2004, 10 pages.
Miramontes, Pedro et al., "DNA Dimer Correlations Reflect in Vivo Conditions and Discriminate Among Nearest-neighbor Base Pair Free Energy Parameter Measures", Physica A, vol. 321, 2003, pp. 577-586.
Mitra, S. et al., "Chapter 4 Classification Techniques", Introduction to Machine Learning and Bioinformatics, First Edition, 2008, 101-127.

(56) References Cited

OTHER PUBLICATIONS

Morand, et al., "Hesperidin contributes to the vascular protective effects of orange juice: a randomized crossover study in healthy volunteers", Am J Clin Nutr. Jan. 2011;93(1):73-80. Epub Nov. 10, 2010.

Moreau, Valerie et al., "Zip Nucleic Acids: New High Affinity Oligonucleotides as Potent Primers for PCR and Reverse Transcription", Nucleic Acids Research, vol. 37, No. 19, e130, 2009, 14 pages.

Moreira, et al., "Increase In And Clearance Of Cell-free Plasma DNA In Hemodialysis Quantified By Real-time PCR", Clinical Chemistry and Laboratory Medicine, vol. 44, No. 12, Dec. 13, 2006, 1410-1415.

Morris, J. K. et al., "Trends in Down's syndrome live births and antenatal diagnoses in England and Wales from 1989 to 2008: analysis of data from the National Down Syndrome Cytogenetic Register", BMJ Online, vol. 339, Oct. 2009, 5 pages.

Munne, S. et al., "Chromosome Abnormalities in Human Embryos", Textbook of Assisted Reproductive Techniques, 2004, pp. 355-377.

Munne, S. et al., "Chromosome abnormalities in human embryos", European Society of Human Reproduction and Embryology: Human Reproduction Update, vol. 4, No. 6, 1998, 842-855.

Munne, S. et al., "Improved implantation after preimplantation genetic diagnosis of aneuploidy", Reproductive BioMedicine Online, vol. 7., No. 1., May 15, 2003, 91-97.

Murali, R. et al., "Crystal structure of Taq DNA polymerase in complex with an inhibitory Fab: The Fab is directed against an intermediate in the helix-coil dynamics of the enzyme", Proc. Natl. Acad. Sci. USA, vol. 95, Oct. 1998, 12562-12567.

Murtaza, M. et al., "Non-Invasive Analysis of Acquired Resistance to Cancer Therapy by Sequencing of Plasma DNA", Nature (doi: 10.1038/nature12065), 2013, 6 pgs.

Muse, Spencer V., "Examining rates and patterns of nucleotide substitution in plants", Plant Molecular Biology 42: 25-43, 2000.

Myers, Chad L. et al., "Accurate Detection of Aneuploidies in Array CGH and Gene Expression Microarray Data", Bioinformatics, 20(18), 2004, 3533-3543.

Nagalla, S. R. et al., "Proteomic Analysis of Maternal Serum in Down Syndrome: Identification of Novel Protein Biomarkers", Journal of Proteome Research, vol. 6, Mar. 21, 2007, 1245-1257.

Nakamura, N. et al., "Ex Vivo Liver Perfusion with Arterial Blood from A Pig with Ischemic Liver Failure", Artificial Organs, vol. 23, No. 2, 1999, 153-160.

Namlos, H. M. et al., "Noninvasive Detection of ctDNA Reveals Intratumor Heterogeneity and Is Associated with Tumor Burden in Gastrointestinal Stromal Tumor", Molecular Cancer Therapeutics, vol. 17, No. 11, 2018, 2473-2480.

Nannya, Yasuhito et al., "A Robust Algorithm for Copy Number Detection Using High-density Oligonucleotide Single Nucleotide Polymorphism Genotyping Arrays", Cancer Res., 65, 14, 2005, 6071-6079.

Narayan, A. et al., "Ultrasensitive measurement of hotspot mutations in tumor DNA in blood using error-suppressed multiplexed deep sequencing", Cancer Research, vol. 72, No. 14, Jul. 15, 2012, 3492-3498.

Natera, Inc., "Declaration of Sandra L. Haberny", May 16, 2019, 3 pages.

Natera, Inc., "Defendant Natera, Inc.'s Invalidity Contentions Under Patent L.R. 3-3; Document Production Accompanying Invalidity Contentions Under Patent L.R. 3-4", Aug. 20, 2018, 17 pages.

Natera, Inc., "Exhibit 8 Ehrich Invalidity Chart", Aug. 20, 2018, 16 pages.

Natera, Inc., "Exhibits A-H to Haberny Declaration", May 16, 2019, 192 pages.

Natera, Inc., "Motion to Dismiss", May 16, 2019, 2 pages.

Natera, Inc., "Natera Inc.'s First Amended Answer, Affirmative Defenses and Counterclaims", Aug. 16, 2018, 28 pages.

Natera, Inc., "Natera, Inc.'s Supplemental Objections and Response To Plaintiff Illumina, Inc.'s Interrogatory No. 8", Mar. 20, 2019, 29 pages.

Natera, Inc., "Opening Brief in Support of Motion to Dismiss", May 16, 2019, 26 pages.

Natera, Inc., , "Petitioner Reply Per Board Order of Nov. 2, 2018 (Paper No. 10)", Nov. 9, 2018, 8 pgs.

National Institutes of Health, , "Genetics Home Reference: Your Guide to Understanding Genetic Conditions", Feb. 28, 2014, 2 pgs.

Nawroz, H et al., "Microsatellite Alterations in Serum DNA of Head and Neck Cancer Patients", Nature Medicine, vol. 2, No. 9, Sep. 1996, 1035-1037.

NCBI, "Blast of AAAAAAAAATTTAAAAAAAAATTT", 2015, 9 pages.

NCBI, "db SNP rs2056688", 2015, 3 pages.

NCBI, "dbSNP record for rs1294331", Retrieved from the Internet: <URL: www.ncbi.nlm.nih.gov/snp/?term=rs 1294331 >, 2019, 2 pgs.

NCBI, "dbSNP record for rs1872575", Retrieved from the Internet: <URL: www.ncbi.nlm.nih.gov/snp/?term=rs1872575, 2019, 2 pgs.

NCBI, "dbSNP record for rs2362450", Retrieved from the Internet: <URL: www.ncbi.nlm.nih.gov/snp/?term=rs2362450>, 2019, 1 pg.

NCBI, "dbSNP record for rs2384571", Retrieved from the Internet: <URL: www.ncbi.nlm.nih.gov/snp/?term=rs2384571>, 2019, 2 pgs.

NCBI, "dbSNP record for rs2498982", Retrieved from the Internet: <URL: www.ncbi.nlm.nih.gov/snp/?term=rs2498982>, 2019, 3 pgs.

NCBI, "dbSNP record for rs3731877", Retrieved from the Internet: <URL: www.ncbi.nlm.nih.gov/snp/?term=rs3731877>, 2019, 2 pgs.

Neve, B. et al., "Rapid SNP Allele Frequency Determination in Genomic DNA Pools by Pyrosequencing", BioTechniques, vol. 32, No. 5, May 1, 2002, 1138-1142.

New England Biolabs, "NucleicAcids, Linkers and Primers: Random Primers", 1998/99Catalog, 1998, 121 and 284.

Newman, A. M. et al., "Integrated digital error suppression for improved detection of circulating tumor DNA", Nature Biotechnology, vol. 34, No. 5, May 2016, 547-555.

Ng, et al., "Multiplex Sequencing Of Paired-end Ditags (MS-PET): A Strategy For The Ultra-high-throughput Analysis Of Transcriptomes And Genomes", Nucleic Acids Research, vol. 34, No. 12, Jul. 13, 2006, 1-10.

Ng, S. B. et al., "Individualised multiplexed circulating tumour DNA assays for monitoring of tumour presence in patients after colorectal cancer surgery", Scientific Reports, vol. 7, No. 40737, Jan. 19, 2017, 11 pages.

Nguyen-Dumont, T. , "A high-plex PCR approach for massively parallel sequencing", BioTechniques, vol. 55, No. 2, Aug. 2013, 69-74.

Nicolaides, K. et al., "Noninvasive Prenatal Testing for Fetal Trisomies in a Routinely Screened First-Trimester Population", American Journal of Obstetrics (article in press), 207, 2012, 1.e1-1.e6.

Nicolaides, K.H et al., "Validation of Targeted Sequencing of Single-Nucleotide Polymorphisms for Non-Invasive Prenatal Detection of Aneuploidy of Chromosomes 13, 18, 21, X, and Y", Prenatal Diagnosis, 33, 2013, 575-579.

Nicolaides, Kypros H. et al., "Prenatal Detection of Fetal Triploidy from Cell-Free DNA Testing in Maternal Blood", Fetal Diagnosis and Therapy, 2013, 1-6.

Nilsson, M. et al., "Padlock Probes: Circularizing Oligonucleotides for Localized DNA Detection", Science, vol. 265, Sep. 10, 1994, 2085-2088.

Nishigaki, K. et al., "Random PCR-Based Genome Sequencing: A Non-Divide-and-Conquer Strategy", DNA Research, vol. 7, 2000, 19-26.

Nishiwaki, Morie et al., "Genotyping of Human Papillomaviruses by A Novel One-step Typing Method With Multiplex PCR and Clinical Applications", Journal of Clinical Microbiology, vol. 46, 2008, pp. 1161-1168.

Norton, S. E. et al., "A stabilizing reagent prevents cell-free DNA contamination by cellular DNA in plasma during blood sample storage and shipping as determined by digital PCR", Clin Biochem., vol. 46, No. 15, Oct. 2013, 1561-1565.

Nui, A. et al., "The Functional Integrity of a Normothermic Perfusion System Using Artificial Blood in Pig Liver", Journal of Surgical Research, Vo. 131, 2006, 189-198.

(56) References Cited

OTHER PUBLICATIONS

Nygren, et al., "Quantification of Fetal DNA by Use of Methylation-Based DNA Discrimination", Clinical Chemistry 56:10 1627-1635 (2010).
O'connell, G. C. et al., "High Interspecimen Variability in Nucleic Acid Extraction Efficiency Necessitates the Use of Spike-In Control for Accurate qPCR-based Measurement of Plasma Cell-Free DNA Levels", Lab Medicine, vol. 48, 2017, 332-338.
Oeth, et al., "iPLEX™ Assay: Increased Plexing Efficiency and Flexibility for MassARRAY System Through Single Base Primer Extension with Mass-Modified Terminators", Sequenom Application Note Doc. No. 8876-006, Apr. 28, 2005, 1-12.
Ogino, S. et al., "Bayesian Analysis and Risk Assessment in Genetic Counseling and Testing", Journal of Molecular Diagnostics, 6 (1), 2004, 9 pgs.
Ohara, O et al., "One-sided Polymerase Chain Reaction: The Amplification of cDNA", Proceedings of the National Academy of Sciences, vol. 86, 1989, 5673-5677.
Ohira, T. et al., "Tumor volume determines the feasibility of cell-free DNA sequencing for mutation detection in non-small cell lung cancer", Cancer Science, vol. 107, 2016, 1660-1666.
Ohsawa, M. et al., "Prenatal Diagnosis of Two Pedigrees of Fukuyama Type Congenital Muscular Dystrophy by Polymorphism Analysis", The Health and Welfare Ministry, 1994, 5 pgs.
Okou, et al., "Microarray-based Genomic Selection For High-throughput Resequencing", Nature Methods, vol. 4, No. 11, Oct. 14, 2007, 907-909.
Okou, David T. et al., "Combining Microarray-based Genomic Selection (MGS) with The Illumina Genome Analyzer Platform To Sequence Diploid Target Regions", Annals of Human Genetics, vol. 73, No. 5, Aug. 6, 2009, 502-513.
Olerup, O. et al., "HLA-DR typing by PCR amplification with sequence-specific primers (PCR-SSP) in 2 hours: an alternative to serological DR typing in clinical practice including donor-recipient matching in cadaveric transplantation", Tissue Antigens, vol. 39, No. 5, May 1992, 225-235.
Oliphant, A. et al., "Bead.Array™ Technology: Enabling an Accurate, Cost-Effective Approach to High-Throughput Genotyping", Bio Techniques, vol. 32, Jun. 2002, S56-S6.
Olivarius, S et al., "High-throughput Verification of Transcriptional starting Sites by Deep-RACE", Bio Techniques, vol. 46, No. 2, Feb. 2009, 130-132.
Olive, M. et al., "Characterization of the DiFi Rectal Carcinoma Cell Line Derived from a Familial Adenomatous Polyposis Patient", In Vitro Cellular & Developmental Biology, vol. 29A, No. 3, Part 1, Mar. 1993, 239-248.
Oliver, Dwight H. et al., "Use of Single Nucleotide Polymorphisms (SNP) and Real-time Polymerase Chain Reaction for Bone Marrow Engraftment Analysis", The Journal of Molecular Diagnostics, vol. 2, No. 4, Nov. 1, 2000, 202-208.
Olivier, et al., "The Invader Assay for SNP Genotyping", Mutation Research, vol. 573, No. 1-2, Jun. 3, 2005, 103-110.
Olney, R. S. et al., "Chorionic Villus Sampling and Amniocentesis: Recommendations for Prenatal Counseling", MMWR: Recommendations and Reports, 44(RR-9), Jul. 21, 1995, 1-12.
O'Malley, R. et al., "An adapter ligation-mediated PCR method for high-throughput mapping of T-DNA inserts in the *Arabidopsis* genome", Nat. Protoc., 2, 2007, 2910-2917.
Orozco A.F., et al., "Placental Release of Distinct DNA-Associated Micro-Particles into Maternal Circulation: Reflective of Gestation Time and Preeclampsia", Placenta, 30, 2009, 891-897.
Orsouw, et al., "Complexity Reduction Of Polymorphic Sequences (Crops): A Novel Approach For Large-scale Polymorphism Discovery In Complex Genomes", PLoS One, vol. 11:e1172, Nov. 14, 2017, 1-10.
Owczarzy, Richard et al., "Melting Temperatures of Nucleic Acids: Discrepancies in Analysis", Biophysical Chemistry, vol. 117, 2005, pp. 207-215.
Ozawa, Makiko et al., "Two Families with Fukuyama Congenital Muscular Dystrophy that Underwent In Utero Diagnosis Based on Polymorphism Analysis", Clinical Muscular Dystrophy: Research in Immunology and Genetic Counseling—FY 1994 Research Report, (including copy of text in Japanese), 1994, 8.
Paez, Guillermo J. et al., "Genome coverage and sequence fidelity of Φ29 polymerase-based multiple strand displacement whole genome amplification", Nucleic Acids Research, 32(9), 2004, 1-11.
Page, S. L. et al., "Chromosome Choreography: The Meiotic Ballet", Science, 301, 2003, 785-789.
Paik, P. K. et al., "Next-Generation Sequencing of Stage IV Squamous Cell Lung Cancers Reveals an Association of P13K Aberrations and Evidence of Clonal Heterogeneity in Patients with Brain Metastases", Cancer Discovery, vol. 5, Apr. 30, 2015, 610-621.
Pakstis, et al., "Candidate SNPs For A Universal Individual Identification Panel", Human Genetics, vol. 121, No. 3-4,, Feb. 27, 2007, 305-317.
Pakstis, et al., "SNPS for Individual Identification", Forensic Science International, vol. 1, May 22, 2008, 479-481.
Palka-Santini, Maria et al., "Large Scale Multiplex PCR Improves Pathogen Detection by DNA Microarrays", BMC Microbiology, vol. 9, No. 1, 2009, 14 pages.
Palomaki, G. E et al., "DNA sequencing of maternal plasma to detect Down syndrome: An international clinical validation study", Genetics In Medicine, vol. 13, No. 1, Nov. 2011, 913-920.
Palomaki, Glenn et al., "DNA Sequencing of Maternal Plasma Reliably Identifies Trisomy 18 and Trisomy 13 as Well as Down Syndrome: an International Collaborative Study", Genetics in Medicine, 2012, 10.
Palomaki, Glenn E. et al., "DNA Sequencing of Maternal Plasma to Detect Down Syndrome: An International Clinical Validation Study", Genetics in Medicine (pre-print version), 13, 2011, 8 pgs.
Panjkovich, Alejandro et al., "Comparison of Different Melting Temperature Calculation Methods for Short DNA Sequences", Bioinformatics, vol. 21, 2005, pp. 711-722.
Papadopoulou, E. et al., "Cell-Free DNA and RNA in Plasma as a New Molecular Marker for Prostate Cancer", Oncology Research, vol. 14, 2004, 439-445.
Papageorgiou, Elisavet A. et al., "Fetal-Specific DNA Methylation Ratio Permits Noninvasive Prenatal Diagnosis of Trisomy 21", Nature Medicine (advance online publication), 17, 2011, 5 pgs.
Parameswaran, P. et al., "A pyrosequencing-tailored nucleotide barcode design unveils opportunities for large-scale sample multiplexing", Nucleic Acids Research, vol. 35, No. 19, Oct. 11, 2007, 9 pages.
Parker, A. V. et al., "The Effect of Sodium Citrate on the Stimulation of Polymorphonuclear Leukocytes", Investigative Ophthalmology & Visual Science, vol. 26, 1985, 1257-1261.
Paruzynski, A. et al., "Genome-wide high-throughput integrome analyses by nrLAM-PCR and next-generation sequencing", Nature Protocols, vol. 5, No. 8, Jul. 8, 2010, 1379-1395.
Pask, R. et al., "Investigating the utility of combining 29 whole genome amplification and highly multiplexed single nucleotide polymorphism BeadArray TM genotyping", BMC Biotechnology, vol. 4, No. 15, Jul. 27, 2004, 8 pages.
Pastinen, T. et al., "Minisequencing: A Specific Tool for DNA Analysis and Diagnostics on Oligonucleotide Arrays", Genome Research, vol. 7, 1997, 606-614.
Pathak, A. et al., "Circulating Cell-Free DNA in Plasma/Serum of Lung Cancer Patients as a Potential Screening and Prognostic Tool", Clinical Chemistry, 52, 2006, 1833-1842.
Patil, N. et al., "Blocks of Limited Haplotype Diversity Revealed by High-Resolution Scanning of Human Chromosome 21", Science, vol. 294, Nov. 23, 2001, 1719-1723.
Paunio, T. et al., "Preimplantation diagnosis by whole-genome amplification, PCR amplification, and solid-phase minisequencing of blastomere DNA", Clinical Chemistry, vol. 42, No. 9, 1996, 1382-1390.
PCT/US2006/045281, "International Preliminary Report on Patentability", mailed May 27, 2008, 1 pg.
PCT/US2006/045281, "International Search Report and Written Opinion", mailed Sep. 28, 2007, 7 pgs.
PCT/US2008/003547, "International Search Report", mailed Apr. 15, 2009, 5 pgs.

(56) References Cited

OTHER PUBLICATIONS

PCT/US2009/034506, "International Search Report", mailed Jul. 8, 2009, 2 pgs.
PCT/US2009/045335, "International Search Report", mailed Jul. 27, 2009, 1 pg.
PCT/US2009/052730, "International Search Report", mailed Sep. 28, 2009, 1 pg.
PCT/US2010/050824, "International Search Report", mailed Nov. 15, 2010, 2 pgs.
PCT/US2011/037018, "International Search Report", mailed Sep. 27, 2011, 2 pgs.
PCT/US2011/061506, "International Search Report", mailed Mar. 16, 2012, 1 pgs.
PCT/US2011/066938, "International Search Report", mailed Jun. 20, 2012, 1 pg.
PCT/US2012066339, "International Search Report", mailed Mar. 5, 2013, 1 pg.
PCT/US2013/028378, "International Search Report and Written Opinion", mailed May 28, 2013, 11 pgs.
PCT/US2013/57924, "International Search Report and Written Opinion", mailed Feb. 18, 2014, 8 pgs.
PCT/US2014/051926, "International Search Report and Written Opinion", Dec. 9, 2014, 3 pgs.
Pearson, K., "On the criterion that a given system of deviations from the probable in the case of a correlated system of variables is such that it can be reasonably supposed to have arisen from random sampling", Philosophical Magazine Series 5, vol. 50, Issue 302, 1900, 157-175.
Pelizzari, C. A. et al., "Quantitative analysis of DNA array autoradiographs", Nucleic Acids Research, vol. 28, No. 22, 2000, 4577-4581.
Pena, Sergio D.J et al., "Paternity Testing in the DNA Era", Trends In Genetics, 10, 6, 1994, 204-209.
Perakis, S. et al., "Advances in Circulating Tumor DNA Analysis", Advances in Clinical Chemistry, vol. 80, 2017, 73-153.
Pergament, E. et al., "Single-Nucleotide Polymorphism-Based Non-invasive Prenatal Screening in a High-Risk and Low-Risk Cohort", Obstetrics & Gynecology, vol. 124, No. 2, Part 1, Aug. 2014, 210-218 + Appendices.
Perkel, Jeffrey M., "Overcoming the Challenges of Multiplex PCR", Biocompare Editorial Article, 2012, 1-5.
Perry, George H. et al., "The Fine-Scale and Complex Architecture of Human Copy-Number Variation", The American Journal of Human Genetics, 82, 2008, 685-695.
Pertl, B. et al., "Detection of Male and Female Fetal DNA in Maternal Plasma by Multiplex Fluorescent Polymerase Chain Reaction Amplification of Short Tandem Repeats", Hum. Genet., 106, 2000, 45-49.
Peters, D., "List of Materials Considered By David Peters, Ph.D.", Jun. 13, 2019, 2 pages.
Peters, David P. et al., "Noninvasive Prenatal Diagnosis of a Fetal Microdeletion Syndrome", New England Journal of Medicine, 365(19), 2011, 1847-1848.
Pfaffl, Michael W., "Quantification Strategies in Real-time PCR", A-Z of quantitative PCR, 2004, pp. 87-112.
Pfaffl, Michael W., "Relative Expression Software Tool (REST©) for Group-Wise Comparison and Statistical Analysis of Relative Expression Results in real-Time PCR", Nucleic Acids Research, 30(9), 2002, 10 pgs.
Philip, J. et al., "Late First-Trimester Invasive Prenatal Diagnosis: Results of an International Randomized Trial", American College of Obstetricians and Gynecologists, vol. 103, No. 6, Jun. 2004, 1164-1173.
Phillips, C. et al., "Resolving Relationship Tests that Show Ambiguous STR Results Using Autosomal SNPs as Supplementary Markers", Forensic Science International: Genetics 2, 2008, 198-204.
Pinard, et al., "Assessment of Whole Genome Amplification-induced Bias Through High-throughput, Massively Parallel Whole Genome Sequencing", BMC Genomics, vol. 7:216, Aug. 23, 2006, 1-21.
Pirker, C. et al., "Whole Genome Amplification for CGH Analysis: Linker-Adapter PCR as the Method of Choice for Difficult and Limited Samples", Cytometry Part A, vol. 61A, 2004, 26-34.
Podder, Mohua et al., "Robust Sn P genotyping by multiplex PCR and arrayed primer", BMC Medical Genomics, 1(5), 2008, 1-15.
Poirier, K. et al., "Maternal mosaicism for mutations in the ARX gene in a family with X linked mental retardation", Human Genetics, vol. 118, Aug. 3, 2005, 45-48.
Pont-Kingdon, G. et al., "Rapid Detection of Aneuploidy (Trisomy 21) by Allele Quantification Combined with Melting Curves Analysis of Single-Nucleotide Polymorphism Loci", Clinical Chemistry, vol. 49, No. 7, 2003, 1087-1094.
Poon, L. L. et al., "Differential DNA Methylation between Fetus and Mother as a Strategy for Detecting Fetal DNA in Maternal Plasma", Clinical Chemistry, vol. 48, No. 1, 2002, 35-41.
Popova, T. et al., "Genome Alteration Print (GAP): a tool to visualize and mine complex cancer genomic profiles obtained by SNP arrays", Genome Biology, vol. 10, R128, Nov. 11, 2009, 1-14.
Porreca, Gregory J et al., "Multiplex Amplification of Large Sets of Human Exons", Nature Methods, 4, (advance online publication), 2007, 6.
Pourmand, et al., "Multiplex Pyrosequencing", Nucleic Acid Research, vol. 30, No. 7, Apr. 1, 2002, 1-5.
Prabhu, et al., "Overlapping Pools for High-throughput Targeted Resequencing", Genome Research, vol. 19, May 15, 2009, 1254-1261.
Price, T.S. et al., ""SW-ARRAY: a dynamic programming solution for the identification of copy-number changes in genomic DNA using array comparative genome hybridization data",", Nucleic Acids Research, vol. 33, No. 11, Jun. 16, 2005, 3455-3464.
Primdahl, H. et al., "Allelic Imbalances in Human Bladder Cancer: Genome-Wide Detection With High-Density Single-Nucleotide Polymorphism Arrays", Journal of the National Cancer Institute, vol. 94, No. 3, Feb. 6, 2002, 216-223.
Profitt, J et al., "Isolation And Characterisation of Recombination Events Involving Immunoglobulin Heavy Chain Switch Regions in Multiple Myeloma Using Long Distance Vectorette PCR (Ldv-pcr)", Leukemia, vol. 13, No. 7, Jul. 1999, 1100-1107.
Puszyk, William M. et al., "Noninvasive Prenatal Diagnosis Of Aneuploidy Using Cell-free Nucleic Acids In Maternal Blood: Promises And Unanswered Questions", Prenatal Diagnosis, vol. 28, No. 1, Nov. 16, 2007, 1-6.
Qiagen, "QIAamp DNA Mini Kit and QIAamp DNA Blood Mini Kit Handbook", QIAamp DNA Mini Kit and QIAamp DNA Blood Mini Kit Handbook, Feb. 2003 ("Qiagen (2003)"), 2003, 68 pages.
Qin, Z. S. et al., "Partition-Ligation-Expectation-Maximization Algorithm for Haplotype Inference with Single-Nucleotide Polymorphisms", Am. J. Hum Genet., vol. 71, 2002, 1242-1247.
Quan, P. C. et al., "Studies on the mechanism of NK cell lysis", The Journal of Immunology, vol. 128, 1982, 1786-1791.
Quinlan, M. P., "Amniocentesis: Indications and Risks", American Medical Association Journal of Ethics: Virtual Mentor, vol. 10, No. 5, May 2008, 304-306.
Quinn, G. P. et al., "Experimental Design and Data Analysis for Biologists", Graphical Exploration of Data, 2002, 64-67.
Rabinowitz, et al., "Accurate Prediction of HIV-1 Drug Response from the Reverse Transcriptase and Protease Amino Acid Sequences Using Sparse Models Created by Convex Optimization", Bioinformatics, 22, 5, 2006, 541-549.
Rabinowitz, M., "A System and Method for Integrating, Validating and Applying Genetic and Clinical Data to Enhance Medical Decisions", Nov. 29, 2005, 155 pgs.
Rabinowitz, Matthew et al., "Origins and rates of aneuploidy inhuman blastomeres", Fertility and Sterility, vol. 97, No. 2, Feb. 2012, 395-401.
Rabinowitz, Matthew. et al., "Non-Invasive Prenatal Aneuploidy Testing of Chromosomes 13, 18, 21, X, and Y Using Targeted Sequencing of Polymorphic Loci", The American Society of Human Genetics, meeting poster, 2012, 1 pg.
Rachlin, J. et al., "Computational tradeoffs in multiplex PCR assay design for SNP genotyping", BMC Genomics, vol. 6, No. 102, Jul. 25, 2005, 11 pages.

(56) References Cited

OTHER PUBLICATIONS

Ragoussis, J., "Genotyping Technologies for Genetic Research", Annual Review of Genomics and Human Genetics, vol. 10 (1), Sep. 1, 2009, 117-133.

Rahmann, Sven et al., "Mean and variance of the Gibbs free energy of oligonucleotides in the nearest neighbor model under varying conditions", Bioinformatics, 20(17), 2004, 2928-2933.

Raindance Technologies, "Multiplexing with RainDrop Digital PCR", Application Note, 2013, 2 pgs.

Raindance Technologies, et al., "RainDance Technologies Introduces the RDT 1000", RainDance Technologies, Nov. 12, 2008.

Rava, Richard P. et al., "Circulating Fetal Cell-Free DNA Fraction Differ in Autosomal Aneuploidies and Monosomy X", Clinical Chemistry, 60(1), (papers in press), 2013, 8 pgs.

Ravipati, Goutham et al., "Comparison of Sensitivity, Specificity, Positive Predictive Value, and Negative Predictive Value of Stress Testing Versus 64-Multislice Coronary Computed Tomography Angiography in Predicting Obstructive Coronary Artery Disease Diagnosed by Coronary Angiogr", The American Journal of Cardiology, Coronary Artery Disease. vol. 101, Issue 6, Mar. 15, 2008, 774-775.

Rechitsky, Svetlana et al., "Preimplantation Genetic Diagnosis with HLA Matching", Reproductive Bio Medicine Online, 9, 2, 2004, 210-221.

Reeves, R. H. et al., "Too much of a good thing: mechanisms of gene action in Down syndrome", Trends in Genetics, vol. 17, No. 2, Feb. 2, 2001, 83-88.

Reinert, T. et al., "Analysis of circulating tumour DNA to monitor disease burden following colorectal cancer surgery", Gut, vol. 65, 2016, 625-634.

Renwick, P. et al., "Proof of Principle and First Cases Using Preimplantation Genetic Haplotyping—A Paradigm Shift for Embryo Diagnosis", Reproductive BioMedicine Online, 13 (1), 2006, 110-119.

Rhoads, A. et al., "PacBio Sequencing and Its Applications", Genomics Proteomics Bioinformatics, vol. 13, Nov. 2, 2015, 278-289.

Ricciotti, Hope, "Eating by Trimester", Online]. Retrieved from Internet:<http://www.youandyourfamily.com/article.php?story=Eating+by+Trimester>, 2014, 3.

Riley, D. E., "DNA Testing: An Introduction For Non-Scientists An Illustrated Explanation", Scientific Testimony: An Online Journal, http://www.scientific.org/tutorials/articles/riley/riley.html, Apr. 6, 2005, 22 pages.

Riva, F., "Patient-Specific Circulating Tumor DNA Detection during Neoadjuvant Chemotherapy in Triple-Negative Breast Cancer", Clinical Chemistry, vol. 63, No. 3, 2017, 691-699.

Robertson, G. et al., "Genome-wide profiles of STAT1 DNA association using chromatin immunoprecipitation and massively parallel sequencing", Nature Methods, vol. 4, No. 8, Aug. 2007, 651-657.

Roche Diagnostics, et al., "Versatile Nucleic Acid Purification", MagnaPure Manual, Feb. 3, 2012.

Rogaeva, E. et al., "The Solved and Unsolved Mysteries of the Genetics of Early-Onset Alzheimer's Disease", NeuroMolecular Medicine, vol. 2, 2002, 1-10.

Roman, B. L. et al., "Non-Radioisotopic AFLP Method Using PCR Primers Fluorescently Labeled with CyA 5", BioTechniques, vol. 26, Feb. 1999, 236-238.

Roper, Stephen M. et al., "Forensic Aspects of DNA-Based Human Identity Testing", Journal of Forensic Nursing, 4, 2008, 150-156.

Rosado, J. A. et al., "Tyrosine kinases activate store-mediated Ca2+ entry in human platelets through the reorganization of the actin cytoskeleton", Biochem. J., vol. 351, 2000, 429-437.

Rosen, D. R. et al., "Mutations in Cu/Zn superoxide dismutase gene are associated with familial amyotrophic lateral sclerosis", Nature, vol. 362, Mar. 4, 1993, 59-62.

Ross, P. et al., "Quantitative Approach to Single-Nucleotide Polymorphism Analysis Using MALDI-TOF Mass Spectrometry", BioTechniques, vol. 29, Sep. 2000, 620-629.

Rothberg, et al., "The Development and Impact of 454 Sequencing", Nature Biotechnology, vol. 26, No. 10, Oct. 9, 2008, 1117-1124.

Roux, K., "Optimization and Troubleshooting in PCR", PCR Methods Appl. 4, 1995, 185-194.

Rozen, Steve et al., "Primer3 on the WWW for General Users and for Biologis Programmers", Methods in Molecular Biology, 132: Bioinformatics Methods and Protocols, 1999, 365-386.

Ruano, G. et al., "Haplotype of multiple polymorphisms resolved by enzymatic amplification of single DNA molecules", Proc. Nati. Acad. Sci. USA, vol. 87, Aug. 1990, 6296-6300.

Rubio, J. M. et al., "Semi-nested, Multiplex Polymerase Chain Reaction for Detection of Human Malaria Parasites and Evidence of Plasmodium Vivax Infection in Equatorial Guinea", The American Journal of Tropical Medicine And Hygiene, vol. 60, 1999, pp. 183-187.

Ruschendorf, et al., "Alohomora: A Tool For Linkage Analysis Using 10K SNP Array Data", Bioinformatics Applications Notes, vol. 21, No. 9, Jan. 12, 2005, 2123-2125.

Russell, L. M., "X Chromosome Loss and Ageing", Cytogenetic and Genome Res., 116, 2007, 181-185.

Ryan, A. et al., "Informatics-Based, Highly Accurate, Noninvasive Prenatal Paternity Testing", Genetics in Medicine (advance online publication), 2012, 5 pgs.

Ryan, B. M. et al., "A prospective study of circulating mutant KRAS2 in the serum of patients with colorectal neoplasia: strong prognostic indicator in postoperative follow up", Gut, vol. 52, 2003, 101-108.

Rychlik, et al., "Optimization of the annealing temperature for DNA amplification in vitro", Nucleic Acids Research, 18(21), 1990, 6409-6412.

Sahota, A., "Evaluation of Seven PCR-Based Assays for the Analysis of Microchimerism", Clinical Biochemistry, vol. 31, No. 8., 1998, 641-645.

Sahukhal, G. S. et al., "msaABCR operon positively regulates biofilm development by repressing proteases and autolysis in *Staphlococcus aureus*", FEMS Microbiology Letters, vol. 362, No. 4, 2015, 1-10.

Saito, H. et al., "Prenatal DNA diagnosis of a single-gene disorder from maternal plasma", The Lancet, vol. 356, Sep. 30, 2000, 1170.

Saker, A. et al., "Genetic characterisation of circulating fetal cells allows non-invasive prenatal diagnosis of cystic fibrosis", Prenatal Diagnosis, vol. 26, Jul. 11, 2006, 906-916.

Samango-Sprouse, C. et al., "SNP-Based Non-Invasive Prenatal Testing Detects Sex Chromosome Aneuploidies with High Accuracy", Prenatal Diagnosis, 33, 2013, 1-7.

Samura, O. et al., "Diagnosis of Trisomy 21 in Fetal Nucleated Erythrocytes from Maternal Blood by Use of Short Tandem Repeat Sequences", Clinical Chemistry, vol. 47, No. 9, 2001, 1622-1626.

Sanchez, C. et al., "New insights into structural features and optimal detection of circulating tumor DNA determined by single-strand DNA analysis", Nature Partner Journals, vol. 3, No. 31, Nov. 23, 2018, 12 pgs.

Sander, Chris, "Genetic Medicine and the Future of Health Care", Science, 287(5460), 2000, 1977-1978.

Sanger, et al., "Nucleotide Sequence of Bacteriophage Lambda DNA", Journal of Molecular Biology, vol. 162, No. 4, Dec. 25, 1982, 729-773.

Santalucia, J. et al., "The Thermodynamics of DNA Structural Motifs", Annu. Rev. Biophys. Biomol. Struct., 33, 2004, 415-440.

Santalucia, John J.R et al., "Improved Nearest-Neighbor Parameters for Predicting DNA Duplex Stability", Biochemistry, 35, 1996, 3555-3562.

Santalucia, Jr., J., "Physical Principles and Visual-OMP Software for Optimal PCR Design", Methods in Molecular Biology, vol. 402, 2007, 3-33.

Sasabe, Yutaka, "Genetic Diagnosis of Gametes and Embryos Resulting from ART", Japanese Journal of Fertility and Sterility, vol. 46, No. 1, 2001, 43-46.

Scarpa, A. et al., "Molecular Typing of Lung Adenocarcinoma on Cytological Samples Using a Multigene Next Generation Sequencing Panel", PLOS One, vol. 8, No. 11, Nov. 13, 2013, 6 pgs.

(56) References Cited

OTHER PUBLICATIONS

Schaaf, C. P. et al., "Copy Number and SNP Arrays In Clinical Diagnostics", Annu. Rev. Genomics Hum. Genet., vol. 12, 2011, 25-51.
Scheet, P. et al., "A Fast and Flexible Statistical Model for Large-Scale Population Genotype Data: Applications to Inferring Missing Genotypes and Haplotypic Phase", The American Journal of Human Genetics, vol. 78, Apr. 2006, 629-644.
Schmitt, M. W. et al., "Detection of ultra-rare mutations by next-generation sequencing", PNAS, vol. 109, No. 36, Sep. 4, 2012, 14508-14513.
Schoske, R et al., "Multiplex PCR Design Strategy used for the Simultaneous Amplification of 10 Y Chromosome Short Tandem Repeat (STR) Loci", Analytical and Bioanalytical Chemistry, vol. 375, 2003, 333-343.
Schoumans, J et al., "Detection of chromosomal imbalances in children with idiopathic mental retardation by array based comparative genomic hybridisation (array-CGH)", JMed Genet, 42, 2005, 699-705.
Schubert, "Picking out prenatal DNA", Nature Medicine, vol. 10, No. 785, Aug. 2004, 1 page.
Schwarzenbach, H. et al., "Cell~free nucleic acids as biomarkers in cancer patients", Nature Reviews: Cancer, vol. 11, Jun. 2011, 426-437.
Schwarzenbach, H. et al., "Detection and Characterization of Circulating Microsatellite-DNA in Blood of Patients with Breast Cancer", Ann. N.Y. Acad. Sci., vol. 1022, 2004, 25-32.
Schwarzenbach, H. et al., "Evaluation of cell-free tumour DNA and RNA in patients with breast cancer and benign breast disease", Molecular BioSystems, vol. 7, 2011, 2848-2854.
Sebat, Jonathan et al., "Strong Association of De Novo Copy Number Mutations with Autism", Science, 316, 2007, 445-449.
Sehnert, A. et al., "Optimal Detection of Fetal Chromosomal Abnormalities by Massively Parallel DNA Sequencing of Cell-Free Fetal DNA from Maternal Blood", Clinical Chemistry (papers in press), 57 (7), 2011, 8 pgs.
Seppo, A. et al., "Detection of circulating fetal cells utilizing automated microscopy: potential for noninvasive prenatal diagnosis of chromosomal aneuploidies", Prenatal Diagnosis, vol. 28, Jul. 22, 2008, 815-821.
Sermon, Karen et al., "Preimplantation genetic diagnosis", The Lancet, Lancet Limited. 363(9421), 2000, 1633-1641.
Servin, B et al., "MOM: A Program to Compute Fully Informative Genotype Frequencies in Complex Breeding Schemes", Journal of Heredity, vol. 93, No. 3, Jan. 1, 2002 (Jan. 1, 2002), pp. 227-228.
Sham, P. et al., "DNA Pooling: A Tool for Large-Scale Association Studies", Nature Reviews Genetics, vol. 3, Nov. 2002, 862-871.
Shapero, M. H. et al., "Mara: A Novel Approach for Highly Multiplexed Locus-specific SNP Genotyping Using High-density DNA Oligonucleotide Arrays", Nucleic Acids Research, vol. 32, No. 22, 2004, 1-9.
Sharples, et al., "Diagnostic Accuracy Of Coronary Angiography And Risk Factors For Post-heart-transplant Cardiac Allograft Vasculopathy", Transplantation, vol. 76, No. 4, Aug. 27, 2003, 679-682.
Shaw-Smith, et al., "Microarray Based Comparative Genomic Hybridisation (array-CGH) Detects Submicroscopic Chromosomal Deletions and Duplications in Patients with Learning Disability/Mental Retardation and Dysmorphic Features", J. Med. Genet., 41, 2004, 241-248.
Shen, et al., "High-quality DNA sequence capture of 524 disease candidate genes", High-quality DNA sequence capture of 524 disease candidate genes, Proceedings of the National Academy of Sciences, vol. 108, No. 16, Apr. 5, 2011 (Apr. 5, 2011), pp. 6549-6554.
Shen, R. et al., "High-throughput SNP genotyping on universal bead arrays", Mutation Research, vol. 573, Feb. 11, 2005, 70-82.
Shen, Zhiyong , "MPprimer: a program for reliable multiplex PCR primer design", BMC Bioinformatics 2010, 11:143, 1-7.
Shendure, J. et al., "Accurate Multiplex Polony Sequencing of an Evolved Bacterial Genome", Science, Nov. 30, 2007, 18-24.
Shendure, J. et al., "Next-generation DNA sequencing", Nature Biotechnology, vol. 26, No. 10, Oct. 2008, 1135-1145.
Sherlock, J et al., "Assessment of Diagnostic Quantitative Fluorescent Multiplex Polymerase Chain Reaction Assays Performed on Single Cells", Annals of Human Genetics, 62, 1, 1998, 9-23.
Shi, H. et al., "Melanoma whole-exome sequencing identifies V600E B-RAF amplification-mediated acquired B-RAF inhibitor resistance", Nature Communications, vol. 3, No. 724, Mar. 6, 2012, 8 pages.
Shinozaki, M. et al., "Utility of Circulating B-RAF DNA Mutation in Serum for Monitoring Melanoma Patients Receiving Biochemotherapy", Clin Cancer Res, vol. 13, No. 7, Apr. 1, 2007, 2068-2074.
Shiroguchi, K. et al., "Digital RNA sequencing minimizes sequence-dependent bias and amplification noise with optimized single-molecule barcodes", PNAS, vol. 109, No. 4, Jan. 24, 2012, 1347-1352.
Shokralla, S. et al., "Next-generation DNA barcoding: using next-generation sequencing to enhance and accelerate DNA barcode capture from single specimens", Molecular Ecology Resources, vol. 14, 2014, 892-901.
Short, N. J. et al., "Targeted next-generation sequencing of circulating cell-free DNA vs bone marrow in patients with acute myeloid leukemia", Blood Advances, vol. 4, No. 8, Apr. 23, 2020, 1670-1677.
Shyamala, Venkatakrishna et al., "Genome Walking by Single-Specific-Primer Polymerase Chain Reaction: SSP-PCR", Gene, vol. 84, 1989, pp. 1-8.
Siebert, P. D. et al., "An improved PCR method for walking in uncloned genomic DNA", Nucleic Acids Research, vol. 23, No. 6, 1995, 1087-1088.
Sigdel, T. et al., "Plasma Donor-Derived Cell-Free DNA Quantification by massively multiplex PCR Distinguishes Kidney Transplant Acute Rejection", Transplantation, vol. 102, No. 7S, Jul. 2018, S178-S179.
Sigdel, T. K. et al., "Optimizing Detection of Kidney Transplant Injury by Assessment of Donor-Derived Cell-Free DNA via Massively Multiplex PCR", Journal of Clinical Medicine, vol. 8, No. 19, Dec. 23, 2018, 17 pages.
Simpson, J. et al., "Fetal Cells in Maternal Blood: Overview and Historical Perspective", Annals New York Academy of Sciences, 731, 1994, 1-8.
Singh, Vinayak K. et al., "PCR Primer Design", Molecular Biology Today, vol. 2, 2001, pp. 27-32.
Sint, Daniela et al., "Advances in Multiplex PCR: Balancing Primer Efficiencies and Improving Detection Success", Methods in Ecology and Evolution, 3, 2012, 898-905.
Sivertsson, A. et al., "Pyrosequencing as an Alternative to Single-Strand Conformation Polymorphism Analysis for Detection of N-ras Mutations in Human Melanoma Metastases", Clinical Chemistry, vol. 48, No. 12, 2002, 2164-2170.
Slater, Howard et al., "High-Resolution Identification of Chromosomal Abnormalities Using Oligonucleotide Arrays Containing 116,204 SNPs", Am. J. Hum. Genet., 77, 5, 2005, 709-726.
Smith, et al., "Rapid Whole-genome Mutational Profiling using Next- generation Sequencing Technologies", Genome Research, vol. 18, Sep. 4, 2008, 1638-1642.
Smith, James F et al., "Cell-free Fetal DNA in Maternal Plasma", Neo Reviews, vol. 9, No. 8, Aug. 1, 2008, e332-e337.
Snijders, Antoine et al., "Assembly of Microarrays for Genome-Wide Measurement of DNA Copy Number", Nature Genetic, 29, 2001, 263-264.
Snyder, T. M. et al., "Universal noninvasive detection of solid organ transplant rejection", PNAS, vol. 108, No. 15, Apr. 12, 2011, 6229-6234.
Societies Related To Genetic Med, , "Guideline related to genetic examination", Japanese Society for Genetic Counseling, Japanese Society for Gene Diagnosis and Therapy, Japan Society of Obstetrics and Gynecology, 2003, 2-15.
Solexa, "Application Note: DNA Sequencing", 2006, 1-2.

(56) References Cited

OTHER PUBLICATIONS

Solomon, M. J. et al., "Formaldehyde-mediated DNA-protein crosslinking: A probe for in vivo chromatin structures", Proc. Natl. Acad. Sci. USA, vol. 82, 1985, 6470-6474.
Sorenson, G. D. et al., "Soluble Normal and Mutated DNA Sequences from Single-Copy Genes in Human Blood", Cancer Epdemiology, Biomarkers & Prevention, vol. 3, Jan./Feb. 1994, 67-71.
Sourceforge.net, "Primer3", 2009, 1 pg.
Sparks, A. et al., "Non-Invasive Prenatal Detection and Selective Analysis of Cell-Free DNA Obtained from Maternal Blood: Evaluation for Trisomy 21 and Trisomy 18", American Journal of Obstetrics & Gynecology 206, 2012, 319.e1-319.e9.
Sparks, Andrew B. et al., "Selective Analysis of Cell-Free DNA in Maternal Blood for Evaluation of Fetal Trisomy", Prenatal Diagnosis, 32, 2012, 1-7.
Spencer, K. et al., "Maternal serum levels of dimeric inhibin A in pregnancies affected by trisomy 21 in the first trimester", Prenatal Diagnosis, vol. 21, 2001, 441-444.
Spencer, K. et al., "Maternal serum levels of total activin-A in first-trimester trisomy 21 pregnancies", Prenatal Diagnosis, vol. 21, 2001, 270-273.
Spertini, D. et al., "Screening of Transgenic Plants by Amplification of Unknown Genomic DNA Flanking T-DNA", BioTechniques, vol. 27, Aug. 1999, 308-314.
Spes, et al., "Diagnostic And Prognostic Value Of Serial Dobutamine Stress Echocardiography For Noninvasive Assessment Of Cardiac Allograft Vasculopathy: A Comparison With Coronary Angiography And Intravascular Ultrasound", Circulation, vol. 100, No. 5, Aug. 3, 1999, 509-515.
Spindler, K.L. G. et al., "Cell-free DNA in healthy individuals, noncancerous disease and strong prognostic value in colorectal cancer", International Journal of Cancer, vol. 135, 2014, 2984-2991.
Spindler, K.-L. G. et al., "Cell-Free DNA in Metastatic Colorectal Cancer: A Systematic Review and Meta-Analysis", The Oncologist, vol. 22, 2017, 1049-1055.
Spiro, Alexander et al., "A Bead-Based Method for Multiplexed Identification and Quantitation of DNA Sequences Using Flow Cytometry", Applied and Environmental Microbiology, 66, 10, 2000, 4258-4265.
Spits, C et al., "Optimization and Evaluation of Single-Cell Whole Genome Multiple Displacement Amplification", Human Mutation, 27(5), 496-503, 2006.
Srinivasan, et al., "Noninvasive Detection of Fetal Subchromosome Abnormalities via Deep Sequencing of Maternal Plasma", The American Journal of Human Genetics 92, 167-176, Feb. 7, 2013.
Stephens, M. et al., "Accounting for Decay of Linkage Disequilibrium in Haplotype Inference and Missing-Data Imputation", Am. J. Hum. Genet., vol. 76, 2005, 449-462.
Stephens, Mathews. et al., "A Comparison of Bayesian Methods for Haplotype Reconstruction from Population Genotype Data", Am. J. Hum. Genet.,73, 2003, 1162-1169.
Stevens, Robert et al., "Ontology-Based Knowledge Representation for Bioinformatics", Briefings in Bioinformatics, 1, 4, 2000, 398-414.
Stewart, C. M. et al., "Circulating cell-free DNA for non-invasive cancer management", Cancer Genetics, vol. 228-229, 2018, 169-179.
Stewart, S. et al., "Revision of the 1990 Working Formulation for the Standardization of Nomenclature in the Diagnosis of Heart Rejection", The Journal of Heart and Lung Transplantation, vol. 24, No. 11, Nov. 2005, 1710-1720.
Steyerberg, E.W et al., "Application of Shrinkage Techniques in Logistic Regression Analysis: A Case Study", Statistica Neerlandica, 55(1), 2001, 76-88.
Stiller, et al., "Direct Multiplex Sequencing (DMPS)—A Novel Method For Targeted High-thoroughput Sequencing Of Ancient And Highly Degraded DNA", Genome Research, vol. 19, No. 10, Jul. 27, 2009, 1843-1848.
Stolerman, Elliot S. et al., "Haplotype structure of the ENPP1 Gene and Nominal Association of the K121Q missense single nucleotide polymorphism with glycemic traits in the Framingham Heart Study", Diabetes, vol. 57, Issue 7, Jul. 1, 2008, 1971-1977.
Stone, J. P. et al., "Ex Vivo Normothermic Perfusion Induces Donor-Derived Leukocyte Mobilization and Removal Prior to Renal Transplantation", Kidney Int Rep., vol. 1, No. 4, Aug. 6, 2016, 230-239.
Strom, C. et al., "Three births after preimplantation genetic diagnosis for cystic fibrosis with sequential first and second polar body analysis", American Journal of Obstetrics and Gynecology, 178 (6), 1998, 1298-1306.
Strom, Charles M. et al., "Neonatal Outcome of Preimplantation Genetic Diagnosis by Polar Body Removal: The First 109 Infants", Pediatrics, 106( 4), 2000, 650-653.
Stroun, Maurice et al., "Prehistory of the Notion of Circulating Nucleic Acids in Plasma/Serum (CNAPS): Birth of a Hypothesis", Ann. N.Y. Acad. Sci., 1075, 2006, 10-20.
Su, S.Y. et al., ""Inferring combined CNV/SNP haplotypes from genotype data"", Bioinformatics, vol. 26, No. 11,1, Jun. 1, 2010, 1437-1445.
Su, Z. et al., "A Platform for Rapid Detection of Multiple Oncogenic Mutations With Relevance to Targeted Therapy in Non-Small-Cell Lung Cancer", The Journal of Molecular Diagnostics,, vol. 13, No. 1, Jan. 2011, 74-84.
Sun, Guihua et al., "SNPs in human miRNA genes affect biogenesis and function", RNA, 15(9), 2009, 1640-1651.
Swarup, V. et al., "Circulating (cell-free) nucleic acids—A promising, non-invasive tool for early detection of several human diseases", FEBS Letters, vol. 581, 2007, 795-799.
Sweet-Kind Singer, J. A. et al., "Log-penalized linear regression", IEEE International Symposium on Information Theory, 2003. Proceedings, 2003, 286.
Swinkels, D. W. et al., "Effects of Blood-Processing Protocols on Cell-free DNA Quantification in Plasma", Clinical Chemistry, vol. 49, No. 3, 2003, 525-526.
Syvanen, A.C. , "Toward genome-wide SNP genotyping", Nature Genetics Supplement, vol. 37, Jun. 2005, S5-S10.
Taback, B. et al., "Quantification of Circulating DNA in the Plasma and Serum of Cancer Patients", Ann. N.Y. Acad. Sci, vol. 1022, 2004, 17-24.
Takala, et al., "A High-throughput Method for Quantifying Alleles and Haplotypes of The Malaria Vaccine Candidate Plasmodium Falciparum Merozoite Surface Protein-1 19 kDa", Malaria Journal, vol. 5:31, Apr. 20, 2006, 1-10.
Takano, T. et al., "Epidermal Growth Factor Receptor Gene Mutations and Increased Copy Numbers Predict Gefitinib Sensitivity in Patients With Recurrent Non-Small-Cell Lung Cancer", Journal of Clinical Oncology, vol. 23, No. 28, Oct. 1, 2005, 6829-6837.
Takara Biomedicals, "Competitive PCR Guide", Lit. # L0126, Aug. 1999, 9 pages.
Takashima, Y. et al., "Expansion-contraction of photoresponsive artificial muscle regulated by host-guest interactions", Nature Communications, vol. 3, No. 1270, Dec. 11, 2012, 8 pages.
Taliun, D. et al., "Efficient haplotype block recognition of very long and dense genetic sequences", BMC Bioinformatics, vol. 15 (10), 2014, 1-18.
Tamura, et al., "Sibling Incest and formulation of paternity probability: case report", Legal Medicine, 2000, vol. 2, p. 189-196.
Tang, et al., "Multiplex fluorescent PCR for noninvasive prenatal detection of fetal-derived paternally inherited diseases using circulatory fetal DNA in maternal plasma, Eur J Obstet Gynecol Reprod Biol, 2009, v. 144, No. 1, p. 35-39.
Tang, N. et al., "Detection of Fetal-Derived Paternally Inherited X-Chromosome Polymorphisms in Maternal Plasma", Clinical Chemistry, 45 (11), 1999, 2033-2035.
Tebbutt, S. J. et al., "Microarray genotyping resource to determine population stratification in genetic association studies of complex disease", BioTechniques, vol. 37, Dec. 2004, 977-985.
Ten Bosch, J. , "Keeping Up With the Next Generation Massively Parallel Sequencing in Clinical Diagnostics", Journal of Molecular Diagnostics, vol. 10, No. 6, 2008, 484-492.
Tewhey, R. et al., "Microdroplet-based PCR enrichment for large-scale targeted sequencing", Nature Biotechnology, vol. 27, No. 11, Nov. 2009, 1025-1031.

(56) References Cited

OTHER PUBLICATIONS

Tewhey, R. et al., "The importance of phase information for human genomics", Nature Reviews Genetics, vol. 12, No. 3, Mar. 1, 2011, 215-223.
Thavarajah, R. et al., "Chemical and physical basics of routine formaldehyde fixation", Journal of Oral and Maxillofacial Pathology, vol. 16, No. 3, 2012, 400-405.
The Bump Message Boards, The Bump (Panorama Test, attached), Jul. 1, 2013, 8 pages.
The International Hapmap Consort, "The International HapMap Project", Nature, vol. 426, Dec. 18, 2003, 789-796.
Thermofisher Scientific, "Ion AmpliSeq Cancer Hotspot Panel v2", Retrieved from the Internet: https://tools.thermofisher.com/content/sfs/brochures/Ion-AmpliSeq-Cancer-Hotspot-Panel-Flyer.pdf, 2015, 2 pages.
Thomas, M.R et al., "The Time of Appearance and Disappearance of Fetal DNA from the Maternal Circulation", Prenatal Diagnosis, 15, 1995, 641-646.
Thompson, J. C. et al., "Detection of Therapeutically Targetable Driver and Resistance Mutations in Lung Cancer Patients by Next-Generation Sequencing of Cell-Free Circulating Tumor DNA", Clin Cancer Res, vol. 22, No. 23, Dec. 1, 2016, 5772-5782.
Thornton, Brenda et al., "Real-time Pcr (qPCR) Primer Design Using Free Online Software", Biochemistry and Molecular Biology Education, vol. 39, 2011, pp. 145-154.
Tiersch, T. R. et al., "Reference Standards for Flow Cytometry and Application in Comparative Studies of Nuclear DNA Content", Cytometry, vol. 10, Mar. 21, 1989, 706-710.
Tong, et al., "Diagnostic Developments Involving Cell-free (Circulating) Nucleic Acids", Clinica Chimica Acta, vol. 363, No. (1-2), Aug. 26, 2005, 187-196.
Tong, Yu et al., "Noninvasive Prenatal Detection of Fetal Trisomy 18 by Epigenetic Allelic Ratio Analysis in Maternal Plasma: Theoretical and Empirical Considerations", Clinical Chemistry, 52(12), 2006, 2194-2202.
Tong, Yu K. et al., "Noninvasive Prenatal Detection of Trisomy 21 by Epigenetic-Genetic Chromosome-Dosage Approach", Clinical Chemistry, 56(1), 2010, 90-98.
Toshikazu, et al., "Estimation Of Haplotype Frequencies, Linkage-disequilibrium Measures, And Combination of Haplotype Copies in Each Pool By Use Of Pooled DNA Data", American Journal of Human Genetics, vol. 72, Jan. 17, 2003, 384-398.
Tounta, G et al., "Non-invasive prenatal diagnosis using cell-free fetal nucleic acids in maternal plasma: Progress overview beyond predictive and personalized diagnosis", EPMA Journal, vol. 2, Issue 2, 2011, 163-171.
Tounta, G. et al., "A Multiplex PCR for Non-invasive Fetal RHD Genotyping Using Cell-free Fetal DNA", in vivo, vol. 25, 2011, 411-418.
Treff, N. R. et al., "Single Cell Whole Genome Amplification Technique Significantly Impacts the Accuracy and Precision of Microarray Based 23 Chromosome Aneuploidy Screening", Poster Presentations Preimplantation Genetic Diagnosis, vol. 88, Supplement 1, Sep. 1, 2007, S231.
Troeger, C. et al., "Approximately Half of The Erythroblasts in Maternal Blood are of Fetal Origin", Molecular Human Reproduction, vol. 5, No. 12, Dec. 1, 1999, 1162-1165.
Troutt, et al., "Ligation-anchored PCR: A Simple Amplification Technique with Single-sided Specificity", Proceedings of the National Academy of Sciences, vol. 89, Oct. 1992, 9823-9825.
Troyanskaya, Olga G. et al., "A Bayesian Framework for Combining Heterogeneous Data Sources for Gene Function Prediction (in *Saccharomyces cerevisiae*)", PNAS, 100(14), 2003, 8348-8353.
Tsang, Jason C. et al., "Circulating Nucleic Acids in Plasma/Serum", Pathology, vol. 39, No. 2, Apr. 1, 2007, 197-207.
Tsangaris, G. T. et al., "Proteomic analysis of amniotic fluid in pregnancies with Down syndrome", Proteomics, vol. 6, 2006, 4410-4419.
Tsui, N. B. et al., "Systematic micro-array based identification of placental mRNA in maternal plasma: towards non-invasive prenatal gene expression profiling", J. Med. Genet, vol. 41, 2004, 461-467.
Tsui, Nancy B.Y et al., "Non-Invasive Prenatal Detection of Fetal Trisomy 18 by RNA-SNP Allelic Ratio Analysis Using Maternal Plasma SERPINB2 mRNA: A Feasibility Study", Prenatal Diagnosis, 29, 2009, 1031-1037.
Tu, J. et al., "Pair-barcode high-throughput sequencing for large-scale multiplexed sample analysis", BMC Genomics, vol. 13, No. 43, Jan. 25, 2012, 1-9.
Tufan, N L. et al., "Analysis of Cell-Free Fetal DNA from Maternal Plasma and Serum Using a Conventional Multiplex PCR: Factors Influencing Success", The Turkish Journal of Medical Sciences, vol. 35, 2005, 85-92.
Turner, E. et al., "Massively Parallel Exon Capture and Library-Free Resequencing Across 16 Genomes", Nature Methods, 6 (5), 2009, 315-316.
Tuzcu, et al., "Intravascular Ultrasound Evidence Of Angiographically Silent Progression In Coronary Atherosclerosis Predicts Long-term Morbidity And Mortality After Cardiac Transplantation", The American Journal of Cardiology, vol. 45, No. 9, May 3, 2005, 1538-1542.
Tynan, J. A. et al., "Restriction Enzyme-Mediated Enhanced Detection of Circulating Cell-Free Fetal DNA in Maternal Plasma", The Journal of Molecular Diagnostics, vol. 13, No. 4, Jul. 2011, 382-389.
Tzimagiorgis, G. et al., "Recovering circulating extracellular or cell-free RNA from bodily fluids", Cancer Epidemiology, vol. 35, 2011, 580-589.
Umetani, N. et al., "Increased Integrity of Free Circulating DNA in Sera of Patients with Colorectal or Periampullary Cancer: Direct Quantitative PCR for ALU Repeats", Clinical Chemistry, vol. 52, No. 6, 2006, 1062-1069.
Urbaniak, S. J. et al., "RhD haemolytic disease of the fetus and the newborn", Blood Reviews, vol. 14, 2000, 44-61.
Urbanova, M. et al., "Circulating Nucleic Acids as a New Diagnostic Tool", Cellular & Molecular Biology Letters, vol. 15, 2010, 242-259.
Vallone, P. M. et al., "A multiplex allele-specific primer extension assay for forensically informative SNPs distributed throughout the mitochondrial genome", Int J Legal Medicine, vol. 118, Feb. 4, 2004, 147-157.
Vallone, Peter, "AutoDimer: a Screening Tool for Primer-Dimer and Hairpin Structures", Bio Techniques, 37, 2004, 226-231.
Vallone, Peter M. et al., "Demonstration of Rapid Multiplex PCR Amplification Involving 16 Genetic Loci", Forensic Science International: Genetics, vol. 3, 2008, pp. 42-45.
Van Den Oever, J. M. et al., "Single Molecule Sequencing of Free DNA from Maternal Plasma for Noninvasive Trisomy 21 Detection", Clinical Chemistry, vol. 58, No. 4, 2012, 699-706.
Van Uitert, I. et al., "The influence of different membrane components on the electrical stability of bilayer lipid membranes", Biochimica et Biophysica Acta, vol. 1798, 2010, 21-31.
Vanneste, Marion et al., "Functional Genomic Screening Independently Identifies CUL3 as a Mediator of Vemurafenib Resistance via Src-RAC1 Signaling Axis", Frontiers in Oncology, vol. 10, 2020, 16 pages.
Varley, Katherine Elena et al., "Nested Patch PCR Enables Highly Multiplexed Mutation Discovery in Candidate Genes", Genome Res., 18(11), 2008, 1844-1850.
Verlaan, et al., "Allele-specific Chromatin Remodeling in The ZPBP22/GSDMB/ORMDL3 Locus Associated with the Risk of Asthma And Autoimmune Disease", The American Journal of Human Genetics, vol. 85, No. 3, Sep. 11, 2009, 377-393.
Verlaan, et al., "Targeted Screening of Cis-Regulatory Variation in Human Haplotypes", Genome Research, vol. 19, No. 1, Jan. 1, 2009, 118-127.
Verlinsky, Y. et al., "Over a Decade of Experience with Preimplantation Genetic Diagnosis", Fertility and Sterility, 82 (2), 2004, 302-303.
Vlaminck, I. D. et al., "Circulating Cell-Free DNA Enables Non-invasive Diagnosis of Heart Transplant Rejection", Sci Transl Med., vol. 6, No. 241, Jun. 18, 2018, 26 pages.

(56) References Cited

OTHER PUBLICATIONS

Voelkerding, et al., "Next-generation Sequencing: From Basic Research To Diagnostics", Clinical Chemistry, vol. 55, No. 4, Apr. 1, 2009, 641-658.
Vogelstein, B. et al., "Digital PCR", Proc. Natl. Acad. Sci. USA, vol. 96, Aug. 1999, 9236-9241.
Von Ahsen, Nicolas et al., "Oligonucleotide Melting Temperatures under PCR Conditions: Nearest-Neighbor Corrections for Mg2+, Deoxynucleotide Triphosphate, and Dimethyl Sulfoxide Concentrations with Comparison to Alternative Empirical Formulas", Clinical Chemistry, vol. 47, 2001, pp. 1956-1961.
Von Eggeling, F. et al., "Applications of Random PCR", Cellular and Molecular Biology, vol. 41, No. 5, 1995, 653-670.
Wagner, Jasenka et al., "Non-Invasive Prenatal Paternity Testing from Maternal Blood", Int. J. Legal Med., 123, 2009, 75-79.
Wang, D. G. et al., "Large-Scale Identification, Mapping, and Genotyping of Single-Nucleotide Polymorphisms in the Human Genome", Science, vol. 280, May 15, 1998, 1077-1082.
Wang, Eric et al., "Gestational Age and Maternal Weight Effects on Fetal Cell-Free DNA in Maternal Plasma", Prenatal Diagnosis, 33, 2013, 662-666.
Wang, Hui-Yun et al., "A genotyping system capable of simultaneously analyzing >1000 single nucleotide polymorphisms in a haploid genome", Genome Res., 15, 2005, 276-283.
Wang, J. et al., "Genome-wide Single-Cell Analysis of Recombination Activity and De Novo Mutation Rates in Human Sperm", Cell, vol. 150, Jul. 20, 2012, 402-412.
Wang, S. et al., "Potential Clinical Significance of a Plasma-Based KRAS Mutation Analysis in Patients with Advanced Non-Small Cell Lung Cancer", Clin Cancer Res, vol. 16, No. 4, Feb. 15, 2010, 1324-1330.
Wang, T.L. et al., "Digital karyotyping", PNAS, vol. 99, No. 25, Dec. 10, 2002, 16156-16161.
Wang, W.-P. et al., "Multiplex single nucleotide polymorphism genotyping by adapter ligation-mediated allele-specific amplification", Analytical Biochemistry, vol. 355, May 5, 2006, 240-248.
Wang, Yuker et al., "Allele quantification using molecular inversion probes (MIP)", Nucleic Acids Research, vol. 33, No. 21, Nov. 28, 2005, 14 pgs.
Wapner, R. et al., "Chromosomal Microarray Versus Karyotyping for Prenatal Diagnosis", The New England Journal of Medicine, 367 (23), 2012, 2175-2184.
Wapner, R. et al., "First-Trimester Screening for Trisomies 21 and 18", The New England Journal of Medicine, vol. 349, No. 15, Oct. 9, 2003, 1405-1413.
Wapner, R. J. et al., "Expanding the scope of noninvasive prenatal testing: detection of fetal microdeletion syndromes", American Journal of Obstetrics & Gynecology, vol. 212, Dec. 17, 2014, 1.e1-1.e9.
Wartell, Roger M. et al., "Thermal Denaturation of DNA Molecules: A Comparison of Theory with Experiment", Physics Reports, vol. 126, 1985, pp. 67-107.
Wasson, Jon et al., "Assessing Allele Frequencies of Single Nucleotide Polymorphisms in DNA Pools by Pyrosequencing Technology", BioTechniques, vol. 32, No. 5, May 1, 2002, 1144-1152.
Watkins, N. et al., "Thermodynamic contributions of single internal rA • dA, rC • dC, rG • dG and rU • dT mismatches in RNA/DNA duplexes", Nucleic Acids Research, 9 (5),, 2010, 1894-1902.
Watt, Heather L. , "Sex Diagnosis of Preimplantation Porcine Embryos through PCR Amplification of The Sry Gene", Sex Diagnosis of Preimplantation Porcine Embryos Through PCR Amplification of the SRY Gene (1998) ("Watt (1998)"), 1998, 151 pages.
Wei, C. et al., "Detection and Quantification by Homogeneous PCR of Cell-free Fetal DNA in Maternal Plasma", Clinical Chemistry, vol. 47, No. 2, 2001, 336-338.
Wei, Ting et al., "Novel Approaches to Mitigate Primer Interaction and Eliminate Inhibitors in Multiplex PCR, Demonstrated Using an Assay for Detection of three Strawberry Viruses", Journal of Virological Methods, vol. 151, 2008, pp. 132-139.
Weiss, C. A. , "Chapter 8: Confidence Intervals for One Population Mean", Introductory Statistics, Sixth Edition, 2002, 340-381.
Wellnhofer, et al., "Angiographic Assessment Of Cardiac Allograft Vasculopathy: Results Of A Consensus Conference Of The Task Force For Thoracic Organ Transplantation of the German Cardiac Society", Transplant International, vol. 23, No. 11, Aug. 19, 2010, 1094-1104.
Wells, D , "Microarray for Analysis and Diagnosis of Human Embryos", 12th International Congress on Prenatal Diagnosis and Therapy, Budapest, Hungary, 2004, 9-17.
Wells, Dagan , "Advances in Preimplantation Genetic Diagnosis", European Journal of Obstetrics and Gynecology and Reproductive Biology, 115S, 2004, S97-S101.
Wells, Dagan , "Detailed Chromosomal and Molecular Genetic Analysis of Single Cells by Whole Genome Amplification and Comparative Genomic Hybridisation", Nucleic Acids Research, 27, 4, 1999, 1214-1218.
Wen, Daxing et al., "Universal Multiples PCR: A Novel Method of Simultaneous Amplification of Multiple DNA Fragments", Plant Methods, 8(32), Null, 2012, 1-9.
What To Expect Message Boards, What To Expect (Weird Harmony results), May 1, 2015, 7 pages.
Widlak, P. et al., "Cleavage Preferences of the Apoptotic Endonuclease DFF 40 (Caspase~activated DNase or Nuclease) on Naked DNA and Chromatin Substrates", The Journal of Biological Chemistry, vol. 275, No. 11, Mar. 17, 2000, 8228-8232.
Wiedmann, Ralph T. et al., "SNP Discovery in Swine by Reduced Representation and High Throughput Pyrosequencing", BMC Genetics, vol. 9, Article No. 81, Dec. 4, 2008, 1-7.
Wikipedia, "Buffy coat", Retrieved from "https://en.wikipedia.orgJw/index.php?title=Buffy_coat&oldid=900992886 ", Jun. 9, 2019, 2 pgs.
Wikipedia, "Maximum a posteriori estimation", https://en.wikipedia.org/w/index.php?title=Maximum_a_posteriori_estimat ion&oldid=26878808, [retrieved on 2017-08-01], Oct. 30, 2005, 2 pages.
Wikipedia, "Stimulant", 17 pages.
Wilkening, Stefan et al., "Determination of Allele Frequency In Pooled DNA: Comparison of Three PCR-based Methods", Bio Techniques, vol. 39, No. 6, May 30, 2005, 853-857.
Wilkinson, Sarah T et al., "Decreased MHC Class II Expression in Diffuse Large B-Cell Lymphoma does not Correlate with CPG Methylation of Ciita Promoters III and IV", Leuk Lymphoma, vol. 50, 2009, pp. 1875-1878.
Wilton, et al., "Birth of a Healthy Infant After Preimplantation Confirmation of Euploidy by Comparative Genomic Hybridization", N. Engl. J. Med., 345(21), 2001, 1537-1541.
Wilton, L. , "Preimplantation Genetic Diagnosis and Chromosome Analysis of Blastomeres Using Comparative Genomic Hybridization", Human Reproduction Update, 11 (1), 2005, 33-41.
Winsor, E. J. et al., "Maternal Cell Contamination in Uncultured Amniotic Fluid", Prenatal Diagnosis, vol. 16, 1996, 49-54.
Witherspoon, David J. et al., "Mobile Element Scanning (Me-scan) by Targeted High-throughput Sequencing", BMC Genomics, vol. 410, 2010, 15 pages.
Wittwer, C. T. et al., "Real-Time Multiplex PCR Assays", Methods, vol. 25, 2001, 430-448.
Wong, K. H. et al., "Multiplex Illumina Sequencing Using DNA Barcoding", Current Protocols in Molecular Biology, vol. 101, Jan. 2013, 7.11.1-7.11.11.
Wong, K. K. et al., "Allelic imbalance analysis by high-density single nucleotide polymorphic allele (SNP) array with whole genome amplified DNA", Nucleic Acids Research, vol. 32, No. 9, May 17, 2004, 8 pages.
Wright, C. et al., "The use of cell-free fetal nucleic acids in maternal blood for non-invasive prenatal diagnosis", Human Reproduction Update, vol. 15, No. 1, 2009, 139-151.
Wright, C. F. et al., "Cell-free fetal DNA and RNA in maternal blood: implications for safer antenatal testing", BMJ, vol. 39, Jul. 18, 2009, 161-165.
Wright, Caroline et al., "Cell-free Fetal Nucleic Acids for Noninvasive Prenatal Diagnosis", PHG Foundation, Jan. 1, 2009, 1-64.

(56) References Cited

OTHER PUBLICATIONS

Wu, T.L. et al., "Cell-free DNA: measurement in various carcinomas and establishment of normal reference range", Clinica Chimica Acta, vol. 321, 2002, 77-87.

Wu, Y. Y. et al., "Rapid and/or high-throughput genotyping for human red blood cell, platelet and leukocyte antigens, and forensic applications", Clinica Chimica Acta, vol. 363, 2006, 165-176.

Xia, et al., "Simultaneous Quantitative Assessment Of Circulating Cell-free Mitochondrial And Nuclear DNA By Multiplex Real-time PCR", Genetics and Molecular Biology, vol. 32, No. 1, Mar. 1, 2009, 20-24.

Xia, Tianbing et al., "Thermodynamic Parameters for an Expanded Nearest-Neighbor Model for Formation of RNA Duplexes with Watson-Crick Base Pairs", Biochemistry, 37, 1998, 14719-14735.

Xian, et al., "Advances On Circulating Fetal DNA In Maternal Plasma", Chinese Medical Journal, vol. 120, No. 14, Jul. 2, 2007, 1256-1259.

Xie, et al., "CNV-SEQ, A New Method to Detect Copy Number Variation Using Highthroughput Sequencing", BMC Bioinformatics, vol. 10:80, Mar. 6, 2009, 1-9.

Xu, N. et al., "A Mutation in the Fibroblast Growth Factor Receptor 1 Gene Causes Fully Penetrant Normosmic Isolated Hypogonadotropic Hypogonadism", The Journal of Clinical Endocrinology & Metabolism, vol. 92, No. 3, 2007, 1155-1158.

Xu, S. et al., "Circulating tumor DNA identified by targeted sequencing in advanced-stage non-small cell lung cancer patients", Cancer Letters, vol. 370, 2016, 324-331.

Xu, W. et al., "A Novel Universal Primer-Multiplex-PCR Method with Sequencing Gel Electrophoresis Analysis", PLOS One, vol. 7, No. 1, Jan. 17, 2012, 10 pgs.

Xue, et al., "Optimizing The Yield And Utility Of Circulating Cell-free DNA From Plasma And Serum", Clinica Chimica Acta, vol. 404, No. 2, Jun. 27, 2009, 100-104.

Yamada, T. et al., "Detection of K-ras Gene Mutations in Plasma DNA of Patients with Pancreatic Adenocarcinoma: Correlation with Clinicopathological Features", Clinical Cancer Research, vol. 4, Jun. 1998, 1527-1532.

Yamada, T. et al., "PrimerStation: a highly specific multiplex genomic PCR primer design server for the human genome", Nucleic Acids Research, vol. 34, 2006, W665-W669.

Yang, Lin et al., "64-MDCT Coronary Angiography of Patients With Atrial Fibrillation: Influence of Heart Rate On Image Quality and Efficacy In Evalution of Coronary Artery Disease", AJR, vol. 193, No. 3, Sep. 1, 2009, 795-801.

Yaron, Y., "The implications of non-invasive prenatal testing failures: a review of an under-discussed phenomenon", Prenatal Diagnosis, vol. 36, 2016, 391-396.

Yeh, Iwei et al., "Knowledge Acquisition, Consistency Checking and Concurrency Control for Gene Ontology (GO)", Bioinformatics, 19, 2, 2003, 241-248.

Yijen, et al., "Noninvasive Evaluation Of Cardiac Allograft Rejection By Cellular And Functional Cardiac Magnetic Resonance", JACC: Cardiovacular Imaging, vol. 2, No. 6, Jun. 1, 2009, 731-741.

Yilmaz, A. et al., "Comparative Evaluation of Left and Right Ventricular Endomyocardial Biopsy", Circulation, vol. 122, No. 9, Aug. 31, 2010, 900-909.

You, Frank M. et al., "BatchPrimer3: A high throughput web application for PCR and sequencing primer design", BMC Bioinformatics, Biomed Central, London, GB, vol. 9, No. 1, May 29, 2008 (May 29, 2008), p. 253.

Yuan, X. et al., "Probability Theory-based SNP Association Study Method for Identifying Susceptibility Loci and Genetic Disease Models in Human Case-Control Data", IEEE Trans Nanobioscience, vol. 9, No. 4, Dec. 2010, 232-241.

Yuanxin, Yan et al., "T-linker-specific Ligation PCR (T-linker Pcr): An Advanced PCR Technique for Chromosome Walking or for Isolation of Tagged DNA Ends", Nucleic Acids Research, vol. 31, No. 12, e68, 2003, 7 pages.

Yung, T. K. et al., "Single-Molecule Detection of Epidermal Growth Factor Receptor Mutations in Plasma by Microfluidics Digital PCR in Non-Small Cell Lung Cancer Patients", Clinical Cancer Research, vol. 15, Mar. 10, 2009, 2076-2084.

Zachariah, R. et al., "Circulating cell-free DNA as a potential biomarker for minimal and mild endometriosis", Reproductive BioMedicine Online, vol. 18, No. 3, Jan. 27, 2009, 4007-411.

Zhang, et al., "Diagnosis of Acute Rejection by Analysis of Urinary DNA of Donor Origin in Renal Transplant Recipients", Transplantation Proceedings, vol. 33, No. 1-2, Feb. 2001, 380-381.

Zhang, et al., "Use Of PCR And PCR-SSP For Detection Of Urinary Donor-Origin Dna In Renal Transplant Recipients With Acute Rejection", Chinese Medical Journal, vol. 116, No. 2, Feb. 2003, 191-194.

Zhang, J. et al., "Presence of Donor-and Recipient-derived DNA in Cell-free Urine Samples of Renal Transplantation Recipients: Urinary DNA Chimerism", Clinical Chemistry, vol. 45, No. 10, 1999, 1741-1746.

Zhang, Kun et al., "Digital RNA Alleotyping Reveals Tissue-specific and Allele-specific Gene Expression in Human", Nature Methods, vol. 6, No. 8, Jul. 20, 2009, 613-618.

Zhang, L. et al., "Whole genome amplification from a single cell: Implications for genetic analysis", Proc. Nat'l. Acad. Sci. USA, vol. 89, Jul. 1992, 5847-5851.

Zhang, Rui et al., "Quantifying RNA allelic ratios by microfluidic multiplex PCR and sequencing", Nature Methods, 11(1), 2014, 51-56.

Zhao, et al., "Urinary Thromboxane B2 In Cardiac Transplant Patients As A Screening Method Of Rejection", Prostaglandins, vol. 54, No. 6, Dec. 1, 1997, 881-889.

Zhao, Xiaojun et al., "An Integrated View of Copy Number and Allelic Alterations in the Cancer Genome Using Single Nucleotide Polymorphism Arrays", Cancer Research, 64, 2004, 3060-3071.

Zheng, S. et al., "Whole Genome Amplification Increases the Efficiency and Validity of Buccal Cell Genotyping in Pediatric Populations1", Cancer Epidemiology, Biomarkers & Prevention, vol. 10, Jun. 2001, 697-700.

Zheng, Z et al., "Anchored Multiplex PCR for Targeted Next-generation Sequencing", Nature Medicine, vol. 20, No. 12, Dec. 2014, 1479-1486.

Zhong, X Y. et al., "Detection of Fetal Rhesus D And Sex Using Fetal DNA from Maternal Plasma by Multiplex Polymerase Chain Reaction", British Journal of Obstetrics and Gynaecology, vol. 107, Jun. 2000, 766-769.

Zhong, X. et al., "Risk free simultaneous prenatal identification of fetal Rhesus D status and sex by multiplex real-time PCR using cell free fetal DNA in maternal plasma", Swiss Medical Weekly, vol. 131, Mar. 2001, 70-74.

Zhong, Xiao Y. et al., "Cell-free DNA In Urine: A Marker for Kidney Graft Rejection, but Not for Prenatal Diagnosis ?", Annals of the New York Academy of Sciences, vol. 945, Sep. 1, 2001, 250-257.

Zhou, et al., "Pyrosequencing, A High-throughput Method For Detecting Single Nucleotide Polymorphisms In The Dihydrofolate Reductase And Dihydropteroate Synthetase Genes Of Plasmodiym Falciparum", Journal of Clinical Microbiology, vol. 44, No. 11, Nov. 1, 2006, 3900-3910.

Zhou, W. et al., "Counting Alleles Reveals a Connection Between Chromosome 18q Loss and Vascular Invasion", Nature Biotechnology, 19, 2001, 78-81.

Zhou, W. et al., "Counting alleles to predict recurrence of early-stage colorectal cancers", The Lancet, vol. 359, Jan. 19, 2002, 219-225.

Zimmer, et al., "Transplant Coronary Artery Disease", JACC: Cardiovascular Interventions, vol. 3, No. 4, Apr. 1, 2010, 367-377.

Zimmermann, et al., "Noninvasive Prenatal Aneuploidy Testing of Chromosomes 13, 18, 21 X, and Y, Using targeted Sequencing of Polymorphic Loci", Prenatal Diagnosis, 32, 2012, 1-9.

Zimmermann, B., "Declaration Under 37 CFR 1.32", filed in U.S. Appl. No. 14/171,587, filed Feb. 3, 2014, 4 pgs.

Zimmermann, B. et al., "Digital PCR: a powerful new tool for noninvasive prenatal diagnosis?", Prenatal Diagnosis, vol. 28, Nov. 10, 2008, 1087-1093.

(56) References Cited

OTHER PUBLICATIONS

Zimmermann, B., "Noninvasive prenatal aneuploidy testing of chromosomes 13, 18, 21, X, and Y, using targeted sequencing of polymorphic loci, Supplemental Information", Prenatal Diagnosis, vol. 32, 2012, 7 pages.

Zimmermann, B. et al., "Novel Real-Time Quantitative PCR Test for Trisomy 21", Clinical Chemistry, vol. 48, No. 2, 2002, 362-363.

Zimmermann, B. et al., "Optimized Real-Time Quantitative PCR Measurement of Male Fetal DNA in Maternal Plasma", Clinical Chemistry, vol. 51, No. 9, 2005, 1598-1604.

Zimmermann, B. et al., "Real-Time Quantitative Polymerase Chain Reaction Measurement of Male Fetal DNA in Maternal Plasma", Methods in Molecular Medicine, vol. 132, 2007, 43-49.

Zimmermann, B. et al., "Use of Real-Time Polymerase Chain Reaction for the Detection of Fetal Aneuploidies", Methods in Molecular Biology, vol. 336, Feb. 2006, 83-100.

Zlotogora, J. , "Penetrance and expressivity in the molecular age", Genetics in Medicine, vol. 5, No. 5, 2003, 347-352.

\* cited by examiner

METHODS FOR DETECTING IMMUNE CELL DNA AND MONITORING IMMUNE SYSTEM

CROSS-REFERENCE TO RELATED APPLICATIONS

This application claims the benefit of U.S. Provisional Application Ser. No. 62/857,966, filed Jun. 6, 2019, which is hereby incorporated by reference in its entirety.

SEQUENCE LISTING

The instant application contains a Sequence Listing which has been submitted electronically in ASCII format and is hereby incorporated by reference in its entirety. Said ASCII copy, created on May 29, 2020, is named N_031_WO_01_SL.txt and is 25,064 bytes in size.

BACKGROUND

The adaptive immune system generates highly specific immune responses against invading pathogens and plays an important role in maintaining the balance with commensal microorganisms. It also provides protection against cancer and can prevent future infections through the formation of memory, the underlying principle of vaccination strategies.

Adaptive immune responses are mediated by B and T cells that express unique antigen receptor with defined specificity to antigens. The unique capacity of immunoglobulin genes encoding B cell receptors (BCRs in B cells) and T-cell receptors (TCRs in T cells) to recognize antigens is a result of recombination of the variable (V), diversity (D), and joining (J) gene segments, as well as subsequent somatic hypermutation events during early differentiation and selection processes of B and T cells. The recombination process occurs separately for both subunit chains of each receptor and subsequent heterodimeric pairing creates still greater combinatorial diversity.

The antigen-reactivity of T cells is limited to recognizing short linear peptide antigens presented by either class I (for CD8 cytotoxic T cells) or class II (for CD4 helper T cells) major histocompatibility complex molecules (MHC). In contrast, B cells can recognize a wide variety of molecules, including larger 3-dimensional proteins and small molecules.

B cells can inhibit tumor development by producing antibodies that attack cancer cells or oncogenic viruses, such as human papillomavirus (HPV). Alternatively, B cells may release immunosuppressive cytokines that stifle an antitumor response. On the other hand, B cells may mutate into cancer cells themselves to form for example chronic lymphocytic leukemia (CLL) or B-cell lymphoma.

T cells come in two major categories. The CD8 positive T cells are also called killer T cells because they directly kill infected cells. The CD4 positive helper T cells stimulate B cells to produce antibodies and help developing killer T cells. T cells can be activated against cancer cells that otherwise evade being recognized by T cells by so called immunotherapy drugs that have been approved for treating lung cancer, melanoma, and other cancers. Technology to engineer T-cells into attacking specific cancer cells has also been developed. So called chimeric antigen receptor (CAR) T cells can be made by genetically modifying a T cell receptor to recognize a specific protein on the tumor cells. These engineered CAR T cells can be produced in large amounts in laboratories and infused into the patient's body. On the other hand, T cells can also mutate into various forms of cancer, and pathological forms of T cells may attack healthy cells of the body to cause autoimmune diseases.

Since B and T cells are both critical to the body's defense against disease and infection on the one hand and can transformed into pathological cells causing diseases on the other hand, there is a great medical need for methods of detecting and monitoring the quantity and diversity of B and T cells.

SUMMARY OF THE INVENTION

In one aspect, this disclosure relates to a method of detecting or monitoring immune cells in a subject, comprising: performing a multiplex amplification reaction on nucleic acids isolated from a biological sample of the subject to generate a set of amplicons, wherein each of the set of amplicons comprises recombined V(D)J gene segments at a gene locus of interest, wherein the multiplex amplification reaction is capable of amplifying at least about 50% of all possible V(D)J recombinations at the gene locus of interest; and sequencing the set of amplicons, wherein sequences of the recombined V(D)J gene segments are indicative of presence of an immune cell in the biological sample.

In some embodiments, the gene locus of interest is the B cell receptor (BCR) gene locus or the T cell receptor (TCR) gene locus.

In some embodiments, the multiplex amplification reaction is capable of amplifying at least about 70% of all V(D)J recombinations at a gene locus of interest in the immune cell. In some embodiments, the multiplex amplification reaction is capable of amplifying at least about 80% of all V(D)J recombinations at a gene locus of interest in the immune cell. In some embodiments, the multiplex amplification reaction is capable of amplifying at least about 85% of all V(D)J recombinations at a gene locus of interest in the immune cell. In some embodiments, the multiplex amplification reaction is capable of amplifying at least about 90% of all V(D)J recombinations at a gene locus of interest in the immune cell. In some embodiments, the multiplex amplification reaction is capable of amplifying at least about 95% of all V(D)J recombinations at a gene locus of interest in the immune cell. In some embodiments, the multiplex amplification reaction is capable of amplifying at least about 98% all V(D)J recombinations at a gene locus of interest in the immune cell. In some embodiments, the multiplex amplification reaction is capable of amplifying at least about 100% all V(D)J recombinations at a gene locus of interest in the immune cell.

In some embodiments, the method comprises collecting and sequencing samples from the subject longitudinally.

In some embodiments, the multiplex amplification reaction is performed by using a first set of primers covering a set of V genes of the immune cell and a second set of primers covering a set of J genes of the immune cell. In some embodiments, the first set of primers targets conserved region within the set of V genes, and wherein the second set of primers targets conserved region within the set of J genes. In some embodiments, the first and second sets of primers do not hybridize to sequences located outside of the rearranged V(D)J genes.

In some embodiments, the biological sample comprises a peripheral blood mononuclear cell (PBMCs) sample, a plasma sample, or a combination thereof.

In some embodiments, the nucleic acids isolated from the biological sample comprises cell-free DNA (cfDNA).

In some embodiments, the nucleic acids isolated from the biological sample comprises cellular DNA obtained from PBMCs.

In some embodiments, the amount of immune cells in the biological sample is less than 1.0%, less than 0.5%, or less than 0.1% of the PBMCs in the sample.

In some embodiments, the method is capable of detecting 100 or less V(D)J recombinations per milliliter of the plasma sample. In some embodiments, the method is capable of detecting 50 or less V(D)J recombinations per milliliter of the plasma sample. In some embodiments, the method is capable of detecting 20 or less V(D)J recombinations per milliliter of the plasma sample. In some embodiments, the method is capable of detecting 10 or less V(D)J recombinations per milliliter of the plasma sample. In some embodiments, the method is capable of detecting 5 V(D)J or less recombinations per milliliter of the biological sample. In some embodiments, the method is capable of detecting 2 or less V(D)J recombinations per milliliter of the plasma sample. In some embodiments, the method is capable of detecting a single V(D)J recombination per milliliter of the biological sample.

In some embodiments, the nucleic acids isolated from the biological sample are tagged and amplified before being used as input in the multiplex PCR reaction to detect recombinant events. In some embodiments, adapters with MITs are ligated to extracted nucleic acids and subject to amplification using universal primers.

In some embodiments, the subject is administered a cytotoxic treatment of a disease, wherein the cytotoxic treatment leads to depletion of the immune cells.

In some embodiments, the disease is a malignancy, and the cytotoxic treatment comprises a chemotherapy, a radiotherapy, and/or an immune cell targeted therapy.

In some embodiments, the disease is an autoimmune disease, and the cytotoxic treatment comprise an immunosuppressive therapy.

In some embodiments, the subject suffers from a disease, disorder, or condition that depletes immune cells.

In some embodiments, the disease or condition is a malignancy or an immunodeficiency disorder.

In some embodiments, the method further comprises measuring minimal residual disease in the subject to monitor treatment response or relapse of the disease. In some embodiments, the disease being monitored is a blood cancer such as leukemia, lymphoma, or myeloma.

In some embodiments, the subject has been administered a therapeutic compositing comprising immune cells, and wherein the method further comprises analyzing V(D)J nucleic acid segment sequences to determine the presence of the administered immune cells.

In some embodiments, the immune cell comprises a B cell, a transplanted B cell, a T cell, a transplanted T cell, a CAR-T cell, an engineered B cell, and engineered T cell, a circulating bone marrow B cell, a circulating tumor B cell, a circulating tumor T cell, and/or a tumor infiltrating lymphocyte (TIL).

In some embodiments, the methods disclosed herein further comprise analyzing the V(D)J nucleic acid segment sequences to determine a diversity of the V(D)J nucleic acid segments in the sample obtained from the subject and a control sample, wherein the diversity of the V(D)J nucleic acid segments is indicative of an immune receptor repertoire.

In some embodiments, the immune cell is a B cell, and the diversity of the V(D)J nucleic acid segment sequences is indicative of the diversity of a B cell receptor (BCR)-repertoire.

In some embodiments, the sample is a single isolated B cell or a clonally expanded single isolated B cell, and the diversity of the V(D)J nucleic acid segment sequences is indicative of the diversity of the BCR-repertoire of the single isolated B cell or the clonally expanded single isolated B cell.

In some embodiments, the immune cell is a T cell, and the diversity of the V(D)J nucleic acid segment sequences is indicative of the diversity of a T cell receptor (TCR)-repertoire.

In some embodiments, the sample is a single isolated T cell or a clonally expanded single isolated T cell, and the diversity of the V(D)J nucleic acid segment sequences is indicative of the diversity of the TCR-repertoire of the single isolated T cell or the clonally expanded single isolated T cell.

In some embodiments, the subject is administered a cytotoxic treatment of a disease, leading to depletion of the immune cells, and wherein the control sample is obtained from the subject prior to administration of the cytotoxic treatment or from a second subject not administered the cytotoxic treatment.

BRIEF DESCRIPTION OF THE DRAWINGS

FIG. 5A shows a graph depicting the melting temperature distribution of the PCR primers in the assay. FIG. 5B shows a graph depicting the primer GC percent distribution. FIG. 5C shows the average VDG length of the amplicons produced by the B cell detection PCR assay.

DETAILED DESCRIPTION

Figure 1:
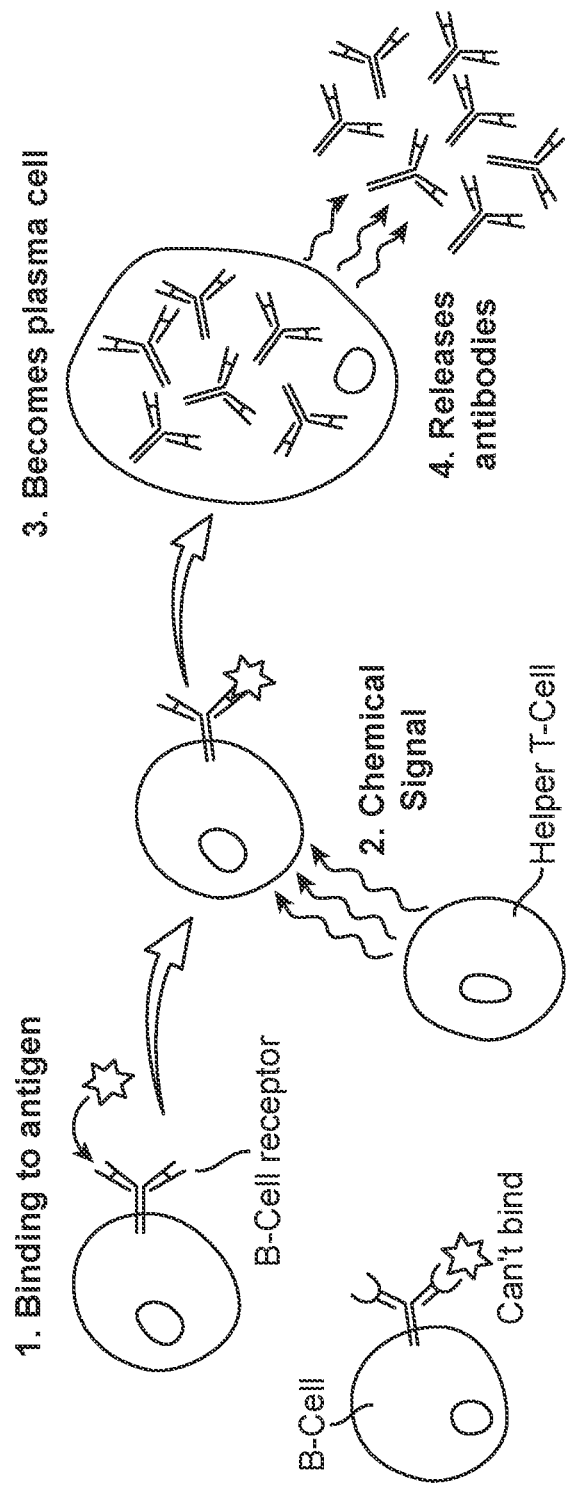
FIG. 1 is a graphic representation showing activation of B cells by antigen recognition.

Reference will now be made in detail to some specific embodiments of the invention contemplated by the inventors for carrying out the invention. Certain examples of these specific embodiments are illustrated in the accompanying drawings. While the invention is described in conjunction with these specific embodiments, it will be understood that it is not intended to limit the invention to the described embodiments. On the contrary, it is intended to cover alternatives, modifications, and equivalents as may be included within the spirit and scope of the invention as defined by the appended claims.

In the following description, numerous specific details are set forth in order to provide a thorough understanding of the present invention. Particular example embodiments of the present invention may be implemented without some or all of these specific details.

The present disclosure provides a next-generation sequencing workflow for detection of B and T cells having undergone VDJ recombination. Provided methods, compositions, systems, and kits are for use in high accuracy amplification and sequencing of genomic DNA (gDNA) or cell-free DNA (cfDNA) having rearranged immune cell receptor gene sequences (e.g., T cell receptor (TCR), B cell receptor (antibody or BCR)) in detecting or monitoring immune cells such as B and T cells in samples from a subject in need thereof.

In one aspect, this disclosure relates to performing a multiplex amplification reaction on nucleic acids isolated from a biological sample of the subject to generate a set of amplicons, wherein each of the set of amplicons comprises recombined V(D)J gene segments at a gene locus of interest, wherein the multiplex amplification reaction is capable of amplifying at least about 50% of all possible V(D)J recombinations at the gene locus of interest; and sequencing the set of amplicons, wherein sequences of the recombined V(D)J gene segments are indicative of presence of an immune cell in the biological sample.

In some embodiments, the multiplex amplification reaction is performed using a set of primers capable of amplifying at least about 70% of all V(D)J recombinations at a gene locus of interest in the immune cell. In some embodiments, the multiplex amplification reaction is performed using a set of primers capable of amplifying at least about 80% of all V(D)J recombinations at a gene locus of interest in the immune cell. In some embodiments, the multiplex amplification reaction is performed using a set of primers capable of amplifying at least about 85% of all V(D)J recombinations at a gene locus of interest in the immune cell. In some embodiments, the multiplex amplification reaction is performed using a set of primers capable of amplifying at least about 90% of all V(D)J recombinations at a gene locus of interest in the immune cell. In some embodiments, the multiplex amplification reaction is performed using a set of primers capable of amplifying at least 95% of all V(D)J recombinations at a gene locus of interest in the immune cell. In some embodiments, the multiplex amplification reaction is performed using a set of primers capable of amplifying at least about 98% all V(D)J recombinations at a gene locus of interest in the immune cell. In some embodiments, the multiplex amplification reaction is performed using a set of primers capable of amplifying at least about 100% all V(D)J recombinations at a gene locus of interest in the immune cell The method of claim 1, wherein the gene locus of interest is the B cell receptor (BCR) gene locus or the T cell receptor (TCR) gene locus.

As referred to herein, terms "VDJ recombination" or "VDJ rearrangement" are used interchangeably to refer the process of combining V, D, and J gene segments to produce immune cell receptors. As used herein, "immune cell receptor" and "immune receptor" are used interchangeably. In certain embodiments, the present disclosure provides methods, compositions, and systems that use nucleic acid amplification, such as polymerase chain reaction (PCR), to enrich rearranged target immune cell receptor gene sequences from cellular gDNA or cell-free DNA (cfDNA) for subsequent sequencing. In particular, provided methods described herein may improve accuracy and performance in sequencing applications with nucleotide sequences associated with genomic recombination and high variability. In some embodiments, methods, compositions, systems, and kits provided herein are for use in amplification and sequencing of the complementarily determining regions (CDRs) of rearranged immune cell receptors such as BCRs or TCRs gDNA or cfDNA in a sample. Thus, provided herein are multiplex immune cell receptor gene-directed compositions for multiplex library preparation from rearranged immune cell receptor gDNA, used in combination with next generation sequencing technologies for effective detection and monitoring of immune cell populations.

In some embodiments, methods and compositions are provided for amplifying the rearranged variable regions of immune cell receptor cellular gDNA or cfDNA, e.g., rearranged TCR and BCR gene DNA. Multiplex amplification is used to enrich for a portion of rearranged TCR or BCR cellular gDNA or cfDNA which includes at least a portion of the variable region of the receptor. In some embodiments, the amplified gDNA includes one or more complementarity determining regions CDR1, CDR2, and/or CDR3 for the target receptor. In some embodiments, the amplified gDNA includes one or more complementarily determining regions CDR1, CDR2, and/or CDR3 for TCR beta. In some embodiments, the amplified gDNA includes primarily CDR3 for the target receptor, e.g., CDR3 for TCR beta.

1. Immune Receptor Terminology and Description

The complementarity determining regions of a TCR or BCR results from genomic DNA undergoing recombination of the V(D)J gene segments as well as addition and/or deletion of nucleotides at the gene segment junctions. Recombination of the V(D)J gene segments and subsequent hypermutation events lead to extensive diversity of the expressed immune cell receptors.

As used herein, the terms "complementarity determining region" and "CDR" refer to regions of a T cell receptor or an antibody where the molecule complements an antigen's conformation, thereby determining the molecule's specificity and contact with a specific antigen. In the variable regions of T cell receptors and antibodies, the CDRs are interspersed with regions that are more conserved, termed framework regions (FR). Each variable region of a T cell receptor and an antibody contains 3 CDRs, designated CDR1, CDR2 and CDR3, and also contains 4 framework sub-regions, designated FR1, FR2, FR3 and FR4.

As used herein, the term "framework" or "framework region" or "FR" refers to the residues of the variable region other than the CDR residues as defined herein. There are four separate framework sub-regions that make up the framework: FR1, FR2, FR3, and FR4.

Systems for standard designation of the exact location of the CDRs and FRs within the receptor molecule (TCR or immunoglobulin) are well-known in the art. For example, the IMGT designations may be used to describing the CDR and FR regions as described in Brochet et al. (2008) Nucleic Acids Res. 36:W503-508, specifically incorporated herein by reference). As one example of CDR/FR amino acid designations, the residues that make up the FRs and CDRs of T cell receptor beta have been characterized by IMGT as follows: residues 1-26 (FR1), 27-38 (CDR1), 39-55 (FR2), 56-65 (CDR2), 66-104 (FR3), 105-117 (CDR3), and 118-128 (FR4).

Designation of CDRs in immunoglobulins may be standardized according to Kabat et al., (1991) Sequences of Proteins of Immunological Interest, 5th Ed. Public Health Service, National Institutes of Health, Bethesda, Md., or according to Chothia and Lesk (1987) J. Mol. Biol. 196: 901-917; herein specifically incorporated by reference. As one example of CDR designations, the residues that make up the six immunoglobulin CDRs have been characterized by Kabat as follows: residues 24-34 (CDRL1), 50-56 (CDRL2) and 89-97 (CDRL3) in the light chain variable region and 31-35 (CDRH1), 50-65 (CDRH2) and 95-102 (CDRH3) in the heavy chain variable region; and by Chothia as follows: residues 26-32 (CDRL1), 50-52 (CDRL2) and 91-96 (CDRL3) in the light chain variable region and 26-32 (CDRH1), 53-55 (CDRH2) and 96-101 (CDRH3) in the heavy chain variable region.

The term "T cell receptor" or "T cell antigen receptor" or "TCR," as used herein interchangeably to refer to the antigen/MHC binding heterodimeric protein product of a vertebrate, e.g., mammalian, TCR gene complex, including the human TCR alpha, beta, gamma and delta chains.

The term "antibody" or immunoglobulin" or "B cell receptor" or "BCR," as used herein, is intended to refer to immunoglobulin molecules comprised of four polypeptide chains, two heavy (H) chains and two light (L) chains (lambda or kappa) inter-connected by disulfide bonds. An antibody has a known specific antigen with which it binds. Each heavy chain of an antibody is comprised of a heavy chain variable region (abbreviated herein as HCVR, HV or VH) and a heavy chain constant region. The heavy chain constant region is comprised of three domains, CHL CH2 and CH3. Each light chain is comprised of a light chain variable region (abbreviated herein as LCVR or VL or KV or LV to designate kappa or lambda light chains) and a light chain constant region. The light chain constant region is comprised of one domain, CL.

As noted, the diversity of the TCR and BCR chain CDRs is created by recombination of germline variable (V), diversity (D), and joining (J) gene segments, as well as by independent addition and deletion of nucleotides at each of the gene segment junctions during the process of TCR and BCR gene rearrangement. In the rearranged DNA encoding a TCR beta receptor and a TCR delta receptor, for example, CDR1 and CDR2 are found in the V gene segment and CDR3 includes some of the V gene segment, and the D and J gene segments. In the rearranged DNA encoding a TCR alpha receptor and a TCR gamma receptor, CDR1 and CDR2 are found in the V gene segment and CDR3 includes some of the V gene segment and the J gene segment. In the rearranged DNA encoding a BCR heavy chain, CDR1 and CDR2 are found in the V gene segment and CDR3 includes some of the V gene segment and the D and J gene segments. In the rearranged DNA encoding a BCR light chain, CDR1 and CDR2 are found in the V gene segment and CDR3 includes some of the V gene segment and the J gene segment.

2. Multiplex Amplification of TCR or BCR Genomic DNA Having Undergone V(D)J Rearrangement In some embodiments, amplification is performed using direct multiplexed PCR, sequential PCR, nested PCR, doubly nested PCR, one-and-a-half sided nested PCR, fully nested PCR, one sided fully nested PCR, one-sided nested PCR, hemi-nested PCR, hemi-nested PCR, triply hemi-nested PCR, semi-nested PCR, one sided semi-nested PCR, reverse semi-nested PCR method, or one-sided PCR, which are described in U.S. application Ser. No. 13/683,604, filed Nov. 21, 2012, U.S. Publication No. 2013/0123120, U.S. application Ser. No. 13/300,235, filed Nov. 18, 2011, U.S. Publication No 2012/0270212, and U.S. Ser. No. 61/994, 791, filed May 16, 2014, which are hereby incorporated by reference in their entirety. If desired, any of these methods can be used for mini-PCR. In some embodiments, a multiplex amplification reaction is used to amplify TCR or BCR genomic DNA having undergone V(D)J rearrangement.

In some embodiments, the multiplex amplification reaction is performed by using a first set of primers covering a set of V genes of the immune cell and a second set of primers covering a set of J genes of the immune cell. In some embodiments, the first set of primers targets a conserved region within the set of V genes, and wherein the second set of primers targets a conserved region within the set of J genes. The conserved region may for example be any region within the V or J genes except for the CDRs. As used herein, the term "conserved region" refers to regions that are relatively conserved or relatively invariant compared to the CDRs. Conserved regions may be identified by comparing relevant sequences from different species by using bioinformatics tools that are well-known in the art. Non-limiting examples of the first and set of primers are provided in Table 2.

In some embodiments, a multiplex amplification reaction is used to amplify nucleic acid molecule(s) comprising at least a portion of a TCR or BCR CDR from cellular gDNA or cfDNA derived from a biological sample obtained from a subject. In some embodiments, a multiplex amplification reaction is used to amplify nucleic acid molecule(s) comprising at least two CDRs of a TCR or BCR from cellular gDNA or cfDNA derived from a biological sample. In some embodiments, a multiplex amplification reaction is used to amplify nucleic acid molecules comprising at least three CDRs of a TCR or BCR from cellular gDNA or cfDNA derived from a biological sample. In some embodiments, the resulting amplicons are used to determine the nucleotide sequences of the rearranged TCR or BCR CDRs in the sample.

In some embodiments, at least one primer set includes primers to cover all V genes of the BCR or TCR gene locus. In some embodiments, the primer set covering all V genes of the BCR gene locus includes 64 forward primers. In some embodiments, at least one primer set includes primers to cover all J genes of the BCR or TCR gene locus. In some embodiments, the primer set covering all J genes of the BCR gene locus includes 12 reverse primers. The number of V, D, and J genes in B cells are shown in table 1 below.

TABLE 1

VDJ genes in B cells

| IMGT DB | V genes | D genes | J genes |
|---|---|---|---|
| Functional | 264 | 30 | 13 |
| Orphans | 39 | 14 | — |
| Pseudogenes | 58 | — | — |

Housekeeping genes (HKG) are conserved, have a single copy, have no homologs, and therefore, housekeeping genes show no variability in sequencing read counts between different cell types and samples. In some embodiments, a primer set covering one or more housekeeping genes is provided to normalize for variation in DNA input to the amplification reaction. In some embodiments, the primer set covers 2 housekeeping genes. In some embodiments, the primer set covers 4 housekeeping genes. In some embodiments, the primer set covers 6 housekeeping genes. In some embodiments, the primer set covers 8 housekeeping genes.

In some embodiments, multiplex amplification reactions are performed with primer sets designed to generate amplicons which include CDR1, CDR2, and/or CDR3 regions of the rearranged target immune receptor gDNA. In some embodiments, multiplex amplification reactions are performed using one set of primers, wherein each primer is directed to at least a portion of a V gene and one set of primers, wherein each primer is directed to at least a portion of the J gene of the target immune receptor.

In some embodiments, a multiplex amplification reaction is used to amplify rearranged or recombined TCR genomic DNA, including rearranged TCR beta, TCR alpha, TCR gamma, and TCR delta genomic DNA. In some embodiments, at least a portion of a TCR CDR is amplified from cellular gDNA or cfDNA in a multiplex amplification reaction. In some embodiments, at least two CDR portions of TCR are amplified from cellular gDNA or cfDNA in a multiplex amplification reaction. In certain embodiments, a multiplex amplification reaction is used to amplify at least the CDR1, CDR2, and CDR3 regions of a TCR gDNA. In some embodiments, the resulting amplicons are used to determine the rearranged TCR CDR nucleotide sequence.

In some embodiments, provided are compositions for multiplex amplification of at least a portion of rearranged TCR or BCR variable region comprising V(D)J gene segments. In some embodiments, the composition comprises a plurality of sets of primer pair reagents directed to a portion of a V gene framework region and a portion of a J gene of target immune receptor genes selected from the group consisting of TCR beta, TCR alpha, TCR gamma, TCR delta, immunoglobulin heavy chain, immunoglobulin light chain lambda, and immunoglobulin light chain kappa.

In some embodiments, primer sets used in the multiplex reactions are designed to amplify at least 50% of the known gDNA rearrangements at the locus of interest. In certain embodiments, primer sets used in the multiplex reactions are designed to amplify at least 60%, at least 70%, at least 75%, at least 80%, at least 85%, at least 90%, at least 95%, at least 97%, at least 98% or more of the known gDNA rearrangements at the locus of interest. For example, use of 64 forward primers covering all the V gene segments, in combination with 12 reverse primers each covering all the J genes, will amplify up to 85% of CDR3 sequence as shown in table 3 in the working examples below.

In some embodiments, a multiplex amplification reaction includes at least 10, 20, 25, 30, 40, 45, 50, 55, 60, 65, 70, 75, 80, 85, 90, or more forward primers in which each forward primer is directed to a sequence corresponding to at least a portion of one or more TCR V genes or BCR V genes. In such embodiments, the plurality of reverse primers directed to the TCR or BCR V gene is combined with at least 10, 12, 14, 16, 18, 20, or about 15 to about 20 reverse primers directed to a sequence corresponding to at least a portion of a J gene of the same TCR or BCR gene. In some embodiments of the multiplex amplification reactions, the TCR or BCR V gene directed primers may be the forward primers and the TCR J gene-directed primers may be the reverse primers. Accordingly, in some embodiments, a multiplex amplification reaction includes at least 20, 25, 30, 40, 45, 50, 55, 60, 65, 70, 75, 80, 85, 90, or more reverse primers in which each reverse primer is directed to a sequence corresponding to at least a portion of one or more TCR or BCR V gene regions. In such embodiments, the plurality of forward primers directed to the TCR or BCR V gene regions is combined with at least 10, 12, 14, 16, 18, 20, or about 15 to about 20 reverse primers directed to a sequence corresponding to at least a portion of a J gene of the same TCR or BCR gene.

In some embodiments, the V gene FR and J gene target-directed primers combine as amplification primer pairs to amplify target rearranged immune receptor gDNA sequences and generate target amplicons. Generally, the length of a target amplicon will depend upon which V gene primer set is paired with the J gene primers. Accordingly, in some embodiments, target amplicons (including TCR beta amplicons) can range from about 50 nucleotides to about 350 nucleotides in length. In some embodiments, target amplicons are about 50 to about 200, about 70 to about 170, about 100 to about 170, about, 150 to about 200, about 200 to about 350, about 250 to about 320, about 270 to about 300, about 225 to about 300, about 250 to about 275, about 200 to about 235, about 200 to about 250, or about 175 to about 275 nucleotides in length. In some embodiments, generating amplicons of such short lengths allows the provided methods and compositions to effectively detect and analyze the immune repertoire from cfDNA or highly degraded gDNA template material, such as that derived from an FFPE sample.

cfDNA (such as necroptically- or apoptotically-released cancer cfDNA) is highly fragmented. For fetal cfDNA, the fragment sizes are distributed in approximately a Gaussian fashion with a mean of 160 bp, a standard deviation of 15 bp, a minimum size of about 100 bp, and a maximum size of about 220 bp. The polymorphic site of one particular target locus may occupy any position from the start to the end among the various fragments originating from that locus. The amplicon length is the distance between the 5-prime ends of the forward and reverse priming sites. Amplicon length that is shorter than typically used by those known in the art may result in more efficient measurements of the desired polymorphic loci by only requiring short sequence reads. In an embodiment, a substantial fraction of the amplicons are less than 100 bp, less than 90 bp, less than 80 bp, less than 70 bp, less than 65 bp, less than 60 bp, less than 55 bp, less than 50 bp, or less than 45 bp.

In some embodiments, multiplex amplification is performed with target-directed amplification primers which do not include a tagging sequence. In other embodiments, multiplex amplification is performed with amplification primers each of which include a target-directed sequence and a tagging sequence such as, for example, the forward primer or primer set includes tagging sequence 1 and the reverse primer or primer set includes tagging sequence 2. In still other embodiments, multiplex amplification is performed with amplification primers where one primer or primer set includes target directed sequence and a tagging sequence and the other primer or primer set includes a target-directed sequence but does not include a tagging sequence, such as, for example, the forward primer or primer set includes a tagging sequence and the reverse primer or primer set does not include a tagging sequence.

In some embodiments, a plurality of target gDNA template molecules are amplified in a single multiplex amplification reaction mixture with TCR or BCR directed amplification primers and the resultant amplicons contain only TCR or BCR sequences. In some embodiments, a tagging sequence is added to the ends of such amplicons through, for example, adapter ligation. In some embodiments, a barcode sequence is added to one or both ends of such amplicons through, for example, adapter ligation.

Nucleotide sequences suitable for use as barcodes and for barcoding libraries are known in the art. Adapters and amplification primers and primer sets including a barcode sequence are commercially available. Oligonucleotide adapters containing a barcode sequence are also commercially available including, for example, IonXpress™, IonCode™ and Ion Select barcode adapters (Thermo Fisher Scientific). Similarly, additional and other universal adapter/primer sequences described and known in the art (e.g., Illumina universal adapter/primer sequences, PacBio universal adapter/primer sequences, etc.) can be used in conjunction with the methods and compositions provided herein and the resultant amplicons sequenced using the associated analysis platform.

In some embodiments, two or more barcodes are added to amplicons when sequencing multiplexed samples. In some embodiments, at least two barcodes are added to amplicons prior to sequencing multiplexed samples to reduce the frequency of artefactual results (e.g., immune receptor gene rearrangements or clone identification) derived from barcode cross-contamination or barcode bleed-through between samples. In some embodiments, at least two bar codes are used to label samples when tracking low frequency clones of the immune repertoire. Methods for characterizing the immune repertoire which benefit from a high sequencing depth per clone and/or detection of clones at such low frequencies include, but are not limited to, monitoring a patient with a hyperproliferative disease undergoing treatment and testing for minimal residual disease following treatment.

In some embodiments, target amplicons using the amplification methods (and associated compositions, systems, and kits) disclosed herein, are used in the preparation of an immune receptor repertoire library. In some embodiments, the immune receptor repertoire library includes introducing adapter sequences to the termini of the target amplicon sequences. In certain embodiments, a method for preparing an immune receptor repertoire library includes generating target immune receptor amplicon molecules according to any of the multiplex amplification methods described herein, treating the amplicon molecule by digesting a modified nucleotide within the amplicon molecules' primer sequences, and ligating at least one adapter to at least one of the treated amplicon molecules, thereby producing a library of adapter-ligated target immune receptor amplicon molecules comprising the target immune receptor repertoire. In some embodiments, the steps of preparing the library are carried out in a single reaction vessel involving only addition steps. In certain embodiments, the method further includes clonally amplifying a portion of the at least one adapter-ligated target amplicon molecule.

3. Amplification Mixtures for Performing Multiplex PCR

As used herein, "amplify", "amplifying" or "amplification reaction" and their derivatives, refer to any action or process whereby at least a portion of a nucleic acid molecule (referred to as a template nucleic acid molecule) is replicated or copied into at least one additional nucleic acid molecule. The additional nucleic acid molecule optionally includes sequence that is substantially identical or substantially complementary to at least some portion of the template nucleic acid molecule. The template nucleic acid molecule can be single-stranded or double-stranded and the additional nucleic acid molecule can independently be single-stranded or double-stranded. In some embodiments, amplification includes a template-dependent in vitro enzyme-catalyzed reaction for the production of at least one copy of at least some portion of the nucleic acid molecule or the production of at least one copy of a nucleic acid sequence that is complementary to at least some portion of the nucleic acid molecule. Amplification optionally includes linear or exponential replication of a nucleic acid molecule. In some embodiments, such amplification is performed using isothermal conditions; in other embodiments, such amplification can include thermocycling. In some embodiments, the amplification is a multiplex amplification that includes the simultaneous amplification of a plurality of target sequences in a single amplification reaction. At least some of the target sequences can be situated on the same nucleic acid molecule or on different target nucleic acid molecules included in the single amplification reaction. In some embodiments, "amplification" includes amplification of at least some portion of DNA- and RNA-based nucleic acids alone, or in combination. The amplification reaction can include single or double-stranded nucleic acid substrates and can further including any of the amplification processes known to one of ordinary skill in the art. In some embodiments, the amplification reaction includes polymerase chain reaction (PCR).

An amplification reaction mixture useful for the present invention includes components known in the art for nucleic acid amplification, especially for PCR amplification. For example, the reaction mixture typically includes nucleotide triphosphates, a polymerase, and magnesium. Polymerases that are useful for the present invention can include any polymerase that can be used in an amplification reaction especially those that are useful in PCR reactions. In certain embodiments, hot start Taq polymerases are especially useful Amplification reaction mixtures useful for practicing the methods provided herein, such as AmpliTaq Gold master mix (Life Technologies, Carlsbad, CA), are available commercially.

Methods of the present invention, in certain embodiments, include forming an amplification reaction mixture. The reaction mixture typically is formed by combining a polymerase, nucleotide triphosphates, nucleic acid fragments from a nucleic acid library generated from the sample, a series of forward target-specific outer primers and a first strand reverse outer universal primer. Another illustrative embodiment is a reaction mixture that includes forward target-specific inner primers instead of the forward target-specific outer primers and amplicons from a first PCR reaction using the outer primers, instead of nucleic acid fragments from the nucleic acid library. The reaction mixtures provided herein, themselves forming in illustrative embodiments, a separate aspect of the invention. In illustrative embodiments, the reaction mixtures are PCR reaction mixtures. PCR reaction mixtures typically include magnesium.

In some embodiments, the reaction mixture includes ethylenediaminetetraacetic acid (EDTA), magnesium, tetramethyl ammonium chloride (TMAC), or any combination thereof. In some embodiments, the concentration of TMAC is between 20 and 70 mM, inclusive. While not meant to be bound to any particular theory, it is believed that TMAC binds to DNA, stabilizes duplexes, increases primer specificity, and/or equalizes the melting temperatures of different primers. In some embodiments, TMAC increases the uniformity in the amount of amplified products for the different targets. In some embodiments, the concentration of magnesium (such as magnesium from magnesium chloride) is between 1 and 8 mM.

The large number of primers used for multiplex PCR of a large number of targets may chelate a lot of the magnesium (2 phosphates in the primers chelate 1 magnesium). For example, if enough primers are used such that the concentration of phosphate from the primers is ~9 mM, then the primers may reduce the effective magnesium concentration by ~4.5 mM. In some embodiments, EDTA is used to decrease the amount of magnesium available as a cofactor for the polymerase since high concentrations of magnesium can result in PCR errors, such as amplification of non-target loci. In some embodiments, the concentration of EDTA reduces the amount of available magnesium to between 1 and 5 mM (such as between 3 and 5 mM).

In some embodiments, the concentration of the primers in the multiplex amplification reaction. In some embodiments, the concentration of the primers is about 1 nM to about 1000 nM. In some embodiments, the concentration of the primers is about 1 nM to about 800 nM. In some embodiments, the concentration of the primers is about 1 nM to about 600 nM. In some embodiments, the concentration of the primers is about 1 nM to about 400 nM. In some embodiments, the concentration of the primers is about 1 nM to about 200 nM.

In some embodiments, the concentration of the primers is about 1 nM to about 100 nM. In some embodiments, the concentration of the primers is about 1 nM to about 20 nM. In some embodiments, the concentration of the primers is about 1 nM, 2 nM, 4 nM, 6 nM, 8 nM, 10 nM, 12 nM, 14 nM, 16 nM, 18 nM, or 20 nM. In one particular embodiment, the concentration of the primers is about 16 nM.

In any of the methods for detecting VDJ recombination DNA segments herein that include a cellular DNA or cfDNA amplification/sequencing workflow, improved amplification parameters for multiplex PCR can be employed. For example, wherein the amplification reaction is a PCR reaction and the annealing temperature is between 1, 2, 3, 4, 5, 6, 7, 8, 9, or 10° C. greater than the melting temperature on the low end of the range, and 2, 3, 4, 5, 6, 7, 8, 9, 10, 11, 12, 13, 14 or 15° on the high end the range for at least 10, 20, 25, 30, 40, 50, 06, 70, 75, 80, 90, 95 or 100% the primers of the set of primers.

Accordingly, in an example of any of the methods herein that include an amplification step, the amplification reaction is a PCR reaction, the annealing temperature is between 1 and 10° C. greater than the melting temperature of at least 90% of the primers of the set of primers, the length of the annealing step in the PCR reaction is between 15 and 60 minutes, the primer concentration in the amplification reaction is between 1 and 10 nM, and the primers in the set of primers, are designed to minimize primer dimer formation. In a further aspect of this example, the multiplex amplification reaction is performed under limiting primer conditions.

In some embodiments, the pH is between 7.5 and 8.5, such as between 7.5 and 8, 8 and 8.3, or 8.3 and 8.5, inclusive. In some embodiments, Tris is used at, for example, a concentration of between 10 and 100 mM, such as between 10 and 25 mM, 25 and 50 mM, 50 and 75 mM, or 25 and 75 mM, inclusive. In some embodiments, any of these concentrations of Tris are used at a pH between 7.5 and 8.5. In some embodiments, a combination of KCl and $(NH_4)_2SO_4$ is used, such as between 50 and 150 mM KCl and between 10 and 90 mM $(NH_4)_2SO_4$, inclusive. In some embodiments, the concentration of KCl is between 0 and 30 mM, between 50 and 100 mM, or between 100 and 150 mM, inclusive. In some embodiments, the concentration of $(NH_4)_2SO_4$ is between 10 and 50 mM, 50 and 90 mM, 10 and 20 mM, 20 and 40 mM, 40 and 60 mM, or 60 and 80 mM $(NH_4)_2SO_4$, inclusive. In some embodiments, the ammonium $[NH_4^+]$ concentration is between 0 and 160 mM, such as between 0 to 50, 50 to 100, or 100 to 160 mM, inclusive. In some embodiments, the sum of the potassium and ammonium concentration ($[K^+]+[NH_4^+]$) is between 0 and 160 mM, such as between 0 to 25, 25 to 50, 50 to 150, 50 to 75, 75 to 100, 100 to 125, or 125 to 160 mM, inclusive. An exemplary buffer with $[K^+]+[NH_4^+]=120$ mM is 20 mM KCl and 50 mM $(NH_4)_2SO_4$. In some embodiments, the buffer includes 25 to 75 mM Tris, pH 7.2 to 8, 0 to 50 mM KCl, 10 to 80 mM ammonium sulfate, and 3 to 6 mM magnesium, inclusive. In some embodiments, the buffer includes 25 to 75 mM Tris pH 7 to 8.5, 3 to 6 mM $MgCl_2$, 10 to 50 mM KCl, and 20 to 80 mM $(NH_4)_2SO_4$, inclusive. In some embodiments, 100 to 200 Units/mL of polymerase are used. In some embodiments, 100 mM KCl, 50 mM $(NH_4)_2SO_4$, 3 mM $MgCl_2$, 7.5 nM of each primer in the library, 50 mM TMAC, and 7 ul DNA template in a 20 ul final volume at pH 8.1 is used In some embodiments, a crowding agent is used, such as polyethylene glycol (PEG, such as PEG 8,000) or glycerol. In some embodiments, the amount of PEG (such as PEG 8,000) is between 0.1 to 20%, such as between 0.5 to 15%, 1 to 10%, 2 to 8%, or 4 to 8%, inclusive. In some embodiments, the amount of glycerol is between 0.1 to 20%, such as between 0.5 to 15%, 1 to 10%, 2 to 8%, or 4 to 8%, inclusive. In some embodiments, a crowding agent allows either a low polymerase concentration and/or a shorter annealing time to be used. In some embodiments, a crowding agent improves the uniformity of the DOR and/or reduces dropouts (undetected alleles). Polymerases In some embodiments, a polymerase with proof-reading activity, a polymerase without (or with negligible) proof-reading activity, or a mixture of a polymerase with proof-reading activity and a polymerase without (or with negligible) proof-reading activity is used. In some embodiments, a hot start polymerase, a non-hot start polymerase, or a mixture of a hot start polymerase and a non-hot start polymerase is used. In some embodiments, a HotStarTaq DNA polymerase is used (see, for example, QIAGEN catalog No. 203203). In some embodiments, AmpliTaq Gold® DNA Polymerase is used. In some embodiments a PrimeSTAR GXL DNA polymerase, a high fidelity polymerase that provides efficient PCR amplification when there is excess template in the reaction mixture, and when amplifying long products, is used (Takara Clontech, Mountain View, CA). In some embodiments, KAPA Taq DNA Polymerase or KAPA Taq HotStart DNA Polymerase is used; they are based on the single-subunit, wild-type Taq DNA polymerase of the thermophilic bacterium *Thermus aquaticus*. KAPA Taq and KAPA Taq HotStart DNA Polymerase have 5'-3' polymerase and 5'-3' exonuclease activities, but no 3' to 5' exonuclease (proofreading) activity (see, for example, KAPA BIOSYSTEMS catalog No. BK1000). In some embodiments, Pfu DNA polymerase is used; it is a highly thermostable DNA polymerase from the hyperthermophilic archaeum *Pyrococcus furiosus*. The enzyme catalyzes the template-dependent polymerization of nucleotides into duplex DNA in the 5'→3' direction. Pfu DNA Polymerase also exhibits 3'→5' exonuclease (proofreading) activity that enables the polymerase to correct nucleotide incorporation errors. It has no 5'→3' exonuclease activity (see, for example, Thermo Scientific catalog No. EP0501). In some embodiments Klentaql is used; it is a Klenow-fragment analog of Taq DNA polymerase, it has no exonuclease or endonuclease activity (see, for example, DNA POLYMERASE TECHNOLOGY, Inc, St. Louis, Missouri, catalog No. 100). In some embodiments, the polymerase is a PHUSION DNA polymerase, such as PHUSION High Fidelity DNA polymerase (M0530S, New England BioLabs, Inc.) or PHUSION Hot Start Flex DNA polymerase (M0535S, New England BioLabs, Inc.). In some embodiments, the polymerase is a Q5® DNA Polymerase, such as Q5® High-Fidelity DNA Polymerase (M0491S, New England BioLabs, Inc.) or Q5® Hot Start High-Fidelity DNA Polymerase (M0493S, New England BioLabs, Inc.). In some embodiments, the polymerase is a T4 DNA polymerase (M0203S, New England BioLabs, Inc.).

In some embodiment, between 5 and 600 Units/mL (Units per 1 mL of reaction volume) of polymerase is used, such as between 5 to 100, 100 to 200, 200 to 300, 300 to 400, 400 to 500, or 500 to 600 Units/mL, inclusive.

4. Method of Primer Design

As used herein, the term "primer" and its derivatives refer to any polynucleotide that can hybridize to a target sequence of interest. In some embodiments, the primer can also serve to prime nucleic acid synthesis. Typically, the primer functions as a substrate onto which nucleotides can be polymerized by a polymerase; in some embodiments, however, the primer can become incorporated into the synthesized nucleic acid strand and provide a site to which another primer can hybridize to prime synthesis of a new strand that is complementary to the synthesized nucleic acid molecule. The primer may be comprised of any combination of nucleotides or analogs thereof, which may be optionally linked to form a linear polymer of any suitable length. In some embodiments, the primer is a single-stranded oligonucleotide or polynucleotide. (For purposes of this disclosure, the terms "polynucleotide" and "oligonucleotide" are used interchangeably herein and do not necessarily indicate any difference in length between the two).

In some embodiments, the primer is single-stranded but it can also be double-stranded. The primer optionally occurs naturally, as in a purified restriction digest, or can be produced synthetically. In some embodiments, the primer acts as a point of initiation for amplification or synthesis when exposed to amplification or synthesis conditions; such amplification or synthesis can occur in a template-dependent fashion and optionally results in formation of a primer extension product that is complementary to at least a portion of the target sequence. Exemplary amplification or synthesis conditions can include contacting the primer with a polynucleotide template (e.g., a template including a target sequence), nucleotides and an inducing agent such as a polymerase at a suitable temperature and pH to induce polymerization of nucleotides onto an end of the target-specific primer. If double-stranded, the primer can optionally be treated to separate its strands before being used to prepare primer extension products. In some embodiments, the primer is an oligodeoxyribonucleotide or an oligoribonucleotide. In some embodiments, the primer can include one or more nucleotide analogs.

The exact length and/or composition, including sequence, of the target-specific primer can influence many properties, including melting temperature (Tm), GC content, formation of secondary structures, repeat nucleotide motifs, length of predicted primer extension products, extent of coverage across a nucleic acid molecule of interest, number of primers present in a single amplification or synthesis reaction, presence of nucleotide analogs or modified nucleotides within the primers, and the like. In some embodiments, a primer can be paired with a compatible primer within an amplification or synthesis reaction to form a primer pair consisting or a forward primer and a reverse primer. In some embodiments, the forward primer of the primer pair includes a sequence that is substantially complementary to at least a portion of a strand of a nucleic acid molecule, and the reverse primer of the primer of the primer pair includes a sequence that is substantially identical to at least of portion of the strand. In some embodiments, the forward primer and the reverse primer are capable of hybridizing to opposite strands of a nucleic acid duplex. Optionally, the forward primer primes synthesis of a first nucleic acid strand, and the reverse primer primes synthesis of a second nucleic acid strand, wherein the first and second strands are substantially complementary to each other, or can hybridize to form a double-stranded nucleic acid molecule. In some embodiments, one end of an amplification or synthesis product is defined by the forward primer and the other end of the amplification or synthesis product is defined by the reverse primer. In some embodiments, where the amplification or synthesis of lengthy primer extension products is required, such as amplifying an exon, coding region, or gene, several primer pairs can be created than span the desired length to enable sufficient amplification of the region. In some embodiments, a primer can include one or more cleavable groups. In some embodiments, primer lengths are in the range of about 10 to about 60 nucleotides, about 12 to about 50 nucleotides and about 15 to about 40 nucleotides in length. Typically, a primer is capable of hybridizing to a corresponding target sequence and undergoing primer extension when exposed to amplification conditions in the presence of dNTPs and a polymerase. In some embodiments, the primer includes one or more cleavable groups at one or more locations within the primer.

Primer designs can be generated with Primer3 (Untergrasser A, Cutcutache I, Koressaar T, Ye J, Faircloth B C, Remm M, Rozen S G (2012) "Primer3—new capabilities and interfaces." Nucleic Acids Research 40(15):e115 and Koressaar T, Remm M (2007) "Enhancements and modifications of primer design program Primer3." Bioinformatics 23(10):1289-91) source code available at primer3.sourceforge.net). Primer specificity can be evaluated by BLAST and added to existing primer design pipeline criteria:

Primer specificities can be determined using the BLASTn program from the ncbi-blast-2.2.29+ package. The task option "blastn-short" can be used to map the primers against hg19 human genome. Primer designs can be determined as "specific" if the primer has less than 100 hits to the genome and the top hit is the target complementary primer binding region of the genome and is at least two scores higher than other hits (score is defined by BLASTn program). This can be done in order to have a unique hit to the genome and to not have many other hits throughout the genome.

The final selected primers can be visualized in IGV (James T. Robinson, Helga Thorvaldsdóttir, Wendy Winckler, Mitchell Guttman, Eric S. Lander, Gad Getz, Jill P. Mesirov. Integrative Genomics Viewer. Nature Biotechnology 29, 24-26 (2011)) and UCSC browser (Kent W J, Sugnet C W, Furey T S, Roskin K M, Pringle T H, Zahler A M, Haussler D. The human genome browser at UCSC. Genome Res. 2002 June; 12(6):996-1006) using bed files and coverage maps for validation.

If desired, multiplex PCR may be performed using primers with a decreased likelihood of forming primer dimers. In particular, highly multiplexed PCR can often result in the production of a very high proportion of product DNA that results from unproductive side reactions such as primer dimer formation. In an embodiment, the particular primers that are most likely to cause unproductive side reactions may be removed from the primer library to give a primer library that will result in a greater proportion of amplified DNA that maps to the genome. The step of removing problematic primers, that is, those primers that are particularly likely to firm dimers has unexpectedly enabled extremely high PCR multiplexing levels for subsequent analysis by sequencing.

There are a number of ways to choose primers for a library where the amount of non-mapping primer dimer or other primer mischief products are minimized Empirical data indicate that a small number of 'bad' primers are responsible for a large amount of non-mapping primer dimer side reactions. Removing these 'bad' primers can increase the percent of sequence reads that map to targeted loci. One way to identify the 'bad' primers is to look at the sequencing data of DNA that was amplified by targeted amplification; those primer dimers that are seen with greatest frequency can be removed to give a primer library that is significantly less likely to result in side product DNA that does not map to the genome. There are also publicly available programs that can calculate the binding energy of various primer combinations, and removing those with the highest binding energy will also give a primer library that is significantly less likely to result in side product DNA that does not map to the genome.

The use of tags on the primers may reduce amplification and sequencing of primer dimer products. In some embodiments, the primer contains an internal region that forms a loop structure with a tag. In particular embodiments, the primers include a 5' region that is specific for a target locus, an internal region that is not specific for the target locus and forms a loop structure, and a 3' region that is specific for the target locus. In some embodiments, the loop region may lie between two binding regions where the two binding regions are designed to bind to contiguous or neighboring regions of template DNA. In various embodiments, the length of the 3' region is at least 7 nucleotides. In some embodiments, the length of the 3' region is between 7 and 20 nucleotides, such as between 7 to 15 nucleotides, or 7 to 10 nucleotides, inclusive. In various embodiments, the primers include a 5' region that is not specific for a target locus (such as a tag or a universal primer binding site) followed by a region that is specific for a target locus, an internal region that is not specific for the target locus and forms a loop structure, and a 3' region that is specific for the target locus. Tag-primers can be used to shorten necessary target-specific sequences to below 20, below 15, below 12, and even below 10 base pairs. This can be serendipitous with standard primer design when the target sequence is fragmented within the primer binding site or, or it can be designed into the primer design. Advantages of this method include: it increases the number of assays that can be designed for a certain maximal amplicon length, and it shortens the "non-informative" sequencing of primer sequence. It may also be used in combination with internal tagging.

5. Samples and Preparation of Cellular and Cell-Free DNA for Sequencing

A sample or biological sample, as used herein, refers to a composition from an individual that contains or may contain cells related to the immune system. Exemplary biological samples, include without limitation, tissue (for example, lymph node, organ tissue, bone marrow), whole blood, synovial fluid, cerebral spinal fluid, tumor biopsy, and other clinical specimens containing cells. The sample may include normal and/or diseased cells and be a fine needle aspirate, fine needle biopsy, core sample, or other sample. In some embodiments, the sample may be fresh (e.g., not preserved), frozen, or formalin-fixed paraffin-embedded tissue (FFPE). Some samples comprise cancer cells, such as carcinomas, melanomas, sarcomas, lymphomas, myelomas, leukemias, and the like.

The biological sample can be a mix of tissue or cell types, a preparation of cells enriched for at least one particular category or type of cell, or an isolated population of cells of a particular type or phenotype. Samples can be separated by centrifugation, elutriation, density gradient separation, apheresis, affinity selection, panning, FACS, centrifugation with Hypaque, etc. prior to analysis. Methods for sorting, enriching for, and isolating particular cell types are well-known and can be readily carried out by one of ordinary skill. In some embodiments, these methods can be used to identify and isolate a single cell of interest.

Methods and reagents for extracting or isolating nucleic acid from biological samples are well known and commercially available. In some embodiments, DNA extraction from biological samples is performed by any method described herein or otherwise known to those of skill in the art, e.g., methods involving proteinase K tissue digestion and alcohol-based nucleic acid precipitation, treatment with RNAse to digest contaminating RNA, and DNA purification using silica-gel-membrane technology, or any combination thereof. Exemplary methods for DNA extraction from biological samples using commercially available kits including Ion AmpliSeq™ Direct FFPE DNA Kit, MagMAX™ FFPE DNA/RNA Ultra Kit, TRI Reagent™ (Invitrogen), PureLink™ Genomic DNA Mini kit (Invitrogen), RecoverAll™ Total Nucleic Acid Isolation Kit (Invitrogen), MagMAX™ DNA Multi-Sample Kit (Invitrogen) and DNA extraction kits from BioChain Institute Inc. (e.g., FFPE Tissue DNA Extraction Kit, Genomic DNA Extraction Kit, Blood and Serum DNA Isolation Kit).

In some embodiments, genomic DNA (gDNA) is obtained from a biological sample using conventional methods. The gDNA may in some embodiments be cellular gDNA. In some embodiments, the gDNA is cell-free DNA (cfDNA) obtained by liquid biopsy of the subject.

Cell-free DNA may be obtained from a variety of tissues, such as tissues that are in liquid form, e.g., blood, plasma, lymph, ascites fluid, or cerebral spinal fluid. In some embodiments, the cfDNA is isolated from plasma that has been isolated from whole blood that has been centrifuged to remove cellular material. The hemolysis grade of each pooled plasma sample was evaluated visually (no hemolysis, mild hemolysis or severe hemolysis). cfDNA may be extracted using the Qiagen NA™ kit (Valencia, CA) following a protocol optimized for 5 ml of plasma. All cfDNA samples were QCed on Bioanalyzer™ High Sensitivity chips (Agilent, Santa Clara, CA).

Cellular DNA may be obtained from any cell type. In some embodiments, the sample comprises a peripheral blood mononuclear cell (PBMCs) sample. In some embodiments, the plurality of nucleic acid comprises cellular DNA obtained from PBMCs. In some embodiments, the sample comprises an amount of immune cells less than 1.0%, less than 0.5%, or less than 0.1% of the PBMCs in the sample. In some embodiments, the method of the present invention is capable of detecting 100 or less V(D)J recombinations per milliliter of the biological sample. In some embodiments, the method of the present invention is capable of detecting 50 or less V(D)J recombinations per milliliter of the biological sample. In some embodiments, the method of the present invention is capable of detecting 20 or less V(D)J recombinations per milliliter of the biological sample. In some embodiments, the method of the present invention is capable of detecting 10 or less V(D)J recombinations per milliliter of the biological sample. In some embodiments, the method is capable of detecting 5 or less V(D)J recombinations per milliliter of the biological sample. In some embodiments, the method is capable of detecting 2 or less V(D)J recombinations per milliliter of the biological sample. In some embodiments, the method is capable of detecting a single V(D)J recombination per milliliter of the biological sample.

For preparing libraries of cfDNA, the isolated cfDNA may be end-repaired, A-tailed, and ligated with custom adapters. The purified ligation product was amplified for 20 cycles and purified using AMPURE® XP beads (Agencourt/Beckman Coulter).

The library material from each plasma sample was used as input into multiplex PCR (mPCR) using the relevant assay pool and an optimized plasma mPCR protocol. In some embodiments, the mPCR protocol utilized an annealing time of 15 minutes at a temperature of 60° C., 62.5° C., or 65° C., which was above the Tm of the primers. The Tms of the primers using theoretical calculations was 52.5 to 59 C. In some embodiments, a 10 nM primer concentration was used. The mPCR products were barcoded in a separate PCR step, and the barcoded PCR products were pooled according to the assay pooling information. The pools were purified using Ampure™ beads following the manufacturer's protocol, QCed on a Bioanalyzer™ DNA1000™ chip (Agilent, Santa Clara, CA), and quantified using the Qubit™ dsDNA Broad Range kit (Thermo Fisher Scientific, Waltham, MA). In some embodiments, each pool was sequenced on a separate HiSeq 2500 Rapid run (Illumina, San Diego, CA) with 50 cycle paired end single index reads.

gDNA multiplex PCR and sequencing. The genomic DNA samples were used as input into a similar mPCR using the relevant assay pools and an optimized genomic mPCR protocol. The mPCR products were barcoded in a separate PCR step, and all the barcoded products were combined into one pool. The pool was purified using Ampure™ beads following the manufacturer's protocol, QCed on a Bioanalyzer DNA1000 chip, and quantified using the Qubit dsDNA Broad Range kit. The pool was sequenced on a single HiSeq2500 Rapid run with 50 cycle single end single index reads.

6. Methods for Detecting or Monitoring an Immune Cell Population

In certain embodiments, methods and compositions are provided for detecting or monitoring the immune cell population of a patient undergoing cytotoxic treatment of a disease, leading to depletion of the patient's immune cells. In some embodiments, the subject is administered a cytotoxic treatment of a disease, wherein the cytotoxic treatment leads to depletion of the immune cells. In some embodiments, the disease is a malignancy, and the cytotoxic treatment comprises a chemotherapy, a radiotherapy, and/or an immune cell targeted therapy. In some embodiments, the disease is an autoimmune disease, and the cytotoxic treatment comprise an immunosuppressive therapy.

In some embodiments, the subject is suffering from a disease, disorder, or condition that depletes immune cells. In some embodiments, the disease or condition is a malignancy or an immunodeficiency disorder.

Suitable cells for analysis include, without limitation, various hematopoietic cells, lymphocytes, and tumor cells, such as peripheral blood mononuclear cells (PBMCs), T cells, B cells, circulating tumor cells, and tumor infiltrating lymphocytes (TILs). Lymphocytes expressing immunoglobulin include pre-B cells, B-cells, e.g. memory B cells, and plasma cells. Lymphocytes expressing T cell receptors include thymocytes, NK cells, pre-T cells and T cells, where many subsets of T cells are known in the art, e.g. Th1, Th2, Th17, CTL, T reg, etc.

In some embodiments, the methods and compositions are used to detect or monitor immune cells populations of tumor infiltrating lymphocytes (TILs) before, during, and/or following cytotoxic treatment. In some embodiments, the methods and compositions for detecting and monitoring immune cell populations may be used to identify and/or track therapeutic T cell population(s) and B cell population(s). In some embodiments, the subject is administered a therapeutic compositing comprising immune cells, and wherein the method further comprises analyzing V(D)J nucleic acid segment sequences to determine the presence of the administered immune cells. In some embodiments, the methods and compositions provided are used to detect or monitor the persistence of cell-based therapies following patient treatment, including but not limited to, presence of engineered T cell populations including without limitation CAR-T cell populations, TCR engineered T cell populations, persistent CAR-T expression, presence of administered TIL populations, TIL expression following adoptive T-cell therapy, and/or immune reconstitution after allogeneic hematopoietic cell transplantation.

In some embodiments, the methods and compositions provided are used to detect or monitor T cell clones or populations present in patient sample following administration of cell-based therapies to the patient, including but not limited to, e.g., cancer vaccine cells, CAR-T, TIL, and/or other engineered T cell-based therapy.

The methods and compositions provided herein may be used for monitoring and detection of immune cell population in subjects undergoing cytotoxic treatment of diseases and conditions that lead to immune cell depletion. Many treatments of diseases and conditions are known to cause immune cell depletions. For example, commonly used chemotherapy, radiotherapy, and immune cell targeted therapies may result in immune cell depletion. Cytotoxic treatments include but are not limited to induction chemotherapy, neoadjuvant chemotherapy, adjuvant chemotherapy, maintenance chemotherapy, or salvage chemotherapy. Commonly known types of cytotoxic drugs leading to cell depletions include but are not limited to alkylating agents, antimetabolites, anti-microtubule agents, topoisomerase inhibitors, and cytotoxic antibiotics such as anthracyclines, bleomycines, mitomycin C, mitoxantrone, and actinomycin.

Conditions associated with immunodeficiency are also of interest for analysis with the provided methods, including congenital and acquired immunodeficiency syndromes.

In some embodiments, the methods and compositions are used to identify and/or track B cell lineage malignancies or T cell lineage malignancies. In some embodiments, the methods and compositions provided are used for minimal residual disease (MRD) monitoring for a patient following treatment. Accordingly, in some embodiments, the method further comprises measuring minimal residual disease in the subject to monitor treatment response or relapse of the disease. As used herein, the term "minimal residual disease (MRD)" refers to a small number of disease cells that remain in a patient during or after treatment when the patient is in remission. In remission, the patient may no longer display obvious symptoms or signs of disease, but MRD cells may remain and cause relapse of the disease. These MRD cells are a major cause of relapse of diseases such as cancer and in particular leukemia, lymphoma, and myeloma. Testing for MRD may be useful for determining whether treatment has eradicated the cancer or whether traces remain, comparing efficacy of different treatments, monitoring patient remission status as well as detecting recurrence of the disease, and choosing the treatment that will best meet those needs. The number of MRD cells in a sample from a patient may be as low as one disease cell in a million normal cells.

In some embodiments, the methods and compositions are used to detect and/or monitor immune cells in patients diagnosed with leukemia or lymphoma, including without limitation, acute lymphoblastic leukemia, chronic myeloid leukemia, chronic lymphocytic leukemia, chronic myelogenous leukemia, cutaneous T cell lymphoma, B cell lymphoma, mantle cell lymphoma, and multiple myeloma. In some embodiments, the methods and compositions are used to detect and/or monitor MRD in patients diagnosed with solid tumors, including without limitation, breast cancer, lung cancer, colorectal, and neuroblastoma. In some embodiments, the methods and compositions are used to detect and/or monitor MRD in patients following cancer treatment including without limitation bone marrow transplant, lymphocyte infusion, adoptive T-cell therapy, other cell-based immunotherapy, and antibody-based immunotherapy.

B cell lineage malignancies of interest include, without limitation, multiple myeloma; acute lymphocytic leukemia (ALL); relapsed/refractory B cell ALL, chronic lymphocytic leukemia (CLL); diffuse large B cell lymphoma; mucosa-associated lymphatic tissue lymphoma (MALT); small cell lymphocytic lymphoma; mantle cell lymphoma (MCL); Burkitt lymphoma; mediastinal large B cell lymphoma; Waldenström macroglobulinemia; nodal marginal zone B cell lymphoma (NMZL); splenic marginal zone lymphoma (SMZL); intravascular large B-cell lymphoma; primary effusion lymphoma; lymphomatoid granulomatosis, etc. Non-malignant B cell hyperproliferative conditions include monoclonal B cell lymphocytosis (MBL).

T cell lineage malignancies of interest include, without limitation, precursor T-cell lymphoblastic lymphoma; T-cell prolymphocytic leukemia; T-cell granular lymphocytic leukemia; aggressive NK cell leukemia; adult T-cell lymphoma/leukemia (HTLV 1-positive); extranodal NK/T-cell lymphoma; enteropathy-type T-cell lymphoma; hepatosplenic γδ T-cell lymphoma; subcutaneous panniculitis-like T-cell lymphoma; mycosis fungoides/Sezary syndrome; anaplastic large cell lymphoma, T/null cell; peripheral T-cell lymphoma; angioimmunoblastic T-cell lymphoma; chronic lymphocytic leukemia (CLL); acute lymphocytic leukemia (ALL); prolymphocytic leukemia; and hairy cell leukemia.

Other malignancies of interest include, without limitation, acute myeloid leukemia, head and neck cancers, brain cancer, breast cancer, ovarian cancer, cervical cancer, colorectal cancer, endometrial cancer, gallbladder cancer, gastric cancer, bladder cancer, prostate cancer, testicular cancer, liver cancer, lung cancer, kidney (renal cell) cancer, esophageal cancer, pancreatic cancer, thyroid cancer, bile duct cancer, pituitary tumor, wilms tumor, kaposi sarcoma, osteosarcoma, thymus cancer, skin cancer, heart cancer, oral and larynx cancer, neuroblastoma and non-hodgkin lymphoma.

7. Methods of Determining Immune Receptor Repertoire

In some embodiments, the methods disclosed herein further comprise analyzing the V(D)J nucleic acid segment sequences to determine a diversity of the V(D)J nucleic acid segments in the sample obtained from the subject and a control sample, wherein the diversity of the V(D)J nucleic acid segments is indicative of an immune receptor repertoire.

In some embodiments, the immune cell is a B cell, and the diversity of the V(D)J nucleic acid segment sequences is indicative of the diversity of a B cell receptor (BCR)-repertoire. In some embodiments, the sample is a single isolated B cell or a clonally expanded single isolated B cell, and the diversity of the V(D)J nucleic acid segment sequences is indicative of the diversity of the BCR-repertoire of the single isolated B cell or the clonally expanded single isolated B cell. In some embodiments, the immune cell is a T cell, and the diversity of the V(D)J nucleic acid segment sequences is indicative of the diversity of a T cell receptor (TCR)-repertoire. In some embodiments, the sample is a single isolated T cell or a clonally expanded single isolated T cell, and the diversity of the V(D)J nucleic acid segment sequences is indicative of the diversity of the TCR-repertoire of the single isolated T cell or the clonally expanded single isolated T cell. Single cells may be obtained by using commonly known cell sorting techniques or limited dilution methods and as described in section 5 herein.

In some embodiments, the methods disclosed herein may be used to monitor the immune receptor diversity in a subject undergoing cytotoxic treatments, wherein the subject is administered a cytotoxic treatment of a disease, leading to depletion of the immune cells, and wherein the control sample is obtained from the subject prior to administration of the cytotoxic treatment or from a second subject not administered the cytotoxic treatment, and wherein changes in the diversity of the immune receptors are evaluated by using the control sample as a reference.

8. Exemplary Kits

In one aspect, the invention features a kit, such as a kit for amplifying gene loci of interest in a nucleic acid sample for detecting deletions and/or duplications of chromosome segments or entire chromosomes using any of the methods described herein). In some embodiments, the kit can include any of the primer libraries of the invention. In an embodiment, the kit comprises a plurality of inner forward primers and optionally a plurality of inner reverse primers, and optionally outer forward primers and outer reverse primers, where each of the primers is designed to hybridize to the region of DNA immediately upstream and/or downstream from one of the target sites (e.g., V(D)J recombination generated gene segments) on the target chromosome(s) or chromosome segment(s), and optionally additional chromosomes or chromosome segments. In some embodiments, the kit includes instructions for using the primer library to amplify the target loci, such as for detecting one or more deletions and/or duplications of one or more chromosome segments or entire chromosomes using any of the methods described herein.

Kits for immune cell receptor DNA detection according to some embodiments of the present invention, include standards and/or controls such as primer for amplifying housekeeping genes. For example, in certain embodiments, the standards and/or controls are sold and optionally shipped and packaged together with primers used to perform the amplification reactions provided herein.

9. Molecular Barcodes

In some embodiments, the adaptors or primers describe herein may comprise one or more molecular barcodes. Molecular barcodes or molecular indexing sequences have been used in next generation sequencing to reduce quantitative bias introduced by replication, by tagging each nucleic acid fragment with a molecular barcode or molecular indexing sequence. Sequence reads that have different molecular barcodes or molecular indexing sequences represent different original nucleic acid molecules. By referencing the molecular barcodes or molecular indexing sequences, PCR artifacts, such as sequence changes generated by polymerase errors that are not present in the original nucleic acid molecules can be identified and separated from real variants/mutations present in the original nucleic acid molecules.

In some embodiments, molecular barcodes are introduced by ligating adaptors carrying the molecular barcodes to the isolated cfDNA or cellular DNA to obtain adaptor-ligated and molecular barcoded DNA. In some embodiments, molecular barcodes are introduced by amplifying the adaptor-ligated DNA with primers carrying the molecular barcodes to obtain amplified adaptor-ligated and molecular barcoded DNA.

In some embodiments, the molecular barcoding adaptor or primers may comprise a universal sequence, followed by a molecular barcode region, optionally followed by a target specific sequence in the case of a primer. The sequence 5' of molecular barcode may be used for subsequence PCR amplification or sequencing and may comprise sequences useful in the conversion of the amplicon to a library for sequencing. The random molecular barcode sequence could be generated in a multitude of ways. The preferred method synthesizes the molecule tagging adaptor or primer in such a way as to include all four bases to the reaction during synthesis of the barcode region. All or various combinations of bases may be specified using the IUPAC DNA ambiguity codes. In this manner the synthesized collection of molecules will contain a random mixture of sequences in the molecular barcode region. The length of the barcode region will determine how many adaptors or primers will contain unique barcodes. The number of unique sequences is related to the length of the barcode region as $N^L$ where N is the number of bases, typically 4, and L is the length of the barcode. A barcode of five bases can yield up to 1024 unique sequences; a barcode of eight bases can yield 65536 unique barcodes. In an embodiment, the DNA can be measured by a sequencing method, where the sequence data represents the sequence of a single molecule. This can include methods in which single molecules are sequenced directly or methods in which single molecules are amplified to form clones detectable by the sequence instrument, but that still represent single molecules, herein called clonal sequencing.

In some embodiments, the molecular barcodes described herein are Molecular Index Tags ("MITs"), which are attached to a population of nucleic acid molecules from a sample to identify individual sample nucleic acid molecules from the population of nucleic acid molecules (i.e. members of the population) after sample processing for a sequencing reaction. MITs are described in detail in U.S. Pat. No. 10,011,870 to Zimmermann et al., which is incorporated herein by reference in its entirety. Unlike prior art methods that relate to unique identifiers and teach having a diversity of unique identifiers that is greater than the number of sample nucleic acid molecules in a sample in order to tag each sample nucleic acid molecule with a unique identifier, the present disclosure typically involves many more sample nucleic acid molecules than the diversity of MITs in a set of MITs. In fact, methods and compositions herein can include more than 1,000, $1 \times 10^6$, $1 \times 10^9$, or even more starting molecules for each different MIT in a set of MITs. Yet the methods can still identify individual sample nucleic acid molecules that give rise to a tagged nucleic acid molecule after amplification.

In the methods and compositions herein, the diversity of the set of MITs is advantageously less than the total number of sample nucleic acid molecules that span a target locus but the diversity of the possible combinations of attached MITs using the set of MITs is greater than the total number of sample nucleic acid molecules that span a target locus. Typically, to improve the identifying capability of the set of MITs, at least two MITs are attached to a sample nucleic acid molecule to form a tagged nucleic acid molecule. The sequences of attached MITs determined from sequencing reads can be used to identify clonally amplified identical copies of the same sample nucleic acid molecule that are attached to different solid supports or different regions of a solid support during sample preparation for the sequencing reaction. The sequences of tagged nucleic acid molecules can be compiled, compared, and used to differentiate nucleotide mutations incurred during amplification from nucleotide differences present in the initial sample nucleic acid molecules.

Sets of MITs in the present disclosure typically have a lower diversity than the total number of sample nucleic acid molecules, whereas many prior methods utilized sets of "unique identifiers" where the diversity of the unique identifiers was greater than the total number of sample nucleic acid molecules. Yet MITs of the present disclosure retain sufficient tracking power by including a diversity of possible combinations of attached MITs using the set of MITs that is greater than the total number of sample nucleic acid molecules that span a target locus. This lower diversity for a set of MITs of the present disclosure significantly reduces the cost and manufacturing complexity associated with generating and/or obtaining sets of tracking tags. Although the total number of MIT molecules in a reaction mixture is typically greater than the total number of sample nucleic acid molecules, the diversity of the set of MITs is far less than the total number of sample nucleic acid molecules, which substantially lowers the cost and simplifies the manufacturability over prior art methods. Thus, a set of MIT's can include a diversity of as few as 3, 4, 5, 10, 25, 50, or 100 different MITs on the low end of the range and 10, 25, 50, 100, 200, 250, 500, or 1000 MITs on the high end of the range, for example. Accordingly, in the present disclosure this relatively low diversity of MITs results in a far lower diversity of MITs than the total number of sample nucleic acid molecules, which in combination with a greater total number of MITs in the reaction mixture than total sample nucleic acid molecules and a higher diversity in the possible combinations of any 2 MITs of the set of MITs than the number of sample nucleic acid molecules that span a target locus, provides a particularly advantageous embodiment that is cost-effective and very effective with complex samples isolated from nature.

In some embodiments, the population of nucleic acid molecules has not been amplified in vitro before attaching the MITs and can include between $1 \times 10^8$ and $1 \times 10^{13}$, or in some embodiments, between $1 \times 10^9$ and $1 \times 10^{12}$ or between $1 \times 10^{10}$ and $1 \times 10^{12}$, sample nucleic acid molecules. In some embodiments, a reaction mixture is formed including the population of nucleic acid molecules and a set of MITs, wherein the total number of nucleic acid molecules in the population of nucleic acid molecules is greater than the diversity of MITs in the set of MITs and wherein there are at least three MITs in the set. In some embodiments, the diversity of the possible combinations of attached MITs using the set of MITs is more than the total number of sample nucleic acid molecules that span a target locus and less than the total number of sample nucleic acid molecules in the population. In some embodiments, the diversity of set of MITs can include between 10 and 500 MITs with different sequences. The ratio of the total number of nucleic acid molecules in the population of nucleic acid molecules in the sample to the diversity of MITs in the set, in certain methods and compositions herein, can be between 1,000:1 and 1,000,000,000:1. The ratio of the diversity of the possible combinations of attached MITs using the set of MITs to the total number of sample nucleic acid molecules that span a target locus can be between 1.01:1 and 10:1. The MITs typically are composed at least in part of an oligonucleotide between 4 and 20 nucleotides in length as discussed in more detail herein. The set of MITs can be designed such that the sequences of all the MITs in the set differ from each other by at least 2, 3, 4, or 5 nucleotides.

In some embodiments, provided herein, at least one (e.g. 2, 3, 5, 10, 20, 30, 50, 100) MIT from the set of MITs are attached to each nucleic acid molecule or to a segment of each nucleic acid molecule of the population of nucleic acid molecules to form a population of tagged nucleic acid molecules. MITs can be attached to a sample nucleic acid molecule in various configurations, as discussed further herein. For example, after attachment one MIT can be located on the 5' terminus of the tagged nucleic acid molecules or 5' to the sample nucleic acid segment of some, most, or typically each of the tagged nucleic acid molecules, and/or another MIT can be located 3' to the sample nucleic acid segment of some, most, or typically each of the tagged nucleic acid molecules. In other embodiments, at least two MITs are located 5' and/or 3' to the sample nucleic acid segments of the tagged nucleic acid molecules, or 5' and/or 3' to the sample nucleic acid segment of some, most, or typically each of the tagged nucleic acid molecules. Two MITs can be added to either the 5' or 3' by including both on the same polynucleotide segment before attaching or by performing separate reactions. For example, PCR can be performed with primers that bind to specific sequences within the sample nucleic acid molecules and include a region 5' to the sequence-specific region that encodes two MITs. In some embodiments, at least one copy of each MIT of the set of MITs is attached to a sample nucleic acid molecule, two copies of at least one MIT are each attached to a different sample nucleic acid molecule, and/or at least two sample nucleic acid molecules with the same or substantially the same sequence have at least one different MIT attached. A skilled artisan will identify methods for attaching MITs to nucleic acid molecules of a population of nucleic acid molecules. For example, MITs can be attached through ligation or appended 5' to an internal sequence binding site of a PCR primer and attached during a PCR reaction as discussed in more detail herein.

After or while MITs are attached to sample nucleic acids to form tagged nucleic acid molecules, the population of tagged nucleic acid molecules are typically amplified to create a library of tagged nucleic acid molecules. Methods for amplification to generate a library, including those particularly relevant to a high-throughput sequencing workflow, are known in the art. For example, such amplification can be a PCR-based library preparation. These methods can further include clonally amplifying the library of tagged nucleic acid molecules onto one or more solid supports using PCR or another amplification method such as an isothermal method. Methods for generating clonally amplified libraries onto solid supports in high-throughput sequencing sample preparation workflows are known in the art. Additional amplification steps, such as a multiplex amplification reaction in which a subset of the population of sample nucleic acid molecules are amplified, can be included in methods for identifying sample nucleic acids provided herein as well.

In some embodiments, a nucleotide sequence of the MITs and at least a portion of the sample nucleic acid molecule segments of some, most, or all (e.g. at least 2, 3, 4, 5, 6, 7, 8, 9, 10, 20, 25, 50, 75, 100, 150, 200, 250, 500, 1,000, 2,500, 5,000, 10,000, 15,000, 20,000, 25,000, 50,000, 100,000, 1,000,000, 5,000,000, 10,000,000, 25,000,000, 50,000,000, 100,000,000, 250,000,000, 500,000,000, $1 \times 10^9$, $1 \times 10^{10}$, $1 \times 10^{11}$, $1 \times 10^{12}$, or $1 \times 10^{13}$ tagged nucleic acid molecules or between 10, 20, 25, 30, 40, 50, 60, 70, 80, or 90% of the tagged nucleic acid molecules on the low end of the range and 20, 25, 30, 40, 50, 60, 70, 80, or 90, 95, 96, 97, 98, 99, and 100% on the high end of the range) of the tagged nucleic acid molecules in the library of tagged nucleic acid molecules is then determined. The sequence of a first MIT and optionally a second MIT or more MITs on clonally amplified copies of a tagged nucleic acid molecule can be used to identify the individual sample nucleic acid molecule that gave rise to the clonally amplified tagged nucleic acid molecule in the library.

In some embodiments, sequences determined from tagged nucleic acid molecules sharing the same first and optionally the same second MIT can be used to identify amplification errors by differentiating amplification errors from true sequence differences at target loci in the sample nucleic acid molecules. For example, in some embodiments, the set of MITs are double stranded MITs that, for example, can be a portion of a partially or fully double-stranded adapter, such as a Y-adapter. In these embodiments, for every starting molecule, a Y-adapter preparation generates 2 daughter molecule types, one in a + and one in a − orientation. A true mutation in a sample molecule should have both daughter molecules paired with the same 2 MITs in these embodiments where the MITs are a double stranded adapter, or a portion thereof. Additionally, when the sequences for the tagged nucleic acid molecules are determined and bucketed by the MITs on the sequences into MIT nucleic acid segment families, considering the MIT sequence and optionally its complement for double-stranded MITs, and optionally considering at least a portion of the nucleic acid segment, most, and typically at least 75% in double-stranded MIT embodiments, of the nucleic acid segments in an MIT nucleic acid segment family will include the mutation if the starting molecule that gave rise to the tagged nucleic acid molecules had the mutation. In the event of an amplification (e.g. PCR) error, the worst-case scenario is that the error occurs in cycle 1 of the $1^{st}$ PCR. In these embodiments, an amplification error will cause 25% of the final product to contain the error (plus any additional accumulated error, but this should be <<1%). Therefore, in some embodiments, if an MIT nucleic acid segment family contains at least 75% reads for a particular mutation or polymorphic allele, for example, it can be concluded that the mutation or polymorphic allele is truly present in the sample nucleic acid molecule that gave rise to the tagged nucleic acid molecule. The later an error occurs in a sample preparation process, the lower the proportion of sequence reads that include the error in a set of sequencing reads grouped (i.e. bucketed) by MITs into a paired MIT nucleic acid segment family. For example, an error in a library preparation amplification will result in a higher percentage of sequences with the error in a paired MIT nucleic acid segment family, than an error in a subsequent amplification step in the workflow, such as a targeted multiplex amplification. An error in the final clonal amplification in a sequencing workflow creates the lowest percentage of nucleic acid molecules in a paired MIT nucleic acid segment family that includes the error.

In some embodiments disclosed herein, the ratio of the total number of the sample nucleic acid molecules to the diversity of the MITs in the set of MITs or the diversity of the possible combinations of attached MITs using the set of MITs can be between 10:1, 20:1, 30:1, 40:1, 50:1, 60:1, 70:1, 80:1, 90:1, 100:1 200:1, 300:1, 400:1, 500:1, 600:1, 700:1, 800:1, 900:1, 1,000:1, 2,000:1, 3,000:1, 4,000:1, 5,000:1, 6,000:1, 7,000:1, 8,000:1, 9,000:1, 10,000:1, 15,000:1, 20,000:1, 25,000:1, 30,000:1, 40,000:1, 50,000:1, 60,000:1, 70,000:1, 80,000:1, 90,000:1, 100,000:1, 200,000:1, 300,000:1, 400,000:1, 500,000:1, 600,000:1, 700,000:1, 800,000:1, 900,000:1, and 1,000,000:1 on the low end of the range and 100:1 200:1, 300:1, 400:1, 500:1, 600:1, 700:1, 800:1, 900:1, 1,000:1, 2,000:1, 3,000:1, 4,000:1, 5,000:1, 6,000:1, 7,000:1, 8,000:1, 9,000:1, 10,000:1, 15,000:1, 20,000:1, 25,000:1, 30,000:1, 40,000:1, 50,000:1, 60,000:1, 70,000:1, 80,000:1, 90,000:1, 100,000:1, 200,000:1, 300,000:1, 400,000:1, 500,000:1, 600,000:1, 700,000:1, 800,000:1, 900,000:1, 1,000,000:1, 2,000,000:1, 3,000,000:1, 4,000,000:1, 5,000,000:1, 6,000,000:1, 7,000,000:1, 8,000,000:1, 9,000,000:1, 10,000,000:1, 50,000,000:1, 100,000,000:1, and 1,000,000,000:1 on the high end of the range.

In some embodiments, the sample is a human cfDNA sample. In such a method, as disclosed herein, the diversity is between about 20 million and about 3 billion. In these embodiments, the ratio of the total number of sample nucleic acid molecules to the diversity of the set of MITs can be between 100,000:1, $1 \times 10^6$:1, $1 \times 10^7$:1, $2 \times 10^7$:1, and $2.5 \times 10^7$:1 on the low end of the range and $2 \times 10^7$:1, $2.5 \times 10^7$:1, $5 \times 10^7$:1, $1 \times 10^8$:1, $2.5 \times 10^8$:1, $5 \times 10^8$:1, and $1 \times 10^9$:1 on the high end of the range.

In some embodiments, the diversity of possible combinations of attached MITs using the set of MITs is preferably greater than the total number of sample nucleic acid molecules that span a target locus. For example, if there are 100 copies of the human genome that have all been fragmented into 200 bp fragments such that there are approximately 15,000,000 fragments for each genome, then it is preferable that the diversity of possible combinations of MITs be greater than 100 (number of copies of each target locus) but less than 1,500,000,000 (total number of nucleic acid molecules). For example, the diversity of possible combinations of MITs can be greater than 100 but much less than 1,500,000,000, such as 200, 300, 400, 500, 600, 700, 800, 900, or 1,000 possible combinations of attached MITs. While the diversity of MITs in the set of MITs is less than the total number of nucleic acid molecules, the total number of MITs in the reaction mixture is in excess of the total number of nucleic acid molecules or nucleic acid molecule segments in the reaction mixture. For example, if there are 1,500,000,000 total nucleic acid molecules or nucleic acid molecule segments, then there will be more than 1,500,000,000 total MIT molecules in the reaction mixture. In some embodiments, the ratio of the diversity of MITs in the set of MITs can be lower than the number of nucleic acid molecules in a sample that span a target locus while the diversity of the possible combinations of attached MITs using the set of MITs can be greater than the number of nucleic acid molecules in the sample that span a target locus. For example, the ratio of the number of nucleic acid molecules in a sample that span a target locus to the diversity of MITs in the set of MITs can be at least 10:1, 25:1, 50:1, 100:1, 125:1, 150:1, or 200:1 and the ratio of the diversity of the possible combinations of attached MITs using the set of MITs to the number of nucleic acid molecules in the sample that span a target locus can be at least 1.01:1, 1.1:1, 2:1, 3:1, 4:1, 5:1, 6:1, 7:1, 8:1, 9:1, 10:1, 20:1, 25:1, 50:1, 100:1, 250:1, 500:1, or 1,000:1.

Typically, the diversity of MITs in the set of MITs is less than the total number of sample nucleic acid molecules that span a target locus whereas the diversity of the possible combinations of attached MITs is greater than the total number of sample nucleic acid molecules that span a target locus. In embodiments where 2 MITs are attached to sample nucleic acid molecules, the diversity of MITs in the set of MITs is less than the total number of sample nucleic acid molecules that span a target locus but greater than the square root of the total number of sample nucleic acid molecules that span a target locus. In some embodiments, the diversity of MITs is less than the total number of sample nucleic acid molecules that span a target locus but 1, 2, 3, 4, or 5 more than the square root of the total number of sample nucleic acid molecules that span a target locus. Thus, although the diversity of MITs is less than the total number of sample nucleic acid molecules that span a target locus, the total number of combinations of any 2 MITs is greater than the total number of sample nucleic acid molecules that span a target locus. The diversity of MITs in the set is typically less than one half the number of sample nucleic acid molecules than span a target locus in samples with at least 100 copies of each target locus. In some embodiments, the diversity of MITs in the set can be at least 1, 2, 3, 4, or 5 more than the square root of the total number of sample nucleic acid molecules that span a target locus but less than $\frac{1}{5}$, $\frac{1}{10}$, $\frac{1}{20}$, $\frac{1}{50}$, or $\frac{1}{100}$ the total number of sample nucleic acid molecules that span a target locus. For samples with between 2,000 and 1,000,000 sample nucleic acid molecules that span a target locus, the number of MITs in the set does not exceed 1,000. For example, in a sample with 10,000 copies of the genome in a genomic DNA sample such as a circulating cell-free DNA sample such that the sample has 10,000 sample nucleic acid molecules that span a target locus, the diversity of MITs can be between 101 and 1,000, or between 101 and 500, or between 101 and 250. In some embodiments, the diversity of MITs in the set of MITs can be between the square root of the total number of sample nucleic acid molecules that span a target locus and 1, 10, 25, 50, 100, 125, 150, 200, 250, 300, 400, 500, 600, 700, 800, 900, or 1,000 less than the total number of sample nucleic acid molecules that span a target locus. In some embodiments, the diversity of MITs in the set of MITs can be between 0.01%, 0.05%, 0.1%, 0.5%, 1%, 2%, 3%, 4%, 5%, 10%, 15%, 20%, 25%, 30%, 35%, 40%, 45%, 50%, 55%, 60%, 65%, 70%, 75%, and 80% of the number of sample nucleic acid molecules that span a target locus on the low end of the range and 1%, 2%, 3%, 4%, 5%, 10%, 15%, 20%, 25%, 30%, 35%, 40%, 45%, 50%, 55%, 60%, 65%, 70%, 75%, 80%, 85%, 90%, 95%, 96%, 97%, 98%, and 99% of the number of sample nucleic acid molecules that span a target locus on the high end of the range.

In some embodiments, the ratio of the total number of MITs in the reaction mixture to the total number of sample nucleic acid molecules in the reaction mixture can be between 1.01, 1.1:1, 2:1, 3:1, 4:1, 5:1, 6:1, 7:1, 8:1, 9:1, 10:1, 25:1 50:1, 100:1, 200:1, 300:1, 400:1, 500:1, 600:1, 700:1, 800:1, 900:1, 1,000:1, 2,000:1, 3,000:1, 4,000:1, 5,000:1, 6,000:1, 7,000:1, 8,000:1, 9,000:1, and 10,000:1 on the low end of the range and 25:1 50:1, 100:1, 200:1, 300:1, 400:1, 500:1, 600:1, 700:1, 800:1, 900:1, 1,000:1, 2,000:1, 3,000:1, 4,000:1, 5,000:1, 6,000:1, 7,000:1, 8,000:1, 9,000:1, 10,000:1, 15,000:1, 20,000:1, 25,000:1, 30,000:1, 40,000:1, and 50,000:1 on the high end of the range. In some embodiments, the total number of MITs in the reaction mixture is at least 50%, 60%, 70%, 80%, 90%, 95%, 96%, 97%, 98% 99%, or 99.9% of the total number of sample nucleic acid molecules in the reaction mixture. In other embodiments, the ratio of the total number of MITs in the reaction mixture to the total number of sample nucleic acid molecules in the reaction mixture can be at least enough MITs for each sample nucleic acid molecule to have the appropriate number of MITs attached, i.e. 2:1 for 2 MITs being attached, 3:1 for 3 MITs, 4:1 for 4 MITs, 5:1 for 5 MITs, 6:1 for 6 MITs, 7:1 for 7 MITs, 8:1 for 8 MITs, 9:1 for 0 MITs, and 10:1 for 10 MITs.

In some embodiments, the ratio of the total number of MITs with identical sequences in the reaction mixture to the total number of nucleic acid segments in the reaction mixture can be between 0.1:1, 0.2:1, 0.3:1, 0.4:1, 0.5:1, 0.6:1, 0.7:1, 0.8:1, 0.9:1, 1:1, 1.1:1, 1.2:1, 1.3:1, 1.4:1, 1.5:1, 1.6:1, 1.7:1, 1.8:1, 1.9:1, 2:1, 2.25:1, 2.5:1, 2.75:1, 3:1, 3.5:1, 4:1, 4.5:1, and 5:1 on the low end of the range and 0.5:1, 0.6:1, 0.7:1, 0.8:1, 0.9:1, 1:1, 1.1:1, 1.2:1, 1.3:1, 1.4:1, 1.5:1, 1.6:1, 1.7:1, 1.8:1, 1.9:1, 2:1, 2.25:1, 2.5:1, 2.75:1, 3:1, 3.5:1, 4:1, 4.5:1, 5:1, 6:1, 7:1, 8:1, 9:1, 10:1, 20:1, 30:1, 40:1, 50:1, 60:1, 70:1, 80:1, 90:1, and 100:1 on the high end of the range.

The set of MITs can include, for example, at least three MITs or between 10 and 500 MITs. As discussed herein in some embodiments, nucleic acid molecules from the sample are added directly to the attachment reaction mixture without amplification. These sample nucleic acid molecules can be purified from a source, such as a living cell or organism, as disclosed herein, and then MITs can be attached without amplifying the nucleic acid molecules. In some embodiments, the sample nucleic acid molecules or nucleic acid segments can be amplified before attaching MITs. As discussed herein, in some embodiments, the nucleic acid molecules from the sample can be fragmented to generate sample nucleic acid segments. In some embodiments, other oligonucleotide sequences can be attached (e.g. ligated) to the ends of the sample nucleic acid molecules before the MITs are attached.

In some embodiments disclosed herein the ratio of sample nucleic acid molecules, nucleic acid segments, or fragments that include a target locus to MITs in the reaction mixture can be between 1.01:1, 1.05, 1.1:1, 1.2:1 1.3:1, 1.4:1, 1.5:1, 1.6:1, 1.7:1, 1.8:1, 1.9:1, 2:1, 2.5:1, 3:1, 4:1, 5:1, 6:1, 7:1, 8:1, 9:1, 10:1, 15:1, 20:1, 25:1, 30:1, 35:1, 40:1, 45:1, and 50:1 on the low end and 5:1, 6:1, 7:1, 8:1, 9:1, 10:1, 15:1, 20:1, 25:1, 30:1, 35:1, 40:1, 45:1, 50:1 60:1, 70:1, 80:1, 90:1, 100:1, 125:1, 150:1, 175:1, 200:1, 300:1, 400:1 and 500:1 on the high end. For example, in some embodiments, the ratio of sample nucleic acid molecules, nucleic acid segments, or fragments with a specific target locus to MITs in the reaction mixture is between 5:1, 6:1, 7:1, 8:1, 9:1, 10:1, 15:1, 20:1, 25:1, 30:1, 35:1, 40:1, 45:1, and 50:1 on the low end and 20:1, 25:1, 30:1, 35:1, 40:1, 45:1, 50:1, 60:1, 70:1, 80:1, 90:1, 100:1, and 200:1 on the high end. In some embodiments, the ratio of sample nucleic acid molecules or nucleic acid segments to MITs in the reaction mixture can be between 25:1, 30:1, 35:1, 40:1, 45:1, 50:1 on the low end and 50:1 60:1, 70:1, 80:1, 90:1, 100:1 on the high end. In some embodiments, the diversity of the possible combinations of attached MITs can be greater than the number of sample nucleic acid molecules, nucleic acid segments, or fragments that span a target locus. For example, in some embodiments, the ratio of the diversity of the possible combinations of attached MITs to the number of sample nucleic acid molecules, nucleic acid segments, or fragments that span a target locus can be at least 1.01, 1.1:1, 2:1, 3:1, 4:1, 5:1, 6:1, 7:1, 8:1, 9:1, 10:1, 20:1, 25:1, 50:1, 100:1, 250:1, 500:1, or 1,000:1.

Reaction mixtures for tagging nucleic acid molecules with MITs (i.e. attaching nucleic acid molecules to MITs), as provided herein, can include additional reagents in addition to a population of sample nucleic acid molecules and a set of MITs. For example, the reaction mixtures for tagging can include a ligase or polymerase with suitable buffers at an appropriate pH, adenosine triphosphate (ATP) for ATP-dependent ligases or nicotinamide adenine dinucleotide for NAD-dependent ligases, deoxynucleoside triphosphates (dNTPs) for polymerases, and optionally molecular crowding reagents such as polyethylene glycol. In certain embodiments the reaction mixture can include a population of sample nucleic acid molecules, a set of MITs, and a polymerase or ligase, wherein the ratio of the number of sample nucleic acid molecules, nucleic acid segments, or fragments with a specific target locus to the number of MITs in the reaction mixture can be any of the ratios disclosed herein, for example between 2:1 and 100:1, or between 10:1 and 100:1 or between 25:1 and 75:1, or is between 40:1 and 60:1, or between 45:1 and 55:1, or between 49:1 and 51:1.

In some embodiments disclosed herein the number of different MITs (i.e. diversity) in the set of MITs can be between 3, 4, 5, 6, 7, 8, 9, 10, 11, 12, 13, 14, 15, 16, 17, 18, 19, 20, 25, 30, 35, 40, 45, 50, 60, 70, 80, 90, 100, 125, 150, 175, 200, 250, 300, 350, 400, 450, 500, 600, 700, 800, 900, 1,000, 1,500, 2,000, 2,500, and 3,000 MITs with different sequences on the low end and 4, 5, 6, 7, 8, 9, 10, 11, 12, 13, 14, 15, 16, 17, 18, 19, 20, 25, 30, 35, 40, 45, 50, 60, 70, 80, 90, 100, 125, 150, 175, 200, 250, 300, 350, 400, 450, 500, 600, 700, 800, 900, 1,000, 2,000, 3,000, 4,000, and 5,000 MITs with different sequences on the high end. For example, the diversity of different MITs in the set of MITs can be between 20, 25, 30, 35, 40, 45, 50, 60, 70, 80, 90, and 100 different MIT sequences on the low end and 50, 60, 70, 80, 90, 100, 125, 150, 175, 200, 250, and 300 different MIT sequences on the high end. In some embodiments, the diversity of different MITs in the set of MITs can be between 50, 60, 70, 80, 90, 100, 125, and 150 different MIT sequences on the low end and 100, 125, 150, 175, 200, and 250 different MIT sequences on the high end. In some embodiments, the diversity of different MITs in the set of MITs can be between 3 and 1,000, or 10 and 500, or 50 and 250 different MIT sequences. In some embodiments, the diversity of possible combinations of attached MITs using the set of MITs can be between 4, 5, 6, 7, 8, 9, 10, 15, 20, 25, 30, 40, 50, 75, 100, 150, 200, 250, 300, 400, 500, and 1,000, 2,000, 3,000, 4,000, 5,000, 6,000, 7,000, 8,000, 9,000, 10,000, 20,000, 30,000, 40,000, 50,000, 60,000, 70,000, 80,000, 90,000, 100,000, 250,000, 500,000, 1,000, 000, possible combinations of attached MITs on the low end of the range and 10, 15, 20, 25, 30, 40, 50, 75, 100, 150, 200, 250, 300, 400, 500, 1,000, 2,000, 3,000, 4,000, 5,000, 6,000, 7,000, 8,000, 9,000, 10,000, 20,000, 30,000, 40,000, 50,000, 60,000, 70,000, 80,000, 90,000, 100,000, 250,000, 500,000, 1,000,000, 2,000,000, 3,000,000, 4,000,000, 5,000,000, 6,000,000, 7,000,000, 8,000,000, 9,000,000, and 10,000,000 possible combinations of attached MITs on the high end of the range.

The MITs in the set of MITs are typically all the same length. For example, in some embodiments, the MITs can be any length between 2, 3, 4, 5, 6, 7, 8, 9, 10, 11, 12, 13, 14, 15, 16, 17, 18, 19, and 20 nucleotides on the low end and 4, 5, 6, 7, 8, 9, 10, 11, 12, 13, 14, 15, 16, 17, 18, 19, 20, 21, 22, 23, 24, 25, 26, 27, 28, 29, and 30 nucleotides on the high end. In certain embodiments, the MITs are any length between 3, 4, 5, 6, 7, or 8 nucleotides on the low end and 5, 6, 7, 8, 9, 10, or 11 nucleotides on the high end. In some embodiments, the lengths of the MITs can be any length between 4, 5, or 6, nucleotides on the low end and 5, 6, or 7 nucleotides on the high end. In some embodiments, the length of the MITs is 5, 6, or 7 nucleotides.

As will be understood, a set of MITs typically includes many identical copies of each MIT member of the set. In some embodiments, a set of MITs includes between 10, 20, 25, 30, 40, 50, 100, 500, 1,000, 10,000, 50,000, and 100,000 times more copies on the low end of the range, and 100, 500, 1,000, 10,000, 50,000, 100,000, 250,000, 500,000 and 1,000,000 more copies on the high end of the range, than the total number of sample nucleic acid molecules that span a target locus. For example, in a human circulating cell-free DNA sample isolated from plasma, there can be a quantity of DNA fragments that includes, for example, 1,000-100,000 circulating fragments that span any target locus of the genome. In certain embodiments, there are no more than $\frac{1}{10}$, $\frac{1}{4}$, $\frac{1}{2}$, or $\frac{3}{4}$ as many copies of any given MIT as total unique MITs in a set of MITs. Between members of the set, there can be 1, 2, 3, 4, 5, 6, 7, 8, 9, or 10 differences between any sequence and the rest of the sequences. In some embodiments, the sequence of each MIT in the set differs from all the other MITs by at least 1, 2, 3, 4, 5, 6, 7, 8, 9, or 10 nucleotides. To reduce the chance of misidentifying an MIT, the set of MITs can be designed using methods a skilled artisan will recognize, such as taking into consideration the Hamming distances between all the MITs in the set of MITs. The Hamming distance measures the minimum number of substitutions required to change one string, or nucleotide sequence, into another. Here, the Hamming distance measures the minimum number of amplification errors required to transform one MIT sequence in a set into another MIT sequence from the same set. In certain embodiments, different MITs of the set of MITs have a Hamming distance of less than 1, 2, 3, 4, 5, 6, 7, 8, 9, or 10 between each other.

In certain embodiments, a set of isolated MITs as provided herein is one embodiment of the present disclosure. The set of isolated MITs can be a set of single stranded, or partially, or fully double stranded nucleic acid molecules, wherein each MIT is a portion of, or the entire, nucleic acid molecule of the set. In certain examples, provided herein is a set of Y-adapter (i.e. partially double-stranded) nucleic acids that each include a different MIT. The set of Y-adapter nucleic acids can each be identical except for the MIT portion. Multiple copies of the same Y-adapter MIT can be included in the set. The set can have a number and diversity of nucleic acid molecules as disclosed herein for a set of MITs. As a non-limiting example, the set can include 2, 5, 10, or 100 copies of between 50 and 500 MIT-containing Y-adapters, with each MIT segment between 4 and 8 nucleic acids in length and each MIT segment differing from the other MIT segments by at least 2 nucleotides, but contain identical sequences other than the MIT sequence. Further details regarding Y-adapter portion of the set of Y-adapters is provided herein.

In other embodiments, a reaction mixture that includes a set of MITs and a population of sample nucleic acid molecules is one embodiment of the present disclosure. Furthermore, such a composition can be part of numerous methods and other compositions provided herein. For example, in further embodiments, a reaction mixture can include a polymerase or ligase, appropriate buffers, and supplemental components as discussed in more detail herein. For any of these embodiments, the set of MITs can include between 25, 50, 100, 200, 250, 300, 400, 500, or 1,000 MITs on the low end of the range, and 100, 200, 250, 300, 400, 500, 1,000, 1,500, 2,000, 2,500, 5,000, 10,000, or 25,000 MITs on the high end of the range. For example, in some embodiments, a reaction mixture includes a set of between 10 and 500 MITs.

Molecular Index Tags (MITs) as discussed in more detail herein can be attached to sample nucleic acid molecules in the reaction mixture using methods that a skilled artisan will recognize. In some embodiments, the MITs can be attached alone, or without any additional oligonucleotide sequences. In some embodiments, the MITs can be part of a larger oligonucleotide that can further include other nucleotide sequences as discussed in more detail herein. For example, the oligonucleotide can also include primers specific for nucleic acid segments or universal primer binding sites, adapters such as sequencing adapters such as Y-adapters, library tags, ligation adapter tags, and combinations thereof. A skilled artisan will recognize how to incorporate various tags into oligonucleotides to generate tagged nucleic acid molecules useful for sequencing, especially high-throughput sequencing. The MITs of the present disclosure are advantageous in that they are more readily used with additional sequences, such as Y-adapter and/or universal sequences because the diversity of nucleic acid molecules is less, and therefore they can be more easily combined with additional sequences on an adapter to yield a smaller, and therefore more cost effective set of MIT-containing adapters.

In some embodiments, the MITs are attached such that one MIT is 5' to the sample nucleic acid segment and one MIT is 3' to the sample nucleic acid segment in the tagged nucleic acid molecule. For example, in some embodiments, the MITs can be attached directly to the 5' and 3' ends of the sample nucleic acid molecules using ligation. In some embodiments disclosed herein, ligation typically involves forming a reaction mixture with appropriate buffers, ions, and a suitable pH in which the population of sample nucleic acid molecules, the set of MITs, adenosine triphosphate, and a ligase are combined. A skilled artisan will understand how to form the reaction mixture and the various ligases available for use. In some embodiments, the nucleic acid molecules can have 3' adenosine overhangs and the MITs can be located on double-stranded oligonucleotides having 5' thymidine overhangs, such as directly adjacent to a 5' thymidine.

In further embodiments, MITs provided herein can be included as part of Y-adapters before they are ligated to sample nucleic acid molecules. Y-adapters are well-known in the art and are used, for example, to more effectively provide primer binding sequences to the two ends of the nucleic acid molecules before high-throughput sequencing. Y-adapters are formed by annealing a first oligonucleotide and a second oligonucleotide where a 5' segment of the first oligonucleotide and a 3' segment of the second oligonucleotide are complementary and wherein a 3' segment of the first oligonucleotide and a 5' segment of the second oligonucleotide are not complementary. In some embodiments, Y-adapters include a base-paired, double-stranded polynucleotide segment and an unpaired, single-stranded polynucleotide segment distal to the site of ligation. The double-stranded polynucleotide segment can be between 3, 4, 5, 6, 7, 8, 9, 10, 11, 12, 13, 14, 15, 16, 17, 18, 19, or 20 nucleotides in length on the low end of the range and 4, 5, 6, 7, 8, 9, 10, 11, 12, 13, 14, 15, 16, 17, 18, 19, 20, 21, 22, 23, 24, 25, 26, 27, 28, 29, and 30 nucleotides in length on the high end of the range. The single-stranded polynucleotide segments on the first and second oligonucleotides can be between 3, 4, 5, 6, 7, 8, 9, 10, 11, 12, 13, 14, 15, 16, 17, 18, 19, or 20 nucleotides in length on the low end of the range and 4, 5, 6, 7, 8, 9, 10, 11, 12, 13, 14, 15, 16, 17, 18, 19, 20, 21, 22, 23, 24, 25, 26, 27, 28, 29, and 30 nucleotides in length on the high end of the range. In these embodiments, MITs are typically double stranded sequences added to the ends of Y-adapters, which are ligated to sample nucleic acid segments to be sequenced. In some embodiments, the non-complementary segments of the first and second oligonucleotides can be different lengths.

In some embodiments, double-stranded MITs attached by ligation will have the same MIT on both strands of the sample nucleic acid molecule. In certain aspects the tagged nucleic acid molecules derived from these two strands will be identified and used to generate paired MIT families. In downstream sequencing reactions, where single stranded nucleic acids are typically sequenced, an MIT family can be identified by identifying tagged nucleic acid molecules with identical or complementary MIT sequences. In these embodiments, the paired MIT families can be used to verify the presence of sequence differences in the initial sample nucleic acid molecule as discussed herein.

In some embodiments, MITs can be attached to the sample nucleic acid segment by being incorporated 5' to forward and/or reverse PCR primers that bind sequences in the sample nucleic acid segment. In some embodiments, the MITs can be incorporated into universal forward and/or reverse PCR primers that bind universal primer binding sequences previously attached to the sample nucleic acid molecules. In some embodiments, the MITs can be attached using a combination of a universal forward or reverse primer with a 5' MIT sequence and a forward or reverse PCR primer that bind internal binding sequences in the sample nucleic acid segment with a 5' MIT sequence. After 2 cycles of PCR, sample nucleic acid molecules that have been amplified using both the forward and reverse primers with incorporated MIT sequences will have MITs attached 5' to the sample nucleic acid segments and 3' to the sample nucleic acid segments in each of the tagged nucleic acid molecules. In some embodiments, the PCR is done for 2, 3, 4, 5, 6, 7, 8, 9, or 10 cycles in the attachment step.

In some embodiments disclosed herein the two MITs on each tagged nucleic acid molecule can be attached using similar techniques such that both MITs are 5' to the sample nucleic acid segments or both MITs are 3' to the sample nucleic acid segments. For example, two MITs can be incorporated into the same oligonucleotide and ligated on one end of the sample nucleic acid molecule or two MITs can be present on the forward or reverse primer and the paired reverse or forward primer can have zero MITs. In other embodiments, more than two MITs can be attached with any combination of MITs attached to the 5' and/or 3' locations relative to the nucleic acid segments.

As discussed herein, other sequences can be attached to the sample nucleic acid molecules before, after, during, or with the MITs. For example, ligation adapters, often referred to as library tags or ligation adaptor tags (LTs), appended, with or without a universal primer binding sequence to be used in a subsequent universal amplification step. In some embodiments, the length of the oligonucleotide containing the MITs and other sequences can be between 5, 6, 7, 8, 9, 10, 11, 12, 13, 14, 15, 16, 17, 18, 29, 20, 21, 22, 23, 24, 25, 26, 27, 28, 29, 30, 35, 40, 45, 50, 55, 60, 65, 70, 75, 80, 85, 90, 95, and 100 nucleotides on the low end of the range and 10, 11, 12, 13, 14, 15, 16, 17, 18, 29, 20, 21, 22, 23, 24, 25, 26, 27, 28, 29, 30, 35, 40, 45, 50, 55, 60, 65, 70, 75, 80, 85, 90, 95, 100, 110, 120, 130, 140, 150, 160, 170, 180, 190, and 200 nucleotides on the high end of the range. In certain aspects the number of nucleotides in the MIT sequences can be a percentage of the number of nucleotides in the total sequence of the oligonucleotides that include MITs. For example, in some embodiments, the MIT can be at most 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, or 100% of the total nucleotides of an oligonucleotide that is ligated to a sample nucleic acid molecule.

After attaching MITs to the sample nucleic acid molecules through a ligation or PCR reaction, it may be necessary to clean up the reaction mixture to remove undesirable components that could affect subsequent method steps. In some embodiments, the sample nucleic acid molecules can be purified away from the primers or ligases. In other embodiments, the proteins and primers can be digested with proteases and exonucleases using methods known in the art.

After attaching MITs to the sample nucleic acid molecules, a population of tagged nucleic acid molecules is generated, itself forming embodiments of the present disclosure. In some embodiments, the size ranges of the tagged nucleic acid molecules can be between 10, 20, 30, 40, 50, 60, 70, 80, 90, 100, 125, 150, 175, 200, 250, 300, 400, and 500 nucleotides on the low end of the range and 100, 125, 150, 175, 200, 250, 300, 400, 500, 600, 700, 800, 900, 1,000, 2,000, 3,000, 4,000, and 5,000 nucleotides on the high end of the range.

Such a population of tagged nucleic acid molecules can include between 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 110, 120, 130, 140, 150, 160, 170, 180, 190, 200, 225, 250, 300, 350, 400, 450, 500, 600, 700, 800, 900, 1,000, 2,000, 3,000, 4,000, 5,000, 6,000, 7,000, 8,000, 9,000, 10,000, 15,000, 20,000, 30,000, 40,000, 50,000, 100,000, 200,000, 300,000, 400,000, 500,000, 600,000, 700,000, 800,000, 900,000, 1,000,000, 1,250,000, 1,500,000, 2,000,000, 2,500,000, 3,000,000, 4,000,000, 5,000,000, 10,000,000, 20,000,000, 30,000,000, 40,000,000, 50,000,000, 50,000,000, 100,000,000, 200,000,000, 300,000,000, 400,000,000, 500,000,000, 600,000,000, 700,000,000, 800,000,000, 900,000,000, and 1,000,000,000 tagged nucleic acid molecules on the low end of the range and 10, 15, 20, 25, 30, 40, 50, 60, 70, 80, 90, 100, 150, 200, 250, 300, 400, 500, 600, 700, 800, 900, 1,000, 2,000, 3,000, 4,000, 5,000, 6,000, 7,000, 8,000, 9,000, 10,000, 15,000, 20,000, 30,000, 40,000, 50,000, 100,000, 200,000, 300,000, 400,000, 500,000, 600,000, 700,000, 800,000, 900,000, 1,000,000, 1,250,000, 1,500,000, 2,000,000, 2,500,000, 3,000,000, 4,000,000, 5,000,000, 6,000,000, 7,000,000, 8,000,000, 9,000,000, 10,000,000, 20,000,000, 30,000,000, 40,00,000, 50,000,000, 100,000,000, 200,000,000, 300,000,000, 400,000,000, 500,000,000, 600,000,000, 700,000,000, 800,000,000, 900,000,000, 1,000,000,000, 2,000,000,000, 3,000,000,000, 4,000,000,000, 5,000,000,000, 6,000,000,000, 7,000,000,000, 8,000,000,000, 9,000,000,000, and 10,000,000,000, tagged nucleic acid molecules on the high end of the range. In some embodiments, the population of tagged nucleic acid molecules can include between 100,000,000, 200,000,000, 300,000,000, 400,000,000, 500,000,000, 600,000,000, 700,000,000, 800,000,000, 900,000,000, and 1,000,000,000 tagged nucleic acid molecules on the low end of the range and 500,000,000, 600,000,000, 700,000,000, 800,000,000, 900,000,000, 1,000,000,000, 2,000,000,000, 3,000,000,000, 4,000,000,000, 5,000,000,000 tagged nucleic acid molecules on the high end of the range.

In certain aspects a percentage of the total sample nucleic acid molecules in the population of sample nucleic acid molecules can be targeted to have MITs attached. In some embodiments, at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 96%, 97%, 98%, 99%, or 99.9% of the sample nucleic acid molecules can be targeted to have MITs attached. In other aspects a percentage of the sample nucleic acid molecules in the population can have MITs successfully attached. In any of the embodiments disclosed herein at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 96%, 97%, 98%, 99%, or 99.9% of the sample nucleic acid molecules can have MITs successfully attached to form the population of tagged nucleic acid molecules. In any of the embodiments disclosed herein at least 1, 2, 3, 4, 5, 6, 7, 8, 9, 10, 15, 20, 25, 30, 40, 50, 75, 100, 200, 300, 500, 600, 700, 800, 900, 1,000, 2,000, 3,000, 4,000, 5,000, 6,000, 7,000, 8,000, 9,000, 10,000, 15,000, 20,000, 30,000, 40,000, or 50,000 of the sample nucleic acid molecules can have MITs successfully attached to form the population of tagged nucleic acid molecules.

In some embodiments disclosed herein, MITs can be oligonucleotide sequences of ribonucleotides or deoxyribonucleotides linked through phosphodiester linkages. Nucleotides as disclosed herein can refer to both ribonucleotides and deoxyribonucleotides and a skilled artisan will recognize when either form is relevant for a particular application. In certain embodiments, the nucleotides can be selected from the group of naturally-occurring nucleotides consisting of adenosine, cytidine, guanosine, uridine, 5-methyluridine, deoxyadenosine, deoxycytidine, deoxyguanosine, deoxythymidine, and deoxyuridine. In some embodiments, the MITs can be non-natural nucleotides. Non-natural nucleotides can include: sets of nucleotides that bind to each other, such as, for example, d5SICS and dNaM; metal-coordinated bases such as, for example, 2,6-bis(ethylthiomethyl)pyridine (SPy) with a silver ion and mondentate pyridine (Py) with a copper ion; universal bases that can pair with more than one or any other base such as, for example, 2'-deoxyinosine derivatives, nitroazole analogues, and hydrophobic aromatic non-hydrogen-bonding bases; and xDNA nucleobases with expanded bases. In certain embodiments, the oligonucleotide sequences can be pre-determined while in other embodiments, the oligonucleotide sequences can be degenerate.

In some embodiments, MITs include phosphodiester linkages between the natural sugars ribose and/or deoxyribose that are attached to the nucleobase. In some embodiments, non-natural linkages can be used. These linkages include, for example, phosphorothioate, boranophosphate, phosphonate, and triazole linkages. In some embodiments, combinations of the non-natural linkages and/or the phosphodiester linkages can be used. In some embodiments, peptide nucleic acids can be used wherein the sugar backbone is instead made of repeating N-(2-aminoethyl)-glycine units linked by peptide bonds. In any of the embodiments disclosed herein non-natural sugars can be used in place of the ribose or deoxyribose sugar. For example, threose can be used to generate α-(L)-threofuranosyl-(3'-2') nucleic acids (TNA). Other linkage types and sugars will be apparent to a skilled artisan and can be used in any of the embodiments disclosed herein.

In some embodiments, nucleotides with extra bonds between atoms of the sugar can be used. For example, bridged or locked nucleic acids can be used in the MITs. These nucleic acids include a bond between the 2'-position and 4'-position of a ribose sugar.

In certain embodiments, the nucleotides incorporated into the sequence of the MIT can be appended with reactive linkers. At a later time, the reactive linkers can be mixed with an appropriately-tagged molecule in suitable conditions for the reaction to occur. For example, aminoallyl nucleotides can be appended that can react with molecules linked to a reactive leaving group such as succinimidyl ester and thiol-containing nucleotides can be appended that can react with molecules linked to a reactive leaving group such as maleimide. In other embodiments, biotin-linked nucleotides can be used in the sequence of the MIT that can bind streptavidin-tagged molecules.

Various combinations of the natural nucleotides, non-natural nucleotides, phosphodiester linkages, non-natural linkages, natural sugars, non-natural sugars, peptide nucleic acids, bridged nucleic acids, locked nucleic acids, and nucleotides with appended reactive linkers will be recognized by a skilled artisan and can be used to form MITs in any of the embodiments disclosed herein.

10. Advantages and Applications

The detection assay described herein leverages recombination of V, D and J genes. The recombination principle is similar in B-cells as well as T-cells using different V, D and J genes. Exemplary advantages and applications of the methods and compositions described herein include: (i) useful for detecting B-cell DNA using plasma or extracted cellular DNA; (ii) useful for detecting other immune cells such as T-cells in plasma DNA or in from the cellular fraction; (iii) useful for monitoring the immune system status in response to cytotoxic treatment such as chemotherapy for malignancies and immunosuppressive therapies for autoimmune disorders; (iv) the highly sensitive plasma-based B-cell detection assay can be applied to monitor B-cell counts in the bone marrow thereby avoiding painful and expensive bone marrow biopsies, which is useful for minimal residual disease detection and treatment monitoring; and (v) analysis of all detected VDJ reads can be used to determine B-cell receptor repertoire of patients for situations such as therapy selection and neo-antigen design.

WORKING EXAMPLES

Example 1: Designing Primers for Maximal Coverage of the B Cell Receptor V and J Genes to Detect VDJ Recombination Background B-cells are components of the adaptive immune system that originate in the bone marrow. Each B-cell has a unique B-cell receptor (BCR) on the surface that is used to interface with antigens. FIG. 1 summarizes the mechanism for B cell activation by antigen binding to the BCR.

Figure 2:
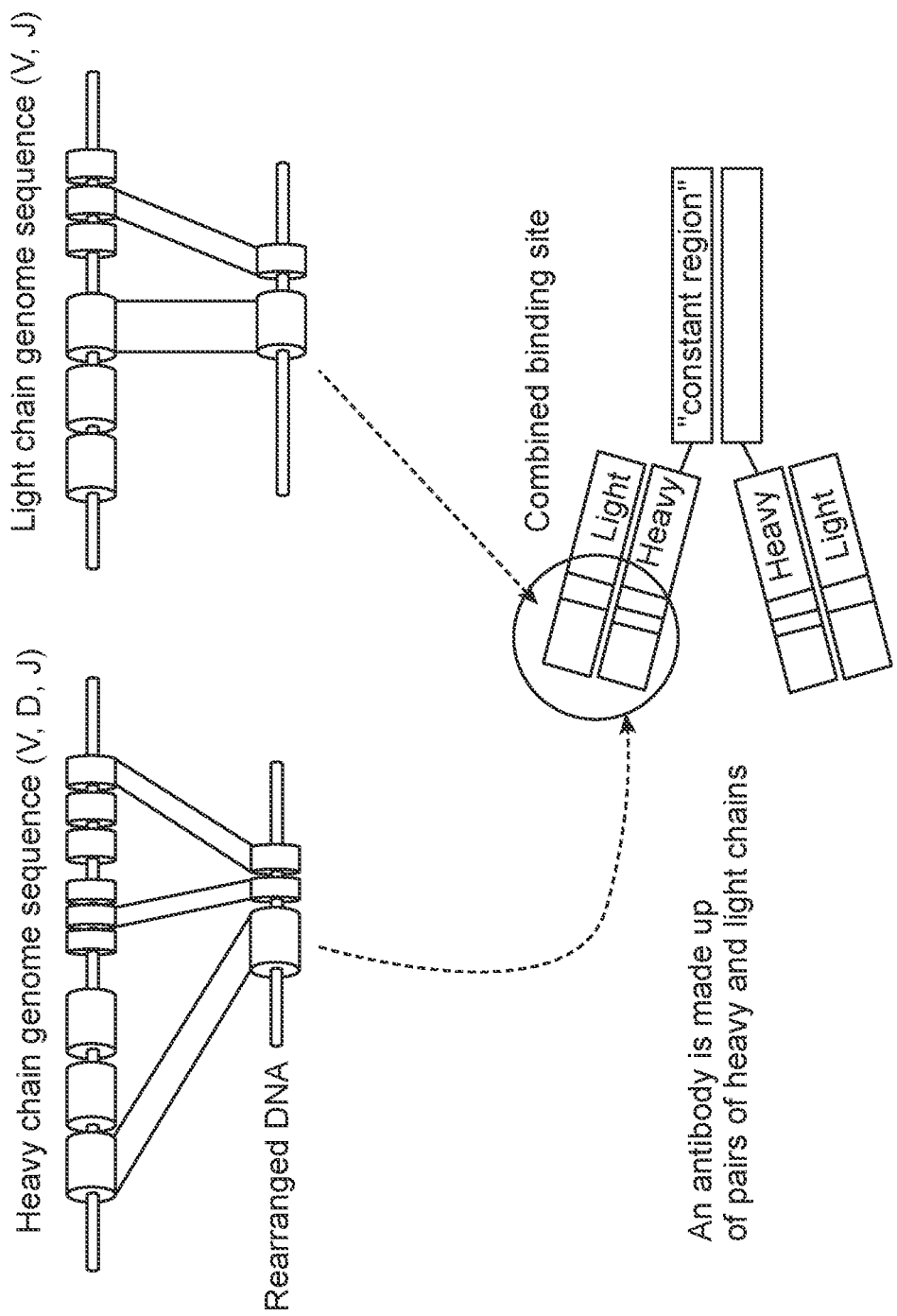
FIG. 2 is a graphic representation of VDJ recombination at the BCR locus.

Every human being has a unique set of BCRs. The BCRs are made of light and heavy chains assembled from V(variable), D (diversity) and J (joining) gene segments. There are many different V, D and J genes in the human genome. The uniqueness of each BCR is due to the recombination event that selects and combines one each of V, D and J genes per BCR (FIG. 2). This results in approximately 3×10^11 possible combinations. This process is specific to B-cells and was leveraged to design multiplex PCR primers to measure B-cell amounts.

Figure 3:
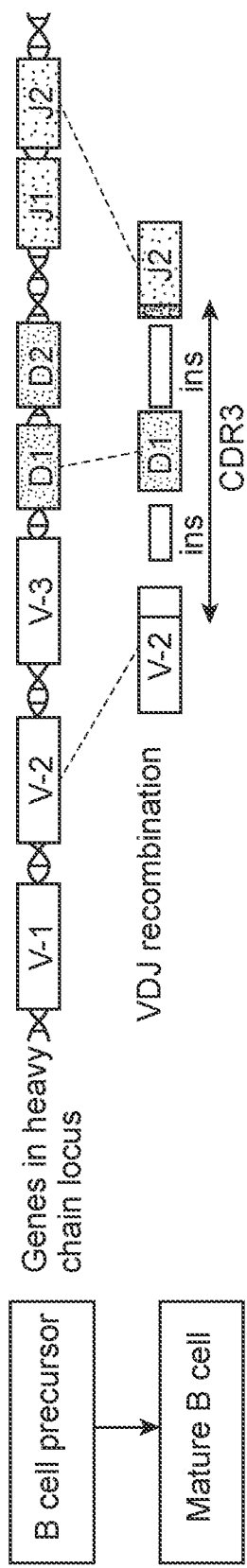
FIG. 3 is a graphic representation of VDJ recombination at the heavy chain locus.

FIG. 3 shows a graphic representation of a heavy chain locus. During maturation of B cells, the V genes combine with the J genes to generate about $3 \times 10^{11}$ different combinations. Different humans will have a different repertoire of V(D)J combinations. The insert (referred to as "ins" in FIG. 3) between the V-D and D-J genes also vary in length.

Primer Design Strategy. The V, D and J genes are found to be organized tandemly forming the IGH locus on chromosome 14. All forward primers are designed on the invariant regions of V genes and all reverse primers on J genes such that a short PCR product is formed only upon successful V(D)J recombination as shown in FIG. 2.

Heavy chain V, D and J gene sequences and annotations were obtained by using ImMunoGeneTics Informationsystem© (IMGT©) described in Lefranc, M.-P., IMGT® databases, web resources and tools for immunoglobulin and T cell receptor sequence analysis, 17: 260-266 (2003).

Figure 4:
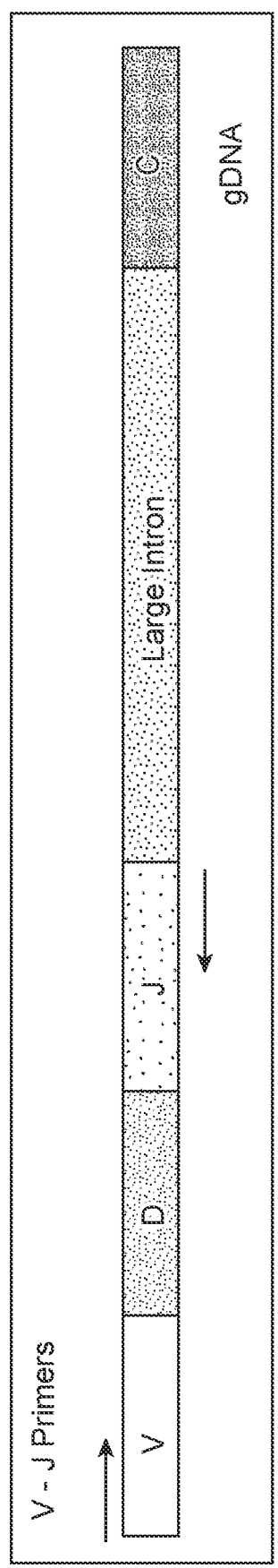
FIG. 4 is a B-cell assay primer design schematics showing localization of forward and reverse primers as indicated with arrows. The V, D and J genes are found to be organized tandemly forming the IGH locus on chromosome 14. All forward primers are designed on the invariant regions of V genes and all reverse primers on J genes such that a short PCR product is formed only upon successful VDJ recombination. IMGT, a web resource for immunoglobulin gene sequences and tools was used to obtain heavy chain V, D and J gene sequences and annotations. 64 forward primers were designed to cover all 361 annotated V genes (including pseudogenes and orphans) such that each primer maps exactly to 15 V genes with the last 15 bases potentially binding to as many as 35 V genes. 12 reverse primers were designed to cover all J genes. 12 primers were designed to target generic housekeeping genes with similar specifications to match V & J primers. A subset of these primers will be used to normalize input levels while calculating B-cell DNA concentrations. Housekeeping genes (HKG) were chosen to be unique and essential genes. In total there are 76 forward primer (64 V and 12 HKG) and 24 reverse primers (12 J and 12 HKG) for a total of 100 primers in the B-cell detection assay pool. The sequences for 76 forward primer (64 V and 12 HKG) and 24 reverse primers (12 J and 12 HKG) are provided in SEQ ID Nos: 1-100. The primer design was optimized to detect B-cell DNA using long gDNA extracted from blood as well as short cfDNA extracted from plasma. This is possible due to the short size of the expected VDJ amplicons. In-silico performance evaluation runs estimate that the assay pool covers 79-85% of all possible VDJ recombinations.

64 forward primers were designed to cover all 361 annotated V genes (including pseudogenes and orphans) such that each primer maps exactly to 15 V genes with the last 15 bases potentially binding to as many as 35 V genes, and 12 reverse primers were designed to cover all J genes as outlined in FIG. 4. Accordingly, the 64 forward primers targeting the V genes and the 12 reverse primers covering the J genes will cover 100% of V and J genes. An exemplary list of primers used in the methods of the present disclosure is provided in the Table 2 below.

TABLE 2

Primer sequences

| Primer | Name Sequence (5' to 3') |
|---|---|
| F_v_primer_1 | TCTAGCCTTCTCGCAGCACAGGCTGTGTATTACTGTGCGAG |
| F_v_primer_2 | TCTAGCCTTCTCGCAGCACACACGGCTGTGTATTACTGTGC |
| F_v_primer_3 | TCTAGCCTTCTCGCAGCACACGGCTGTTTATTACTGTGCGAG |
| F_v_primer_4 | TCTAGCCTTCTCGCAGCACAGAGGACATGGCTGTGTATTACTGT |
| F_v_primer_5 | TCTAGCCTTCTCGCAGCACATCTGAGGACACGGCCGTGTATTA |
| F_v_primer_6 | TCTAGCCTTCTCGCAGCACATAAAGGCTGAGGACACTGCC |
| F_v_primer_7 | TCTAGCCTTCTCGCAGCACAGAGCAGCCTGAGATCTGAAGA |
| F_v_primer_8 | TCTAGCCTTCTCGCAGCACACGGCCGTGTATTACTGTGC |
| F_v_primer_9 | TCTAGCCTTCTCGCAGCACACGGCCGTATATTACTGTGCGAA |
| F_v_primer_10 | TCTAGCCTTCTCGCAGCACAGCCTTGTATCACTGTGCGAG |
| F_v_primer_11 | TCTAGCCTTCTCGCAGCACAGCAGCCTGAGATCTGAGGAC |
| F_v_primer_12 | TCTAGCCTTCTCGCAGCACAACAGCCACATATTACTGTGCAC |
| F_v_primer_13 | TCTAGCCTTCTCGCAGCACACACTGCCGTGTATTACTGTGC |
| F_v_primer_14 | TCTAGCCTTCTCGCAGCACAGCCGTGTATTACTGTACCACAGA |
| F_v_primer_15 | TCTAGCCTTCTCGCAGCACAGCCGTGTATTACTGTACCACAGG |
| F_v_primer_16 | TCTAGCCTTCTCGCAGCACACGGCCGTGTATTACTGTACTAGA |

TABLE 2-continued

Primer sequences

| Primer Name | Sequence (5' to 3') |
|---|---|
| F_v_primer_17 | TCTAGCCTTCTCGCAGCACACACAGCCGTGTATTACTGTACC |
| F_v_primer_18 | TCTAGCCTTCTCGCAGCACACCGCCTTGTATTACTGTGCAA |
| F_v_primer_19 | TCTAGCCTTCTCGCAGCACACGGCCTTGTATTACTGTGCAA |
| F_v_primer_20 | TCTAGCCTTCTCGCAGCACAGAGCAGCCTGAGATCTGACG |
| F_v_primer_21 | TCTAGCCTTCTCGCAGCACACACGGCCGTGTATTACTGTAC |
| F_v_primer_22 | TCTAGCCTTCTCGCAGCACACACGGCCGTGTATTACTGTTC |
| F_v_primer_23 | TCTAGCCTTCTCGCAGCACACACGGCCGTGTATTACTGTG |
| F_v_primer_24 | TCTAGCCTTCTCGCAGCACACTCGGACACCGCCATGT |
| F_v_primer_25 | TCTAGCCTTCTCGCAGCACACACGGCTGTGTATTACTGTGTG |
| F_v_primer_26 | TCTAGCCTTCTCGCAGCACATGAGAGCTGAGGACATGGC |
| F_v_primer_27 | TCTAGCCTTCTCGCAGCACATGAGCAGCCTGAGATCCG |
| F_v_primer_28 | TCTAGCCTTCTCGCAGCACAGCTGAGCAGCCTGAGATCC |
| F_v_primer_29 | TCTAGCCTTCTCGCAGCACACTGCCGTGTATTACTGTGCG |
| F_v_primer_30 | TCTAGCCTTCTCGCAGCACAACAGCCGTGTATTACTGTACTAGAG |
| F_v_primer_31 | TCTAGCCTTCTCGCAGCACACACAGCCGTGTATTACTGTACTAGA |
| F_v_primer_32 | TCTAGCCTTCTCGCAGCACAGGCCATGTATTACTGTGCGAG |
| F_v_primer_33 | TCTAGCCTTCTCGCAGCACAGGCCTTGTATTACTGTGCGAG |
| F_v_primer_34 | TCTAGCCTTCTCGCAGCACACGCCATGTATTACTGTGCGAG |
| F_v_primer_35 | TCTAGCCTTCTCGCAGCACACACAGCCTACATGGAGCTGA |
| F_v_primer_36 | TCTAGCCTTCTCGCAGCACAAACCAGTTCTCCCTGAAGCTGA |
| F_v_primer_37 | TCTAGCCTTCTCGCAGCACATGAAGCTGGGCTCTGTGAC |
| F_v_primer_38 | TCTAGCCTTCTCGCAGCACAGGCCGTGTATTACTGTCTAGA |
| F_v_primer_39 | TCTAGCCTTCTCGCAGCACAGTATCTGCAAATGAACAGCCTGA |
| F_v_primer_40 | TCTAGCCTTCTCGCAGCACAAACAGCCTGAAAACCGAGGACA |
| F_v_primer_41 | TCTAGCCTTCTCGCAGCACAAACATGGACCCTGTGGACACA |
| F_v_primer_42 | TCTAGCCTTCTCGCAGCACAGACATCTGAGGACATGGCTGTGTA |
| F_v_primer_43 | TCTAGCCTTCTCGCAGCACATGTGGACACAGCCACACATTAC |
| F_v_primer_44 | TCTAGCCTTCTCGCAGCACACAATGACCAACATGGACCCTGT |
| F_v_primer_45 | TCTAGCCTTCTCGCAGCACAAACTGAGGACATGGCTGTGTATGG |
| F_v_primer_46 | TCTAGCCTTCTCGCAGCACATGCAAATGAACAGCCTGAGAGC |
| F_v_primer_47 | TCTAGCCTTCTCGCAGCACACAGCTGTGTGTTACTGTATGTGAGG |
| F_v_primer_48 | TCTAGCCTTCTCGCAGCACACTAATGAACAGTCTGAGAGCAGCG |
| F_v_primer_49 | TCTAGCCTTCTCGCAGCACAAATGAACAGTCTGAGAGCAGAGGG |
| F_v_primer_50 | TCTAGCCTTCTCGCAGCACAAACAGTCAGAGAGCTGAGGACATG |
| F_v_primer_51 | TCTAGCCTTCTCGCAGCACAGCAAATGAACACTCAGAGAGCTG |
| F_v_primer_52 | TCTAGCCTTCTCGCAGCACAGAACAGTCTGAGAGCTGAGGACAT |
| F_v_primer_53 | TCTAGCCTTCTCGCAGCACATCGGACGCCGCCATGTATTATT |
| F_v_primer_54 | TCTAGCCTTCTCGCAGCACAGTCTTCAGATCAGCAGCCTAAAGG |
| F_v_primer_55 | TCTAGCCTTCTCGCAGCACAATGGCGTATCTGCAGATCAGCA |
| F_v_primer_56 | TCTAGCCTTCTCGCAGCACAACGGCCGTGTATGACTGTATGA |

TABLE 2-continued

Primer sequences

| Primer Name | Sequence (5' to 3') |
|---|---|
| F_v_primer_57 | TCTAGCCTTCTCGCAGCACAAGGACACCTCCAAAAACCAGGT |
| F_v_primer_58 | TCTAGCCTTCTCGCAGCACAAAATGAACAGCCTGAGAGCCGA |
| F_v_primer_59 | TCTAGCCTTCTCGCAGCACAGTCCAAGAACCAGTTCTCCCTGAA |
| F_v_primer_60 | TCTAGCCTTCTCGCAGCACATCTGTCAGCACGGCATATCT |
| F_v_primer_61 | TCTAGCCTTCTCGCAGCACAGCAGTGGAGCAGCCTGAA |
| F_v_primer_62 | TCTAGCCTTCTCGCAGCACATGTGACTGCCGCGGACA |
| F_v_primer_63 | TCTAGCCTTCTCGCAGCACACCGCGTATTACTGTGCCAGATA |
| F_v_primer_64 | TCTAGCCTTCTCGCAGCACACTCAAGAGATGATTCAAAGAACTCACTGT |
| R_j_primer_1 | TCTAGCCTTCTCGTGTGCAGATCCCTGGCCCCAGTAGTC |
| R_j_primer_2 | TCTAGCCTTCTCGTGTGCAGAGCCCTGGCCCCAGTGCTGGAA |
| R_j_primer_3 | TCTAGCCTTCTCGTGTGCAGATCCCTGGCCCCAGGGGTCGAACCA |
| R_j_primer_4 | TCTAGCCTTCTCGTGTGCAGAGCCACGGCCCCAGAGATCGA |
| R_j_primer_5 | TCTAGCCTTCTCGTGTGCAGATTGGCCCCAGACATCAAAAGCA |
| R_j_primer_6 | TCTAGCCTTCTCGTGTGCAGACCCTTGGCCCCAGATATCAAAA |
| R_j_primer_7 | TCTAGCCTTCTCGTGTGCAGATGGCCCCAGTAGTCAAAGTAG |
| R_j_primer_8 | TCTAGCCTTCTCGTGTGCAGACCAGACGTCCATACCGTAGTAGTA |
| R_j_primer_9 | TCTAGCCTTCTCGTGTGCAGATTTGCCCCAGACGTCCATGTAGTA |
| R_j_primer_10 | TCTAGCCTTCTCGTGTGCAGACCCAGGAGTCGAACCAGTT |
| R_j_primer_11 | TCTAGCCTTCTCGTGTGCAGATGGCCCCAGACGTCCAT |
| R_j_primer_12 | TCTAGCCTTCTCGTGTGCAGACCCAGGGGTCGAACCAGTT |

TABLE 2-continued

Primer sequences

| Primer Name | Sequence (5' to 3') |
|---|---|
| R_ANAPC4_1_chr4_25392530_25392623 | TCTAGCCTTCTCGTGTGCAGACTTCTGAAGCACCATTGGTAGAG |
| R_ANAPC4_2_chr4_25411342_25411442 | TCTAGCCTTCTCGTGTGCAGAGGCCAAAATCTGGTTGGTTCATG |
| R_mcm3_1_chr6_52149446_52149506 | TCTAGCCTTCTCGTGTGCAGACGACTTTGGTGGAGGTAGTTCTT |
| R_mcm3_2_chr6_52137983_52138094 | TCTAGCCTTCTCGTGTGCAGAAAGATCAGCAGGACACCCAGAT |
| R_NOP2_1_chr12_6666136_6666219 | TCTAGCCTTCTCGTGTGCAGACCCACCAGCAAAGAGGAAGAAATC |
| R_PSMB2_1_chr1_36068863_36068951 | TCTAGCCTTCTCGTGTGCAGACTGCCAACCTTCAGTGTTCGAA |
| R_PSMB2_2_chr1_36101977_36102084 | TCTAGCCTTCTCGTGTGCAGACGGTCAATGTCTGTTAAGGCAG |
| R_RBM19_1_chr12_114384237_114384309 | TCTAGCCTTCTCGTGTGCAGATTTACTCCCTTCCCGTCATTCC |
| R_RBM19_2_chr12_114364847_114364926 | TCTAGCCTTCTCGTGTGCAGAGCCTCCCAGGATGTACTCTGTTTAT |
| R_UTP20_1_chr12_101702010_101702126 | TCTAGCCTTCTCGTGTGCAGATTTACCTCCTGTAACGGCCCATCA |
| R_UTP20_2_chr12_101740275_101740400 | TCTAGCCTTCTCGTGTGCAGAAGAGGGTCCTTGGTTTCTAGATCT |
| R_UTP20_3_chr12_101685522_101685651 | TCTAGCCTTCTCGTGTGCAGAAGGCGTGGGTATCTTTGTCC |
| F_ANAPC4_1_chr4_25392530_25392623 | TCTAGCCTTCTCGCAGCACACAGATTGCTGGTACTTGTCTTGC |
| F_ANAPC4_2_chr4_25411342_25411442 | TCTAGCCTTCTCGCAGCACAATCTTGTGTCACCCCCTAACAC |
| F_mcm3_1_chr6_52149446_52149506 | TCTAGCCTTCTCGCAGCACAATCGTCCAGCACCACGGTAC |
| F_mcm3_2_chr6_52137983_52138094 | TCTAGCCTTCTCGCAGCACACACATATTTCAGGTTCCCTTGAGG |
| F_NOP2_1_chr12_6666136_6666219 | TCTAGCCTTCTCGCAGCACACCACCCGTCTAGTTTTCAACCA |
| F_PSMB2_1_chr1_36068863_36068951 | TCTAGCCTTCTCGCAGCACATGATGTTAGGAGCCCTGTTTGG |
| F_PSMB2_2_chr1_36101977_36102084 | TCTAGCCTTCTCGCAGCACACCTCTCCAACACACAGGAGTAA |

TABLE 2-continued

Primer sequences

| Primer | Name Sequence (5' to 3') |
|---|---|
| F_RBM19_1_chr12_114384237_114384309 | TCTAGCCTTCTCGCAGCACAGCTTCCTTCTTGATGGTAGATGGT |
| F_RBM19_2_chr12_114364847_114364926 | TCTAGCCTTCTCGCAGCACAGAAACCACTCACTTCCTTCAGC |
| F_UTP20_1_chr12_101702010_101702126 | TCTAGCCTTCTCGCAGCACAGGCAGAACTTGTTCCAGCAACT |
| F_UTP20_2_chr12_101740275_101740400 | TCTAGCCTTCTCGCAGCACATGGAAGGCAAAGTTGTTCTGTC |
| F_UTP20_3_chr12_101685522_101685651 | TCTAGCCTTCTCGCAGCACAATCGCTCTTGGATCTACACACA |

12 forward primers and 12 reverse primers were designed to target generic housekeeping genes with similar specifications to match V & J primers. See Table 2 (F indicates forward primer, and R indicates reverse primer. The name of the oligos also indicates chromosome location in terms of base pairs). A subset of these primers will be used to normalize input levels while calculating B-cell DNA concentrations. Housekeeping genes (HKG) were chosen because they are conserved and have only a single copy and no homologs.

Figure 5:
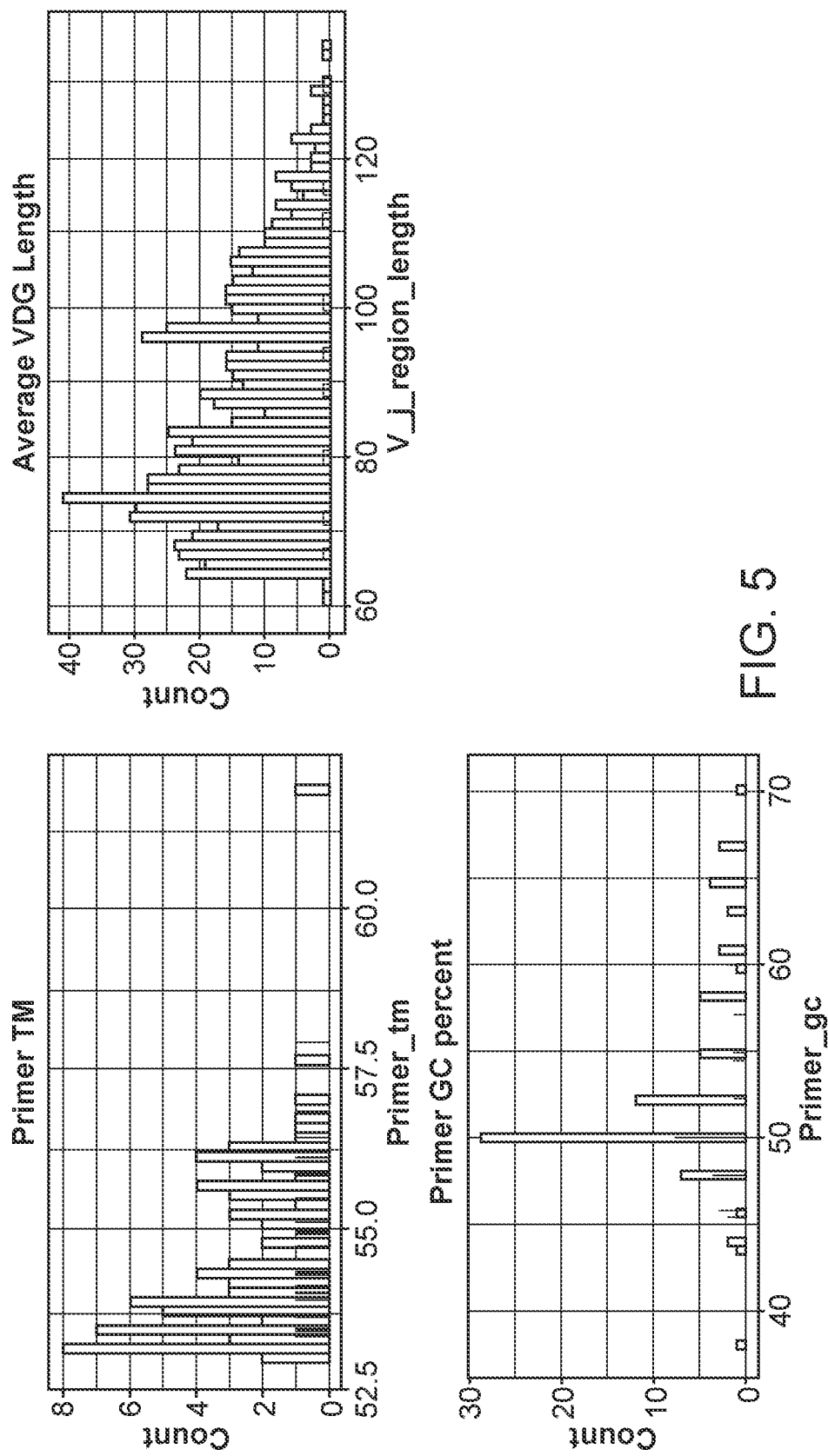
FIG. 5 depicts graphs showing quality control parameters of the B cell detection PCR assay.

The primer design was optimized to detect B-cell DNA using long gDNA extracted from blood as well as short cell-free DNA (cfDNA) extracted from plasma. This is possible due to the short size of the expected VDJ amplicons. FIG. 5 shows the distribution of primer melting temperature (FIG. 5A), the average length of the VDJ region amplified (FIG. 5B), and the GC percentage distribution of the primers (FIG. 5C).

Testing the PCR assay and optimizing PCR conditions. In-silico performance evaluation was performed to test the coverage of the primer assay by comparing the sequence data to post-recombination V(D)J data as shown in Table 3 below. In particular, the evaluation runs estimated that the assay pool covers 79-85% of all possible VDJ recombinations from blood.

TABLE 3

In silico performance evaluation results.

| Cell Type | Total read count | Average estimated pool coverage |
|---|---|---|
| Blood | 94329 | 79-85% |
| Tumor | 117642 | 60-70% |
| Non-tumor | 109805 | 60-68% |
| LN | 80425 | 51-57% |

Quality control experiments were performed to maximize the number of B cells captured and minimize the off-target binding/primer interactions. Table 4 below shows rational for using different annealing temperatures and time of annealing combinations in the PCR protocol.

TABLE 4

Primer Quality Control Test Experiment

| # | Anneal temp. | Primer conc. | Anneal. time | Reasoning |
|---|---|---|---|---|
| 1 | 62.5 C. | 16 nM | 15 mins | Standard condition (control) |
| 2 | 62.5 C. | 16 nM | 30 mins | Improve uniformity |
| 3 | 60 C. | 16 nM | 15 mins | Improve primer efficiency and uniformity |
| 4 | 60 C. | 16 nM | 30 mins | Improve primer efficiency and uniformity |
| 5 | 65 C. | 16 nM | 15 mins | Increase stringency to reduce primer interactions |
| 6 | 65 C. | 16 nM | 30 mins | Reduce primer interaction and improve uniformity |

Figure 6:
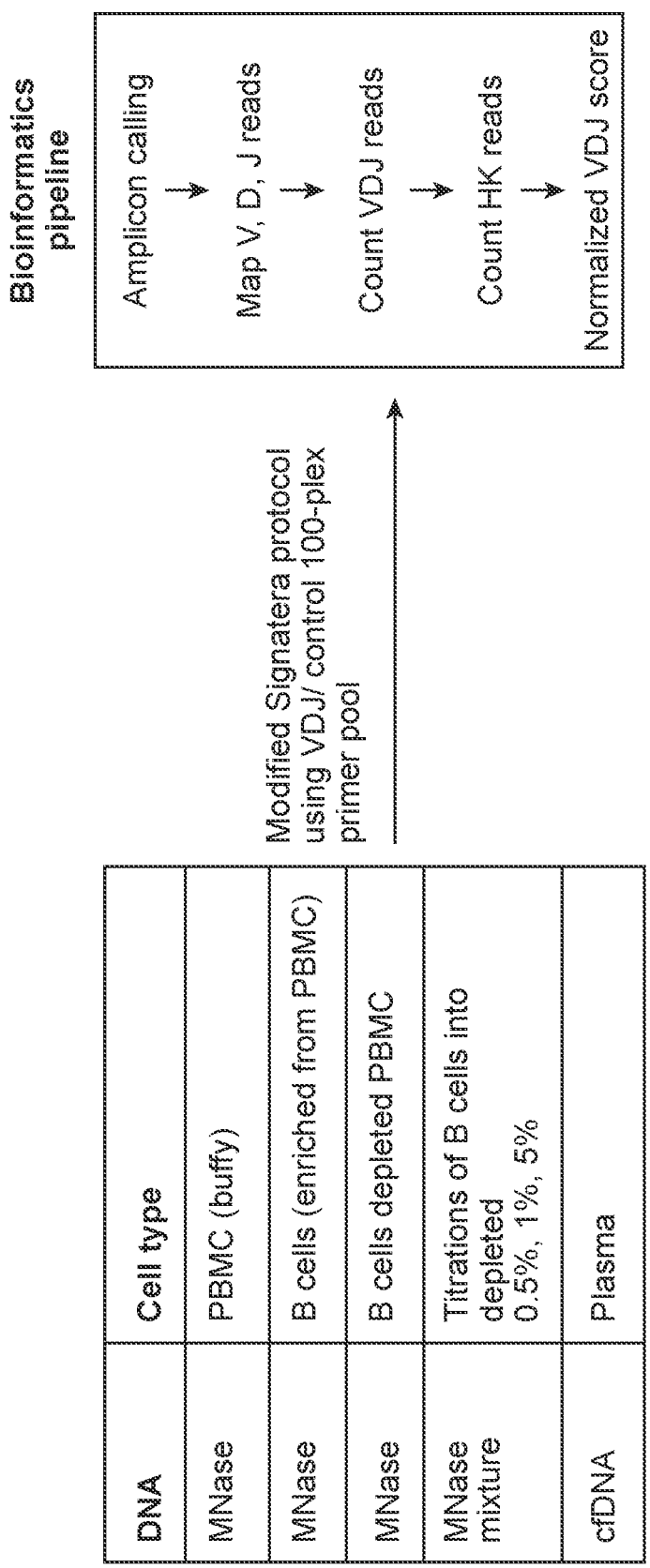
FIG. 6 shows a graphical depiction of an analytic workflow.

Example 2: Methods for Extracting DNA, Preparing DNA Libraries, Performing Multiplex PCR, and Sequencing Extracted genomic DNA (gDNA) from blood digested with MNase to generate approximately 150 bp fragments and cell-free DNA (cfDNA) extracted from plasma are taken as input DNA to generate tagged and amplified libraries as described below and as outlined in FIG. 6. These libraries are subject to multiplex PCR using the B-cell detection assay pool and barcoded for sequencing on an Illumina Hiseq or Nextseq instrument.

cfDNA extraction and QC of Plasma Samples. cfDNA was extracted using the Qiagen NA kit following a protocol optimized for 5 ml of plasma. All cfDNA samples were QCed on Bioanalyzer High Sensitivity chips. The same Bioanalyzer High Sensitivity runs were also used to also quantify the cfDNA samples by interpolation of the mononucleosomal peak height on a calibration curve prepared from a pure cfDNA sample that was quantified previously. This is necessary because cfDNA sometimes contains an intact DNA fraction that overlaps with the high size marker on the chip, making quantification of the mononucleosomal peak unreliable.

Library preparation. The cfDNA from each plasma sample or cellular DNA from the Peripheral Blood Mononuclear Cells (PBMCs) was used as input into Library Prep using Applicant's library prep kit and following the kit instructions. In brief, DNA extracted from plasma or blood were end repaired and A-tailed, and Applicant's custom adapters ligated. The libraries were amplified for 15 cycles to plateau and then purified using Ampure beads following the manufacturer's protocol. The purified libraries were QCed on the LabChip™ cfDNA multiplex PCR and Sequencing. For detection of B cells, the prepared libraries were subjected to multiplex PCR using the B-cell detection assay pool and barcoded for sequencing on an Illumina Hiseq or Nextseq instrument. Generally, the library material from each plasma sample was used as input into multiplex PCR using the relevant assay pool and an optimized plasma mPCR protocol. The mPCR products were barcoded in a separate PCR step, and the barcoded PCR products were pooled according to the assay pooling information.

The resulting data was processed to a custom amplicon caller pipeline and then mapped to V, D and J genes. VDJ matching reads and (housekeeping genes) HKG matching reads are counted. Normalized VDJ count is calculated as the ratio of VDJ read count over HKG read count. A VDJ Score was calculated for each titration as the ratio of the normalized VDJ count for the sample over the normalized VDJ count for a matched sample with 100% B-cells. The VDJ scores represent the B-cell fraction for that sample.

Example 3: B-Cell Assay can Detect B Cell DNA Down to 1-2 Molecules of DNA

In order to evaluate the sensitivity of the B cell assay, MNase samples with known B-cell DNA concentrations were processed. These samples were prepared by titrating DNA isolated from B-cells into DNA from a non-lymphoid cell line at different fractions. B-cells from 5 normal individuals was used for this purpose. The cellular DNA was derived from peripheral blood mononuclear cells (PBMCs), or B cells enriched from PBMCs, or a B cell depleted PBMC. To test the sensitivity of the assay, titrations of 0.5%, 1%, and 5% B cells into depleted B cells were prepared. A VDJ Score was calculated for each titration as the ratio of the normalized VDJ count for the sample over the normalized VDJ count for a matched sample with 100% B-cells. The VDJ scores represent the B-cell fraction for that sample.

Figure 7:
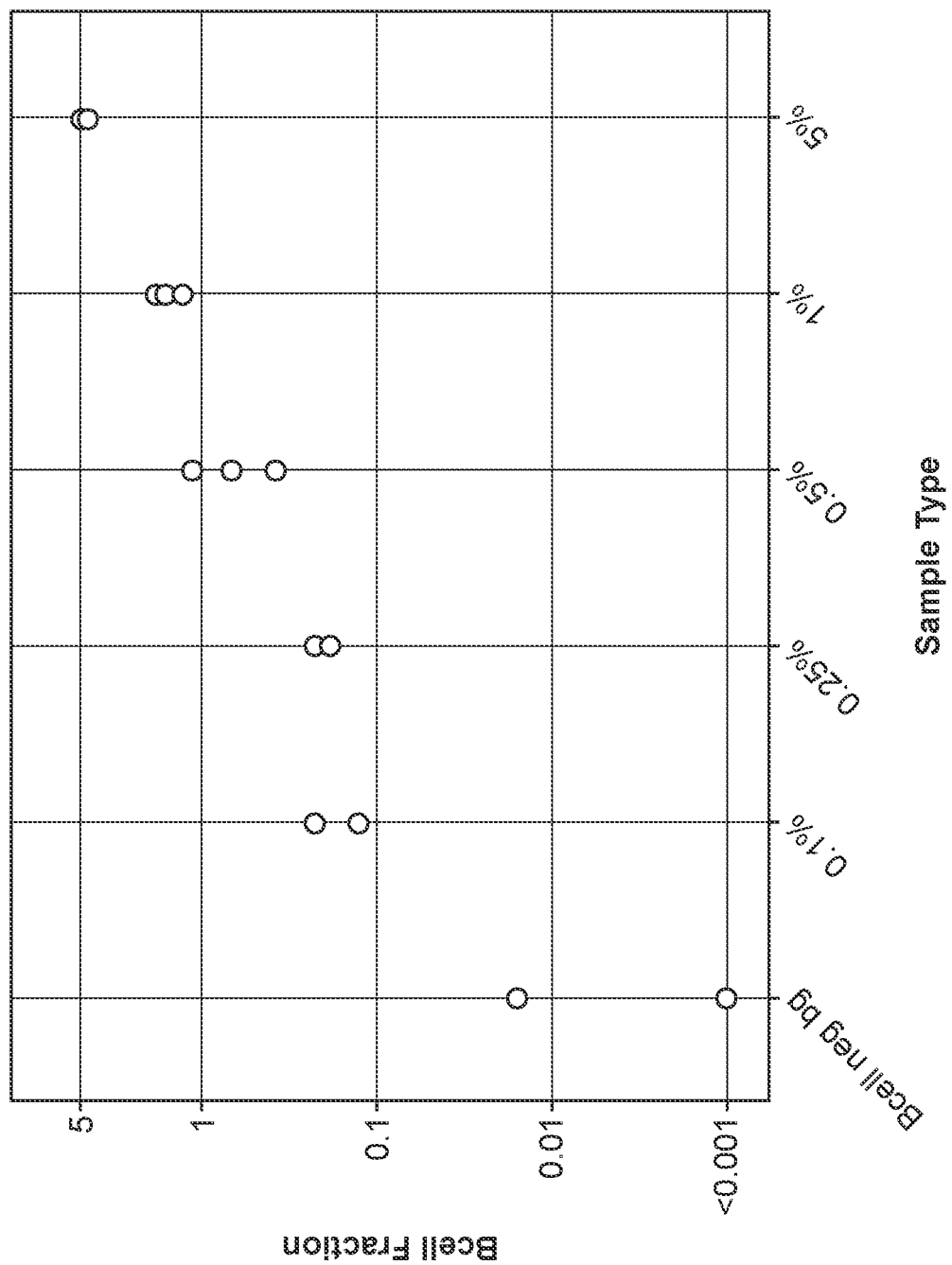
FIG. 7 shows a graphical depiction of the results of detecting B cells in samples titrated with the indicated concentration of B cells. DNA input was cellular DNA from PBMC samples.

FIG. 7 shows that the inventive B cell assay can detect B cell DNA down to 0.1%, which represents 1-2 molecules of DNA.

Figure 8:
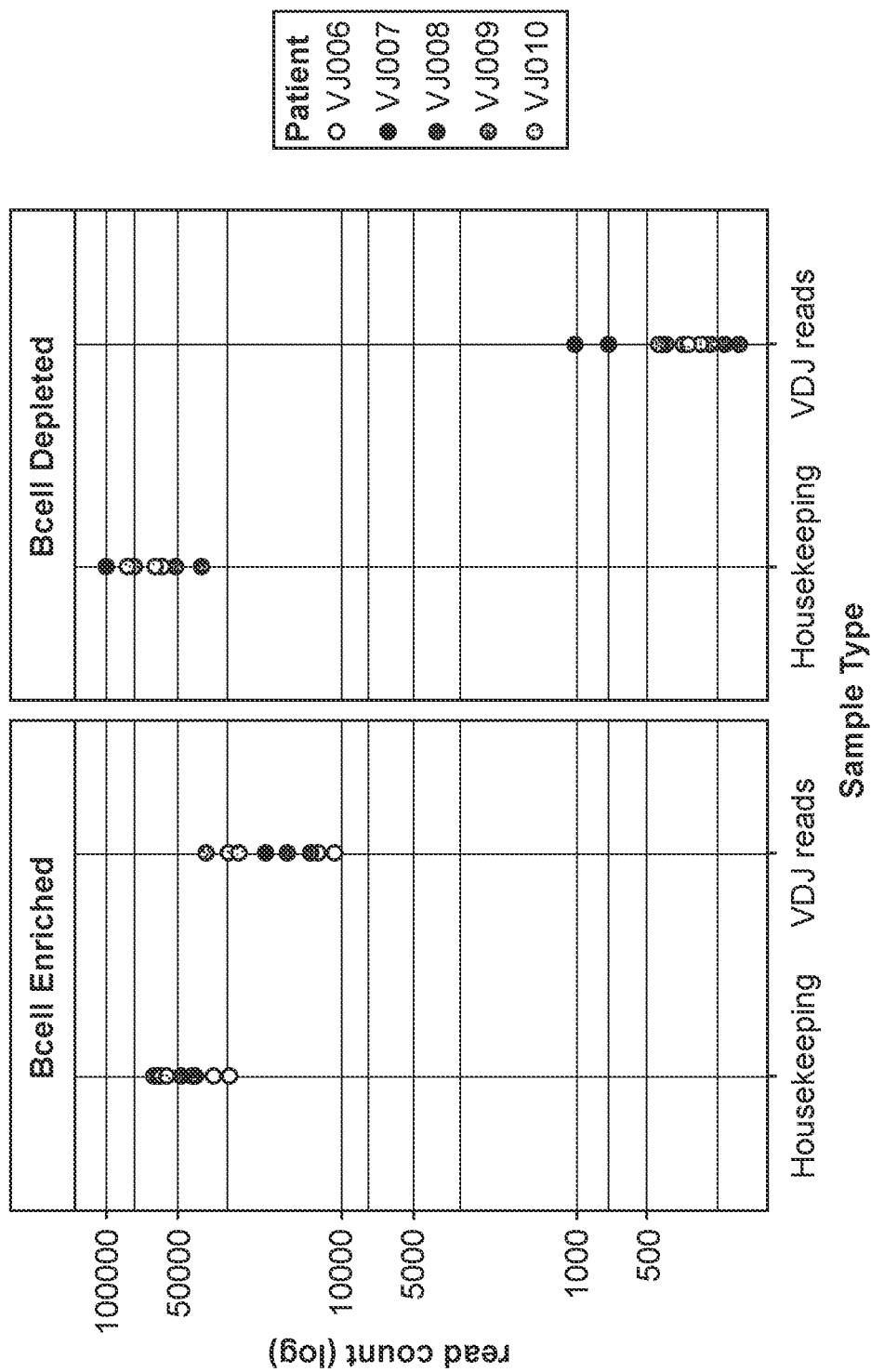
FIG. 8 shows a graphical depiction of VDJ reads and housekeeping gene reads in B cell enriched and B cell depleted samples. DNA input was cellular DNA from PBMC samples.

FIG. 8 shows VDJ and housekeeping read counts from B cell enriched and B cell depleted samples. The VDJ read count in B cell enriched is higher than in B-cell depleted PBMC samples as would be expected. This read count result was reproducible across replicates. This experiments also showed that the housekeeping gene based assay had similar read counts in B cell enriched and B cell depleted samples, so the housekeeping gene based assays can be used to normalize the data.

Figure 9:
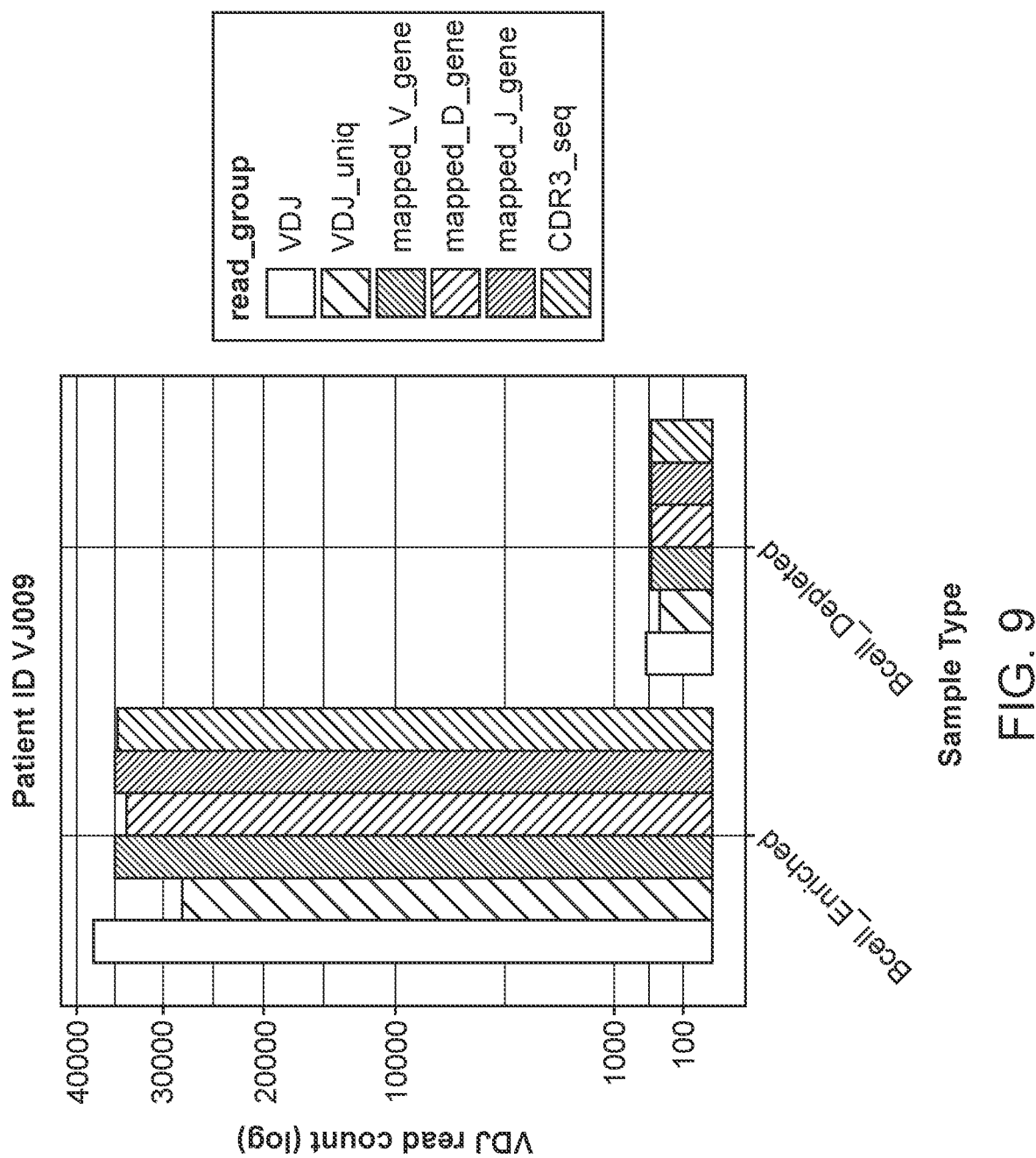
FIG. 9 shows a graphical depiction of VDJ read counts in B cell enriched and B cell depleted samples. DNA input was cellular DNA from PBMC samples.

FIG. 9 shows the custom amplicon caller pipeline described herein correctly map the VDJ reads to V, D, and J genes. The unique count was very close to actual count. Almost all of the reads map to V, D, and J genes. Almost all of the reads have corresponding CDR3 amino acid sequences. This gene mapping was done using the software for comprehensive adaptive immunity profiling, MiXCR, described in Bolotin, Dmitriy A., et al. "MiXCR: software for comprehensive adaptive immunity profiling." Nature methods 12.5 (2015): 380-381, incorporated herein.

Figure 10:
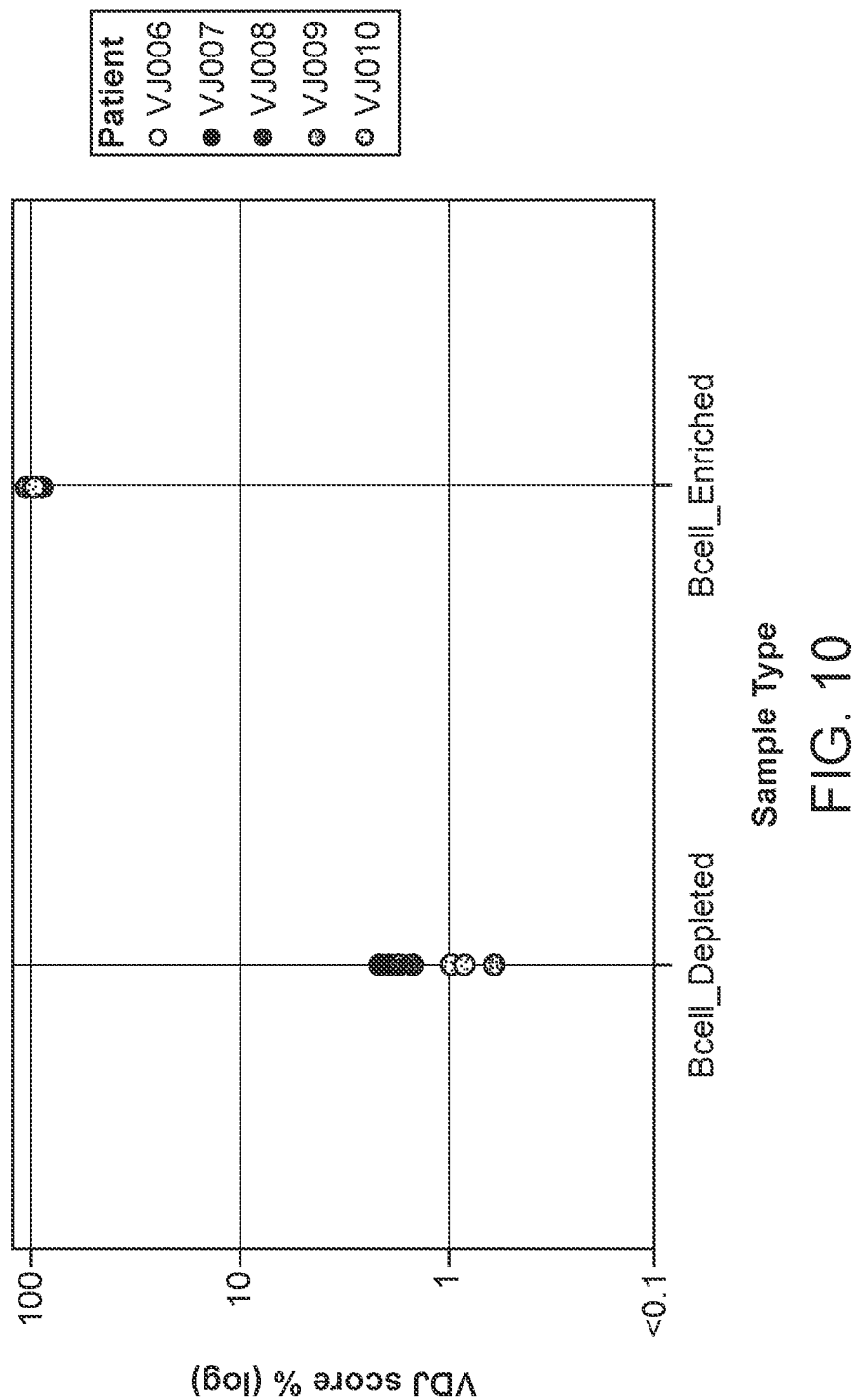
FIG. 10 shows a graphical depiction of VDJ score in B cell enriched and B cell depleted samples. DNA input was cellular DNA from PBMC samples.

FIG. 10 shows graph depicting that the inventive B cell assay can differentiate between B cell enriched and depleted PBMCs by calculating the VDJ score as the normalized V(D)J count divided by the normalized V(D)J count for a matched B cell enriched sample. V(D)J read count are normalized by dividing the V(D)J read count by the housekeeping gene read count. The B cell depleted samples were found to still have residual V(D)J signals.

$$\text{Normalized } VDJ \text{ count} = \frac{VDJ \text{ read count}}{\text{Housekeeping read count}}$$

$$VDJ \text{ Score} = \frac{\text{Normalized } VDJ \text{ count}}{\text{Normalized } VDJ \text{ count for matched } B \text{ cell enriched sample}} \%$$

Figure 11:
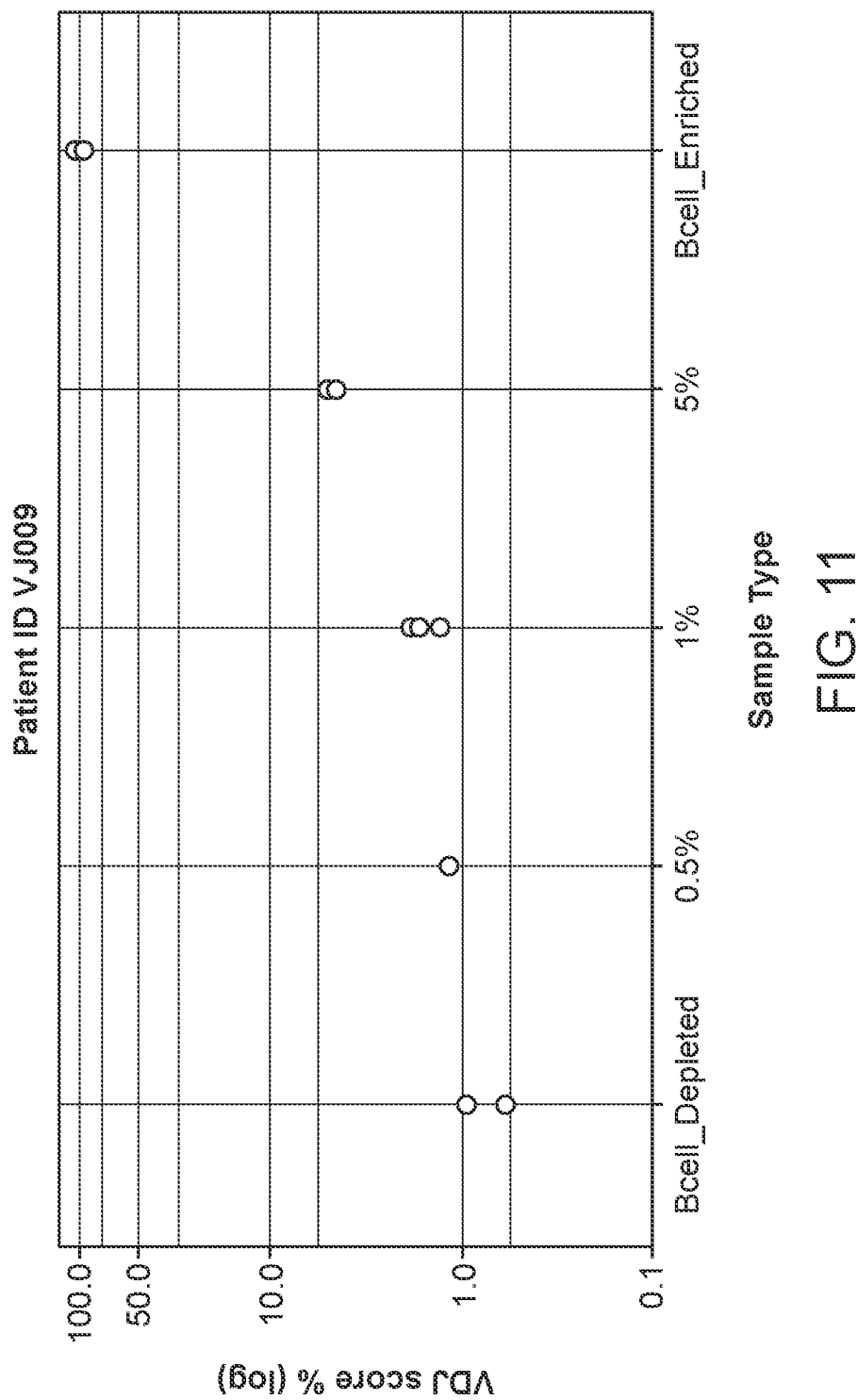
FIG. 11 shows a graphical depiction of VDJ score in B cell enriched and B cell depleted samples, and samples with indicated amounts of B cells. DNA input was cellular DNA from PBMC samples.
Figure 12:
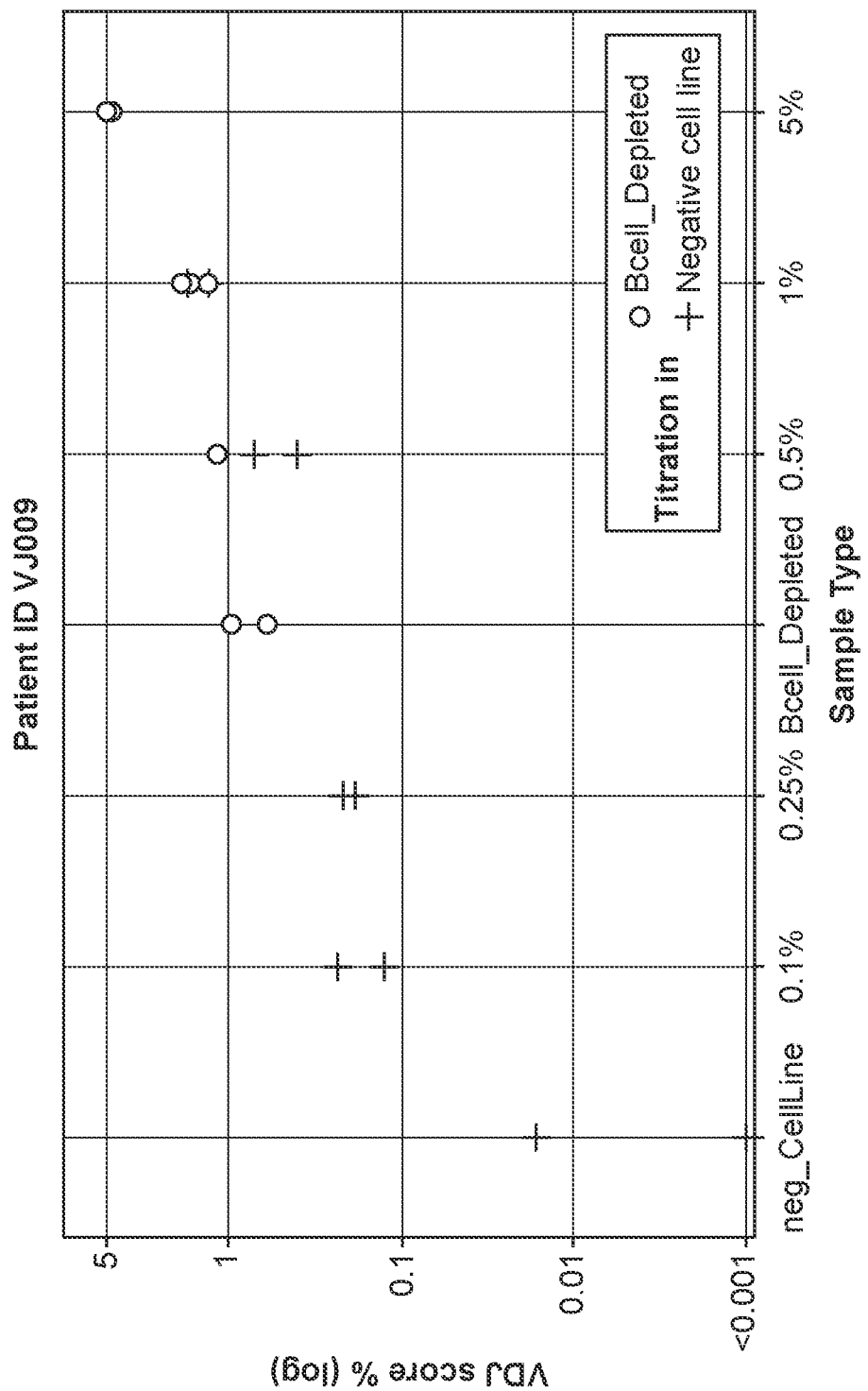
FIG. 12 shows a graphical depiction of VDJ score in B cell enriched and B cell depleted samples, and samples with indicated amounts of B cells as compared to using a negative cell line to determine background levels. DNA input was cellular DNA from PBMC samples.

The sensitivity of the inventive B cell assay was further examined by titrating specified amounts of B cells into B cell depleted samples. As shown in FIG. 11, the inventive B cell assay can detect B cells in sample spiked with only 1% B cells. The B cell depleted PBMCs had 1% background. The measured V(D)J scores matched spiked amount plus background as established by determining the V(D)J score in B cell depleted PBMC samples. To test if the inventive B cell assay could measure V(D)L recombination at even lower spike concentration in a cleaner background, an in-house negative cell line was used as a background, and B cells were titrated into the negative cell line samples at concentrations 0.1%, 0.25%, 0.5%, and 1%. In addition, B cells were titrated into B cell depleted samples at concentration 0.5%, 1%, and 5%. This experimental setup is shown in table 5 below. As shown in FIG. 12, by using a cleaner background, the inventive B cell assay can detect V(D)J recombination in samples spiked with only 0.1% B cells, which likely represent 1 to 2 molecules of V(D)J DNA.

TABLE 5

| DNA | Cell type |
| --- | --- |
| MNase mixture | Titrations of B cells into depleted 0.5%, 1%, and 5%. |
| MNase mixture | Titrations of B cells into in-house negative cell line background 0.1%, 0.25%, 0.5%, and 1%. |

Figure 13:
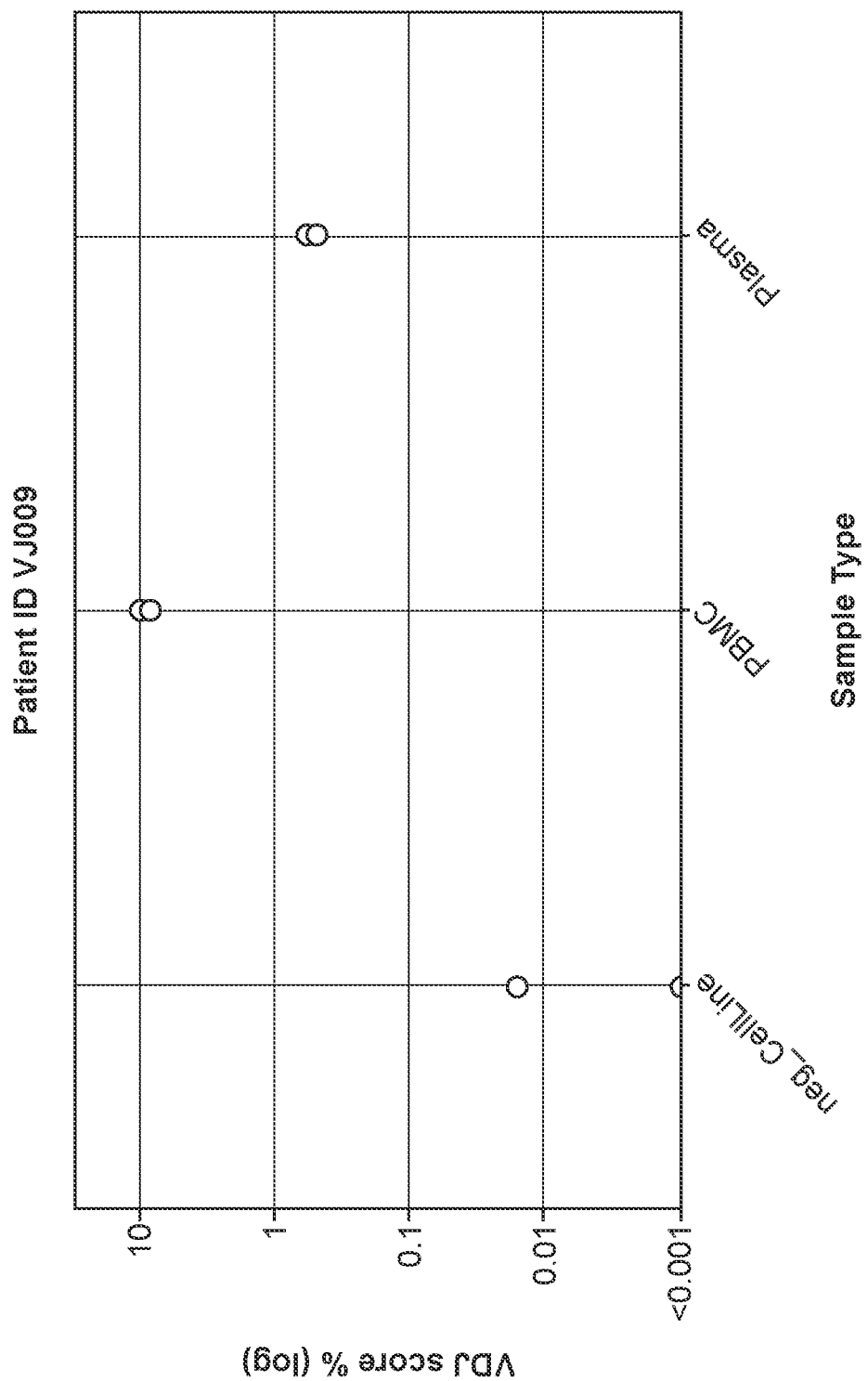
FIG. 13 shows a graphical depiction of VDJ score obtained from using cell-free DNA derived from plasma samples as compared to using cellular DNA from PBMC samples.

In addition to the cellular DNA, the assay was also validated on plasma from normal individuals as shown in FIG. 13. V(D)J recombinations were successfully detected in plasma samples. The V(D)J signal achieved from plasma samples is 3-5% of the signal achieved from PBMC samples. The estimated V(D)J copies per mL plasma is from 1 to 3.8 based on the study of five plasma samples as shown in Table 6 below.

TABLE 6

| Estimated V(D)J copies per mL plasma | |
| --- | --- |
| Patient Plasma sample | Estimated VDJ copies/ml plasma (in 9 ml) |
| VJ006 | 1.0 (9.1) |
| VJ007 | 1.9 (17.2) |
| VJ008 | 1.6 (14.4) |
| VJ009 | 3.5 (31.4) |
| VJ010 | 3.8 (34.5) |

In summary, the B-cell assay design covers 100% of genes annotated in the database and up to 85% of CDR3 sequences. The B-cell assay can differentiate between enriched and depleted B-cell PBMCs, detect as low as 1% spike into a background of depleted B-cell PBMCs, detect as low as 0.1% spike into a cleaner negative cell line background, and detect VDJ recombinations in patient plasma cfDNA.

It is noted that detecting B-cell DNA in plasma can reduce reliance on bone marrow biopsies, which is invasive and expensive. Moreover, the B-cell assay can be a companion assay to a cancer monitoring assay such as Signatera for monitoring immune system status in response to cytotoxic treatment for malignancies such as myeloma, lymphoma and others. Furthermore, the B-cell assay has low COGs (no exome sequencing; assay pool is universal across patients). In addition, the B-cell assay can be run as a cell-based assay to detect <0.1% B-cells (orders of magnitude more sensitive than flow cytometry).

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the present application and relevant art and should not be interpreted in an idealized or overly formal sense unless expressly so defined herein. While not explicitly defined below, such terms should be interpreted according to their common meaning.

Unless the context indicates otherwise, it is specifically intended that the various features of the invention described herein can be used in any combination. Moreover, the disclosure also contemplates that in some embodiments, any feature or combination of features set forth herein can be excluded or omitted. To illustrate, if the specification states that a complex comprises components A, B and C, it is specifically intended that any of A, B or C, or a combination thereof, can be omitted and disclaimed singularly or in any combination.

All numerical designations, e.g., pH, temperature, time, concentration, and molecular weight, including ranges, are approximations which are varied (+) or (−) by increments of 1.0 or 0.1, as appropriate, or alternatively by a variation of +/−15%, or alternatively 10%, or alternatively 5%, or alternatively 2%. It is to be understood, although not always explicitly stated, that all numerical designations are preceded by the term "about." It also is to be understood, although not always explicitly stated, that the reagents described herein are merely exemplary and that equivalents of such are known in the art.

As used in the description of the invention and the appended claims, the singular forms "a," "an" and "the" are intended to include the plural forms as well, unless the context clearly indicates otherwise.

The term "about," as used herein when referring to a measurable value such as an amount or concentration and the like, is meant to encompass variations of 20%, 10%, 5%, 1%, 0.5%, or even 0.1% of the specified amount.

The terms or "acceptable," "effective," or "sufficient" when used to describe the selection of any components, ranges, dose forms, etc. disclosed herein intend that said component, range, dose form, etc. is suitable for the disclosed purpose.

Also as used herein, "and/or" refers to and encompasses any and all possible combinations of one or more of the associated listed items, as well as the lack of combinations when interpreted in the alternative ("or").

As used herein, the term "comprising" is intended to mean that the compositions and methods include the recited elements, but do not exclude others. As used herein, the transitional phrase "consisting essentially of" (and grammatical variants) is to be interpreted as encompassing the recited materials or steps "and those that do not materially affect the basic and novel characteristic(s)" of the recited embodiment. See, In re Herz, 537 F.2d 549, 551-52, 190 U.S.P.Q. 461, 463 (CCPA 1976) (emphasis in the original); see also MPEP § 2111.03. Thus, the term "consisting essentially of" as used herein should not be interpreted as equivalent to "comprising." "Consisting of" shall mean excluding more than trace elements of other ingredients and substantial method steps for administering the compositions disclosed herein. Aspects defined by each of these transition terms are within the scope of the present disclosure.

The terms "nucleic acid," "polynucleotide," and "oligonucleotide" are used interchangeably and refer to a polymeric form of nucleotides of any length, either deoxyribonucleotides or ribonucleotides or analogs thereof. Polynucleotides can have any three dimensional (3D) structure and may perform any function, known or unknown. The following are non-limiting examples of polynucleotides: a gene or gene fragment (for example, a probe, primer, EST or SAGE tag), exons, introns, messenger RNA (mRNA), transfer RNA, ribosomal RNA, RNAi, ribozymes, cDNA, recombinant polynucleotides, branched polynucleotides, plasmids, vectors, isolated DNA of any sequence, isolated RNA of any sequence, nucleic acid probes and primers.

As used herein, the term "subject" includes a person, a patient, an individual, someone being evaluated, etc.

What is claimed is:

1. A method of preparing a non-naturally occurring composition of amplified DNA derived from a biological sample useful for detecting or monitoring immune cells in a subject, comprising:
preparing a non-naturally occurring composition of amplified DNA by performing a multiplex amplification reaction on nucleic acids isolated from a biological sample of the subject to generate a set of amplicons, wherein each of the set of amplicons comprises recombined V(D)J gene segments at a gene locus of interest, wherein the multiplex amplification reaction is capable of amplifying at least about 70% of all possible V(D)J recombinations at the gene locus of interest, wherein the multiplex amplification reaction is performed with a first set of primers targeting V gene sequences targeted by one or more of the primers of SEQ ID NOs: 1-64 and a second set of primers targeting J gene sequences targeted by one or more of the primers of SEQ ID Nos: 65-76; and
analyzing the non-naturally occurring composition of amplified DNA by sequencing the set of amplicons, wherein sequences of the recombed V(D)J gene segments are indicative of presence of an immune cell in the biological sample.

2. The method of claim 1, wherein the multiplex amplification reaction is capable of amplifying at least about 90% of all possible V(D)J recombinations at the B cell receptor gene locus.

3. The method of claim 1, wherein the method comprises collecting and sequencing a plurality of biological samples from the subject longitudinally.

4. The method of claim 1, wherein the biological sample comprises a peripheral blood mononuclear cell (PBMCs) sample, a plasma sample, or a combination thereof.

5. The method of claim 1, wherein the nucleic acids isolated from the biological sample comprises cellular DNA obtained from PBMCs.

6. The method of claim 1, wherein the nucleic acids isolated from the biological sample comprises cell-free DNA (cfDNA).

7. The method of claim 6, wherein the amount of immune cells in the biological sample is less than 1.0%, less than 0.5%, or less than 0.1% of the PBMCs in the sample.

8. The method of claim 1, wherein the method is capable of detecting 5 or less V(D)J recombinations per milliliter of the biological sample.

9. The method of claim 1, wherein the method is capable of detecting a single V(D)J recombination per milliliter of the biological sample.

10. The method of claim 1, wherein the subject has been administered a cytotoxic treatment of a disease, wherein the cytotoxic treatment leads to depletion of the immune cells.

11. The method of claim 10, wherein the disease is a malignancy, and the cytotoxic treatment comprises a chemotherapy, a radiotherapy, or an immune cell targeted therapy; or wherein the disease is an autoimmune disease, and the cytotoxic treatment comprise an immunosuppressive therapy.

12. The method of claim 1, wherein the subject suffers from a disease or disorder that depletes immune cells, wherein the disease or disorder is a malignancy or an immunodeficiency disorder.

13. The method of claim 1, wherein the subject has been administered with a therapeutic composition comprising immune cells, and wherein the method further comprises analyzing sequences of the recombined V(D)J gene segments to determine the presence of the administered immune cells.

14. The method of claim 1, wherein the immune cell comprises a B cell, a transplanted B cell, an engineered B cell, a circulating bone marrow B cell, and/or a circulating tumor B cell.

15. The method of claim 1, further comprising analyzing sequences of the recombined V(D)J gene segments to determine a diversity of V(D)J recombination in the sample obtained from the subject and a control sample, wherein the diversity of V(D)J recombination is indicative of an immune receptor repertoire.

16. The method of claim 15, wherein the immune cell is a B cell, and the diversity of V(D)J recombination is indicative of the diversity of a B cell receptor (BCR)

repertoire; or wherein the sample comprises a single isolated B cell or a clonal expansion thereof, and the diversity of V(D)J recombination is indicative of the diversity of the BCR repertoire of the single isolated B cell or the clonal expansion thereof.

* * * * *

SEQUENCE LISTING

```
<160> NUMBER OF SEQ ID NOS: 100

<210> SEQ ID NO 1
<211> LENGTH: 41
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1
tctagccttc tcgcagcaca ggctgtgtat tactgtgcga g                         41

<210> SEQ ID NO 2
<211> LENGTH: 41
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 2
tctagccttc tcgcagcaca cacggctgtg tattactgtg c                         41
```

```
<210> SEQ ID NO 3
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 3
tctagccttc tcgcagcaca cggctgttta ttactgtgcg ag                        42

<210> SEQ ID NO 4
<211> LENGTH: 44
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 4
tctagccttc tcgcagcaca gaggacatgg ctgtgtatta ctgt                      44

<210> SEQ ID NO 5
<211> LENGTH: 43
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 5
tctagccttc tcgcagcaca tctgaggaca cggccgtgta tta                       43

<210> SEQ ID NO 6
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 6
tctagccttc tcgcagcaca taaaggctga ggacactgcc                           40

<210> SEQ ID NO 7
<211> LENGTH: 41
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 7
tctagccttc tcgcagcaca gagcagcctg agatctgaag a                         41

<210> SEQ ID NO 8
<211> LENGTH: 39
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
```

<400> SEQUENCE: 8
tctagccttc tcgcagcaca cggccgtgta ttactgtgc         39

<210> SEQ ID NO 9
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 9
tctagccttc tcgcagcaca cggccgtata ttactgtgcg aa      42

<210> SEQ ID NO 10
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 10
tctagccttc tcgcagcaca gccttgtatc actgtgcgag         40

<210> SEQ ID NO 11
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 11
tctagccttc tcgcagcaca gcagcctgag atctgaggac         40

<210> SEQ ID NO 12
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 12
tctagccttc tcgcagcaca acagccacat attactgtgc ac      42

<210> SEQ ID NO 13
<211> LENGTH: 41
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 13
tctagccttc tcgcagcaca cactgccgtg tattactgtg c       41

<210> SEQ ID NO 14
<211> LENGTH: 43
<212> TYPE: DNA
<213> ORGANISM: Artificial Sequence

```
<220> FEATURE:
<221> NAME/KEY: source
<223> OTHER INFORMATION: /note="Description of Artificial Sequence:
      Synthetic primer"

<400> SEQUENCE: 14
tctagccttc tcgcagcaca gccgtgtatt actgtaccac aga                43

<210> SEQ ID NO 15
<211> LENGTH: 43
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 15
tctagccttc tcgcagcaca gccgtgtatt actgtaccac agg                43

<210> SEQ ID NO 16
<211> LENGTH: 43
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 16
tctagccttc tcgcagcaca cggccgtgta ttactgtact aga                43

<210> SEQ ID NO 17
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 17
tctagccttc tcgcagcaca cacagccgtg tattactgta cc                 42

<210> SEQ ID NO 18
<211> LENGTH: 41
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 18
tctagccttc tcgcagcaca ccgccttgta ttactgtgca a                  41

<210> SEQ ID NO 19
<211> LENGTH: 41
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 19
tctagccttc tcgcagcaca cggccttgta ttactgtgca a                  41
```

<210> SEQ ID NO 20
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 20
tctagccttc tcgcagcaca gagcagcctg agatctgacg                           40

<210> SEQ ID NO 21
<211> LENGTH: 41
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 21
tctagccttc tcgcagcaca cacggccgtg tattactgta c                         41

<210> SEQ ID NO 22
<211> LENGTH: 41
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 22
tctagccttc tcgcagcaca cacggccgtg tattactgtt c                         41

<210> SEQ ID NO 23
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 23
tctagccttc tcgcagcaca cacggccgtg tattactgtg                           40

<210> SEQ ID NO 24
<211> LENGTH: 37
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 24
tctagccttc tcgcagcaca ctcggacacc gccatgt                              37

<210> SEQ ID NO 25
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

```
<400> SEQUENCE: 25
tctagccttc tcgcagcaca cacggctgtg tattactgtg tg                    42

<210> SEQ ID NO 26
<211> LENGTH: 39
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 26
tctagccttc tcgcagcaca tgagagctga ggacatggc                        39

<210> SEQ ID NO 27
<211> LENGTH: 38
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 27
tctagccttc tcgcagcaca tgagcagcct gagatccg                         38

<210> SEQ ID NO 28
<211> LENGTH: 39
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 28
tctagccttc tcgcagcaca gctgagcagc ctgagatcc                        39

<210> SEQ ID NO 29
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 29
tctagccttc tcgcagcaca ctgccgtgta ttactgtgcg                       40

<210> SEQ ID NO 30
<211> LENGTH: 45
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 30
tctagccttc tcgcagcaca acagccgtgt attactgtac tagag                 45

<210> SEQ ID NO 31
<211> LENGTH: 45
<212> TYPE: DNA
```

<213> ORGANISM: Artificial Sequence
<220> FEATURE:
<221> NAME/KEY: source
<223> OTHER INFORMATION: /note="Description of Artificial Sequence:
    Synthetic primer"

<400> SEQUENCE: 31
tctagccttc tcgcagcaca cacagccgtg tattactgta ctaga         45

<210> SEQ ID NO 32
<211> LENGTH: 41
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic primer"

<400> SEQUENCE: 32
tctagccttc tcgcagcaca ggccatgtat tactgtgcga g             41

<210> SEQ ID NO 33
<211> LENGTH: 41
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic primer"

<400> SEQUENCE: 33
tctagccttc tcgcagcaca ggccttgtat tactgtgcga g             41

<210> SEQ ID NO 34
<211> LENGTH: 41
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic primer"

<400> SEQUENCE: 34
tctagccttc tcgcagcaca cgccatgtat tactgtgcga g             41

<210> SEQ ID NO 35
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic primer"

<400> SEQUENCE: 35
tctagccttc tcgcagcaca cacagcctac atggagctga               40

<210> SEQ ID NO 36
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic primer"

<400> SEQUENCE: 36
tctagccttc tcgcagcaca aaccagttct ccctgaagct ga            42

-continued

```
<210> SEQ ID NO 37
<211> LENGTH: 39
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 37
tctagccttc tcgcagcaca tgaagctggg ctctgtgac                              39

<210> SEQ ID NO 38
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 38
tctagccttc tcgcagcaca ggccgtgtat tactgtgcta ga                          42

<210> SEQ ID NO 39
<211> LENGTH: 43
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 39
tctagccttc tcgcagcaca gtatctgcaa atgaacagcc tga                         43

<210> SEQ ID NO 40
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 40
tctagccttc tcgcagcaca aacagcctga aaaccgagga ca                          42

<210> SEQ ID NO 41
<211> LENGTH: 41
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 41
tctagccttc tcgcagcaca aacatggacc ctgtggacac a                           41

<210> SEQ ID NO 42
<211> LENGTH: 44
<212> TYPE: DNA
<213> ORGANISM: Artificial Sequence
<220> FEATURE:
<221> NAME/KEY: source
<223> OTHER INFORMATION: /note="Description of Artificial Sequence:
```

-continued

Synthetic primer"

<400> SEQUENCE: 42
tctagccttc tcgcagcaca gacatctgag gacatggctg tgta        44

<210> SEQ ID NO 43
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 43
tctagccttc tcgcagcaca tgtggacaca gccacacatt ac        42

<210> SEQ ID NO 44
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 44
tctagccttc tcgcagcaca caatgaccaa catggaccct gt        42

<210> SEQ ID NO 45
<211> LENGTH: 44
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 45
tctagccttc tcgcagcaca aactgaggac atggctgtgt atgg        44

<210> SEQ ID NO 46
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 46
tctagccttc tcgcagcaca tgcaaatgaa cagcctgaga gc        42

<210> SEQ ID NO 47
<211> LENGTH: 45
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 47
tctagccttc tcgcagcaca cagctgtgtg ttactgtatg tgagg        45

<210> SEQ ID NO 48
<211> LENGTH: 44

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 48
tctagccttc tcgcagcaca ctaatgaaca gtctgagagc agcg                    44

<210> SEQ ID NO 49
<211> LENGTH: 44
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 49
tctagccttc tcgcagcaca aatgaacagt ctgagagcag aggg                    44

<210> SEQ ID NO 50
<211> LENGTH: 44
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 50
tctagccttc tcgcagcaca aacagtcaga gagctgagga catg                    44

<210> SEQ ID NO 51
<211> LENGTH: 43
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 51
tctagccttc tcgcagcaca gcaaatgaac actcagagag ctg                     43

<210> SEQ ID NO 52
<211> LENGTH: 44
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 52
tctagccttc tcgcagcaca gaacagtctg agagctgagg acat                    44

<210> SEQ ID NO 53
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 53
```
tctagccttc tcgcagcaca tcggacgccg ccatgtatta tt         42

<210> SEQ ID NO 54
<211> LENGTH: 44
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 54
tctagccttc tcgcagcaca gtcttcagat cagcagccta aagg       44

<210> SEQ ID NO 55
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 55
tctagccttc tcgcagcaca atggcgtatc tgcagatcag ca         42

<210> SEQ ID NO 56
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 56
tctagccttc tcgcagcaca acggccgtgt atgactgtat ga         42

<210> SEQ ID NO 57
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 57
tctagccttc tcgcagcaca aggacacctc caaaaaccag gt         42

<210> SEQ ID NO 58
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 58
tctagccttc tcgcagcaca aaatgaacag cctgagagcc ga         42

<210> SEQ ID NO 59
<211> LENGTH: 44
<212> TYPE: DNA
<213> ORGANISM: Artificial Sequence
<220> FEATURE:
<221> NAME/KEY: source

```
<223> OTHER INFORMATION: /note="Description of Artificial Sequence:
      Synthetic primer"

<400> SEQUENCE: 59
tctagccttc tcgcagcaca gtccaagaac cagttctccc tgaa                    44

<210> SEQ ID NO 60
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 60
tctagccttc tcgcagcaca tctgtcagca cggcatatct                         40

<210> SEQ ID NO 61
<211> LENGTH: 38
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 61
tctagccttc tcgcagcaca gcagtggagc agcctgaa                           38

<210> SEQ ID NO 62
<211> LENGTH: 37
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 62
tctagccttc tcgcagcaca tgtgactgcc gcggaca                            37

<210> SEQ ID NO 63
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 63
tctagccttc tcgcagcaca ccgcgtatta ctgtgccaga ta                      42

<210> SEQ ID NO 64
<211> LENGTH: 49
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 64
tctagccttc tcgcagcaca ctcaagagat gattcaaaga actcactgt               49

<210> SEQ ID NO 65
```

```
<211> LENGTH: 39
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 65
tctagccttc tcgtgtgcag atccctggcc ccagtagtc                                39

<210> SEQ ID NO 66
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 66
tctagccttc tcgtgtgcag agccctggcc ccagtgctgg aa                            42

<210> SEQ ID NO 67
<211> LENGTH: 45
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 67
tctagccttc tcgtgtgcag atccctggcc ccaggggtcg aacca                         45

<210> SEQ ID NO 68
<211> LENGTH: 41
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 68
tctagccttc tcgtgtgcag agccacggcc ccagagatcg a                             41

<210> SEQ ID NO 69
<211> LENGTH: 43
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 69
tctagccttc tcgtgtgcag attggcccca gacatcaaaa gca                           43

<210> SEQ ID NO 70
<211> LENGTH: 43
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 70
```
tctagccttc tcgtgtgcag acccttggcc ccagatatca aaa                43

<210> SEQ ID NO 71
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 71
tctagccttc tcgtgtgcag atggccccag tagtcaaagt ag                 42

<210> SEQ ID NO 72
<211> LENGTH: 45
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 72
tctagccttc tcgtgtgcag accagacgtc cataccgtag tagta              45

<210> SEQ ID NO 73
<211> LENGTH: 45
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 73
tctagccttc tcgtgtgcag atttgcccca gacgtccatg tagta              45

<210> SEQ ID NO 74
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 74
tctagccttc tcgtgtgcag acccaggagt cgaaccagtt                    40

<210> SEQ ID NO 75
<211> LENGTH: 38
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 75
tctagccttc tcgtgtgcag atggccccag acgtccat                      38

<210> SEQ ID NO 76
<211> LENGTH: 40
<212> TYPE: DNA
<213> ORGANISM: Artificial Sequence
<220> FEATURE:

```
<221> NAME/KEY: source
<223> OTHER INFORMATION: /note="Description of Artificial Sequence:
      Synthetic primer"

<400> SEQUENCE: 76
tctagccttc tcgtgtgcag acccagggt cgaaccagtt                              40

<210> SEQ ID NO 77
<211> LENGTH: 44
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 77
tctagccttc tcgtgtgcag acttctgaag caccattggt agag                        44

<210> SEQ ID NO 78
<211> LENGTH: 44
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 78
tctagccttc tcgtgtgcag aggccaaaat ctggttggtt catg                        44

<210> SEQ ID NO 79
<211> LENGTH: 44
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 79
tctagccttc tcgtgtgcag acgactttgg tggaggtagt tctt                        44

<210> SEQ ID NO 80
<211> LENGTH: 43
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 80
tctagccttc tcgtgtgcag aaagatcagc aggacaccca gat                         43

<210> SEQ ID NO 81
<211> LENGTH: 45
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 81
tctagccttc tcgtgtgcag acccaccagc aaagaggaag aaatc                       45
```

```
<210> SEQ ID NO 82
<211> LENGTH: 43
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 82
tctagccttc tcgtgtgcag actgccaacc ttcagtgttc gaa         43

<210> SEQ ID NO 83
<211> LENGTH: 43
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 83
tctagccttc tcgtgtgcag acggtcaatg tctgttaagg cag         43

<210> SEQ ID NO 84
<211> LENGTH: 43
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 84
tctagccttc tcgtgtgcag atttactccc ttcccgtcat tcc         43

<210> SEQ ID NO 85
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 85
tctagccttc tcgtgtgcag agcctcccag gatgtactct gtttat      46

<210> SEQ ID NO 86
<211> LENGTH: 45
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 86
tctagccttc tcgtgtgcag atttacctcc tgtaacggcc catca        45

<210> SEQ ID NO 87
<211> LENGTH: 45
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
```

<400> SEQUENCE: 87
tctagccttc tcgtgtgcag aagagggtcc ttggtttcta gatct        45

<210> SEQ ID NO 88
<211> LENGTH: 41
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 88
tctagccttc tcgtgtgcag aaggcgtggg tatctttgtc c             41

<210> SEQ ID NO 89
<211> LENGTH: 43
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 89
tctagccttc tcgcagcaca cagattgctg gtacttgtct tgc          43

<210> SEQ ID NO 90
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 90
tctagccttc tcgcagcaca atcttgtgtc acccctaac ac            42

<210> SEQ ID NO 91
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 91
tctagccttc tcgcagcaca atcgtccagc accacggtac              40

<210> SEQ ID NO 92
<211> LENGTH: 44
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 92
tctagccttc tcgcagcaca cacatatttc aggttcccctt gagg        44

<210> SEQ ID NO 93
<211> LENGTH: 42
<212> TYPE: DNA
<213> ORGANISM: Artificial Sequence

```
<220> FEATURE:
<221> NAME/KEY: source
<223> OTHER INFORMATION: /note="Description of Artificial Sequence:
      Synthetic primer"

<400> SEQUENCE: 93
tctagccttc tcgcagcaca ccacccgtct agttttcaac ca                    42

<210> SEQ ID NO 94
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 94
tctagccttc tcgcagcaca tgatgttagg agccctgttt gg                    42

<210> SEQ ID NO 95
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 95
tctagccttc tcgcagcaca cctctccaac acacaggagt aa                    42

<210> SEQ ID NO 96
<211> LENGTH: 44
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 96
tctagccttc tcgcagcaca gcttccttct tgatggtaga tggt                  44

<210> SEQ ID NO 97
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 97
tctagccttc tcgcagcaca gaaaccactc acttccttca gc                    42

<210> SEQ ID NO 98
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 98
tctagccttc tcgcagcaca ggcagaactt gttccagcaa ct                    42
```

```
<210> SEQ ID NO 99
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 99
tctagccttc tcgcagcaca tggaaggcaa agttgttctg tc                              42

<210> SEQ ID NO 100
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 100
tctagccttc tcgcagcaca atcgctcttg gatctacaca ca                              42
```